United States Patent
Erion et al.

(10) Patent No.: US 8,080,536 B2
(45) Date of Patent: *Dec. 20, 2011

(54) PHOSPHORUS-CONTAINING PRODRUGS

(75) Inventors: Mark D. Erion, Del Mar, CA (US); K. Raja Reddy, San Diego, CA (US); Serge H. Boyer, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/889,889

(22) Filed: Sep. 24, 2010

(65) Prior Publication Data

US 2011/0009356 A1 Jan. 13, 2011

Related U.S. Application Data

(60) Continuation of application No. 11/779,689, filed on Jul. 18, 2007, now Pat. No. 7,816,345, which is a continuation of application No. 11/601,843, filed on Nov. 20, 2006, now abandoned, which is a division of application No. 09/518,501, filed on Mar. 3, 2000, now Pat. No. 7,205,404.

(60) Provisional application No. 60/153,127, filed on Sep. 8, 1999, provisional application No. 60/123,013, filed on Mar. 5, 1999.

(51) Int. Cl.
A61K 31/66 (2006.01)
C07F 9/02 (2006.01)

(52) U.S. Cl. .......................................... 514/110; 558/81

(58) Field of Classification Search ................ 558/81; 514/110
See application file for complete search history.

(56) References Cited

U.S. PATENT DOCUMENTS

| | | | |
|---|---|---|---|
| 3,018,302 A | 1/1962 | Bielefeld et al. | |
| 3,404,178 A | 10/1968 | Roy | |
| 3,796,700 A | 3/1974 | Yoshioka et al. | |
| 4,255,566 A | 3/1981 | Carrico et al. | |
| 4,318,982 A | 3/1982 | Hornby et al. | |
| 4,340,668 A | 7/1982 | Hornby et al. | |
| 4,376,165 A | 3/1983 | Hornby et al. | |
| 4,447,529 A | 5/1984 | Greenquist et al. | |
| 4,621,077 A | 11/1986 | Rosini et al. | |
| 4,659,825 A | 4/1987 | Holy et al. | |
| 4,705,651 A | 11/1987 | Staibano | |
| 4,724,232 A | 2/1988 | Rideout et al. | |
| 4,724,233 A | 2/1988 | De Clercq et al. | |
| 4,777,163 A | 10/1988 | Bosies et al. | |
| 4,804,655 A | 2/1989 | Müller et al. | |
| 4,808,716 A | 2/1989 | Holy et al. | |
| 4,861,759 A | 8/1989 | Mitsuya et al. | |
| 4,879,277 A | 11/1989 | Mitsuya et al. | |
| 4,882,142 A | 11/1989 | Simon et al. | |
| 4,898,724 A | 2/1990 | Simon et al. | |
| 4,939,130 A | 7/1990 | Jaeggi et al. | |
| 4,952,575 A | 8/1990 | Sauerbier et al. | |
| 4,952,740 A | 8/1990 | Juge et al. | |
| 5,034,394 A | 7/1991 | Daluge | |
| 5,047,533 A | 9/1991 | Reist et al. | |
| 5,089,500 A | 2/1992 | Daluge | |
| 5,130,303 A | 7/1992 | Akiyama et al. | |
| 5,153,183 A | 10/1992 | Kawabe et al. | |
| 5,157,027 A | 10/1992 | Biller et al. | |
| 5,204,355 A | 4/1993 | Zsadon et al. | |
| 5,210,085 A | 5/1993 | Liotta et al. | |
| 5,212,304 A | 5/1993 | Fung et al. | |
| 5,240,946 A | 8/1993 | Kinney et al. | |
| 5,246,937 A | 9/1993 | Hamden et al. | |
| 5,258,538 A | 11/1993 | Fung et al. | |
| 5,366,965 A | 11/1994 | Strein | |
| 5,480,875 A | 1/1996 | Isomura et al. | |
| 5,532,225 A | 7/1996 | Reist et al. | |
| 5,583,122 A | 12/1996 | Benedict et al. | |
| 5,658,889 A | 8/1997 | Gruber et al. | |
| 5,663,159 A | 9/1997 | Starrett, Jr. et al. | |
| 5,681,590 A | 10/1997 | Bechard et al. | |
| 5,721,219 A | 2/1998 | Ingall et al. | |
| 5,814,639 A | 9/1998 | Liotta et al. | |
| 5,840,716 A | 11/1998 | Ubasawa et al. | |
| 5,869,467 A | 2/1999 | Holy et al. | |

(Continued)

FOREIGN PATENT DOCUMENTS

CH 492 738 6/1970

(Continued)

OTHER PUBLICATIONS

Alarcon, "Studies on the In Vivo Formation of Acrolein: 3-Hydroxy-propylmercapturic Acid as an Index of Cyclophosphamide (NSC-26271) Activiation," *Cancer Treatment Reports* 60(4):327-335, U.S. National Cancer Institute (1976).

Alexander et al., "Preparation of 9-(2-Phosphonomethoxyethyl) Adenine Esters as Potential Prodrugs," *Collect. Czech. Chem. Chem. Commun.* 59:1853-1869, Nakladatelstvi Ceskoslovenski Akademie Ved. (1994).

Amin et al., "1-Hydroxy-3-(methylpentylamino)-propylidene-1, 1-bisphosphnic Acid as a Potent Inhibitor of Squalene Synthase," *Arzneim.-Forsch/Drug Res.* 46(8):759-762 Editio Cantor (1996).

(Continued)

*Primary Examiner* — James O. Wilson
*Assistant Examiner* — Ebenezer O Sackey
(74) *Attorney, Agent, or Firm* — Arnold & Porter LLP

(57) ABSTRACT

Novel cyclic phosphoramidate prodrugs of drugs of formula I

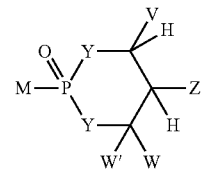

their use in delivery of drugs to the liver, their use in enhancing oral bioavailability, and their method of preparation are described.

26 Claims, No Drawings

U.S. PATENT DOCUMENTS

| | | | |
|---|---|---|---|
| 5,914,331 | A | 6/1999 | Liotta et al. |
| 5,962,522 | A | 10/1999 | Wacher et al. |
| 6,004,927 | A | 12/1999 | Benet et al. |
| 6,028,054 | A | 2/2000 | Benet et al. |
| 6,054,587 | A | 4/2000 | Reddy et al. |
| 6,110,903 | A | 8/2000 | Kasibhatla et al. |
| 6,117,873 | A | 9/2000 | Acklin et al. |
| 6,284,748 | B1 | 9/2001 | Dang et al. |
| 6,294,672 | B1 | 9/2001 | Reddy et al. |
| 6,312,662 | B1 | 11/2001 | Erion et al. |
| 6,399,782 | B1 | 6/2002 | Kasibhatla et al. |
| 6,489,476 | B1 | 12/2002 | Dang et al. |
| 6,752,981 | B1 | 6/2004 | Erion et al. |
| 6,756,360 | B1 | 6/2004 | Erion et al. |
| 6,946,115 | B2 | 9/2005 | Erion et al. |
| 7,205,404 | B1 | 4/2007 | Erion et al. |
| 7,303,739 | B2 | 12/2007 | Erion et al. |

FOREIGN PATENT DOCUMENTS

| | | |
|---|---|---|
| DE | 35 12 781 A1 | 4/1985 |
| EP | 0 002 062 A1 | 5/1979 |
| EP | 0 072 987 A1 | 8/1982 |
| EP | 0 072 531 A1 | 2/1983 |
| EP | 0 158 057 A | 10/1985 |
| EP | 0 161 955 A1 | 11/1985 |
| EP | 0 261 283 A1 | 9/1986 |
| EP | 0 180 276 A1 | 12/1988 |
| EP | 0 338 372 A2 | 10/1989 |
| EP | 0 353 692 A2 | 7/1990 |
| EP | 0 481 214 B1 | 4/1992 |
| EP | 1 165 570 B1 | 1/2002 |
| GB | 987378 | 9/1970 |
| JP | 62-195392 A2 | 8/1987 |
| JP | 62/249996 A2 | 10/1987 |
| WO | WO 90/08155 A1 | 7/1990 |
| WO | WO 90/10636 A1 | 9/1990 |
| WO | WO 91/19721 A1 | 12/1991 |
| WO | 96/01267 | 1/1996 |
| WO | 97/03679 | 2/1997 |
| WO | WO 97/22614 A1 | 6/1997 |
| WO | 98/09668 | 3/1998 |
| WO | 98/39342 | 9/1998 |
| WO | 98/39343 | 9/1998 |
| WO | 98/39344 | 9/1998 |
| WO | WO 99/45016 | 9/1999 |
| WO | WO 01/39724 A2 | 6/2001 |

OTHER PUBLICATIONS

Anderson et al., "Cyclophosphamide and 4-Hydroxycyclophosphamide/Aldophosphamide Kinetics in Patients Receiving High-Dose Cyclophosphamide Chemotherapy," *Clinical Cancer Research* 2:1481-1487 (1996).

Annaert et al., "Transport, Uptake, and Metabolism of the Bis(pivaloyloxymethyl)-Ester Prodrug of 9-(2-Phosphonylmethoxyethyl) Adenine in an In Vitro Cell Culture System of the Intestinal Mucosa (Caco-2)," *Pharm. Res.* 14(4):492-496 (1997).

Arnér et al., Mammalian Deoxyribonculeoside Kinases, *Pharmac. Ther.* 67(2):155-186 (1995).

Arnold et al., "Über Beziehungen zwischen chemischer Konstitution and cancerotoxischer Wirkung in der Reihe der Phosphamidester des Bis-(β-chloräthyl)-amins," *Arzeimittel Forschung. Drug Research* 11:143-158, ECV Editio Cantor Verlag, Aulendorf, Germany (1961).

Atiq et al., "Treatment of Unresectable Primary Liver Cancer with Introhepatic Fluorodeoxyuridine and Mitomycin C Through an Implantable Pump," *Cancer* 69(4):920-924 (1992).

Auberson et al., "N-Phosphonoalkyl-5-Aminomethylquinoxaline-2, 3-Diones: In Vivo Active AMPA and NMDA-(Glycine) Antagonists," *Bioorg. Med. Chem. Lett.* 9:249-254 (1999).

Baker et al., "Microtiter Plate Assay for the Measurement of Glutathione and Glutathione Disulfide in Large Numbers of Biological Samples," *Annal. Biochem.* 190:360-365 (1990).

Balthazor et al., "Nickel-Catalyzed Arbuzov Reaction: Mechanistic Observations," *J. Org. Chem.* 45:5425-5426 (1980).

Banker et al., "Modern Pharmaceutics, 3ed.," Marcel Dekker, New York, 1996, pp. 451 and 596.

Beaucage et al., The Synthesis of Modified Oligonucleotides by the Phosphoramidite Approach and Their Applications, *Tetrahedron* 49(28):6123-6194 (1993).

Bedford et al., "Synthesis of Water-Soluble Prodrugs of the Cytotoxic Agent Combretastatin A4," *Bioorg. Med. Chem. Lett.* 6(2):157-160 (1996).

Beilstein Registry No. 3635189, *Beilstein Institut zur Foerderung der Chemischen Wissenschatten* (1991).

Bentrude et al.. *Am. Chem. Soc.*, 108(21):6669-6675 (1986).

Bentrude et al., *J. Am. Chem. Soc.*, 110(20:7119-7127 (1988).

Bentrude et al., "Stereo- and Reglochemistries of the Oxidations of 2-Methoxy- 5-*tert*-butyl-1,3,2-dioxaphosphorinanes and the Cyclic Methyl 3'5'-Phosphite of Thymidine by $H_2O/I_2$ and $O_2$/AIBN to P-Chiral Phosphates. $^{17}$O NMR Assignment of Phosphorus Configuration to the Diasteromeric Thymidine Cyclic Methyl 3'5'-Monophosphates," *J. Am. Chem. Soc.* 111:3981-3987 (1989).

Berry et al., "High-Yield Preparation of Isolated Rat Liver Parenchymal Cells," *J. of Cell Biology* 43:506-520 (1969).

Bespalov et al., "Prolongation of Morphine Analgesia by Competitive NMDA Receptor Antagonist D-CPPene (SDZ EAA 494) in Rats," *Eur. J. Pharmacol.* 351:299-305 (1998).

Bijsterbosch et al., "Disposition of the Acyclic Nucleoside Phsophonate (S)-9-(3-Hydroxy-2-Phosphonylmethoxypropyl) Adenine," *Antimicrobial Agents and Chemotherapy*, 42:1146-1150(1998).

Bijsterbosch et al., "Disposition of the Acyclic Nucleoside Phosphonate (S)9- (3-Hydroxy-2-Phosphonylmethoxyproply)Adenine," *Antimicrobial Agents and Chemotherapy* 42:1146-1150 (1998).

Bird et al., "Synthesis of Novel *N*-Phosphonoalkyl Dipeptide Inhibitors of Human Collagenase," *J. Med. Chem.* 37:158-169 (1994).

Boddy et al., "Individual Variation in the Activation and Inactivation of Metabolic Pathways of Cyclophosphamide," *J. National Cancer Institute* 84(22):744-748 (1992).

Borch et al., "The Mechanism of Activation of 4-Hydroxycyclophosphamide," *J. Med. Chem.* 30:427-431 (1987).

Borch et al., "Synthesis and Antitumor Properties of Activated Cyclophosphamide Analogues," *J. Med. Chem.* 34:3044-3052 (1991).

Borch et al., "Synthesis, Activation and Cytotoxicity of Aldophosphamide Analogues," *J. Med. Chem.* 34:3052-3058 (1991).

Boyd et al., "Synthesis and Antitumor Activity of Cyclophosphamide Analogues. 3. Preparation, Molecular Structure Determination, and Anticancer Screening of Racemic *cis*- and *trans*-4-Phenylcydophosphamide," *J. Med. Chem.* 23:372-375 (1980).

Brain et al., "Modulation of P450-Dependent Ifosfamide Pharmacokinetics: a Better Understanding of Drug Activation In Vivo," *British J. of Cancer* 77(11):1768-1776 (1998).

Brenna et al., "Affinity-Chromatography Purification of Alkaline Phosphatase from Calf Intestine," *Biochem. J.* 151:291-296 (1975).

Brill et al., "Arbuzov-like Dealkylation Reactions of Transition-Metal-Phosphite Complexes," *Chem. Rev.* 84:577-585 (1984).

Brock et al., "Acrolein, the Causative Factor of Urotoxic Side-effects of Cyclophosphamide, Ifosfamide, Trofosfamide and Sufosfamide," *Arzneimittel Forschung Drug Research* 29(4):659-661 (1979).

Campagne et al., "Synthesis of Mixed Phosphonate Diester Analogues of Dipeptides using BOP or PyBOP Reagents," *Tetrahedron Lett.* 34(42):6743-6744 (1993).

Campbell, "The Synthesis of Phosphonate Esters, an Extension of the Mitsunobu Reaction," *J. Org. Chem.* 57:6331-6335 (1992).

Casara et al, "Synthesis of Acid Stable 5'-O-Fluoromethyl Phosphonates of Nucleosides. Evaluation as Inhibitors of Reverse Transcriptase," *Bioorg. Med..Chem. Lett.* 2(2):145-148 (1992).

Casteel et al., "Steric and Electronic Effects in the Aryl Phosphate to Arylphosphonate Rearrangement," *Synthesis* 691-693 (1991).

Chang et al., "Enhanced Cyclophosphamide and Ifosfamide Activation in Primary Human Hepatocyte Cultures: Response to Cytochrome P-450 Inducers and Autoinduction by Oxazaphosphorines," *Cancer Research* 57:1946-1954 (1997).

Chen et al., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Research* 55:581-589 (1995).

Chen et al, "Sensitization of Human Breast Cancer Cells to Cyclophosphamide and Ifosfamide by Transfer of a Liver Cytochrome P450 Gene," *Cancer Research* 56:1331-1340 (1996).

Clark et al., "Oxidative Metabolism of Cyclophosphamide: Identification of the Hepatic Monooxygenase Catalysts of Drug Activation," *Cancer Research* 49:2344-2350 (1989).

Cooper et al., "Use of Carbohydrate Derivatives for Studies of Phosphorus Stereo-Chemistry. Part II. Synthesis and Configrational Assignments of 1, -3, 2-Oxathiaphosphorinan-2-ones and 1, 3, 2-Dioxaphosphorinan-2-thiones," *J. Chem. Soc. Perk. Trans. I.* 10:1049-1052 (1974).

Coppi et al., "Lewis Acid Mediated Condensation of Alkenols and Aldehydes. A Selective Synthesis of Tetrahydropyrans and Oxepanes," *J. Org. Chem.* 53(4) 911-913 (1988).

Database Beilstein Registry No. 1028505, Beilstein Institute for Organic Chemistry, Frankfurt, Germany, Nov. 29, 1988 (2 pages).

Database Beilstein Registry No. 1083232, Beilstein Institute for Organic Chemistry, Frankfurt, Germany, Nov. 29, 1988 (1 page).

Database Beilstein Registry No. 1085700, Beilstein Institute for Organic Chemistry, Frankfurt, Germany, Nov. 29, 1988 (1 page).

Database Beilstein Registry No. 6530655, Beilstein Institute for Organic Chemistry, Frankfurt, Germany, Apr. 18, 1994 (2 pages).

Davis et al., "Effect of *Withania somnifera* on Cyclosphosphamide-induced Urotoxicity," *Cancer Letters* 148:9-17 (2000).

Dearfield et al., "Analysis of the Genotoxicity of Nine Acrylate/Methacrylate Compounds in L5178Y Mouse Lymphoma Cells," *Mutagenesis* 4:381-393 (1989).

Dechant et al., "Ifosfamide/Mesna. A Review of Its Antineoplastic Activity, Pharmacokinetic Properties and Therapeutic Efficacy in Cancer," *Drugs* 42(3):428-467 (1991).

De Clercq et al., "A Novel Selective Broad-spectrum Anti-DNA Virus Agent," *Nature* 323:464-467 (1986).

Deleve et al., "Cellular Target of Cyclophosphamide Toxicity in the Murine Liver: Role of Glutathione and Site of Metabolic Activation," *Hepatology* 24(4): 830-837 (1996).

DeLombaert et al., "N-Phosphonomethyl Dipeptides and Their Phosphonate Prodrugs, a New Generation of Neutral Endoprptidase (NEP, EC 3.4.24.11) Inhibitors," *J. Med. Chem.* 37:498-511 (1994).

Delombaert et al., "Pharmacological Profile of a Non-Peptidic Dual Inhibitor of Neutral Endopeptidase 24.11 and Endothelin-Converting Enzyme," *Biochem. Biophys. Res. Commun.* 204(1):407-412 (1994).

Delphion English-language abstract of European Patent Publication No. 0 072 987 A1, 2 pages, accessed on Oct. 20, 2005 at https://www.delphion.com/details?pn=EP00072987A1&s FAMILY=1.

Denmark et al., *Tetrahedron* 48(11):2191-2208 (1992).

Desos et al., "Structure-Activity Relationships in a Series of 2(1H)-Quinolones Bearing Different Acidic Function in the 3-Position: 6,7-Dichloro-2(1H)-oxoquinoline-3phosphonic Acid, a New Potent and Selective AMPA/Kainate Antagonist with Neuroprotective Properties," *J. Med. Chem.* 39:197-206 (1996).

de Waziers et al., "Cytochrome P450 Isoenzymes, Epoxide Hydrolase and Glutathlone Transferases in Rat and Human Hepatic and Extrahepatic Tissues1," *The Journal of Pharmacology and Experimental Therapeutics*, 253(1):387-394 (1989).

Dickson et al., "Orally Active Squalene Synthase Inhibitors: Bis((acyloxy)alkyl) Prodrugs of the α-Phosphonosulfonic Acid Moiety," *J. Med. Chem.* 39:661-664 (1996).

Edmunson et al., "Cyclic Organophosphorus Compounds. Part 23. Configurational Assignments in the 4-Phenyl-1, 3, 2λ5-dioxaphosphorinane Series. X-Ray Molecular Structure of *cis*-2-Benzylamino-4-phenyl-1,3, 2-dioxaphosphorinane 2-Oxide," *J. Chem. Res. Synop.* 5:122-123 (1989).

Elliott et al., "Synthesis and Biological Evaluation of Phosphonamidate Peptide Inhibitors of Enkephalinase and Angiotensin-Converting Enzyme," *J. Med. Chem.* 28:1208-1216 (1985).

English-language abstract for EP0002062, esp@cenet Worldwide database (1 page), (May 30, 1979).

English-language abstract for EP0072531, esp@cenet Worldwide database (1 page), (Feb. 23, 1983).

Enriquez et al., "Conjugation of Adenine Arabinoside 5'-Monophosphate to Arabinogalactan: Synthesis, Characterization, and Antiviral Activity," *Bioconjugate Chem.* 6:195-202 (1995).

Erion et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5183 (2004).

Erion et al., "Liver-Targeted Drug Delivery Using HepDirect Prodrugs," *J. of Pharmacology & Experimental Therapeutics* 312(2):554-560 (2005).

Erion et al., "HepDirect Prodrugs for Targeting Nucleoside-Based Antiviral Drugs to the Liver," *Current Opinion in Investigational Drugs* 7(2):109-117 (2006).

Evans "Chemistry 206 Advanced Organic Chemistry," Harvard University, [online] Sep. 11, 2003, [retrieved on Jan. 19, 2005]. Retrieved from the internet, <http://www.courses fas.Harvard.edu/~chem206/Fall_2003/Lectures_and_Handouts/>.

Farquhar et al., "5'-'4-(Pivaloyloxy)-1, 3, 2-dioxaphosphorin an -2y]1-2'-deoxy-5-fluorouridine: a membrane-permeating prodrug of 5-fluoro-2'-deoxyuridylic acid (FDUMP)," *J. Med. Chem.* 38:488-495 (1995).

Farquhar et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36(5):655-658 (1995).

Farquhar et al., "Biologically Reversible Phosphate-Protective Groups," *J. Pharm. Sci.* 72(3):324-325 (1983).

Farquhar et al., "Synthesis and Biological Evaluation of 9-[5'-(2-Oxo-1,3,2- oxazaphosphorinan-2-y1)-β-D-arabinosyl]adenine and 9-5'-(2-Oxo-1,3,2- dioxazaphosphorinan-2-y1)-β-D-arabinosyl]adenine: Potential Neutral Precursors of 9- [β-D-Arabinofuranosyl]adenine]5'-Monophosphate," *J. Med. Chem.* 28:1358-1361 (1985).

Farquhar et al., "Synthesis and Biological Evaluation of Neutral Derivatives of 5-Fluoro-2'-deoxyuridine 5'-Phosphate," *J. Med. Chem.* 26: 1153-1158 (1983).

Farquhar et al., "Synthesis and Antibumor Evaluation of Bis[pivaloyloxy)methyl] 2'-Deoxy-5-fluorouridine 5'-Monophosphate (FdUMP): A Strategy to Introduce Nucleotides into Cells," *J. Med. Chem.* 37:3902-3909 (1994).

Fiume et al., "Inhibition of Hepatitis B Virus Replication by Vidarbine Monophosphate Conjugated with Lactosaminated Serum Albumin," *The Lancet* 13-15 (1988).

Fraiser et al., "Murine Strain Differences in Metabolism and Bladder Toxicity of Cyclophosphamide," *Toxicology* 75:257-272 (1992).

Freed et al., "Evidence for Acyloxymethyl Esters of Pyrimidine 5'-Deoxyribonucleotides as Extracellular Sources of Active 5'-Deoxyribonucleotides in Cultured Cells," *Biochem. Pharmac.* 38:3193-3198 (1989).

Freeman et al., "Prodrug Design for Phosphates and Phosphonates," *Progress in Medicinal Chemistry* 34:111-147 (1997).

Friis et al., "Prodrugs of Phosphates and Phosphonates: Novel Lipophilie α-acloxyalkyl Ester Derivatives of Phosphate—or Phosphonate Containing Drugs Masking the Negative Charges of these Groups," *Euro J. Pharm. Sci,* 4:49-59 (1996).

Gao et al., "Asymmetric Synthesis of Both Enantiomers of Tomoxetine and Fluoxetine. Selective Reduction of 2,3-Epoxycinnamyl Alcohol with Red-A1," *J. Org. Chem.* 53:4081-4084 (1988).

Gilard et al., "Chemical Stability and Fate of the Cytostatic Drug Ifosfamide and Its N-Dechloroethylated Metabolities in Acidic Aqueous Solutions," *J. Med. Chem.* 42:2542-2560 (1999).

Gorenstein et al., "Stereoelectronic Effects in the Reactions of Epimeric 2-Aryloxy-2-oxy-1, 3,2-dioxaphosphorinanes and Oxazaphosphorinanes," *J. Am. Chem. Soc.* 102:5077-5081 (1980).

Groen et al.. "Intracellular Compartmentation and Control of Alanine Metabolism in Rat Liver Parenchymal Cells," *Eur. J. Biochem.* 122:87-93 (1982).

Guida et al., "Structure-Based Design of Inhibitors of Purina Nucleoside Phosphorylase. 4. A Study of Phosphate Mimics," *J. Med. Chem.* 37:1109-1114 (1994).

Gurtoo et al., "Role of Glutathione in the Metabolism-dependent Toxicity and Chemotherapy of Cyclophosphamide," *Cancer Research* 41:3584-3591 (1981).

Gustin et al., "A Rapid, Sensitive Assay for Adenosine Deaminase," *Analytical Biochemistry* 71:527-532 (1976).

Harada et al., "Resolution of 1,3-alkanediols Via Chiral Spiroketals Derived from i-Menthone," *Tetrahedron* 28(41):4843-4846 (1987).

Hayakawa et al., "Benzimidazolium Triflate as an Efficient Promoter for Nucleotide Synthesis via the Phosphoramidite Method," *J. Org. Chem.* 61:7996-7997 (1996).

He et al., Inactivation of Cytochrome P450 3A4 by Bergamottin a Component of Grapefruit Juice, *Chem. Res. Toxicol.* 11(4):252-259 (1998).

Hillers et al., "Analogs of pyrimidinemono-and polynucleotides. IV. Phosphates of 1-(1,4-dihydroxy-2-pentyl)thymine and 1-(1,3-dihydroxy-2-propyl) uracil." *Khim Geterotski Soedin* 5:678-683 (1978) Chem Abstr. vol. 89. No. 17; abst. No. 146864u.

Hilton, "Role of Aldehyde Dehydrogenase in Cyclophosphamide-resistant L1210 Leukemia," *Cancer Research* 44:5156-5160 (1984).

Hirayama et al., "Structure and Conformation of a Novel Inhibitor of Angiotensin I Converting Enzyme—a Tripeptide Containing Phosphonic Acid," *Int. J. Pept Protein Res.* 38:20-24 (1991).

Hulst et al., "A New $^{31}$P NMR Method for the Enantiomeric Excess Determination of Alcohols, Amines and Amino Acid Esters," *Tetrahedron Letters* 34(8):1339-1342 (1993).

Hunston et al., "Synthesis and Biological Properties of Some Cyclic Phosphotriesters Derived from 2'-Deoxy-5-fluorouridine," *J. Med. Chem.* 27:440-444 (1984).

Jain et al., "Sulfonyl-Containing Aldophosphamide Analogues as Novel Anticancer Prodrugs Targeted against Cyclophosphamide-Resistant Tumor Cell Lines," *J. Med. Chem.* 47:3843-3852 (2004).

Jounaidi et al., "Retroviral Transfer of Human Cytochrome P450 Genes for Oxazaphosphorine-based Cancer Gene Therapy," *Cancer Research* 58:4391-4401 (1998).

Jounaidi et al., "Frequent, Moderate-Dose Cyclophosphamide Administration Improves the Efficacy of Cytochrome P-450/Cytochrome P-450 Reductase-based Cancer Gene Therapy," *Cancer Research* 61:4437-4444 (2001).

Kachel et al., "Cyclophosphamide-Induced Lung Toxicity: Mechanism of Endothelial Cell Injury," *J. Pharmacology and Experimental Therapeutics* 268(1):42-46 (1994).

Keenan et al., "Pathology Reevaluation of the Kociba et al. (1978) Bioassay of 2,3,7,8-TCDD: Implications for Risk Assessment," *J. Tox. Envir. Health* 34:279-296 (1991).

Kelley et al., "[[(Guaninylalkyl)phosphinico] methyl)] phosphonic Acids. Multisubstrate Analogue Inhibitors of Human Erythrocyte Purine Nucleoside Phosphorylase," *J. Med. Chem.* 38:1005-1014 (1995).

Khamnei et al., "Neighboring Group Catalysis in the Design of Nucleotide Prodrugs," *J. Med. Chem.* 39:4109-4115 (1996).

Khorana et al., "Cyclic Phosphates. III. Some General Observations on the Formation and Properties of Five-, Six-and Seven-membered Cyclic Phophate Esters," *JACS* 79:430-436 (1957).

Korba et al., "Liver-targeted Antiviral Nucleosides: Enhanced Antiviral Activity of Phosphatidyl-dideoxyguanosine Versus Dideoxyguanosine in Woodchuck Hepatitis Virus Infection In Vivo," *Hepatology* 23(5):958-963 (1996).

Kryuchkov et al., *Izv. Akad. Nauk SSSR. Ser. Khim.* 6:1201-1248 (1987).

Kuriyama et al., "Transient Cyclophosphamide Treatment Before Intraportal Readministration of an Adenoviral Vector can Induce Re-expression of the Original Gene Construct in Rat Liver," *Gene Therapy* 6:749-757 (1999).

Kwon et al., "Effects of N-Substitution on the Activation Mechanisms of 4Hydroxycyclophosphamide Analogues," *J. Med Chem.* 32:1491-1496 (1989).

Lefebvre et al., "Mononucleotide Phosphotriester Derivatives with S-Acyl-2-thioethyl Bioreversible Phosphate-Protecting Groups: Intracellular Delivery of 3'-Azido-2', 3'-dideoxythymidine 5'-Monophosphate," *J. Med. Chem.* 38:3941-3950 (1995).

Lilo et al., "Synthesis and Configurational Assignment of Bicyclic 'Preactivated' Analogues of Cyclophosphamide," *Tetrahedron Letters* 31(6):887-890 (1990).

Lohr et al., "Targeted chemotherapy by intratumor injection of encapsulated cells engineered to produce CYP2B1, and ifosfamide activating cytochrome P450," *Gene Therapy* 5:1070-1078 (1988).

Lok et al., "Neurotoxicity associated with adenine arabinoside monophosphate in the treatment of chronic hepatitis B virus infection," *J. Antimicrob. Chemotherap.* 14:93-99 (1984).

Lorey et al., "A New-Cyclic Phosphoramidate D4T Prodrug Approach *Cyclo*Amb-D4T-Phosphoramidates," *Nucleosides & Nucleotides* 18(4&5):947-948 (1999).

Low et al., "Conversion of 4-Hydroperoxycyclophosphamide and 4-Hydroxycyclophosphamide to Phosphoramide Mustard and Acrolein Mediated, by Bifunctional Catalysts," *Cancer Research* 42:830-837 (1982).

Lu et al., "Palladium-Catalyzed Reaction of Aryl Polyfluoroalkanesulfonates with O,O- Dialkyl Phosphonates," *Synthesis* 726-727 (1987).

Ludeman et al., "Synthesis and Antitumor Activity of Cyclophosphamide Analogs. 1. Benzo Annulated Cyclophosphamide and Related Systems," *J. Med. Chem.* 18(12):1251-1253 (1975).

Ludeman et al., Synthesis and Antitumor Activity of Cyclophosphamide Analogues. 2. Preparation, Hydrolytic Studies, and Anticancer Screening of 5-Bromocyclophosphamide, 3,5-Dehydrocyclophosphamide, and Related Systems; *J. Med Chem.* 22(2):151-158 (1979).

Ludeman et al., "Synthesis and Antitumor Activity of Cyclophosphamide Analogues. 4. Preparation, Kinetic Studies, and Anticancer Screening of "Phenyl ketophos phamide" and Similar Compounds Related to the Cyclophosphamide Metabolyte Aldophosphamide," *J. Med. Chem.* 29:716-727 (1986).

Ludeman et al., "Synthesis of Reactive Metabolite-Analogues of Cyclophosphamide for Comparisons of NMR Kinetic Parameters and Anticancer Screening Data," *Drugs Exptl. Clin. Res.* XII(6/7):527-532 (1986).

May-Manke et al., "Investigation of the Major Human Hepatic Cytochrome P450 Involved in 4-Hydroxylation and N-dechloroethylation of Trofosfamide," *Cancer Chemother. Pharmacol.* 44:327-334 (1999).

Maynard-Faure et al., "New Strategy for the Diastereoselective Synthesis of Bicyclic 'Pre-activated' Analogues of Cyclophosphamide," *Tetrahedron Letters* 39:2315-2318 (1998).

McGuigan et al., "Intracellular Delivery of Bioactive AZT Nucleotides by Aryl Phosphate Derivatives of *AZT*," *J. Med. Chem.* 36:1048-1052 (1993).

McGuigan et al., "Kinase Bypass: A New Strategy for Anti-HIV Drug Design," *Bioorganic & Medicinal Chemistry Letters* 3(6):1207-1210 (1993).

Meier et al., "ADA Bypass by lipophilic Cyclo-Sal-ddAMP Pro-Nucleotides a second Example of the Efficiency of the *cyclo*Sat-Concept," *Bioorg. Med. Chem. Lett.* 7(12):1577-1582 (1997).

Meier et al., "Cyclic Saligenyl Phosphotreisters of 2', 3'-Dideoxy-2', 3'-didehydrothymidine (d4T)—A New Pro-Nucleotide Approach," *Bioorg. Med. Chem. Lett.* 7:99-104 (1997).

Meijer et al., "Covalent and Noncovalent Protein Binding of Drugs: Implications for Hepatic Clearance, Storage, and Cell-Specific Drug Delivery;*Pharm*"). *Res.* 6(2):105- 118 (1989).

Melvin, "An Efficient Synthesis of 2-Hydroxyphenylphosphonates," *Tetrahedron Lett.* 22(35):3375-3376 (1981).

Merckling et al., "Diastereoselectivity in Nucleophilic Displacement Reactions at Phosphorus; Isolation and Characterization of Pentacoordinated Intermediate," *Tetrahedron Letters* 37(13):2217-2220 (1996).

Meyer et al., "2-O'-Acyl-6-thioinosine Cyclic 3', 5'-Phosphates as Prodrugs of Thioinosinic Acid," *J. Med. Chem.* 22:811-815 (1979).

Misiura et al., "Synthesis and Antitumor Activity of Analogues of Ifosfamide Modified in the N-(2-Chloroethyl) Group," *J. Med. Chem.* 31(1):226-230 (1988).

Mitchell et al., "Acetaminophen-Induced Hepatic Necrosis. IV. Protective Role of Glutathione," *J. Pharmacology and Experimental Therapeutics* 187(1):211-217 (1973).

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonacetate,"*J. Chem. Soc. Perkin Trans*.1:2345-2353 (1992).

Mitsunobu, "The Use of Diethyl Azodicarboxylate and Triphenylphosphine in Synthesis and Transformation of Natural Products," *Synthesis* 1-28 (1981).

Moore et al., "Comparison of Mutagenicity Results for Nine Compounds Evaluated at the hgprt Locus In the Standard and Suspension CHO Assays," *Mutagenesis* 6:77-85 (1991).

Mosbo et al., "Dipole Moment, Nuclear Magnetic Resonance, and Infrared Studies of Phosphorus Configurations and Equilibria in 2-R-2-Oxo-1, 3, 2-dioxaphosphorinones," *J. Org. Chem.* 42(9):1549-1555 (1977).

Murray et al., "Cytochrome P450 CYP3A in Human Renal Cell Cancer," *British Journal of Cancer* 79:1836-1842 (1999).

Murray et al., "Cytochrome P450 Expression is a Common Molecular Event in Soft Tissue Sarcomas," *J. Pathology* 171:49-52 (1993).

Nagamatsu et al., "New Phosphorylating Agents for General Synthesis of Mixed Phosphate Esters," *Tetrahedron Lett* 28(21):2375-2378 (1987).

Nakayama et al., "A Highly Enantioselective Synthesis of Phosphate Triesters," *J. Am. Chem. Soc.* 112:6936-6942 (1990).

Neidlein et al., "Mild Preparation of 1-Benzyloxyiminoalkylphosphonic Dichlorides: Application to the Synthesis of Cyclic Phosphonic Deisters and Cyclic Monoester Amides," *Heterocycles* 35:1185-1203 (1993).

Nifant'ev et al., "1,3,2,-Diazaphodsphorinanes," *Zh. Obshch. Khlm.* 49:53-61 (1979).

Nifantyev et al., "Synthesis and Structure of Some Stable Phospholane-Phospholanes," *Phos. Sulfur & Silicon* 113:1-13 (1996).

Ogg et al., "A Reporter Gene Assay to Assess the Molecular Mechanisms of Xenobiotic-dependent Induction of the Human CYP3A4 Gene In Vitro," *Xenobiotica* 29(3):269-279 (1999).

Ohashi et al., "Synthesis of Phosphonosphingoglycolipid Found in Marine Snail *Turbo Cornutis*," *Tetrahedron Lett.* 29(10):1189-1192 (1988).

Partial European Search Report for European Application No. 05 02 3116.6, dated Nov. 17, 2005 (13 pages).

Patent Abstracts of Japan, vol. 1998, No. 1, Jan. 30, 1998 and JP 09241284A (Yamishata Koji, et al.; Nippon Soda Co. Ltd.), Sep. 16, 1997.

Petrakis et al., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833 (1987), (1986).

Petit et al., "Antineoplastic Agents 322. Synthesis of Combretastatin A-4 Prodrugs," *Anti-Cancer Drug Design* 10:299-309 (1995).

Pitcher, "Built-In Bypass," *Nature* 429:39 (2004).

Predvoditelev et al., "Glycero-2-hydroxymethylene phosphates," *Journal of Organic Chemistry of the USSR* (English translation) 13:1489-1492 (1997).

Predvoditelev et al., "Synthesis of lipids and their models on the basis of glycerol alkylene phosphites. V. Cyclic phosphatidylglycerol and phosphatidylhydroxyhomocholine," *Journal of Organic Chemistry of the USSR* (English translation) 17:1156-1165 (1981).

Prosecution history of Dang, Q., et al., U.S. Appl. No. 09/398,698, filed Sep. 3, 1999, now patented as 6,489,476 B1.

Ramachandran et al., "Efficient General Synthesis of 1, 2-2 and 1, 3-diols in High Enantiomeric Excess via the Intramolecular Asymmetric Reduction of the Corresponding Ketoalkyl Diisopinocampheylorinate Intermediates," *Tretrahedron* 38(5):761-764 (1997).

Ramu et al., "Acrolein Mercapturates: Synthesis, Characterization, and Assessment of Their Role in the Bladder Toxicity of Cyclophosphamide," *Chem. Res. Toxicol.* 8:515-524 (1995).

Reddy et al., "Development of a Quantum Mechanics-Based Free-Energy Perturbation Method: Use in the Calculation of Relative Solvation Free Energies," *J. Am. Chem. Soc.* 126:6224-6225 (2004).

Reddy et al., "Stereoselective Synthesis of Nucleoside Monophosphate HepDirect™ Prodrugs," *Tetrahedron Letters* 46:4321-4324 (2005).

Redmore, "Phosphorus Derivatives of Nitrogen Heterocycles. 2. Pyridinephosphonic Acid Derivatives," *J. Org. Chem.* 35(12):4114-4117 (1970).

Ren et al., "Inhibition of Human Aldehyde Dehydrogenase 1 by the 4Hydroxycyclophosphamide Degradation Product Acrolein," *Drug Metabolism and Disposition* 27(1):133-137 (1999).

Ren et al., "Pharmacokinetics of Cyclophosphamide and its Metabolites in Bone Marrow Transplantation Patients," *Clinical Pharmacology and Therapeutics* 64(3):289-301 (1998).

Reusch, "Virtual Text of Organic Chemistry," Michigan State University, [online] Aug. 1, 2004, [retrieved on Jan. 19, 2005]. Retrieved from the internet, <http://www.cem.msu.edu/%7Ereusch/VirtualText/special2.htm#topl>.

Roy et al., "Development of a Substrate-Activity Based Approach to Identify the Major Human Liver P450 Catalysts of Cyclophosphamide and Ifosfamide Activation Based on cDNA-Expressed Activities and Liver Microsomal P450 Profiles," *Drug Metabolism and Disposition* 27(6):655-666 (1999).

Schwartz et al., "Cyclophosphamide Induces Caspase 9-Dependent Apoptosis in 9L Tumor Cells," *Molecular Pharmacology* 60(6):1268-1279 (2001).

Shaw et al., "Biological Screens of PMEA Prodrugs," *Pharm. Res.* 10 (Suppl) S-294 (1993).

Shih et al., "Studies on Potential Antitumor Agents (III). Synthesis of 4Arylcyclophosphamides," *Heterocycles* 9(9):1277-1285 (1978).

Shih et al., Synthesis and Structure of 6-Phenylcyclophosphamides; *Heterocycles* 24(6), 1599-1603 (1986).

Shih et al., "Preparation and Structures of 2-Dimethylamino-4-phenyl-1, 3,2-dioxaphosphorinane-2-oxides," *Bull. Inst. Chem. Acad. Sin.* 41:9-16 (1994).

Sladek et al., "Influence of Diuretics on Urinary General Base Catalytic Activity and Cyclophosphamide-induced Bladder Toxicity," *Cancer Treatment Reports* 66(11):1889-1900 (1982).

Sladek et al., "Restoration of Sensitivity to Oxazaphosphorines by Inhibitors of Aldehyde Dehydrogenase Activity in Cultured Oxazaphosphorine-resistant L1210 and Cross-Linking Agent-resistant P388 Cell Lines," *Cancer Research* 45:1549-1555 (1985).

Springate et al., "Toxicity of Ifosfamide and Its Metabolite Chloroacetaldehyde in Cultured Renal Tubule Cells," *In Vitro Cell Dev. Biol.-Animal* 35:314-317 (1999).

Starrett et al., "Synthesis, Oral Biovailability Determination, and an in Vitro Evaluation of Prodrugs for the Antiviral Agent 9-[2-(Phosphonomethoxy)-ethyl]adenine (PMEA)," *J. Med. Chem.* 37:1857-1834 (1994).

Sumida et al., "Quantitative Analysis of Constitutive and Inducible CYPs mRNA Expression in the HepG2 Cell Line Using Reverse Transcription-Competitive PCR," *Biochem. & Biophys. Res. Comm.* 267:756-780 (2000).

Ten Hoeve et al., "The Design of Resolving Agents. Chiral Cyclic Phosphoric Acids," *J. Org. Chem.* 50:4508-4514 (1985).

Thomson et al., "Synthesis, Bioactivation and Anti-HIV Activity of the Bis(4-acyloxybenzyl) and Mono(4-acyloxybenzyl) Esters of the 5'-monophosphate of AZ," *J. Chem. Soc. Perk. Trans. I.* 11:12391245 (1993).

Turner, "A General Approach to the Synthesis of 1,6-,1,7-, and 1,8-Naphthyridines," *J. Org Chem.* 55(15):4744-4750 (1990).

Unverified English-language translation of European Patent Publication No. 0 072 987 A1, 13 pages, (Aug. 13, 1982).

Venook, "Treatment of Hepatocellular Carcinoma: Too Many Options," *J. Clin. Oncol.* 12(6):1323-1334 (1994).

Vo-Quang et al., "(1-Amino-2-propenyl)phosphonic Acid, an Inhibitor of Alanine Racemase and D-Alanine:D-Alanine Ligase," *J. Med. Chem.* 29(4):579-581 (1986).

Wagner et al., "Direct Conversion of Tetrahydropyranylated Alcohols to the Corresponding Bromides," *Tetrahedron Letters* 30(5):557-558 (1989).

Wallace et al., "Design and Synthesis of Potent, Selective Inhibitors of Endothelin-Converting Enzyme," *J. Med. Chem.* 41:1513-1523 (1998).

Walsh et al., "Phenoxymethylphosphonic Acids and Phosphonic Acid Ion- exchange Resins," *J. Am. Chem. Soc.* 78:4455-4458 (1956).

Watanabe et al., "Dibenzyl Phosphorofluoridate, A New Phosphorylating Agent," *Tetrahedron Letters* 29(45):5763-5764 (1988).

Watkins, "Noninvasive Tests of CYP3A Enzymes," *Pharmacogenetics* 4:171-184 (1994).

Weber et al., "Activation of the Anti-cancer Drug Ifosphamide by Rat Liver Microsomal P450 Enzymes," *Biochem. Pharm.* 45(8):1685-1694 (1993).

Weibel et al., "Potentiating Effect of {2-(2-[(2-Amino-1,6-Dihydro-6-Oxo-9H-Purin-9yl]Methytl-Phenyl]] Ethenyl}Phosphonic Acid (MDL 74,428), A Potent Inhibitor of Purina Nucleoside Phosphorylase, on the Antiretroviral Activities of 2',3'-Dideoxyinosine Combined to Ribavirin in Mice," *Biochem. Pharmacol.* 48(2):245-252 (1994).

Weinhardt et al., "Synthesis and Antidepressant Profiles of Phenyl-Substituted 2- Amino- and 2-[(Alkoxyearbonyl)amino]-1,4,5,6-tetrahydropyrimidines," *J. Med Chem.* 28:694-898 (1985).

Wileman et al., "Receptor-Mediated Endocytosis," *Biochem. J.* 232:1-14 (1985).

Wolff, "Burger's Medicinal Chemistry, 5ed, Part I," John Wiley & Sons, 1995 pp. 975-977.

Yamanaka et al., "Metabolic Studies on BMS-200475, a New Antiviral Compound Active against Hepatitis B Virus," *Antimicrob. Agents Chemoth.* 43:190-193 (1999).

Yip et al., "Use of High-Performance Liquid Chromatography in the Preparation of Flavin Adenine Dinuleotide Analyte Conjugates," *J. of Chromatography* 326:301-310 (1985).

Yu et al., "In vivo Modulation of Alternative Pathways of P-450•Catalyzed Cyclophosphamide Metabolism: Impact on Pharmacokinetics and Antitumor Activity," *J. Pharm. Exp. Ther.* 288(3):928-937 (1999).

Yule et al., "The Effect of Fluconazole on Cyclophosphamide Metabolism in Children," *Drug Metabolism and Disposition* 27(3):417-421 (1999).

Zon et al., "4 Cyclophosphamide Analogues," *Prog. Med. Chem.* 19:205-246 (1982).

Zon et al., "NMR Spectroscopic Studies of Intermediary Metabolites of Cyclophosphamide. A Comprehensive Kinetic Analysis of the Interconversation of *cis*- and *trans*-4-Hydroxycyclophosphamide with Aldophosphamide and Concomitant Partitioning of Aldophosphamide Between Irreversible Fragmentation and Reversible Conjunction Pathways," *J. Med. Chem.* 27:466-485 (1984).

PHOSPHORUS-CONTAINING PRODRUGS

RELATED APPLICATION

This application is a continuation of U.S. application Ser. No. 11/779,689 filed Jul. 18, 2007, now allowed, which is a continuation application of U.S. application Ser. No. 11/601,843 filed Nov. 20, 2006, now abandoned, which is a divisional application of U.S. application Ser. No. 09/518,501 filed Mar. 3, 2000, now patented, which claims priority to U.S. Provisional Application Ser. No. 60/153,127, filed Sep. 8, 1999, and Provisional Application Ser. No. 60/123,013, filed Mar. 5, 1999, and each of which is incorporated by reference in their entirety.

FIELD OF THE INVENTION

The present invention is directed towards novel prodrugs that generate phosph(on)ate compounds which are biologically active or are further phosphorylated to produce biologically active compounds, to their preparation, to their synthetic intermediates, and to their uses. More specifically, the invention relates to the area of substituted cyclic 1,3-propanyl esters wherein the cyclic moiety contains at least one amino attached to the phosphorus.

BACKGROUND OF THE INVENTION

The following description of the background of the invention is provided to aid in understanding the invention, but is not admitted to be, or to describe, prior art to the invention. All cited publications are incorporated by reference in their entirety.

Free phosphorus and phosphonic acids and their salts are highly charged at physiological pH and therefore frequently exhibit poor oral bioavailability, poor cell penetration and limited tissue distribution (e.g. CNS). In addition, these acids are also commonly associated with several other properties that hinder their use as drugs, including short plasma half-life due to rapid renal clearance, as well as toxicities (e.g. renal, gastrointestinal, etc.) (e.g. *Antimicrob Agents Chemother* 1998 May; 42(5): 1146-50). Phosphates have an additional limitation in that they are not stable in plasma as well as most tissues since they undergo rapid hydrolysis via the action of phosphatases (e.g. alkaline phosphatase, nucleotidases).

Prodrugs of phosphorus-containing compounds have been sought primarily to improve the limited oral absorption and poor cell penetration. In contrast to carboxylic acid proesters, many phosphonate and phosphate esters fail to hydrolyze in vivo, including simple alkyl esters. The most commonly used prodrug class is the acyloxyalkyl ester, which was first applied to phosphate and phosphonate compounds in 1983 by Farquhar et al., *J. Pharm. Sci.* 72(3):324 (1983).

Cyclic phosphonate and phosphate esters have also been described for phosphorus-containing compounds. In some cases, these compounds have been investigated as potential phosphate or phosphonate prodrugs. Hunston et al., *J. Med. Chem.* 27: 440-444 (1984). The numbering for these cyclic esters is shown below:

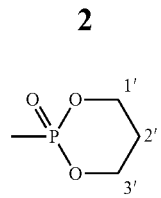

The cyclic 2',2'-difluoro-1',3'-propane ester is reported to be hydrolytically unstable with rapid generation of the ring-opened monoester. Starrett et al. *J. Med. Chem.* 37: 1857-1864 (1994).

Cyclic 3',5'-phosphate esters of araA, araC and thioinosine have been synthesized. Meier et al., *J. Med. Chem.* 22: 811-815 (1979). These compounds are ring-opened through the action of phosphodiesterases which usually require one negative charge.

Cyclic 1',3'-propanyl phosphonate and phosphate esters are reported containing a fused aryl ring, i.e. the cyclosaligenyl ester, Meier et al., *Bioorg. Med. Chem. Lett.* 7: 99-104 (1997). These prodrugs are reported to generate the phosphate by a "controlled, non-enzymatic mechanism[s] at physiological pH according to the designed tandem-reaction in two coupled steps". The strategy was purportedly used to deliver d4-T monophosphate to CEM cells and CEM cells deficient in thymidine kinase infected with HIV-1 and HIV-2.

Unsubstituted cyclic 1',3'-propanyl esters of the monophosphates of 5-fluoro-2'-deoxy-uridine (Farquhar et al., *J. Med. Chem.* 26: 1153 (1983)) and ara-A (Farquhar et al., *J. Med. Chem.* 28: 1358 (1985)) were prepared but showed no in vivo activity. In addition, cyclic 1',3'-propanyl esters substituted with a pivaloyloxy methyloxy group at C-1' was prepared for 5-fluoro-2'-deoxy-uridine monophosphate (5-FdUMP; (Freed et al., *Biochem. Pharmac.* 38: 3193 (1989); and postulated as potentially useful prodrugs by others (Biller et al., U.S. Pat. No. 5,157,027). In cells, the acyl group of these prodrugs underwent cleavage by esterases to generate an unstable hydroxyl intermediate which rapidly broke down to the free phosphate and acrolein following a β-elimination reaction as well as formaldehyde and pivalic acid.

Unsubstituted cyclic phosphoramidate esters, i.e. cyclic phosphonate and phosphate esters wherein one of the ring oxygens is replaced with an NR, are also known. For example, cyclophosphamide (CPA) is representative of a class of mustard oncolytics that utilize this prodrug moiety. Although CPA is activated primarily in the liver via a cytochrome P450-catalyzed oxidation, its biological activity is outside the liver. CPA is an effective immunosuppressive agent as well as an oncolytic agent for extrahepatic cancers because one or more of the intermediate metabolites produced following P450 activation diffuses out of the liver and into the circulation. With time the intermediate(s) enter extrahepatic tissues and are thought to undergo a β-elimination reaction to generate acrolein and the active phosphoramide mustard. Both products are reported to be cytotoxic to cells. The mustard cytotoxicity results from alkylation of DNA (or RNA). Acrolein is reported to exert its toxicity via several mechanisms, including depletion of glutathione, alkylation of DNA and proteins via a Michael reaction. In addition, acrolein produces other toxicities such as the dose-limiting bladder toxicity commonly observed with cyclophosphamide therapy. Since the toxicity of these agents often hampers their use as chemotherapy agents, numerous strategies are under investigation that are designed to enhance P450 activity in or near tumors and thereby localize the activation and antiproliferative effect of these agents to the tumor. One strategy uses retroviruses or other well known techniques for introducing genes into target tissues (e.g. Jounaidi et al., *Cancer Research* 58, 4391 (1998)). Other strategies include the placement of encapsulated cells engineered to produce cytochrome P450s (e.g. Lohr et al., *Gene Therapy* 5, 1070 (1998)) at or near the tumor.

Unsubstituted cyclic phosphoramidate esters have also been prepared as potential prodrugs of the nucleosides araA and 5-fluoro-2'-deoxyuridine (Farquhar et al., *J. Med. Chem.* 28, 1358 1361 (1985); *J. Med. Chem.* 26, 1153-1158 (1983)). The compounds were studied in a mouse model of leukemia where it was assumed that if the prodrug transformation was similar to cyclophosphamide, then these agents would be useful for treating a variety of cancers including leukemias as well as carcinomas of the colon, breast and ovary. In addition, since some of the mechanisms that account for tumor cell drug resistance entail a decrease in the enzymes used to synthesize the monophosphate, the strategy was expected to possibly be beneficial in treating drug resistant tumors. The compounds were only "marginally effective" in prolonging life span in the mouse model.

A variety of substituted 1',3' propanyl cyclic phosphoramidates, wherein 1' represents the carbon alpha to the nitrogen were prepared as cyclophosphamide analogs (Zon, *Progress in Med. Chem.* 19, 1205 (1982)). For example, a number of 2'- and 3'-substituted proesters were prepared in order to decrease the propensity of the $\alpha,\beta$-unsubstituted carbonyl by-product to undergo a Michael reaction. 2'-Substituents included methyl, dimethyl, bromo, trifluoromethyl, chloro, hydroxy, and methoxy whereas a variety of groups were used at the 3'-position including phenyl, methyl, trifluoromethyl, ethyl, propyl, i-propyl, and cyclohexyl. Analogs with a 3'-aryl group e.g. trans-4-phenylcyclophosphamide were "moderately effective in L1210 test system and showed no activity in vivo" G. Zu *Prog. Med. Chem.* 19: 205-246 (1982). A variety of 1'-substituted analogs were also prepared. In general these compounds were designed to be "pre-activated" cyclophosphamide analogs that bypass the oxidation step by already existing as a 1'-substituted analog capable of producing the final compound, e.g. hydroperoxide and 1-thioether. A series of 1'-aryl analogs were also prepared in order to enhance the oxidation potential. In contrast to the 1'-hydroperoxy analogs, the 1'-aryl compounds exhibited either no activity or very poor activity in the standard anticancer in vivo screen assay, i.e. the mouse L1210 assay. The lack of activity was postulated to arise from the steric hindrance of the phenyl and therefore limited oxidation of the prodrug. Support for this postulate was the potent activity of the acyclic phenyl keto analog which exhibited activity similar to cyclophosphamide. Luderman et al. *J. Med. Chem.* 29: 716 (1986).

Cyclic esters of phosphorus-containing compounds are reported in the chemical literature, however they were not tested as prodrugs in biological systems. These cyclic esters include:

[1] di and tri esters of phosphoric acids as reported in Nifantyev et al., *Phosphorus, Sulfur Silicon and Related Elements*, 113: 1 (1996); Wijnberg et al., EP-180276 A1;

[2] phosphorus (III) acid esters. Kryuchkov et al., *Izv. Akad. Nauk SSSR, Ser. Khim.* 6:1244 (1987). Some of the compounds were claimed to be useful for the asymmetric synthesis of L-Dopa precursors. Sylvain et al., DE3512781 A1;

[3] phosphoramidates. Shih et al., *Bull. Inst. Chem. Acad. Sin,* 41: 9 (1994); Edmundson et al., *J. Chem. Res. Synop.* 5: 122 (1989); and

[4] phosphonates. Neidlein et al., *Heterocycles* 35:1185 (1993).

Numerous phosphorus-containing compounds are known to exhibit pharmacological activity but remain far from optimal due to one or more of the above-described limitations. Some of the activities described include phosphonic acids that are useful as antihypertensives and therapy for heart failure via inhibition of NEP 24.11, phosphonic acids that are useful for treating a variety of CNS conditions (stroke, epilepsy, brain and spinal cord trauma, etc.) via binding to excitory amino acid receptors (e.g. NMDA receptor), bisphosphonic acids that are useful for treating osteoporosis, phosphonic acids that are useful as lipid lowering agents (e.g. squalene synthase inhibitors), phosphonates that are useful in treating inflammation (e.g. collagenase inhibitors), phosphonates and phosphates that are useful in treating diabetes, cancer and parasitic and viral infections.

Phosphates and phosphonates that are known to be particularly useful in glucose lowering activity and therefore are anticipated to be useful in treating diabetes are compounds that bind to the AMP site of fructose 1,6-bisphosphatase (FBPase) as described in U.S. Pat. No. 5,658,889, WO 98/39344, WO 98/39343, and WO 98/39342. Other examples of phosphorus-containing drugs include squalene synthetase inhibitor (e.g. BMS 188494).

A large class of drugs known to be active against hepatitis are generally nucleoside or nucleotide analogs that are phosphorylated inside cells to produce the biologically active triphosphate. Examples include Lamivudine (3TC) and Vidarabine (araA). In each case, the drug interferes with viral replication via the triphosphate form through either inhibition of the viral DNA polymerases or DNA chain termination. Some specificity for virus-infected cells is gained by both preferential phosphorylation of the drug by virally-encoded kinases as well as by specific inhibition of viral DNA polymerases. Nevertheless, many of the nucleoside-based drugs are associated with significant non-hepatic toxicity. For example, araA frequently produces neurological toxicity (40%) with many patients showing myalgia or a sensory neuropathy with distressing pain and abnormalities in nerve conduction and a few showing tremor, dysarthria, confusion or even coma. Lok et al., *J Antimicrob. Chemotherap.* 14: 93-99 (1984). In other cases, the efficacy and/or therapeutic index of nucleosides is compromised by poor phosphorylation efficiencies and therefore low levels of the biologically active triphosphate (e.g. Yamanaka et al., *Antimicrob. Agents and Chemother.* 43, 190 (1999)).

Phosphonic acids also show antiviral activity. In some cases the compounds are antivirals themselves (e.g. phosphonoformic acid), whereas in other cases they require phosphorylation to the disphosphate, e.g. 9-(2-phosphonylmethoxyethyl)adenine (PMEA, Adefovir). Frequently, these compounds are reported to exhibit enhanced activity due to either poor substrate activity of the corresponding nucleoside with viral kinases or because the viral nucleoside kinase which is required to convert the nucleoside to the monophosphate is down regulated viral resistance. Monophosphates and phosphonic acids, however, are difficult to deliver to virally-infected cells after oral administration due to their high charge and in the case of the monophosphate instability in plasma. In addition, these compounds often have short half-lives (e.g. PMEA, Adefovir) due in most cases to high renal clearance. In some cases, the high renal clearance can lead to nephrotoxicities or be a major limitation in diseases such as diabetes where renal function is often compromised.

Liver cancer is poorly treated with current therapies. In general, liver tumors are resistant to radiotherapy, respond poorly to chemotherapy and are characterized by a high degree of cell heterogeneity. Oncolytic nucleosides such as 5-fluoro-2'-deoxyuridine, have also shown a poor response against primary liver cancers.

SUMMARY OF THE INVENTION

The present invention is directed towards novel prodrugs that generate phosph(on)ate compounds, their preparation, their synthetic intermediates, and their uses. In one aspect, the invention is directed towards the use of the prodrugs to enhance oral drug delivery. Another aspect of the invention is directed to the use of the prodrugs to enhance the level of the biologically active drug in the liver. Another aspect of the invention is the use of the prodrugs to treat diseases that benefit from enhanced drug distribution or specificity to the liver and like tissues and cells, including hepatitis, cancer, liver fibrosis, malaria, other viral and parasitic infections, and metabolic diseases where the liver is responsible for the overproduction of the biochemical end product, e.g. glucose (diabetes); cholesterol, fatty acids and triglycerides (hyperlipidemia) (atherosclerosis) (obesity). In another aspect, the prodrugs are used to prolong pharmacodynamic half-life of the drug. In addition, the prodrug methodology of the current invention is used to achieve sustained delivery of the parent drug. In another aspect, the prodrugs are used to increase the therapeutic index of the drug. Another aspect of the invention is the use of the prodrugs in combination with techniques that elevate P450 activity in specific tissues. In another aspect of the invention, a method of making these prodrugs is described. A further aspect is the novel intermediates to these prodrugs. In another aspect, the prodrugs are also useful in the delivery of diagnostic imaging agents to the liver.

One aspect of the present invention concerns compounds that are converted in vitro or in vivo to the corresponding $M\text{-}PO_3^{2-}$, $MP_2O_6^{3-}$, $MP_3O_9^{4-}$, and $MP(O)(NHR^6)O^-$ and are of formula

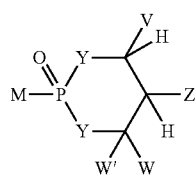

I wherein:

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2_2$)OH, —CH(C≡$CR^2$)OH, $R^2$, —$NR^2_2$, —$OCOR^3$, —$OCO_2R^3$, —$SCOR^3$, —$SCO_2R^3$, —$NHCOR^2$, —$NHCO_2R^3$, —$CH_2$NHaryl, —$(CH_2)_p$-$OR^{12}$, and —$(CH_2)_p$-$SR^{12}$;

p is an integer 2 or 3;

with the provisos that:

a) V, Z, W, W' are not all —H; and b) when Z is —$R^2$, then at least one of V, W, and W' is not —H, alkyl, aralkyl, or alicyclic;

$R^2$ is selected from the group consisting of $R^3$ and —H;

$R_3$ is selected from the group consisting of alkyl, aryl, alicyclic, and aralkyl;

$R^6$ is selected from the group consisting of —H, lower alkyl, acyloxyalkyl, alkoxycarbonyloxyalkyl, and lower acyl;

$R^{12}$ is selected from the group consisting of —H, and lower acyl;

each Y is independently selected from the group consisting of —O—, —$NR^6$— with the proviso that at least one Y is —$NR^6$—;

M is selected from the group that attached to $PO_3^{2-}$, $P_2O_6^{3-}$, $P_3O_9^{4-}$ or $P(O)(NHR^6)O^-$ is a biologically active agent, but is not an FBPase inhibitor, and is attached to the phosphorus in formula I via a carbon, oxygen, sulfur or nitrogen atom;

with the provisos that:

1) M is not —NH(lower alkyl), —N(lower alkyl)$_2$, —NH(lower alkylhalide), —N(lower alkylhalide)$_2$, or —N(lower alkyl)(lower alkylhalide); and 2) $R^6$ is not lower alkylhalide;

and pharmaceutically acceptable prodrugs and salts thereof.

The present invention provides several novel methods of making the prodrugs of the present invention. One method relies on the reaction of the following novel P(III) reagent:

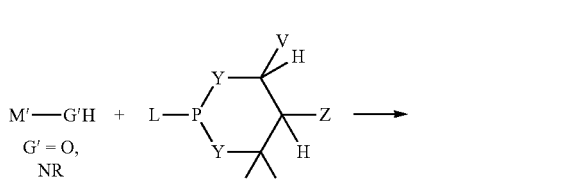

L = leaving groups such as
—$NR_2$, halogen

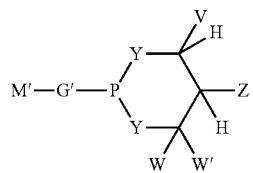

The resulting phosphite is then oxidized to the cyclic phosphoramidate.

A second method relies on the reaction of a novel P(V) reagent:

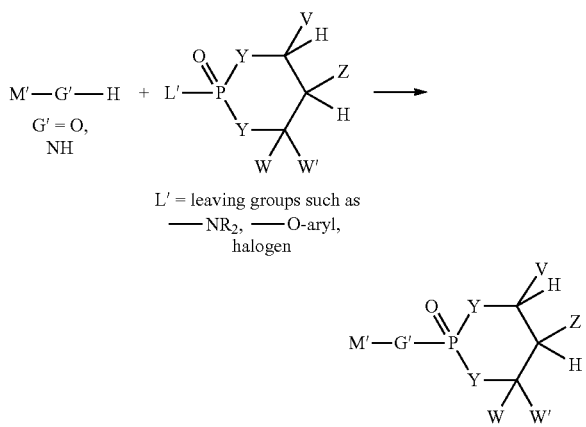

L' = leaving groups such as
—NR$_2$, —O-aryl, halogen

A third method relies on reacting another novel P(V) compound with a diamine or amino alcohol:

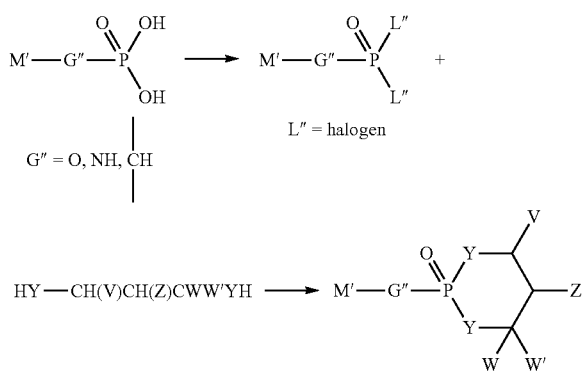

L" = halogen

G" = O, NH, CH

Since these compounds have asymmetric centers, the present invention is directed not only to racemic and diastereomeric mixtures of these compounds, but also to individual stereoisomers. The present invention also includes pharmaceutically acceptable and/or useful salts of the compounds of formula I, including acid addition salts. The present inventions also encompass prodrugs of compounds of formula I.

DEFINITIONS

In accordance with the present invention and as used herein, the following terms are defined with the following meanings, unless explicitly stated otherwise.

The term "aryl" refers to aromatic groups which have 5-14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1-3 substituents. Preferably these substituents are selected from the group consisting of lower alkyl, lower alkoxy, lower perhaloalkyl, halo, hydroxy, and amino.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "-alkylaryl" refers to an aryl group substituted with an alkyl group. "Lower-alkylaryl" refers to such groups where alkyl is lower alkyl.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and R$^1$ can form a cyclic ring system.

The term "-carboxylamido" refers to —CONR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic of 3 to 10 atoms, more preferably 3 to 6 atoms. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The term "phosphono" refers to —PO$_3$R$_2$, where R is selected from the group consisting of —H, alkyl, aryl, aralkyl, and alicyclic.

The term "sulphonyl" or "sulfonyl" refers to —SO$_3$R, where R is H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosphoramidate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosphoramidate, it is attached at the first carbon.

The term "alkylene" refers to a divalent straight chain, branched chain or cyclic saturated aliphatic group.

The term "acyloxy" refers to the ester group —O—C(O)R, where R is H, alkyl, alkenyl, alkynyl, aryl, aralkyl, or alicyclic.

The term "aminoalkyl-" refers to the group NR$_2$-alk- wherein "alk" is an alkylene group and R is selected from H, alkyl, aryl, aralkyl, and alicyclic.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkoxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-", each alkyl and alkylene is lower alkylene.

The terms "alkylthio-" and "alkylthio-" refer to the groups alkyl-S—.

The term "alkylthioalkyl-" refers to the group alkyl-S-alk- wherein "alk" is an alkylene group. In "lower alkylthioalkyl-" each alkyl and alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The terms "amido" or "carboxamido" refer to NR$_2$—C(O)— and RC(O)—NR$^1$—, where R and R$^1$ include H, alkyl, aryl, aralkyl, and alicyclic. The term does not include urea, —NR—C(O)—NR—.

The term "carboxamidoalkylaryl" and "carboxamidoaryl" refers to an aryl-alk-NR$^1$—C(O), and ar-NR$^1$—C(O)-alk-, respectively where "ar" is aryl, "alk" is alkylene, R$^1$ and R include H, alkyl, aryl, aralkyl, and alicyclic.

The term "hydroxyalkyl" refers to an alkyl group substituted with one —OH.

The term "haloalkyl" and "alkylhalide" refers to an alkyl group substituted with one halo. Preferably, the halo is in the 2-position.

The term "cyano" refers to —C≡N.

The term "nitro" refers to —NO$_2$.

The term "acylalkyl" refers to an alkyl-C(O)-alk-, where "alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidino" refers to both —NR—C(NR)—NR$_2$ as well as —N=C(NR$_2$)$_2$ here each R group is independently selected from the group of —H, alkyl, alkenyl, alkynyl, aryl, and alicyclic, all except —H are optionally substituted.

The term "amidino" refers to —C(NR)—NR$_2$ where each R group is independently selected from the group of —H, alkyl, alkenyl, alkynyl, aryl, and alicyclic, all except —H are optionally substituted.

The term "pharmaceutically acceptable salt" includes salts of compounds of formula I and its prodrugs derived from the combination of a compound of this invention and an organic or inorganic acid or base. Suitable acids include HCl.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, R$_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, antiviral agents, and antibiotic agents.

The term "bidentate" refers to an alkyl group that is attached by its terminal ends to the same atom to form a cyclic group. For example, propylene imine contains a bidentate propylene group.

The structure

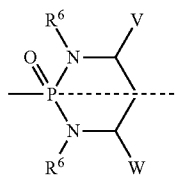

has a plane of symmetry running through the phosphorus-oxygen double bond when R$^6$=R$^6$, V=W, W'=H, and V and W are either both pointing up or both pointing down.

The term "cyclic 1',3'-propane ester", "cyclic 1,3-propane ester", "cyclic 1',3'-propanyl ester", and "cyclic 1,3-propanyl ester" refers to the following:

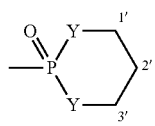

The phrase "together V and Z are connected via an additional 3-5 atoms to form a cyclic group containing 5-7 ring atoms, optionally containing 1 heteroatom, substituted with hydroxy, acyloxy, alkoxycarbonyloxy, or aryloxycarbonyloxy attached to a carbon atom that is three atoms from both Y groups adjacent to V" includes the following:

The structure shown above (left) has an additional 3 carbon atoms that forms a five member cyclic group. Such cyclic groups must possess the listed substitution to be oxidized.

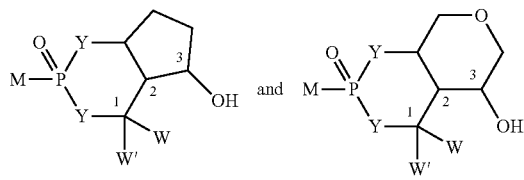

The phrase "together V and Z are connected via an additional 3-5 atoms to form a cyclic group, optionally containing one heteroatom, said cyclic group is fused to an aryl group attached at the beta and gamma position to the Y adjacent to V includes the following:

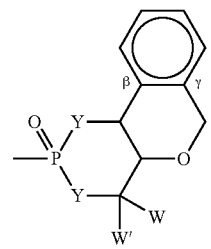

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y adjacent to V includes the following:

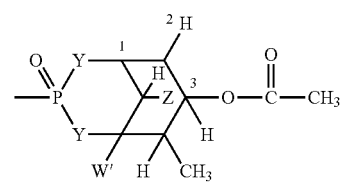

The structure above has an acyloxy substituent that is three carbon atoms from a Y, and an optional substituent, —CH$_3$, on the new 6-membered ring. There has to be at least one hydrogen at each of the following positions: the carbon attached to Z; both carbons alpha to the carbon labeled "3"; and the carbon attached to "OC(O)CH$_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

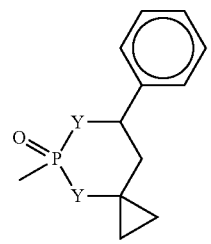

The structure above has V=aryl, and a spiro-fused cyclopropyl group for W and W'.

The term "phosphoramidite" refers to compounds attached via C, O, S, or N to the phosphorus in —P(YR)(YR) including cyclic forms, where Y is independently —O— or —NR$^6$—, but where at least one Y is —NR$^6$—.

The term "phosphoramidate" refers to compounds attached via C, O, S, or N to the phosphorus in —P(O)(YR)

(YR), including cyclic forms, where Y is independently —O— or —NR$^6$—, but where at least one Y is —NR$^6$—.

The term "cyclic phosphoramidate" refers to phosphoramidates where —P(O)(YR)(YR) is

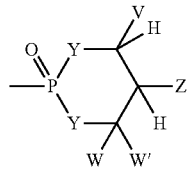

The carbon attached to V must have a C—H bond. The carbon attached to Z must also have a C—H bond.

The term "carbocyclic sugar" refers to sugar analogs that contain a carbon in place of the oxygen normally found in the sugar ring. It includes 5-membered rings such as ribofuranosyl and arabinofuranosyl sugars wherein the ring oxygen is replaced by carbon.

The term "acyclic sugar" refers to sugars that lack a ring, e.g. ribofuranosyl ring. An example is 2-hydroxyethoxymethyl in place of the ribofuranosyl ring.

The term "L-nucleoside" refers to enantiomer of the natural β-D-nucleoside analogs.

The term "arabinofuranosyl nucleoside" refers to nucleoside analogs containing an arabinofuranosyl sugar, i.e. where the 2'-hydroxyl of ribofuranosyl sugars is on the opposite face of the sugar ring.

The term "dioxolane sugar" refers to sugars that contain an oxygen atom in place of the 3' carbon of the ribofuranosyl sugar.

The term "fluorinated sugars" refers to sugars that have 1-3 carbon-fluorine atoms.

The term "P450 enzyme" refers to cytochrome enzymes that oxidize organic compounds and includes naturally occurring P450 isozymes, mutants, truncated enzymes, post-transcriptase modified enzymes, and other variants.

The term "liver" refers to liver and to like tissues and cells that contain the CYP3A4 isozyme or any other P450 isozyme found to oxidize the phosphoramidates of the invention. Based on Example F, we have found that prodrugs of formula VI and VIII are selectively oxidized by the cytochrome P450 isoenzyme CYP3A4. According to DeWaziers et al. (*J. Pharm. Exp. Ther.*, 253, 387-394 (1990)), CYP3A4 is located in humans in the following tissues (determined by immunoblotting and enzyme measurements):

| Tissues | % of liver activity |
|---|---|
| Liver | 100 |
| Duodenum | 50 |
| jejunum | 30 |
| ileum | 10 |
| colon | <5 (only P450 isoenzyme found) |
| stomach | <5 |
| esophagus | <5 |
| kidney | not detectable |

Thus, "liver" more preferably refers to the liver, duodenum, jejunum, ileum, colon, stomach, and esophagus. Most preferably, liver refers to the liver organ.

The term "hepatic" refers to the liver organ cells and not cells from the duodenum, for example.

The term "enhancing" refers to increasing or improving a specific property. It includes the situation where originally there was no activity.

The term "liver specificity" refers to the ratio:

$$\frac{[\text{parent drug or a drug metabolite in liver tissue}]}{\begin{bmatrix}\text{parent drug or a drug metabolite in blood,}\\ \text{urine, or other non-hepatic tissue}\end{bmatrix}}$$

as measured in animals treated with the drug or a prodrug. The ratio can be determined by measuring tissue levels of the parent drug or drug metabolite(s) including the biologically active drug metabolite or both at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug or prodrug (not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "parent drug" refers to MH for phosphoramidates where M is connected to —P(O)(YR)(YR) via oxygen, sulfur or nitrogen and to M-PO$_3^{2-}$ when M is connected to —P(O)(YR)(YR) via carbon. For example, AZT can be thought of as a parent drug in the form of MH. In the body AZT is first phosphorylated to AZT-PO$_3^{2-}$ and then further phosphorylated to form AZT-triphosphate, which is the biologically active form. The parent drug form MH only applies when M is attached via N, S, or O. In the case of PMEA, the parent drug form is M-PO$_3^{2-}$.

The term "drug metabolite" refers to any compound produced in vivo or in vitro from the parent drug, or its prodrugs.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "enhancing the level of the biologically active drug" refers to increasing the level of the biologically active drug in the liver relative to the level achieved after administration of the parent drug where the same mode of administration is used for both the prodrug and the parent drug.

The term "cancer expressing a P450 enzyme" refers to tumor cells having a specific activity, either with or without an agent that induces the P450 activity in the tumor cells, of at least 5% of the liver specific activity.

The term "low levels of enzymes" refers to levels below that necessary to produce the maximal response of the biologically active agent.

The term "inadequate cellular production" refers to levels that are below that necessary to produce the maximal response of the biologically active agent. For example, the response may be viral titre.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biologically active form of the drug at the desired site in the body and to the ability of an agent to bypass this resistance through the use of alternative pathways and cellular activities.

The term "FBPase inhibitors" refers to compounds that inhibit the human enzyme fructose 1,6-bisphosphatase with an IC50 of at least 100 μM and lower glucose in a normal 18-hour fasted rat following a 100 mg/kg dose i.v. The biologically active FBPase inhibitors are M-$PO_3^{2-}$ wherein M is connected via a carbon, or via an oxygen when MH is a imidazole containing nucleoside analog.

The term "biologically active drug or agent" refers to the chemical entity that produces the biological effect. In this invention, biologically active agents refers to M-$PO_3^{2-}$, M-P(O—)$NHR^{6-}$, $MP_2O_6^{3-}$, or $MP_3O_9^{4-}$ where M can be the same M as in the parent drug or a metabolite.

The term "therapeutically effective amount" refers to an amount that has any beneficial effect in treating a disease or condition.

The term "decreased activity of the phosphorylating enzyme" includes decreased production of the enzyme, mutations that lead to decreased efficiency (lower $K_m$ or $V_{max}$), or enhanced production of endogenous inhibitors of the enzyme.

The term "phosph(on)ate" refers to compounds attached via C, O, S, or N to $PO_3^{2-}$ or $P(O)(NHR^6)O^-$. The counterion may be $H^+$ or a metal cation.

The term "nucleoside" refers to a purine or pyrimidine base, including analogs thereof, connected to a sugar, including heterocyclic and carbocyclic analogs thereof.

The following well known drugs are referred to in the specification and the claims. Abbreviations and common names are also provided.

araA; 9-b-D-arabinofuranosyladenine (Vidarabine)
AZT; 3'-azido-2',3'-dideoxythmdine (Zidovudine)
d4T; 2',3'-didehydro-3'-deoxythymidine (Stavudine)
ddI; 2',3'-dideoxyinosine (Didanosine)
ddA; 2',3'-dideoxyadenosine
ddC; 2',3'-dideoxycytidine (Zalcitabine)
L-ddC; L-2',3'-dideoxycytidine
L-FddC; L-2',3'-dideoxy-5-fluorocytidine
L-dT; b-L-thymidine (NV-02B)
L-dC; b-L-2-deoxycytidine (NV-02C)
L-d4C; L-3'-deoxy-2',3'-didehydrocytidine
L-Fd4C; L-3'-deoxy-2',3'-didehydro-5-fluorocytidine
3TC; (−)-2',3'-dideoxy-3'-thiacytidine; 2'R,5'S(−)-1-[2-(hydroxymethyl)oxathiolan-5-yl]cytosine (Lamivudine)
1-b-D-ribofuranosyl-1,2,4-triazole-3-carboxamide (Ribavirin)
FIAU; 1-(2-deoxy-2-fluoro-b-D-arabinofuranosyl)-5-iodouridine
FIAC; 1-(2-deoxy-2-fluoro-b-D-arabinofuranosyl)-5-iodocytosine
BHCG; (±)-(1a,2b,3a)-9-[2,3-bis(hydroxymethyl)cyclobutyl]guanine
FMAU; 2'-Fluoro-5-methyl-b-L-arabino-furanosyluracil
BvaraU; 1-b-D-arabinofuranosyl-E-5-(2-bromovinyl)uracil (Sorivudine)
E-5-(2-bromovinyl)-2'-deoxyuridine
TFT; Trifluorothymidine (Trifluorothymidine)
5-propynyl-1-arabinosyluracil (Zonavir)
CDG; carbocyclic 2'-deoxyguanosine
DAPD; (−)-B-D-2,6-diaminopurine dioxolane
FDOC; (−)-B-D-5-fluoro-1-[2-(hydroxymethyl)-1,3-dioxolane]cytosine
d4C; 3'-deoxy-2',3'-didehydrocytidine
DXG; dioxolane guanosine
FEAU; 2'-deoxy-2'-fluoro-1-b-D-arabinofuranosyl-5-ethyluracil
FLG; 2',3'-dideoxy-3'-fluoroguanosine
FLT; 3'-deoxy-3'-fluorothymidine
FTC; (−)-cis-5-fluoro-1-[2-(hydroxymethyl)-1,3-oxathiolan-5-yl]cytosine
5-yl-carbocyclic 2'-deoxyguanosine (BMS200,475)
[1-(4'-hydroxy-1',2'-butadienyl)cytosine] (Cytallene)
Oxetanocin A; 9-(2-deoxy-2-hydroxymethyl-beta-D-erythro-oxetanosyl)adenine
Oxetanocin G; 9-(2-deoxy-2-hydroxymethyl-beta-D-erythro-oxetanosyl)guanine
ddAPR: 2,6-diaminopurine-2',3'-dideoxyriboside
3TC; (−)-2',3'-dideoxy-3' thiacytidine; (2R,5S) 1-[2-(hydroxymethyl)-1,3-oxathiolane-5-yl]cytosine (Lamivudine)
Cyclobut A; (+/−)-9-[(1 beta,2 alpha,3 beta)-2,3-bis(hydroxymethyl)-1-cyclobutyl]adenine
Cyclobut G; (+/−)-9-[(1 beta,2 alpha,3 beta)-2,3-bis(hydroxymethyl)-1-cyclobutyl]guanine (Lobucavir)
5-fluoro-2'-deoxyuridine (Floxuridine)
dFdC; 2',2'-difluorodeoxycytidine (Gemcitabine)
araC; arabinosylcytosine (Cytarabine)
bromodeoxyuridine
IDU; 5-iodo-2'-deoxyuridine (Idoxuridine)
CdA; 2-chlorodeoxyadenosine (Cytadribine)
F-ara-A; fluoroarabinosyladenosine (Fludarabine)
ACV; 9-(2-hydroxyethoxylmethyl)guanine (Acyclovir)
GCV; 9-(1,3-dihydroxy-2-propoxymethyl)guanine (gancyclovir)
9-(4-hydroxy-3-hydroxymethylbut-1-yl)guanine (Penciclovir)
(R)-9-(3,4-dihydroxybutyl)guanine (Buciclovir)
phosphonoformic acid (Foscarnet)
PPA; phosphonoacetic acid
PMEA; 9-(2-phosphonylmethoxyethyl) adenine (Adefovir)
PMEDAP; 9-(2-phosphonylmethoxyethyl)-2,6-diaminopurine
HPMPC; (S)-9-(3-hydroxy-2-phosphonylmethoxypropyl) cytosine (Cidofovir)
HPMPA; (S)-9-(3-hydroxy-2-phosphonylmethoxypropyl) adenine
FPMPA; 9-(3-fluoro-2-phosphonylmethoxypropyl) adenine
PMPA; 9-[2-(R)-phosphonylmethoxy)propyl]adenine (Tenofovir)
araT; 9-b-D-arabinofuranosylthymidine
FMdC; (E)-2'-deoxy-2'(fluoromethylene)cytidine
AICAR; 5-aminoimidazole-4-carboxamido-1-ribofuranosyl

DETAILED DESCRIPTION OF THE INVENTION

The invention is directed to the use of new cyclic phosphoramidate methodology which allows compounds to be efficiently converted to phosph(on)ate containing compounds by P450 enzymes found in large amounts in the liver and other tissues containing these specific enzymes. This methodology can be applied to various drugs and to diagnostic imaging agents. More specifically, the invention is directed to the use of prodrugs that undergo non-esterase-mediated hydrolysis reactions to produce $MP(O)(NHR^6)O^-$ which is either biologically active or is transformed into the biologically active agent $M\text{-}PO_3^{2-}$, $M\text{-}P_2O_6^{3-}$ or $M\text{-}P_3O_9^{4-}$. Because highly charged phosph(on)ate containing compounds are not readily absorbed in the gastrointestinal tract, this prodrug methodology can be used to enhance absorption after oral administration.

In another aspect of the invention, this prodrug methodology can also be used to enhance the pharmacodynamic half-life relative to the parent drug because the cyclic phosph(on)ates of the invention can avoid metabolism by enzymes which metabolize the parent drug. Similarly, prodrugs of the invention can enhance the pharmacodynamic half-life of the phosph(on)ate-containing compound because the prodrug avoids clearance pathways used to clear negatively-charged compounds from the bloodstream.

In another aspect of the invention, this prodrug methodology can also be used to achieve sustained delivery of the parent drug because oxidation of the novel prodrugs proceeds in the liver at different rates and therefore selection of prodrugs that oxidize slowly but at a rate suitable for maintaining therapeutically effective levels will produce a sustained therapeutic effect.

The novel cyclic 1,3-propanylester methodology of the present invention may also be used to increase the distribution of a particular drug or imaging agent to the liver which contains abundant amounts of the P450 isozymes responsible for oxidizing the cyclic 1,3-propanylester of the present invention so that the free phosph(on)ate is ultimately produced. Accordingly, this prodrug technology should prove useful in the treatment of liver diseases or diseases where the liver is responsible for the overproduction of the biochemical end product such a glucose, cholesterol, fatty acids and triglycerides. Such diseases include viral and parasitic infections, liver cancer, liver fibrosis, diabetes, hyperlipidemia, and obesity. In one aspect, preferably the disease is not diabetes. In addition, the liver specificity of the prodrugs should also prove useful in the delivery of diagnostic agents to the liver. High levels of the biologically active drug are achieved in tissues expressing P450 enzymes capable of cleaving the prodrug due to significant retention by these cells of the activated prodrug, subsequent prodrug cleavage intermediates as well as the biologically active drug. In addition, high levels of the biologically active drug are achieved relative to the levels achieved after administration of the parent drug when the parent drug is poorly phosphorylated in the tissue or has a relatively short pharmacokinetic half-life due to metabolism or other clearance mechanisms.

The use of certain prodrug analogs of cyclophosphamide are also envisioned for treatment of cancers of the GI tract (e.g. primary and secondary liver cancers) as well as cancers where cytochrome P450s are introduced artificially, e.g. by retrovirus and other well known gene therapy strategies as well as via implanted cells engineered to express cytochrome P450s.

These specific P450 enzymes are also found in other specific tissues and cells, and thus this methodology may also be used to increase the delivery of these agents to those tissues.

In another aspect of the invention, the characteristic that most of the cyclic phosphoramidates of the present invention are metabolized in the liver to produce the phosph(on)ate can enable the use of the prodrug methodology of the present invention to increase the therapeutic index of various drugs which have side effects related to the amount of the drug or its metabolites which are distributed in extrahepatic tissues. Increased therapeutic index can also result from increased liver levels of the biologically active agent and therefore greater efficacy relative to the parent drug administered at similar doses.

In another aspect of the invention, prodrugs can be used to deliver phosph(on)ates to tissues that generate suboptimal levels of phosph(on)ates and their associated higher phosphorylated metabolites due to poor substrate activity of the parent compound and/or poor expression of enzymes used to phosphorylate the parent compound. Poor expression of the phosphorylating enzyme occurs naturally or from down regulation of the phosphorylating enzyme following chronic administration of the drug or other agents.

In another aspect of the invention, novel phosphoramidite and phosphoramidate intermediates are described.

In another aspect, methods of preparing the cyclic phosphoramidate prodrugs are described.

These aspects are described in greater detail below.

Phosphoramidate Drugs:

Compounds of the formula $M\text{-}P(O)(NHR^6)O^-$ are useful compounds for binding to nucleotide binding sites, such as AMP-binding sites, and certain sites known to recognize negatively charged compounds, e.g. carboxylic and phosphonic acids. Enzymes that catalyze the addition of water to a carbonyl compound, specifically a peptide carbonyl, an ester, a ketone or an aldehyde, are of particular interest since these enzymes recognize compounds that have a tetrahedral group containing a negatively charged oxygen. An example is the zinc metalloproteinase class of enzymes which add water across a peptide carbonyl using a zinc-assisted catalytic mechanism. These enzymes are inhibited by phosphoramidates, e.g. NEP 24.11 is inhibited by the natural product Phosphoramidon. The prodrug strategy can provide a useful means for delivery of these compounds orally, or delivery of certain compounds to the liver in order to achieve greater efficacy or a greater therapeutic window. Enzymes inhibitors that may be suitable for delivery as prodrugs include certain phosphoramidates that inhibit NEP24.11, collagenase, stromolysin, gelatinase, ACE, endothelin converting enzyme, and metalloproteinases involved in matrix remodeling such as occurs in Rheumatoid arthritis and osteoarthritis and in the heart following an acute myocardial infarction, and tumor metastasis.

Phosphonic Acids and Phosphoric Acids:

Cleavage of the prodrug of formula I produces the phosphoramidate $M\text{-}P(O)(NHR)O^-$ which in some cases is further converted to the corresponding $M\text{-}PO_3^{2-}$ via either chemical hydrolysis or enzyme catalyzed hydrolysis (phosphatases, amidases). The product $M\text{-}PO_3^{2-}$ can either be the drug or itself may be further metabolized to produce higher order phosphates, e.g. $M\text{-}P_2O_6^{3-}$ or $M\text{-}P_3O_9^{4-}$ via cellular kinases. In some cases the intermediate $M\text{-}P(O)(NHR)O^-$ may be converted to higher order phosphates via initial conversion to M-H.

Enhancing Oral Bioavailability

The invention pertains to certain cyclic phosphoramidates and their use to deliver, most preferably via oral administration, a therapeutically effective amount of the corresponding phosph(on)ate compounds, preferably to an animal in need thereof. Prodrugs of the invention enhance oral bioavailability of certain drugs by changing the physical property of the drug as a consequence of the prodrug moiety and its substituents V, Z, W, and W'. The active drug may be $M\text{-}P(O)(NHR^6)O^-$ or $M\text{-}PO_3^{2-}$. Alternatively, both may instead undergo further metabolism, e.g. phosphorylation by kinases to form $M-P_2O_6^{3-}$ and/or $M-P_3O_9^{4-}$ as the active drug substance.

Compounds containing a free phosphonic acid or a phosphoric acid group generally exhibit poor (<2%) oral bioavailability since these groups are highly charged at physiological pH. Charged groups on compounds with molecular weights greater than 250 Daltons impede passive diffusion across cell membranes as well as absorption across the gut epithelial cell layer. Neutral prodrugs of these compounds have therefore been studied since these compounds would be more lipophilic and therefore more likely to exhibit improved intestinal permeability. Although many prodrug classes have been reported, few have been found that exhibit properties suitable for drug development.

The most common prodrug class, and the class almost exclusively used for clinical candidates, is the acyloxyalkyl esters. These prodrugs, however, often exhibit only a modest improvement in oral bioavailability due to poor aqueous stability, poor stability to acidic/basic pH and rapid degradation by esterases in the gastrointestinal tract (Shaw & Cundy, *Pharm. Res.* 10, (Suppl), S294 (1993). Another class of prodrugs are the bis-aryl prodrugs (e.g. DeLombert et al. *J. Med. Chem.* 37, 498 (1994)) which have shown in a few isolated cases to provide good to modest improvements in oral bioavailability. The major limitation with this class of compounds is that the prodrug ester often is degraded to the monoacid rapidly in vivo but conversion to the parent drug occurs only slowly (sometimes over days) if at all.

The prodrugs of the invention exhibit improved properties that lead to enhanced oral bioavailability relative to the parent drug. Several characteristics of the present cyclic phosphoramidate prodrugs may contribute to their ability to enhance oral bioavailability. First, the prodrugs exhibit good stability in aqueous solutions across a wide range of pHs. (Example A) This pH stability prevents immediate hydrolysis in the mouth and GI tract prior to absorption. The pH stability can also be beneficial during formulation of the product.

Second, the prodrugs are resistant to esterases and phosphatases which are abundant in the gastrointestinal tract. Because much of the administered dose remains intact in the G.I. tract, the compound remains less highly charged than a free phosph(on)ate which means more of the drug can be absorbed by passive diffusion and enter the blood stream. (Example B)

Last, the prodrug can limit metabolism at other sites on the molecule. For example, the prodrugs of the invention eliminate metabolism of the purine base of araA by adenosine deaminase which is also abundant in the GI tract. (Example B) The amine of araA which is normally deaminated by the enzyme is protected by the cyclic phosphate moiety which is located on the 5'-ribofuranosyl hydroxyl. Reduced metabolism at other sites of the molecule enables more of the drug to circulate in the blood stream. Although not all of these properties will be applicable to every prodrug of every drug, each of these properties can enable more drug to survive the GI tract and be available for absorption.

The novel prodrug strategy of the invention will be useful for the oral delivery of drugs that act in the liver as well as certain drugs that act on targets located in the vascular system or extrahepatic tissues. Because the highest concentration of CYP3A4 (the enzyme responsible for activating the novel prodrugs) is in the liver, the biologically active drug has a high concentration in the liver, relative to other tissues. In one aspect, parent drugs which act in the liver are preferred.

However, some of the phosph(on)ates are exported by organic anion transporters in the liver and enter the blood stream. Many phosph(on)ates in the blood stream are cleared quickly by the kidneys. Such compounds probably will not reach therapeutic levels in extrahepatic tissues. However, there are some phosph(on)ates and phosphates that are able to remain in circulation because they are not rapidly cleared by the kidneys (e.g. NEP inhibitors). Such compounds are able to achieve therapeutically effective levels in blood and extrahepatic tissues. Thus, in another aspect, oral delivery to extrahepatic tissues of phosph(on)ates which are not cleared by the kidneys is preferred. Thus, such parent drugs that act at sites accessible to the free phosph(on)ic acid such as targets within the vasculature system, or enzyme or receptor targets that are located on cell membranes which are exposed to the blood or fluid in the intrastitial space are preferred. Targets suitable for this aspect of the invention would be targets in which the phosphonic acid administered parenterally (e.g. via i.v. injection) produces a pharmacological or biochemical response expected to be useful for treating a disease condition.

Since the inhibitors exhibit poor oral bioavailability (<2%), prodrugs of the type described in this invention could enhance the oral bioavailability and produce the phosphonic acid following prodrug cleavage in the liver. Suitable circulating drug levels are expected after prodrug cleavage in the liver, since the liver is known to excrete phosphonic acids into the circulation.

Oral bioavailability can also be calculated by comparing the area under the curve of prodrug, parent drug, and/or metabolite concentration over time in plasma, liver, or other tissue or fluid of interest following oral and i.v. administration. (Example P)

For example, for drugs excreted renally in large amounts, oral bioavailability can be measured by comparing the amount of the parent drug or metabolite excreted in the urine, for example, after oral and i.v. administration of the prodrug. A lower limit of oral bioavailability can be estimated by comparison with the amount of parent drug excreted in the urine after administration of the prodrug (p.o.) and the parent drug (i.v.). Prodrugs of the invention show improved oral bioavailability across a wide spectrum of prodrugs, with many preferably showing increases of 1.5 to 10-fold in oral bioavailability. More preferably, oral bioavailability is enhanced by at least 2-fold compared to the parent drug.

Agents are known that inhibit CYP3A4 in the gastrointestinal tract. For example, grapefruit juice is known to decrease the activity putatively via a component in the grapefruit juice (e.g. Bergamottin; *Chem Res Toxicol* 1998, 11, 252-259) which results in the inactivation and/or down regulation of the enzyme. Since only GI CYP3A4 is affected, the oral absorption of the prodrugs of this invention should be enhanced. A combination of agents that inhibit, inactivate, or downregulate P450s that metabolize the prodrugs will have the effect of enhancing their absorption and thereby making more prodrug available for metabolism in the liver. The net effect of the combination would therefore be to deliver more drug to the liver after oral absorption.

Sustained Delivery

Drugs that undergo rapid elimination in vivo often require multiple administrations of the drug to achieve therapeutically-effective blood levels over a significant period of time. Other methods are also available including sustained release formulations and devices. Prodrugs that breakdown over time can also provide a method for achieving sustained drug levels. In general, this property has not been possible with the known phosph(on)ate prodrugs since either they undergo rapid hydrolysis in vivo (e.g. acyloxyalkyl esters) or very slow conversion (e.g. di-aryl prodrugs).

The cyclic phosphoramidates of the invention are capable of providing sustained drug release by providing a steady release of the drug over time. For example, most phosphates undergo dephosphorylation in vivo within minutes after systemic administration via the action of phosphatases present in the blood. Similarly, acyloxyalkyl esters of these phosphates undergo rapid esterase-mediated hydrolysis to the phosphate which then is rapidly dephosphorylated. Some prodrugs of the current invention may enable prolonged drug delivery since many of the present prodrugs are oxidized slowly over time to the phosph(on)ate in the livers (Example S). Suitably positioned, prodrug moieties can prevent or slow systemic metabolism associated with the parent drug.

Sustained delivery of the drugs is achievable by selecting the prodrugs of formula I that are hydrolyzed in vivo at a rate capable of maintaining therapeutically effective drug levels over a period of time. The cleavage rate of the drug may depend on a variety of factors, including the rate of the P450 oxidation, which is dependent on both the substituents on the prodrug moiety, the stereochemistry of these substituents and the parent drug. Moreover, sustained drug production will depend on the rate of elimination of the intermediate generated after oxidation and the rate and availability of the prodrug to the liver, which is the major site of oxidation. Identification of the prodrug with the desired properties is readily achieved by screening the prodrugs in an assay that monitors the rate of drug production in the presence of the major P450 enzyme involved in the metabolism, in the presence of liver microsomes or in the presence of hepatocytes. These assays are illustrated in Examples C, D, F, G, I, J, respectively.

It is contemplated that prodrugs of the present invention could be combined to include, for example, one prodrug which produces the active agent rapidly to achieve a therapeutic level quickly, and another prodrug which would release the active agent more slowly over time.

Improved Pharmacodynamic Half-Life

The pharmacodynamic half-life of a drug can be extended by the novel prodrug methodology as a result of both its ability to produce drug over a sustained period and in some cases the longer pharmacokinetic half-life of the prodrug. Both properties can individually enable therapeutic drug levels to be maintained over an extended period resulting in an improvement in the pharmacodynamic half-life. The pharmacodynamic half-life can be extended by impeding the metabolism or elimination pathways followed by the parent drug. For some drugs, the prodrugs of the present invention are able to avoid the metabolism or elimination pathways associated with the parent drug and thereby exist as the prodrug for extended periods in an animal. High levels of the prodrug for an extended period result in sustained production of the parent drug which can result in an improvement in the drug pharmacodynamic half-life.

An example of the ability of the prodrug class to impede metabolic pathways associated with the parent drug is shown by the araAMP prodrugs. In comparison to araAMP, prodrugs show no ara-hypoxanthine ("araH") which is the known metabolic byproduct of araA produced in e.g. plasma and the gastrointestinal tract after oral or i.v./administration. AraAMP on the other hand is rapidly and nearly completely converted to araH, which is produced by first dephosphorylation to araA via phosphatases followed by deamination of the base via adenosine deaminase. The prodrug moiety prevents both dephosphorylation and deamination from occurring.

A common route of elimination of phosph(on)ate drugs is via the kidneys and a transporter that recognizes anionic compounds. Complete elimination of phosphonate and phosphate containing drugs from the circulation often occurs only minutes after drug administration. The prodrugs of this invention slow the elimination of these drugs by masking the negative charge until after oxidation and hydrolysis in liver and like tissues.

Enhanced Selective Delivery of Agents to the Liver and Like Tissues

Delivery of a drug to the liver with high selectivity is desirable in order to treat liver diseases or diseases associated with the abnormal liver properties (e.g. diabetes, hyperlipidemia) with minimal side effects.

Analysis of the tissue distribution of CYP3A4 indicates that it is largely expressed in the liver (DeWaziers et al., *J. Pharm. Exp. Ther.* 253: 387 (1990)). Moreover, analysis of tissue homogenates in the presence of prodrugs indicates that only the liver homogenate cleaves the prodrug and to a lesser degree homogenates from tissues in the upper GI. Kidney, brain, heart, stomach, spleen, muscle, lung, and testes showed no appreciable cleavage of the prodrug (Example D).

Evidence of the liver specificity was also shown in vivo after both oral and i.v. administration of the prodrugs. Administration of a prodrug of araAMP i.v. gives liver levels of the bioactive drug araATP greater than achieved by an equivalent dose of either araA or araAMP. In contrast, the prodrug fails to produce detectable amounts of the araA by-product araH, which, as reported in the literature, is readily detected after either araA or araAMP administration. Similarly, the prodrug achieves high liver levels without production of the metabolite araH after oral administration. Since the prodrugs are cleaved by liver abundant enzymes, oral administration may enable even higher liver specificity via a first pass effect.

The prodrugs described in this invention can be tailored such that the elimination step is fast and therefore the product is produced near the site of oxidation, which for these prodrugs is in the liver or other P450-expressing tissue/cells.

In some cases liver specificity will be achieved most optimally using prodrugs of highly reactive drugs, which after production, act locally at a fast rate relative to diffusion out of the liver.

Agents that induce P450 activity, e.g. CYP3A4 activity, are known. For example, rifampicin, glucocorticoids, phenobarbital, erythromycin are known to enhance CYP3A4 activity in rat and human livers following. P450 activity can be monitored in humans by non-invasive methods e.g. via [14C] erythromycin breath test. These studies are useful in the identification of agents that activate CYP3A4 in humans. Accordingly, for prodrugs where drug delivery is limited by prodrug metabolism rate (e.g. rate of clearance of prodrug is fast relative to rate of prodrug cleavage), agents such as rifampicin can be used in combination or as adjuncts or pre-treatments to enhance CYP3A activity in the liver and thereby to increase liver drug levels. (Examples J and O)

Prodrug Cleavage Mechanism

The prodrugs of the current invention are simple, low molecular weight modifications of the drug which enable liver-selective drug delivery on the basis of the their sensitivity to liver-abundant enzymes. The prodrug cleavage mechanism is postulated to entail an oxidation and β-elimination based on studies analyzing reaction requirements and products. In some cases, M-P(O)(NR$^6$)O$^-$ is further metabolized to M-PO$_3$$^{2-}$ and M-P$_3$O$_9$$^{4-}$. Prodrugs are stable to aqueous solution across a broad pH range and therefore do not undergo a chemical cleavage process to produce the parent drug. In addition the prodrugs are stable to esterases and blood proteins. In contrast, the prodrugs are rapidly cleaved in the presence of liver microsomes from rats (Example C) and humans (Examples D and F). The drug is also produced in freshly isolated rat hepatocytes where it is detected as the corresponding phosph(on)ate and/or biologically active agent (Examples G and J). Moreover, when the parent drug is an FBPase inhibitor, the production of the drug is supported by the ability of the prodrug to result in potent gluconeogenesis inhibition (Example I).

Possible specific enzymes involved in the cleavage process were evaluated through the use of known cytochrome P450 inhibitors (Example E). The studies indicate that the isoenzyme cytochrome CYP3A4 is responsible based on ketoconozole inhibition of drug formation.

The biologically active agent is detected in the liver following administration of drugs of formulae VI-VIII, shown below:

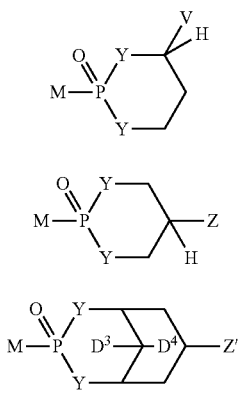

Prodrugs of the following formulas are particularly preferred.

Prodrugs of formula VI cleave to generate aryl vinyl ketone whereas prodrugs of formula VIII cleave to generate phenol (Example L). The mechanism of cleavage could proceed by the following mechanisms, shown for compounds where one Y is $NR^6$.

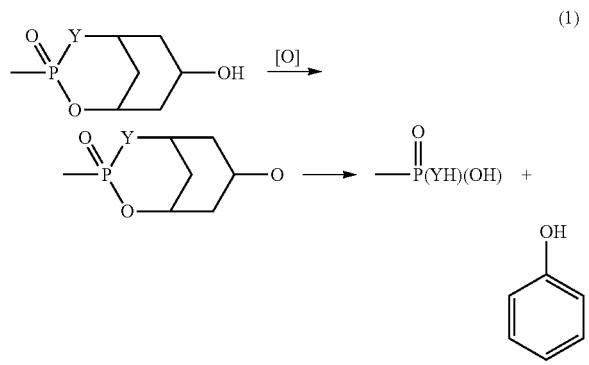

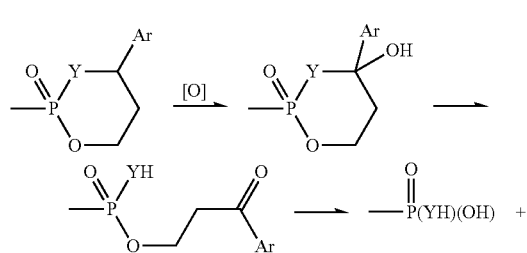

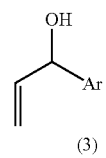

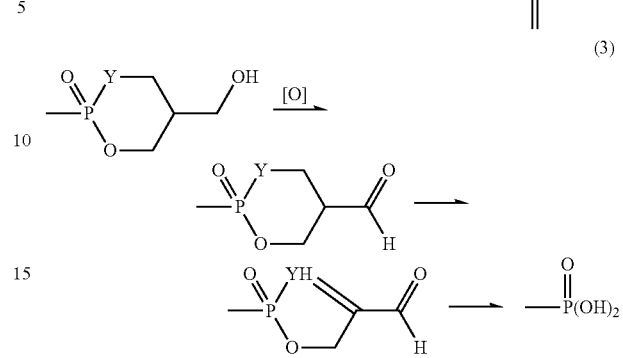

Although the esters in the invention are not limited by the above mechanisms, in general, each ester contains a group or atom susceptible to microsomal oxidation (e.g. alcohol, benzylic methine proton), which in turn generates an intermediate that breaks down to the parent compound in aqueous solution via β-elimination of the $M-P(O)(YH)_2$. This species is either the active component or is further transformed via chemical or enzymatic processes to $M-PO_3^{2-}$, $M-P_2O_6^{3-}$, or $M-P_3O_9^{4-}$. Furthermore, although these specific prodrugs are cleaved by CYP3A4, other prodrugs in the class may be substrates for other P450s. Small changes in structure are known to influence substrate activity and P450 preference. The identification of the isoenzyme(s) activating the prodrug is accomplished according to the procedure described in Example B.

Alternatively, cyclic phosphoramidates can serve as a prodrug of phosph(on)ates or higher order phosph(on)ates since intermediate phosphoramidates can be converted to $MPO_3^{2-}$, $MP_2O_6^{3-}$, or $MP_3O_9^{4-}$ via the action of phosphatases/amidases which can produce MH or $MPO_3^{2-}$ which in turn can be phosphorylated by kinases to the biologically active.

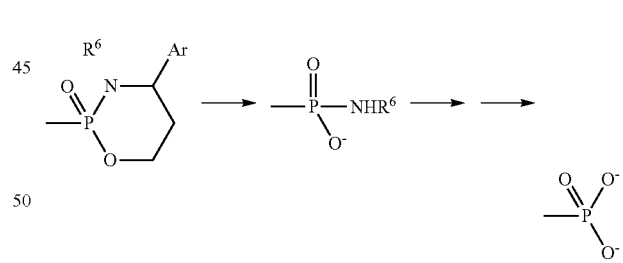

compound.

Increased Therapeutic Index

The prodrugs of this invention can significantly increase the therapeutic index ("TI") of certain drugs. In many cases, the increased TI is a result of the high liver specificity. For example, araA and araAMP are known to produce significant systemic side effects and these side effects are associated with blood levels of the araA byproduct araH. Presumably the side effects are a result of toxicities of araH or araA in extrahepatic tissues (e.g. nerves) which produce e.g. the neuropathies associated with the drug in man (>40% of patients receiving araA). Prodrugs of araA show a substantial shift in the liver (araATP)/urine (araH) ratio in comparison with araAMP.

Renal toxicity is a common toxicity associated with phosphonic acids. The toxicity results from transport, e.g. via the organic anion transporters located on the basolateral membrane of the renal proximal tubule, of the negatively charged drug into e.g. tubular cells which then accumulate the drug to high concentrations unless there is an equally efficient transport of the drug out of the cell via luminal transport mechanisms (e.g., anion exchange or facilitated diffusion). Many examples have been reported in the literature of nephrotoxic phosphonic acids, e.g. PMEA and HPMPA. The novel prodrug of PMEA shows only small amounts of PMEA in the urine relative to either PMEA or bisPOM PMEA at doses that achieved comparable liver drug levels.

Another common toxicity associated with phosphonic acid drugs is gastrointestinal toxicity via in some cases GI erosions. Prodrugs of the current invention can decrease GI toxicities, especially toxicities produced by direct action of the drug on the GI tract after oral administration. Similar to the kidney, gut epithelial cells have organic anion transporters which can result in high intracellular drug levels an cytotoxicity. Since the negatively charged phosph(on)ate is not revealed until after absorption and cleavage in the liver, prodrugs of this invention reduce gut toxicity.

Severe toxicities are also associated with nearly all anticancer agents. In an effort to decrease these toxicities during treatment of primary or secondary liver cancers, drugs are sometimes administered directly into the portal artery in order to increase liver drug exposure. Since oncolytic drugs typically are associated with significant side effects, local administration enables greater hepatic uptake and thereby decreased extrahepatic toxicities. To further increase liver uptake, chemoembolization is sometimes used in conjunction with hepatic artery drug infusion. The high liver specificity of the prodrugs in the current invention suggest that systemic side effects will be similarly minimized by the novel prodrug approach.

Moreover, primary and secondary liver cancers are particularly resistant to both chemotherapy and radiotherapy. Although the mechanism for the resistance is not completely understood, it may arise from increased liver gene products that lead to rapid metabolism and/or export of chemotherapeutic agents. In addition, the liver, which is generally associated with xenobiotic metabolism and generation of cytotoxic intermediates, is equipped by nature with multiple protective mechanism so that damage from these intermediates are minimized. For example, the intracellular concentration of glutathione is very high in the liver relative to other tissues presumably so that intermediates capable of alkylating proteins and DNA are detoxified through a rapid intracellular reaction. Consequently, the liver may be resistant to chemotherapeutic agents because of these mechanisms and therefore require higher than normal concentrations of the oncolytic agent to achieve success. Higher liver concentrations require higher doses of the drug which commonly result in extrahepatic toxicities.

Prodrugs of the current invention can be effective against these cancers because they enable higher levels of the biologically active drug through a variety of mechanisms. For example, the high liver specificity can enable higher doses since the dose-limiting extrahepatic side effects are reduced. Second, sustained delivery of the prodrug can enable high drug levels to be maintained over a sustained period. Third, in some cases, the parent drug is poorly phosphorylated in the target cells. The prodrugs of this invention can bypass this step and deliver the phosph(on)ate which in some cases is further metabolized to the biologically active agent. Last, the therapeutic index can sometimes be further enhanced by co-administration of CYP inducers (e.g. rifampicin, glucocorticoids, phenobarbital, erythromycin) which can enhance conversion in the liver and thereby enable higher levels of the biologically active drug without increasing the dose (Examples J and O). These benefits of the prodrugs enable successful therapy of liver diseases, such as primary and secondary liver cancers as well as other liver diseases.

Byproduct Toxicity

Prodrugs of the invention are also useful because they generate byproducts that are either non-toxic or rapidly detoxified. Some of the byproducts generated by prodrugs of the invention are not considered to be highly toxic at doses expected to be used in the clinic, especially given that the byproduct would be generated in the liver (e.g. phenol). Other byproducts generated by the prodrugs of this invention, e.g. aryl vinyl ketone, can be considered as alkylating agents and therefore could produce either or both cytotoxicity and genotoxicity. These toxicities, however, are eliminated for prodrugs activated in the liver since: 1) the byproduct is produced at or near the site of prodrug activation; and 2) natural defense mechanisms exist at the site of byproduct generation and are able to completely detoxify the byproduct. Other mechanisms may also assist in the detoxification of the byproduct, including reactions that lead to oxidation, reduction or transformation (e.g. sulfation) of the byproduct.

The primary defense system expected to protect cells from the prodrug byproduct involves the natural thiol glutathione and possibly an enzyme that catalyzes the addition of glutathione to electrophiles, i.e. glutathione S-transferase (GST). Glutathione and GST are always co-expressed with CYPs as part of a natural defense mechanism that protects the cell from highly reactive oxygen species generated during CYP-mediated oxidation of organic compounds. CYPs are expressed in certain cells (primarily hepatocytes) to oxidize organic compounds and thereby assist in their elimination from the body. Tissue distribution studies show that CYP3A4 as well as most other P450s are expressed highest in the liver followed by the small intestine. All other tissues have <<2% of the liver CYP3A4 activity. Similarly, analysis of glutathione levels indicates that the liver (10 mM) and GI have nearly 1000-fold higher glutathione levels than other tissues. These levels of glutathione are still high even in diseased livers.

Glutathione reacts rapidly with vinyl ketones, and any alkylating agent, to generate a conjugate which is then eliminated via the bile or kidney. Alkylation of other proteins or nucleic acids in the cell is not expected in cells with glutathione since glutathione is a much better nucleophile than heteroatoms on the bases of nucleic acids and exists at much higher concentration than thiol groups on the surface of proteins.

By products such as acrolein can produce bladder toxicity which these prodrugs can prevent by their ability to generate the byproduct within the hepatocyte. Examples M and N are useful for testing for byproduct toxicity, which is not expected in the liver as long as hepatic glutahione levels remain >20% of normal. Glutathione is readily measured in hepatocytes as well as in vivo (Examples M and N). Cytotoxicity is detected in hepatocytes via testing of cell viability with trypan blue and by analyzing for elevation of live enzymes. In vivo, liver toxicity is evaluated by analysis of liver enzyme elevation in the plasma.

Non-Mutagenic Prodrugs

Prodrugs of the invention are elevated by a postulated mechanism involving an initial oxidation followed by a β-elimination reaction. In some cases, e.g. certain prodrugs of formula VI and formula VII, the biproduct of the reaction is an α,β-unsaturated carbonyl compound, e.g. vinyl phenyl ketone for prodrugs where V=Ph, Z, W and W'=H. Compounds can act as Michael acceptors and react with nucleophiles via a Michael addition. Mutagenesis is observed with some α-β-unsaturated ketones and certain toxicities arise from Michael addition adducts (e.g. acrolein produces bladder toxicities). The degree to which these activities limit the use of compounds of Formula VI is dependent on the severity of the toxicity and the indicated disease.

Prodrugs that produce non-toxic and non-mutagenic biproducts are especially preferred for the treatment of chronic diseases (e.g. diabetes). Frequently, it is difficult to predict the mutagenic properties of a compound. For example, a number of acrylates have been shown to produce positive mutagenic responses as indicated by increased chromosome aberrations and micronucleus frequencies in cultured L5179Y mouse lymphoma cells (Dearfield et al., *Mutagenesis* 4, 381-393 (1989)). Other acrylates, however, are negative in this test (*J. Tox. Envir. Health*, 34, 279-296 (1991)) as well as in the Ames test and the CHO assay which measures newly induced mutations at the hypoxanthine-guanine phosphoribosyltransferase (hgprt) locus (*Mutagenesis* 6, 77-85 (1991)). Phenyl vinyl ketone lacks teratogenic activity in rat embryos in culture suggesting that it may not be mutagenic nor highly toxic (*Teratology* 39, 31-37 (1989)).

Since mutagenicity and toxicity are not highly predictable properties, non-mutagenic prodrugs of formula I and their associated by-products can be readily identified by conducting well known in vitro and in vivo assays. For example, compounds can be tested in non-mammalian cell assays such as the Ames test, a fluctuation test in *Kl. pneumoniae*, a forward mutation assay with *S. typhimurium*, a chromosome loss assay in *Saccharomyces cerevisiae*, or a D3 recombinogenicity assay in *Saccharomyces cerevisiae*. Compounds can also be tested in mammalian cell assays such as the mouse lymphoma cells assay (TK+/−heterozygotes of L5178Y mouse lymphoma cells), assays in Chinese hamster ovary cells (e.g. CHO/HGPRT assay), and an assay in rat liver cell lines (e.g. RL1 or RL4). Each of these assays can be conducted in the presence of activators (e.g. liver microsomes) which may be of particular importance to these prodrugs. By conducting these assays in the presence of the liver microsomes, for example, the prodrug produces products, such as phenol or vinyl ketone. The mutagenicity of the by-product is measured either directly or as a prodrug where the results are compared to the parent drug alone. Assays in liver cell lines are a preferred aspect of the invention since these cells have higher glutathione levels, which can protect the cell from damage caused by a Michael acceptor, as well as greater levels of intracellular enzymes used to detoxify compounds. For example, the liver contains reductases that with some by-products might result in reduction of the carbonyl.

A variety of end points are monitored including cell growth, colony size, gene mutations, micronuclei formation, mitotic chromosome loss, unscheduled DNA synthesis, DNA elongation, DNA breaks, morphological transformations, and relative mitotic activity.

In vivo assays are also known that assess the mutagenicity and carcinogenicity of compounds. For example, a non-mammalian in vivo assay is the *Drosophila* sex-linked recessive lethal assay. Examples of mammalian in vivo assays include the rat bone marrow cytogenetic assay, a rat embryo assay, as well as animal teratology and carcinogenicity assays.

Kinase Bypass

Nucleosides are often converted in cells to mono-, di- and tri-phosphates with the latter usually acting as the biologically active species. In some cases, the triphosphate is a potent inhibitor of the target enzyme but poor to modest efficacy is achieved in vivo because administration of the nucleoside fails to achieve sufficiently high levels of the biologically active phosphate. Often the failure to achieve high levels of the phosphate is because the nucleoside is a poor substrate of the enzymes that catalyze the phosphorylation reaction. Other reasons include the low natural levels of the phosphorylating enzyme in the target cell which may represent low natural expression levels or be a result of chronic therapy with the drug or another drug which results in enzyme down regulation. In some cases, drug resistance results from a decrease in activity of the enzymes responsible for synthesis of a nucleoside monophosphate (e.g. kinases such as thymidylate kinase or enzymes in the biosynthesis pathway of 5-fluoro-2'-deoxy UMP). In other cases nucleoside transporters are downregulated leading to lower intracellular nucleoside drug concentration and therefore less nucleoside is available for phosphorylation. Similarly, increased expression of multidrug resistant gene product is postulated to increase the export of nucleotides from cancer cells. Administration of the prodrug generates the monophosphate by a different pathway avoiding the pathways that cause the resistance to the parent drug. Thus, the prodrugs of the present invention can achieve a therapeutic effect in cells resistant to the parent drug. Some drugs as the mono- or triphosphate analogs are highly potent inhibitors of the target enzyme (e.g. HBV polymerase) but are poorly effective in cells or in vivo due to poor phosphorylation. (Example H) These drugs are especially preferred drugs since the prodrug strategy delivers the monophosphate. Frequently, the first phosphorylation of the nucleoside is the rate-limiting step whereas phosphorylation of the monophosphate to the triphosphate by mammalian kinases is rapid and relatively insensitive to structural variations.

Ring-Substituted Cyclophosphamide Analogs for Treatment of Certain Cancers:

Cyclophosphamide (CPA) and Ifosfamide (IF) are commonly used oncolytic drugs that undergo initial activation in the liver via a P450 mechanism (CYP2B6 and CYP3A4) to intermediate 7. This intermediate exists in equilibrium with the ring-opened species (8), which is the penultimate intermediate for a variety of metabolic pathways, including a β-elimination reaction that generates the alkylating mustard 9 and acrolein. The latter reaction sequence occurs via a non-enzymatic reaction and is thought to proceed with a t½ of ~30-40 minutes at neutral pH.

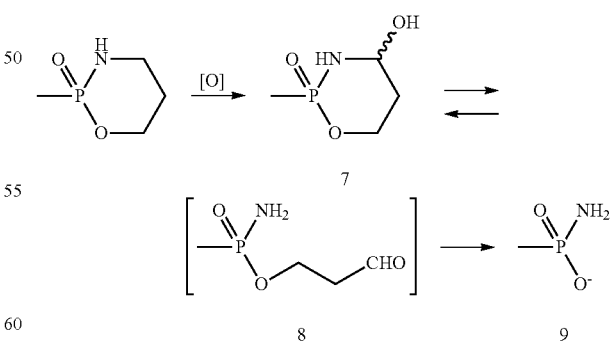

Intermediates 8 and 9 are relatively lipophilic and long-lived. As a consequence, a significant proportion of the activated CPA "escapes" the liver and enters the general circulation. Both the oncolytic activity and the drug-associated side effects are due to extra-hepatic breakdown. Uptake of the intermediate by tumor cells and generation of the mustard results in inhibition of cell proliferation. Similarly, myelosuppression and decreased white cells are side effects associated with CPA therapy that result from inhibition of extra-hepatic cell proliferation.

CPA and IF are under investigation in conjunction with methods useful for the introduction of cytochrome P450s artificially, e.g. by retrovirus and other well known gene therapy strategies as well as via implanted cells engineered to express cytochrome P450s for the treatment of cancer. The hope is that with cells that express the CYP near the tumor, a more local and therefore a potentially more beneficial therapy is possible. Prodrugs of this invention have the advantage for treating primary and secondary liver cancers as well as for tumors with enhanced P450 activity since they generate the active oncolytic agent more locally, i.e. with less "escape" from the tissue containing the P450 activity. The reasons for the greater local effect are due to differences in the prodrug cleavage intermediates which include: (1) a ring-opening reaction that is rapid and irreversible; and (2) the ring-opened product, which can be negatively charged (M-P(O)(NHR$^6$) O$^-$) and therefore unable to exit the cell via passive diffusion.

Types of Parent Drugs

Various kinds of parents drugs can benefit from the prodrug methodology of the present invention. Parent drugs of the form MH, which are phosphorylated to become the biologically active drug are well suited for use in the prodrug methodology of the present invention. There are many well known parent drugs of the form MH which become biologically active via phosphorylation. For example, it is well known that antitumor and antiviral nucleosides are activated through phosphorylation. These compounds include LdC, LdT, araA; AZT; d4T; ddI; ddA; ddC; L-ddC; L FddC; L-d4C; L-Fd4C; 3TC; ribavirin; 5-fluoro-2'-deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2' deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2' fluororibofuranosyl)-2,6-diaminopurine; 9 (arabinofuranosyl) guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; cytallene; PMEA, PMEDAP, HPMPC, HPMPA, FPMPA, and PMPA.

In one preferred aspect, the compounds of formula I does not include compounds where MH is araA or 5-fluoro-2'-deoxyuridine.

Preferred antiviral drugs include:

LdC, LdT, araA; AZT; d4T; ddI; ddA; ddC; L-ddC; L FddC; L-d4C; L-Fd4C; 3TC; ribavirin; FIAU; FIAC; BHCG; L-FMAU; BvaraU; E-5-(2 bromovinyl-2'-deoxyuridine; TFT; 5-propynyl 1-arabinosyluracil; CDG; DAPD; FDOC; d4C; DXG; FEAU; FLG; FLT; FTC; 5-yl-carbocyclic 2'deoxyguanosine; cytallene; oxetanocin A; oxetanocin G; Cyclobut A, Cyclobut G; bromodeoxyuridine; IDU; araT; tiazofurin; ddAPR; 9-(arabinofuranosyl)-2,6 diaminopurine; 9-(2'-deoxyribofuranosyl)-2,6 diaminopurine; 9-(2'-deoxy 2' fluororibofuranosyl)-2,6-diaminopurine; 9 (arabinofuranosyl) guanine; 9-(2'deoxyribofuranosyl)guanine; 9-(2'-deoxy 2' fluororibofuranosyl)guanine; FMdC; 5,6 dihydro-5-azacytidine; 5-azacytidine; 5-aza 2'deoxycytidine; ACV, GCV; penciclovir; (R) 9-(3,4-dihydroxybutyl)guanine; cytallene; 5 PMEA; PMEDAP; HPMPC; HPMPA; FPMPA; PMPA; foscarnet; and phosphonoformic acid.

In one preferred aspect, MH does not include araA.

More preferred antiviral drugs include:

araA; AZT; d4T; ddI; ddA; ddC; L-ddC; L FddC; L-d4C; L-Fd4C; 3TC; ribavirin; FIAU; FIAC; L-FMAU; TFT; CDG; DAPD; FDOC; d4C; DXG; FEAU; FLG; FLT; FTC; 5-yl carbocyclic 2' deoxyguanosine; cytallene; oxetanocin A; oxetanocin G; Cyclobut A, Cyclobut G; araT; ACV, GCV; penciclovir; PMEA; PMEDAP; HPMPC; HPMPA; PMPA; foscarnet.

In one preferred aspect, MH does not include araA.

Most preferred antiviral drugs include:

3TC;
penciclovir;
FMAU;
DAPD;
FTC;
Cyclobut G;
ACV;
GCV;
PMEA;
HPMPA;
5-yl-carbocyclic 2' deoxyguanosine;
ribavirin Preferred anticancer drugs include:
dFdC; 2',2'-difluorodeoxycytidine (gemcitabine);
araC; arabinosylcytosine (cytarabine);
F-ara-A; 2-fluoroarabinosyladenosine (fludarabine); and
CdA; 2-chlorodeoxyadenosine (cladribine).
2'-deoxy-5-iodouridine
Coformycin
2'-deoxycoformycin
Tiazofurin
Ribavirin
5-fluoro-2'deoxyuridine
9-(arabinofuranosyl)-2,6-diaminopurine
9-(2'-deoxyribofuranosyl)-2,6-diaminopurine
9-(2'-deoxy-2'-fluororibofuranosyl)-2,6-diaminopurine
9-(arabinofuranosyl)-guanine
9-(2'-deoxyribofuranosyl)-guanine
9-(2'-deoxy-2'-fluororibofuranosyl)-guanine In one preferred aspect, MH does not include 5-fluoro-2'-deoxyuridine.

In one aspect, preferably the compounds of formula I are not used in the treatment of diabetes.

More preferred anticancer drugs include:
dFdC;
araC;
FaraA;
CdA;
5-fluoro 2'deoxyuridine;
GCV;
5,6-dihydro-5-azacytidine;
5-azacytidine; and
5-aza-2'-deoxycytidine.

In one preferred aspect, ME does not include 5-fluoro-2'-deoxyuridine.

Drugs containing a phosphonic acid (C—PO$_3^{2-}$) moiety are also suitable parent drugs advantageously used in the present invention. These drugs are biologically active either in the form of MPO$_3^{2-}$, MP$_2$O$_6^{3-}$, or MP$_3$O$_9^{4-}$. Phosphonic acids that are also suitable for this prodrug delivery strategy include protease inhibitors that are useful for example as antihypertensives, anticancer or anti-inflammatory agents. The novel prodrug methodology can be applied to NEP inhibitors, (DeLambert et al., *J. Med. Chem.* 37:498 (1994)), ACE inhibitors, endothelin converting enzyme inhibitors, purine nucleoside phosphorylase inhibitors, inhibitors of metalloproteases involved in tumor metastasis, and inhibitors of collagenase (Bird et al., *J. Med. Chem.* 37, 158-169 (1994). Moreover, phosphonic acids useful as NMDA antagonists which are useful for treating a variety of conditions, including stroke, head trauma, pain, and epilepsy. Other phosphonic acids that could benefit from the prodrug strategies are phosphonic acids reported by Squibb that inhibit squalene synthase, by Hoechst that are immunomodulators, by Merck that are antidepressants, by Ciba-Geigy and Marion Merrel Dow that are immunosuppressants via inhibition of purine nucleoside phosphorylase, and by Bristol-Myers Squibb, Gilead that are antivirals. Certain antibiotics might be suitable, especially antibiotics such as D-alanine racemase inhibitors and fosfomycin and associated analogs.

The following compounds and their analogs can be used in the prodrug methodology of the present invention:

NEP Inhibitors
(S)-3-[N-[2-[(phosphonomethyl)amino]-3-(4-biphenylyl)propionyl]amino]propionic acid by DeLombaert et al. in *J Med. Chem.* 1994 Feb. 18; 37(4):498-511

Collagenase Inhibitors
N,[N—((R)-1-phosphonopropyl(-(S)-leucyl]-(S)-phenylalanine N-methyl amide by Bird et al. in *J Med Chem* 1994 Jan. 7; 37(1):158-69

Angiotensin Coverting Enzyme Inhibitors
(IR)-1-(N—(N-acetyl-L-isoleucyl)-L-tyrosyl)amino-2-(4-hydroxyphenyl)ethyl-phosphonic acid by Hirayama et al. in *Int J Pept Protein Res* 1991 July; 38(1):20-4.

Endothelin Inhibitor
CGS 26303 by DeLombaert et al., *Biochem Biophys Res Commun* 1994 Oct. 14; 204(1):407-12
(S,S)-3-Cyclohexyl-2-[[5-(2,4-difluorophenyl)-2-[(phosphonomethyl)amino]pent-4-ynoyl]amino]propionic acid by Wallace et al., *J Med Chem* 1998 Apr. 23; 41(9):1513-23
(S,S)-2-[[5-(2-fluorophenyl)-2-[(phosphonomethyl)amino]pent-4-ynoyl-]amino]-4-methylpentanoic acid
(S,S)-2-[[5-(3-fluorophenyl)-2-[(phosphonomethyl)amino]pent-4-ynoyl]+++amino]-4-methylpentanoic acid NMDA/AMPA Antagonists
N-phosphonoalkyl-5-aminomethylquinoxaline-2,3-diones as described in *Bioorg Med. Chem. Lett.* 1999 Jan. 18; 9(2):249-54
3-(2-carboxypiperazin-4-yl)-1-propenyl-1-phosphonic acid by Bespalov et al. in *Eur J Pharmacol* 1998 Jun. 26; 351 (3):299-305
[2-(8,9-dioxo-2,6-diazabicyclo[5.2.0]non-1(7)-en-2-yl)-ethyl]phosphonic acid D,L-(E)-2-amino-4-[3H]-propyl-5-phosphono-3-pentenoic acid
6,7-dichloro-2(1H)-oxoquinoline-3-phosphonic acid by Desos et al. in *J. Med. Chem.* 1996 Jan. 5; 39(1):197-206.
cis-4-(phosphonomethyl)piperidine-2-carboxylic acid (CGS19755)

Purine Nucleoside Phosphorylase Inhibitors
[7-(2-amino-1,6-dihydro-6-chloro-9H-purin-9-yl)-1,1-fluoroheptyl]phosphonic acid and
[4-(5-amino-6,7-dihydro-7-oxo-3H-1,2,3,-triazolo[4,5-d]-pyrimidin-3-yl)butyl]phosphonic acid.
[[[5-(2-amino-1,6-dihydro-6-oxo-9H-purin-9-yl)pentyl]phosphinico]methyl]phosphonic acid by Kelly et al. in *J Med Chem* 1995 Mar. 17; 38(6):1005-14
(2-[2-[(2-amino-1,6-dihydro-6-oxo-9H-purin-9-yl)methyl]-phenyl]ethenyl)-phosphonic acid by Weibel et al. in *Biochem Pharmacol.* 1994 Jul. 19; 48(2):245-52.
9-(3,3-Dimethyl-5-phosphonopentyl)guanine by Guida et al. in *J Med Chem* 1994 Apr. 15; 37(8):1109-14.

Alanine Racemase Inhibitors
DL-(1-Amino-2-propenyl)phosphonic acid by Vo-Quang et al. in *J Med Chem* 1986 April; 29(4):579-81

Squalene Synthase Inhibitors
1-Hydroxy-3-(methylpentylamino)-propylidene-1,1-bis-phosphonic acid by Amin et al. in *Arzneimittelforschung.* 1996 August; 46(8):759-62.
BMS188494 is POM prodrug of BMS187745 by Dickson et al. in *J Med. Chem.* 1996 Feb. 2; 39(3):661-4.

Treatment of Cancer:

The prodrug strategy in the current invention encompasses several features that are advantageously used in cancer therapies. Many of the known anticancer drugs are nucleosides that undergo phosphorylation to the monophosphate which frequently is further converted to the triphosphate. The prodrug strategy increases the effectiveness of these drugs because the prodrug is cleaved by liver-abundant enzymes and therefore higher levels of the active metabolite are achieved in the liver relative to extrahepatic tissues. The net effect is greater efficacy and/or a greater therapeutic index. In some cases, the prodrug strategy also increases the effectiveness of these drugs by bypassing well-known resistance mechanisms including mechanisms involved in the uptake, intracellular biosynthesis of the active metabolite, export and metabolism of the monophosphate. Examples of preferred drug candidates that are specifically amenable to the strategy include, e.g. dFdC, araC, F-ara, and CdA, and 5-fluoro-2'-deoxyuridine ("5-FU"). In one aspect, MH is not 5-FU.

Some prodrugs may result in some accumulation of the monophosphate in cells. Certain monophosphates are useful for the treatment of cancers, e.g. monophosphates that are potent inhibitors of thymidylate synthase (TS) and IMP dehydrogenase. Some TS inhibitors are reported to be moderately effective in treating liver cancers. For example, 5-FU and 5-FdUMP are effective. These drugs, however, are plagued by drug resistance and severe side effects. To avoid the latter, 5-FU analogs are often delivered via the portal artery to achieve the highest possible liver levels. Accordingly, 5-FdTMP and associated analogs are suitable targets for the prodrug strategy. Other nucleosides such as ribavirin, tiazofurin and coformycin and analogs thereof are also suitable targets for the prodrug strategy.

Liver cancers are also very resistant to radiotherapy. One method for enhancing radiotherapy is to administer radiosensitizers. Radiosensitizers such as 2'-deoxy-5-iodouridine are nucleosides suitable for the prodrug technology since the prodrugs will be cleaved by only P450 containing cells. After cleavage the monophosphate can be further phosphorylated to the triphosphate and trapped inside the cell making the cell more sensitive to radiotherapy.

Treatment of Viral Infections:

Drugs useful for treating viruses that infect the liver and cause liver damage, e.g. hepatitis virus strains, exhibit similar properties to the anticancer nucleoside drugs in terms of efficacy, side effects and resistance. Prodrugs of these nucleosides would therefore be useful in treating hepatitis. In some cases, the drugs are already targeted for hepatitis (e.g. araA, 3TC, L-FMAU, FTC, BMS 200,475). The prodrugs of these compounds could enhance the efficacy, increase the therapeutic index, improve the pharmacodynamic half-life and/or bypass drug resistance. Prodrugs of other agents used to treat viral infections other than hepatitis may also be made useful by administration of the prodrugs of this invention since these drugs are good antivirals (e.g. acyclovir, but useful for other viral infections because they are phosphorylated to the mono-phosphono by a viral kinase. The monophosphate is converted to the biologically active triphosphate by mammalian kinases. Accordingly, delivery of the monophosphate using this clan of prodrugs enables treatment of hepatitis by drugs normally used to treat other viral infections.

Use for the Delivery of Diagnostic Agents:

Nucleoside diagnostic agents, e.g. uridine analogs with the 5H substituted with Tc, are useful as the prodrugs of this invention as liver diagnostic agents. These compounds are converted first to the monophosphate and then onto the triphosphate in cells that contain P450 activity, specifically CYP3A4 activity. Since nearly all of the activity is in the liver, diagnostic agents of this type will primarily be metabolized in the liver and accumulate in cells that metabolize the prodrug. Accordingly, liver tumors that have no CYP3A4 activity or tumors such as hepatocellular carcinomas which have approximately 50% of the normal activity may be differentiated from normal liver tissue.

Agents Used to Modulate CYP Activity

A variety of methods may be used to enhance the in vivo activity of compounds of formula I. For example, various drugs are known that enhance cytochrome P450 (CYP) activity. Enhancement frequently entails increased gene transcription. Four families of CYPs are particularly susceptible to induction, namely CYP1-4. Induction is purportedly via receptors that are activated by various xenobiotics. For example, CYP1 gene activation frequently involves activation of the Ah receptor by polycyclic aromatic hydrocarbons. CYP2-4 are activated via orphan nuclear receptors. Data suggests that the nuclear receptor CAR (constitutively Active Receptor) is responsible for phenobarbital CYP activation, especially CYP2 genes. The pregnane nuclear receptors (PXR or PAR or SXR) are thought to activate CYP3A genes whereas the PPAR (peroxisome proliferator activate receptor) is linked to CYP4 gene activation. All three xenobiotic receptors are highly expressed in the liver which accounts for the liver specificity of the P450 gene induction.

Xenobiotics known to induce CYP3 genes include phenobarbital, a variety of steroids, e.g. dexamethasone, antibiotics, e.g. rifampicin, and compounds such as pregnenolone-16a carbonitrile, phenyloin, carbamazepine, phenylbutazone, etc. A variety of methods are known that enable identification of xenobiotics that induce P450s, including a reporter gene assay in HepG2 cells (Ogg et al., *Xenobiotica* 29, 269-279 (1999). Other inducers of the CYP3A subfamily are known that act at the post-transcriptional level either by mRNA or protein stabilization, e.g. clotrimazole, TA and erythromycin. Compounds known to induce CYPs or identified in in vitro assays are then used to enhance CYP activity in vivo. For example, CYP activity is monitored in rats pre-treated with CYP modulators by e.g. evaluating liver microsomes over a period of time to determine the optimal pre-treatment period, dose and dosing frequency. Rats with enhanced CYP activity, especially the CYP activity responsible for activation of the prodrugs (e.g. CYP3A4), are then treated with compounds of formula I. Enhanced CYP activity can then lead to enhanced prodrug conversion and liver specificity. For example, enhanced metabolism of cyclophosphamide was found with pre-treatment with phenobarbital (Yu et al., *J. Pharm. Exp. Ther.* 288, 928-937 (1999).

In some cases, enhanced CYP activity may lead to unwanted drug metabolism. For example, enhanced activity of CYPs not involved in prodrug activation can result in increased drug metabolism and therefore decreased efficacy. In addition, increased CYP activity in other tissues, e.g. CYP3A4 in the gastrointestinal tract, could result in decreased prodrug absorption and liver drug levels Inhibitors of CYP activity are known that might be useful in minimizing unwanted drug metabolism. For example, grapefruit juice is known to inactivate gastrointestinal CYP3A4 and to result in enhanced absorption of numerous drugs metabolized by CYP3A4. CYP inhibitors are also known for many of the CYP subfamilies that can be useful for attenuating unwanted drug metabolism while maintaining CYP activity important for prodrug cleavage. For example, the CYP3A inhibitor TAO was used to modulate cyclophosphamide metabolism in vivo in a manner that decreased the formation of toxic metabolites that do not contribute to its antitumor activity.

Methods for Monitoring Patient P450 Activity

CYP activity is known to exhibit significant differences across individuals. The range for CYP3A4 is 5- to 20-fold although most individuals are within a 3-fold range. Modest decreases are noted for individuals with liver disease (30-50%) or advanced age (25-50%). Differences for gender are even more modest (<25%). Methods for phenotyping an individual's CYP activity are known and could be useful in predicting who should receive drugs that modulate CYP activity. Evasive procedures include liver biopsy. Non evasive procedures have been reported, including an "erythromycin breath test" which is based on the exhalation of 14CO2 generated from the CYP3A-mediated N-demethylation of radiolabeled erythromycin (iv). (Watkins, *Pharmacogenetics* 4, 171-184 (1994)).

Gene Therapy

Introduction into tumor cells genes that encode for enzymes not normally expressed represents a new therapeutic strategy for increasing the therapeutic effectiveness of anti-cancer chemotherapies. The general strategy entails expression of an enzyme that catalyzes the breakdown of a prodrug of an anticancer drug thereby localizing the drug in or near the tumor mass and limiting exposure elsewhere. The strategy has been demonstrated using the HSV-TK gene wherein the thymidylate kinase specifically expressed in the transfected cells activates ganciclovir to the monophosphate which is then converted by other kinases to the tumor cell killing triphosphate. A similar strategy uses the bacterial cytosine deaminase gene for conversion of 5-fluorouracil to 5-fluorocytosine. Other genes have been considered including carboxypeptidase G2, nitro reductase, purine nucleoside phosphorylation, etc. In addition, CYP gene transfer has been explored as a way to enhance the chemotherapeutic effect of cyclophosphamide and ifosfamide, two drugs known to be activated by CYPs. For example, human breast cancer cells were sensitized by transfection with the CYP2B1 gene (Chen et al., *Cancer Research,* 56, 1331 1340 (1996)). The advantage of this strategy relative to the HSV-TK gene strategy is that the product of the CYP catalyzed oxidation readily diffuses outside of the tumor cell and into nearby cells. In contrast to monophosphate products of the HSV-TK strategy, the product can enter cells that are not in cell-cell contact and therefore produce a more widespread tumor killing effect (Chen and Waxman, *Cancer Research,* 55, 581-589 (1995)).

Compounds of formula I can be made more effective by using gene therapy to introduce the gene that encodes the CYP specifically involved in prodrug cleavage. The specific CYP that breaks down the prodrug is readily determined using some or all of the following steps: 1) demonstrate prodrug cleavage using human microsomes; 2) classify the subfamily by comparing activity with microsomes induced with various subfamily specific inducers (e.g. CYP3 enzymes are induced with a variety of steroids, e.g. dexamethasone, antibiotics, e.g. rifampicin, and compounds such as pregnenolone-16a carbonitrile, phenyloin, carbamazepine, phenylbutazone, etc.; 3) identify the CYP or CYPs responsible for prodrug activation by using known CYP subfamily specific inhibitors (e.g. troleandomycin, erythromycin, ketoconazole and gestodene) and/or by using neutralizing antibodies; 4) confirm CYP subfamily by demonstrating turnover via the recombinant enzyme.

Genes are introduced to the tumor using a suitable vector (e.g. retroviral vectors, adenoviral vectors) or via direct DNA injection. P450 activity can also be introduced into or near the tumor mass using cells engineered to express P450s. Preferred are encapsulated cells (e.g. Lohr et al., *Gene Therapy* 5: 1070 (1998)) The compounds of formula I are then introduced following significant enhancement of the CYP activity in the tumor.

Especially preferred are those prodrugs disclosed in the invention that are converted to the parent phosph(on)ate in cells and tissues, especially hepatocytes and liver, as indicated by measurement of the intracellular drug metabolites in hepatocytes using the procedure described in Examples G and J.

Preferred Compounds

The compounds of the invention are substituted 6-membered cyclic 1,3 propane prodrugs of certain phosph(on)ates as represented by Formula I:

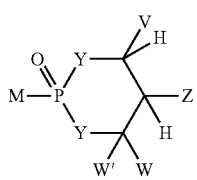

I wherein:

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R, —OR$^2$, —SR$^2$, —CHR$^2$N$_3$, —CH$_2$aryl, —CH(aryl)OH, —CH(CH=CR$^2_2$)OH, —CH(C≡CR$^2$)OH, —R, —NR$^2_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{12}$, and —(CH$_2$)$_p$—SR$^{12}$;

p is an integer 2 or 3;

with the provisos that:

a) V, Z, W, W' are not all —H; and b) when Z is —R$^2$, then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

R$^6$ is selected from the group consisting of —H, and lower alkyl, acyloxyalkyl, alkoxycarbonyloxy alkyl and lower acyl;

R$^{12}$ is selected from the group consisting of —H, and lower acyl;

each Y is independently selected from the group consisting of —O—, —NR$^6$— with the proviso that at least one Y is —NR$^6$—;

M is selected from the group that attached to PO$_3^{2-}$, P$_2$O$_6^{3-}$, P$_3$O$_9^{4-}$ or P(O)(NHR$^6$)O$^-$ is a biologically active agent, but is not an FBPase inhibitor, and is attached to the phosphorus in formula I via a carbon, oxygen, sulfur or nitrogen atom;

with the provisos that:

1) M is not —NH(lower alkyl), —N(lower alkyl)$_2$, —NH(lower alkylhalide), —N(lower alkylhalide)$_2$, or —N(lower alkyl)(lower alkylhalide); and 2) R$^6$ is not lower alkylhalide;

and pharmaceutically acceptable prodrugs and salts thereof.

In general, preferred substituents, V, Z, W, and W' of formula I are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-P450 enzymes;

(3) enhance cell penetration, e.g. substituents are not charged or of high molecular weight since both properties can limit oral bioavailability as well as cell penetration;

(4) promote the β-elimination reaction following the initial oxidation by producing ring-opened products that have one or more of the following properties:
   a) fail to recyclize;
   b) undergo limited covalent hydration;
   c) promote β-elimination by assisting in the proton abstraction;
   d) impede addition reactions that form stable adducts, e.g. thiols to the initial hydroxylated product or nucleophilic addition to the carbonyl generated after ring opening; and
   e) limit metabolism of reaction intermediates (e.g. ring-opened ketone);

(5) lead to a non-toxic and non-mutagenic by-product with one or more of the following characteristics. Both properties can be minimized by using substituents that limit Michael additions, e.g.:
   a) electron donating Z groups that decrease double bond polarization;
   b) W groups that sterically block nucleophilic addition to the β-carbon;
   c) Z groups that eliminate the double bond after the elimination reaction either through retautomerization (enol->keto) or hydrolysis (e.g. enamine);

d) V groups that contain groups that add to the α,β-unsaturated ketone to form a ring;
e) Z groups that form a stable ring via Michael addition to double bond; and
f) groups that enhance detoxification of the by-product by one or more of the following characteristics:
(i) confine to liver; and
(ii) make susceptible to detoxification reactions (e.g. ketone reduction); and
(6) capable of generating a pharmacologically active product.

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, preferably independently selected from nitrogen, oxygen, and sulfur. Suitable heteroaliacyclic groups include groups having from 2 to about twenty carbon atoms and from 1 to 5 heteroatoms, preferably independently selected from nitrogen, oxygen, phosphorous, and sulfur.

In compounds of formula I, preferably one Y is —O— and one Y is —$NR^6$—. When only one Y is —$NR^6$—, preferably the Y closest to W and W' is —O—. In another aspect, preferably the Y closest to V is —O—.

In another aspect, both Y groups are —$NR^6$—.

More preferred are compounds wherein one Y is —O—, and

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus.

More preferred are such compounds where V is selected from the group consisting of aryl, substituted aryl, heteroaryl, and substituted heteroaryl.

More preferred V groups of formula VI are aryl, substituted aryl, heteroaryl, and substituted heteroaryl. Preferably, one Y is —O—. Particularly preferred aryl and substituted aryl groups include phenyl, and phenyl substituted with 1-3 halogens. Especially preferred are 3,5-dichlorophenyl, 3-bromo-4-fluorophenyl, 3-chlorophenyl, and 3-bromophenyl.

It is also especially preferred when V is selected from the group consisting of monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

In another particularly preferred aspect, one Y group is —O—, Z, W, and W' are H, and V is phenyl substituted with 1-3 halogens. Especially preferred are 3,5-dichlorophenyl, 3-bromo-4-fluorophenyl, 3-chlorophenyl, and 3-bromophenyl.

It is also especially preferred when V is selected from the group consisting of heteroaryl and substituted heteroaryl.

Most preferred is when such heteroaryl is 4-pyridyl.

In another aspect, it is preferred when together V and W are connected via an additional 3 carbon atoms to form an optionally substituted cyclic group containing 6 carbon atoms and monosubstituted with one substituent selected from the group consisting of hydroxy, acyloxy, alkoxycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from the group consisting of —$CH_2$—CH(OH)—$CH_2$—, —$CH_2$CH($OCOR^3$)—$CH_2$—, and —$CH_2$CH($OCO_2$)$R^3$)—$CH_2$—.

Another preferred V group is 1-alkene. Oxidation by P450 enzymes is known to occur at benzylic and allylic carbons.

In one aspect, preferred V groups include —H, when Z is —$CHR^2OH$, —$CH_2OCOR^3$, or —$CH_2OCO_2R^3$.

In another aspect, when V is aryl, substituted aryl, heteroaryl, or substituted heteroaryl, preferred Z groups include —$OR^2$, —$SR^2$, —$R^2$, —$NR^2_2$, —$OCOR^3$, —$OCO_2R^3$, —$SCOR^3$, —$SCO_2R^3$, —$NHCOR^2$, —$NHCO_2R^3$, —$(CH_2)_p$-$OR^2$, and —$(CH_2)_p$-$SR^2$. More preferred Z groups include —$OR^2$, $R^2$, —$OCOR^3$, —$OCO_2R^3$, —$NHCOR^2$, —$NHCO_2R^3$, —$(CH_2)_p$-$OR^{12}$, and —$(CH_2)_p$-$SR^{12}$. Most preferred Z groups include —$OR^2$, —H, —$OCOR^3$, —$OCO_2R^3$, and —$NHCOR^2$.

Preferred W and W' groups include H, $R^3$, aryl, substituted aryl, heteroaryl, and substituted aryl. Preferably, W and W' are the same group. More preferred is when W and W' are H.

In one aspect, prodrugs of formula VI which, in addition, are preferred:

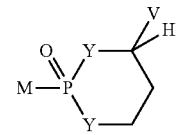

VI wherein

V is selected from the group consisting of aryl, substituted aryl, heteroaryl, and substituted heteroaryl. More preferred are such compounds where M is attached to the phosphorus via an O or N atom. Especially preferred are 3,5-dichlorophenyl, 3-bromo-4-fluorophenyl, 3-chlorophenyl, 3-bromophenyl. Preferably Y is —O—. Particularly preferred aryl and substituted aryl groups include phenyl and substituted phenyl. Particularly preferred heteroaryl groups include monocyclic substituted and unsubstituted heteroaryl groups. Especially preferred are 4-pyridyl and 3-bromopyridyl.

In one aspect, the compounds of formula VI preferably have a group Z which is H, alkyl, alicyclic, hydroxy, alkoxy, $OC(O)R^3$, $OC(O)OR^3$, or $NHC(O)R^2$. Preferred are such groups in which Z decreases the propensity of the by-product, vinylaryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=$OR^{12}$, NHAc, etc. Other groups may also prevent the Michael addition especially groups that result in removal of the double bond altogether such as Z=—OH, —$OC(O)R^3$, —$OCO_2R^3$, and $NH_2$, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. $(CH_2)_pSH$ or $(CH_2)_pOH$ where p is 2 or 3. Yet another preferred group is a group attached to V which is capable of adding to the α,β-unsaturated double bond after the elimination reaction:

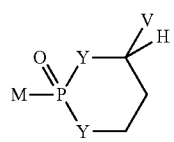

VI

In another aspect, prodrugs of formula VII are preferred:

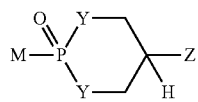

VII wherein

Z is selected from the group consisting of:
—$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, and —$CH_2aryl$. Preferably, M is attached to the phosphorus via a nitrogen. More preferred groups include —$CHR^2OH$, —$CHR^2OC(O)R^3$, and —$CHR^2OCO_2R^3$. Preferably $R^2$ is H.

In another aspect, prodrugs of formula VIII are preferred:

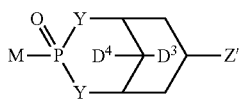

VIII wherein

Z' is selected from the group consisting of —OH, —OC(O)$R^3$, $OCO_2R^3$, and —OC(O)$SR^3$;

$D^4$ and $D^3$ are independently selected from the group consisting of —H, alkyl, —OH, and —OC(O)$R^3$; with the proviso that at least one of $D^4$ and $D^3$ are —H. Preferably Y is —O—. An especially preferred Z' group is OH.

In one preferred embodiment, W' and Z are —H, W and V are both the same aryl, substituted aryl, heteroaryl, or substituted heteroaryl, and both Y groups are the same —$NR^6$—, such that the phosphonate prodrug moiety:

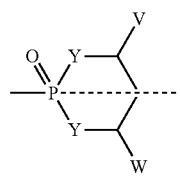

has a plane of symmetry through the phosphorous-oxygen double bond.

In another preferred embodiment, W and W' are H, V is selected from the group consisting of aryl, substituted aryl, heteroaryl, substituted heteroaryl, and Z is selected from the group consisting of —H, $OR^2$, and —$NHCOR^2$. More preferred are such compounds where Z is —H. Preferably, such compound have M attached via oxygen. Most preferred are such compounds where oxygen is in a primary hydroxyl group. Also more preferred, are those compounds where V is phenyl or substituted phenyl.

In one aspect, tumor cells expressing a P450 enzyme can be treated by administering a cyclophosphamide analog selected from the group consisting of

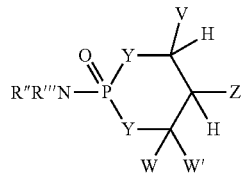

wherein:

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, $OR^2$, —$SR^2$, —$CHR^2N_3$, —$CH_2aryl$, —$CH(aryl)OH$, —$CH(CH=CR^2_2)OH$, —$CH(C≡CR^2)OH$, —$R^2$, $NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$-$OR^{12}$, and —$(CH_2)_p$-$SR^{12}$;

p is an integer 2 or 3;

with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

$R^{66}$ is selected from the group consisting of —H, lower 2-haloalkyl, and lower alkyl;

$R^{12}$ is selected from the group consisting of —H, and lower acyl;

R" is lower 2-haloalkyl;

R'" is selected from the group consisting of H, lower alkyl, and R";

each Y is independently selected from the group consisting of —O—, —NR$^{66}$— with the proviso that at least one Y is —NR$^{66}$—;

and pharmaceutically acceptable prodrugs and salts thereof.

Preferably, the tumor cell is a hepatocellular carcinoma. These cyclophosphamide analogs can also be used to treat tumor cells by enhancing the activity of a P450 enzyme that oxidizes cyclophosphamide analogs and by administering the cyclophosphamide analogs.

In another aspect, the P450 activity is enhanced by the administration of a compound that increases the amount of endogenous P450 enzyme. Preferably, the compound that increases the amount of endogenous P450 enzyme is selected from the group consisting of phenobarbitol, dexamethasone, rifampicin, phentoin, and preganolon-16α-carbonitrile. Preferred cyclophosphoramide analogs include those where R" is 2-chloroethyl, and R'" is selected from the group consisting of —H, and 2-chloroethyl.

Also, preferred are cyclophosphamide analogs where R$^{66}$ is selected from the group consisting of —H, methyl, and 2-chloroethyl.

In one aspect, the activity of a P450 enzyme is enhanced by administration of a compound that increases the amount of endogenous P450 enzyme.

Also preferred cyclophosphamide analogs are those where Z, W, W', and R$^{66}$ are —H, and R" and R'" are 2-chloroethyl.

Preferred cyclophosphamide analogs have V is selected from the group consisting of aryl, substituted aryl, heteroaryl, and substituted heteroaryl. More preferred are those compounds where Z, W, W', and R$^{66}$ are —H, and R" and R'" are 2-chloroethyl. Also more preferred are those wherein V is selected from the group consisting of phenyl, 3-chlorophenyl, and 3-bromophenyl. Also preferred are those wherein V is 4-pyridyl.

Also more preferred, are those compounds where V is an optionally substituted monocyclic heteroaryl containing at least one nitrogen atom. Preferably such compounds have M attached via oxygen. Most preferred are such compounds where said oxygen is in a primary hydroxyl group. Especially preferred are such compounds where V is 4-pyridyl.

Preferably, oral bioavailability is at least 5%. More preferably, oral bioavailability is at least 10%.

P450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry. In contrast, the reaction is relatively insensitive to the group M since cleavage occurred with a variety of phosphonate, phosphate and phosphoramidates. The atom in M attached to phosphorus may be O, S or N. The active drug is M-PO$_3^{2-}$, MP$_2$O$_6^{3-}$, or MP$_3$O$_9^{4-}$ useful for treatment of diseases in which the liver is a target organ, including diabetes, hepatitis, liver cancer, liver fibrosis, malaria and metabolic diseases where the liver is responsible for the overproduction of a biochemical end products such as glucose (diabetes), cholesterol, fatty acids and triglycerides (atherosclerosis). Moreover, M-PO$_3^{2-}$, MP$_2$O$_6^{3-}$, or MP$_3$O$_9^{4-}$ may be useful in treating diseases where the target is outside the liver in tissues or cells that can oxidize the prodrug.

Other preferred M groups include drugs useful in treating diabetes, cancer, viral infections, liver fibrosis, parasitic infections, hypertension, and hyperlipidemia.

The preferred compounds of formula VIII utilize a Z' group that is capable of undergoing an oxidative reaction that yields an unstable intermediate which via elimination reactions breaks down to the corresponding M-P(O)(NHR$^6$)$_2$, or M-P(O)(O$^-$)(NHR$^6$). An especially preferred Z' group is OH. Groups D$^4$ and D$^3$ are preferably hydrogen, alkyl, —OR$^2$, —OCOR$^3$, but at least one of D$^4$ or D$^3$ must be H.

The following compounds and their analogs can be used in the prodrug methodology of the present invention.

In one preferred aspect, M is attached to the phosphorus in formula I via an oxygen atom. Preferably, M is a nucleoside. Preferably, M is attached via an oxygen that is in a primary hydroxyl group on a ribofuranosyl or an arabinofuranosyl group. Preferably such compounds include LdT, LdC, araA; AZT; d4T; ddI; ddA; ddC; L-ddC; L FddC; L-d4C; L-Fd4C; 3TC; ribavirin; 5-fluoro 2' deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2' deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2' fluororibofuranosyl)-2,6-diaminopurine; 9 (arabinofuranosyl) guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; or AICAR. In another aspect, it is preferred when M is attached via an oxygen in a hydroxyl on an acyclic sugar it is preferred when such MH is ACV, GCV; penciclovir; (R)-9-(3,4 dihydroxybutyl)guanine; or cytallene.

In one preferred aspect, the compounds in formula I do not include compounds where MH is araA or 5-fluoro-2'-deoxyuridine.

In general, it is preferred that when M is attached via an oxygen, said oxygen is in a primary hydroxy group. In such an instance, it is preferred that MH is araA; AZT; d4T; ddI; ddA; ddC; L-ddC; L FddC; L-d4C; L-Fd4C; 3TC; ribavirin; 5-fluoro 2' deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2' deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2' fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; or cytallene.

In another aspect, MH is araA.

In another aspect, MH is 5-fluoro-2'-deoxyuridine.

In another aspect, compounds of formula I wherein M is attached to the phosphorus in formula I via a carbon atom are preferred. In such compounds, preferably M-PO$_3^{2-}$ is phosphonoformic acid, or phosphonoacetic acid.

In another preferred aspect, MPO$_3^{2-}$, MP$_2$O$_6^{3-}$, or MP$_3$O$_9^{4-}$ is useful for the treatment of diseases of the liver or metabolic diseases where the liver is responsible for the overproduction of a biochemical end product. Preferably, such disease of the liver is selected from the group consisting of diabetes, hepatitis, cancer, fibrosis, malaria, gallstones, and chronic cholecystalithiasis. It is more preferred when treating such diseases that MH, $MPO_3^{2-}$, $MP2O_6^{3-}$, or $MP_3O^{4-}$ is an antiviral or anticancer agent.

Preferably, the metabolic disease that $MPO_3^{2-}$, $MP_2O_6^{3-}$, or $MP_3O_9^{4-}$ are useful for diabetes, atherosclerosis, and obesity.

In another aspect, it is preferred when the biochemical end product is selected from the group consisting of glucose, cholesterol, fatty acids, and triglycerides. More preferred is when $MP(O)(NHR^6)O^-$ or $MPO_3^{2-}$ is an AMP activated protein kinase activator.

In one preferred embodiment, W' and Z are —H, W and V are both the same aryl, substituted aryl, heteroaryl, or substituted heteroaryl such that the phosphonate prodrug moiety:

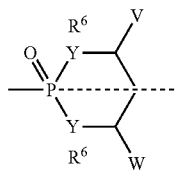

has a plane of symmetry.

In another preferred embodiment, W and W' are H, V is selected from the group consisting of aryl, substituted aryl, heteroaryl, substituted heteroaryl, and Z is selected from the group consisting of —H, $OR^2$, and —$NHCOR^2$. More preferred are such compounds where Z is —H. Preferably, such compound have M attached via oxygen. Most preferred are such compounds where oxygen is in a primary hydroxyl group.

Also more preferred, are those compounds where V is phenyl or substituted phenyl. Most preferred are such compounds where said oxygen is in a primary hydroxyl group.

Preferably, such compounds have M attached via oxygen.

Also more preferred, are those compounds where V is an optionally substituted monocyclic heteroaryl containing at least one nitrogen atom. Preferably such compounds have M attached via oxygen. Most preferred are such compounds where said oxygen is in a primary hydroxyl group.

Especially preferred are such compounds where V is selected from the group consisting of phenyl substituted with 1-3 halogens, and 4-pyridyl. In these compounds it is also preferred when MH is selected from the group consisting of LdT, LdC, araA; AZT; d4T; ddI; ddA; ddC; L-ddC; L FddC; L-d4C; L-Fd4C; 3TC; ribavirin; 5-fluoro 2' deoxyuridine; FIAU; FIAC; BHCG; L FMAU; BvaraU; E-5-(2-bromovinyl-2'deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofaranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2' fluororibofuranosyl)guanine; FMdC; 5,6 dihydro-5-azacytidine; 5-azacytidine; 5-aza 2' deoxycytidine; AICAR; ACV, GCV; penciclovir; (R)-9-(3,4 dihydroxybutyl)guanine; or cytallene. Particularly preferred are such compounds where V is selected from the group consisting of phenyl substituted with 1-3 halogens and 4-pyridyl and MH is selected from the group consisting of araA; AZT; d4T; 3TC; ribavirin; 5 fluoro-2'deoxyuridine; FMAU; DAPD; FTC; 5-yl-carbocyclic 2'deoxyguanosine; Cyclobut G; dFdC; araC; IDU; FaraA; ACV; GCV; or penciclovir.

Also preferred is when MH is selected from the group consisting of ACV, GCV; penciclovir; (R)-9-(3,4 dihydroxybutyl)guanine; cytallene.

When W' and W are H, V is aryl, substituted aryl, heteroaryl, or substituted heteroaryl, and Z is H, $OR^2$, or —NH-$COR^2$, it is also preferred when M is attached to the phosphorus via a carbon atom. Preferred are such compounds wherein $MPO_3^{2-}$ is selected from the group consisting of phosphonoformic acid, and phosphonoacetic acid. Also preferred are MH is selected from the group consisting of PMEA, PMEDAP, HPMPC, HPMPA, FPMPA, and PMPA.

Preferably, oral bioavailability is at least 5%. More preferably, oral bioavailability is at least 10%.

P450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis stereochemistry. In contrast, the reaction is relatively insensitive to the group M since cleavage occurred with a variety of phosphonate, phosphate and phosphoramidates. Accordingly, the group M represents a group that as part of a compound of formula I enables generation of a biologically active compound in vivo via conversion to the corresponding $M-PO_3^{2-}$. The atom in M attached to phosphorus may be O, S, C or N. The active drug may be $M-PO_3^{2-}$ or a metabolite of $M-PO_3^{2-}$ such as the triphosphate useful for treatment of diseases in which the liver is a target organ, including diabetes, hepatitis, liver cancer, liver fibrosis, malaria and metabolic diseases where the liver is responsible for the overproduction of a biochemical end products such as glucose (diabetes), cholesterol, fatty acids and triglycerides (atherosclerosis). Moreover, $M-PO_3^{2-}$ and $MP(O)(NHR^6)O^-$ may be useful in treating diseases where the target is outside the liver but accessible to a phosph(on)ate. Preferred M groups are groups in which M is a nucleoside and the phosphate is attached to a hydroxyl, preferably a primary hydroxyl on a sugar or sugar-analog. More preferred M groups include LdC, LdT, araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2' fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; or cytallene. Especially preferred are lobucavir, FTC, 3TC, BMS 200,475; DAPD, DXG, L-FMAU, LdC, LdT, ribavirin, F-ara-A, araC, CdA, dFdC, 5-fluoro-2'-deoxyuridine, ACV, GCV, and penciclovir.

The preferred M groups include phosphonic acids useful for treating viral infections. Such preferred antivirals include PMEA; PMEDAP; HPMPC; HPMPA; FPMPA; PMPA; foscarnet; phosphonoformic acid. More preferred are PMEA, PMPA, HPMPC, and HPMPA. Especially preferred are PMEA and PMPA.

Other preferred M groups include phosphonic acids useful in treating diabetes, liver fibrosis, e.g. collagenase inhibitors such as reported in Bird et al., *J. Med. Chem.* 37, 158-169 (1994), parasitic infections, diseases responsive to metalloprotease inhibition (e.g. hypertension, liver, cancer), and hyperlipidemia.

In another aspect, preferred MH groups including L-nucleosides. Preferred L-nucleosides include FTC, 3TC, L-FMAU, LdC, and LdT.

In one aspect, preferred MH groups are acyclic nucleosides. Preferred acyclic nucleosides include ACV, GCV; penciclovir; (R)-9-(3,4 dihydroxybutyl)guanine; and cytallene. More preferred are ACV; GCV, and penciclovir.

In another aspect, preferred MH groups include dideoxy nucleosides. Preferred dideoxy nucleosides include AZT; d4T; ddI; ddA; ddC; L-ddC; L-FddC; L d4C; L-Fd4C; d4C; and ddAPR. More preferred are AZT; d4T; ddI; and ddC.

In another aspect, preferred MH groups include arabinofuranosyl nucleosides. Preferred are araA; araT; 5-propynyl-1-arabinosyluracil; araC; FaraA; 9-(arabinofuranosyl)-2,6 diaminopurine; and 9-(arabinofuranosyl)guanine. More preferred are araA; araC; and FaraA.

In another aspect, preferred MH groups include carbocyclic nucleosides. Preferred are 5-yl-carbocyclic 2' deoxyguanosine; CDG; cyclobut A; cyclobut G; and BHCG. More preferred are 5-yl-carbocyclic 2' deoxyguanosine; and cyclobut G.

In another aspect, preferred MH groups include fluorinated sugars on the nucleosides. Preferred fluorinated sugars include FLT; FLG; FIAC; FIAU; FMAU; FEAU; dFdC; 9-(2'-deoxy-2'fluororibofuranosyl) 2,6-diaminopurine; and 9-(2'-deoxy 2'fluororibofuranosyl)guanine More preferred are L-FMAU; and dFdC.

In another aspect, preferred MH groups include dioxolane nucleosides. Preferred dioxolane nucleosides include DAPD; DXG; and FDOC. More preferred is DAPD and DXG.

In another aspect, preferred MH and $MPO_3^2$ for treating viral infections include lobucavir, FTC, 3TC, BMS 200,475; DAPD, DXG, L-FMAU, LdC, LdT, ribavirin, ACV, GCV, penciclovir, PMEA, and PMPA.

In another aspect, preferred MH groups for treating cancer include F-ara-A, araC, CdA, dFdc, and 5-fluoro-2'-deoxyuridine.

The following prodrugs are preferred compounds of the invention. The compounds are shown without depiction of stereochemistry since the compounds are biologically active as the diastereomeric mixture or as a single stereoisomer. Compounds named in Table 1 are designated by numbers assigned to the variables of formula VIa using the following convention:

$M^1.V.L1.L2$ where Y is NH and Y' is oxygen; $M^1$ is a variable that represents compounds of the formula M-H which have a specific hydroxyl group that is phosphorylated with a group P(O)(Y—CH(V)CH2CH2-Y') to make compounds of formula VIa or $M^1$ is a variable that represents phosphonic acids of the formula $M-PO_3^{2-}$ which are transformed to compounds of formula VIa by replacing two oxygens in the $PO_3^{2-}$ group with Y—CH(V)CH2CH2-Y'. V is an aryl or heteroaryl group that has 2 substituents, L1 and L2, at the designated positions.

Variable $M^1$ is divided into three groups with the structures assigned to each group listed below:

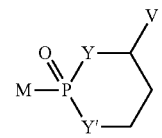

Via

Variable $M^1$: Group $M^1$1:
1) 3TC where —P(O)(Y—CH(V)CH2CH2-Y') is attached to the primary hydroxyl.
2) (–)FTC where —P(O)(Y—CH(V)CH2CH2-Y') is attached to the primary hydroxyl.
3) L-FMAU where —P(O)(Y—CH(V)CH2CH2-Y') is attached to the primary hydroxyl.
4) Penciclovir where —P(O)(Y—CH(V)CH2CH2-Y') is attached to the primary hydroxyl that is phosphorylated in cells.
5) BMS 200,475 where —P(O)(Y—CH(V)CH2CH2-Y') is attached to the primary hydroxyl.
6) L(–)Fd4C where —P(O)(Y—CH(V)CH2CH2-Y') is attached to the primary hydroxyl.
7) Lobucavir where —P(O)(Y—CH(V)CH2CH2-Y') is attached to the primary hydroxyl that is phosphorylated in cells.
8) DXG where —P(O)(Y—CH(V)CH2CH2-Y') is attached to the primary hydroxyl.
9) LdC where —P(O)(Y—CH(V)CH2CH2-Y') is attached to the primary hydroxyl.

Variable $M^1$: Group $M^1$2:
1) ddI where —P(O)(Y—CH(V)CH2CH2-Y') is attached to the primary hydroxyl.
2) LdT where —P(O)(Y—CH(V)CH2CH2-Y') is attached to the primary hydroxyl.
3) ddC where —P(O)(Y—CH(V)CH2CH2-Y') is attached to the primary hydroxyl.
4) AZT where —P(O)(Y—CH(V)CH2CH2-Y') is attached to the primary hydroxyl.
5) d4T where —P(O)(Y—CH(V)CH2CH2-Y') is attached to the primary hydroxyl.
6) DAPD where —P(O)(Y—CH(V)CH2CH2-Y') is attached to the primary hydroxyl.
7) L-FddC where —P(O)(Y—CH(V)CH2CH2-Y') is attached to the primary hydroxyl.
8) Ribavirin where —P(O)(Y—CH(V)CH2CH2-Y') is attached to the primary hydroxyl.
9) CdA where —P(O)(Y—CH(V)CH2CH2-Y') is attached to the primary hydroxyl Variable $M^1$: Group $M^1$3:
1) Ganciclovir where —P(O)(Y—CH(V)CH2CH2-Y') is attached to the primary hydroxyl that is phosphorylated in cells.
2) Acyclovir where —P(O)(Y—CH(V)CH2CH2-Y') is attached to the primary hydroxyl.
3) Cytarabine where —P(O)(Y—CH(V)CH2CH2-Y') is attached to the primary hydroxyl.
4) Gemcitabine where —P(O)(Y—CH(V)CH2CH2-Y') is attached to the primary hydroxyl
5) Fludarabine where —P(O)(Y—CH(V)CH2CH2-Y') is attached to the primary hydroxyl
6) Floxuridine where —P(O)(Y—CH(V)CH2CH2-Y') is attached to primary hydroxyl
7) HPMPC where —P(O)(Y—CH(V)CH2CH2-Y') replaces the $PO_3^=$ group.
8) PMEA where —P(O)(Y—CH(V)CH2CH2-Y') replaces the $PO_3^=$ group.

9) PMPA where —P(O)(Y—CH(V)CH2CH2-Y') replaces the $PO_3^=$ group.

Variable V: Group V1
1) 2-(L1)-3 (L2) phenyl
2) 2-(L1)-4(L2) phenyl
3) 2-(L1)-5(L2) phenyl
4) 2-(L1)-6(L2) phenyl
5) 3-(L1)-4(L2) phenyl
6) 3-(L1)-5(L2) phenyl
7) 3-(L1)-6(L2) phenyl
8) 2-(L1)-6(L2)-4-chlorophenyl
9) 3-(L1)-5 (L2) 4-chlorophenyl Variable V: Group V2
1) 2-(L1)-3(L2) 4-pyridyl
2) 2-(L1)-5(L2) 4-pyridyl
3) 2-(L1)-6(L2) 4-pyridyl
4) 3-(L1)-5(L2) 4-pyridyl
5) 3-(L1)-6(L2) 4-pyridyl
6) 2-(L1)-4(L2) 3-pyridyl
7) 2-(L1)-5(L2) 3-pyridyl
8) 2-(L1)-6(L2) 3-pyridyl
9) 4-(L1)-5(L2) 3-pyridyl Variable V: Group V3
1) 4-(L1)-6(L2) 3-pyridyl
2) 5-(L1)-6(L2) 3-pyridyl
3) 3-(L1)-4(L2) 2-pyridyl
4) 3-(L1)-5(L2) 2-pyridyl
5) 3-(L1)-6(L2) 2-pyridyl
6) 4-(L1)-5(L2) 2-pyridyl
7) 4-(L1)-6(L2) 2-pyridyl
8) 3-(L1)-4 (L2)-2-thienyl
9) 2-(L1)-5(L2) 3-furanyl Variable L1
1) hydrogen
2) chloro
3) bromo
4) fluoro
5) methyl
6) isopropyl
7) methoxy
8) dimethylamino
9) acyloxy Variable L2
1) hydrogen
2) chloro
3) bromo
4) fluoro
5) methyl
6) isopropyl
7) methoxy
8) dimethylamino
9) acyloxy Preferred compounds are compounds listed in Table 1 using groups $M^1 1$ and V1. For example, compound 1.3.6.7 represents structure 1 of group $M^1 1$, i.e. 3TC; structure 3 of group V1, i.e. 2-(L1)-5-(L2) phenyl; structure 6 of variable L1, i.e. isopropyl; and structure 7 of variable L2, i.e. methoxy. The compound 1.3.6.7. therefore is 3TC with the P(O)(Y—CH(V)CH2CH2Y') attached to the primary hydroxyl group being {[1-(2-I-propyl-5-methoxyphenyl)-1,3-propyl]phosphoryl}.

Preferred compounds are also compounds listed in Table 1 using groups $M^1 1$ and V2.

Preferred compounds are also compounds listed in Table 1 using groups $M^1 1$ and V3.

Preferred compounds are also compounds listed in Table 1 using groups $M^1 2$ and V1.

Preferred compounds are also compounds listed in Table 1 using groups $M^1 2$ and V2.

Preferred compounds are also compounds listed in Table 1 using groups $M^1 2$ and V3.

Preferred compounds are also compounds listed in Table 1 using groups $M^1 3$ and V1.

Preferred compounds are also compounds listed in Table 1 using groups $M^1 3$ and V2.

Preferred compounds are also compounds listed in Table 1 using groups $M^1 3$ and V3.

Preferred compounds are represented by all of the above named compounds with the exception that Y is oxygen and Y' is NH.

Preferred compounds are represented by all of the above named compounds with the exception that Y and Y' are NH.

Preferred compounds are represented by all of the above named compounds with the exception that Y is NCH3 and Y' is oxygen.

Preferred compounds are represented by all of the above named compounds with the exception that Y is oxygen and Y' is $NCH_3$.

TABLE 1

| | | | | | | | | | |
|---|---|---|---|---|---|---|---|---|---|
| 1.1.1.1. | 1.1.1.2. | 1.1.1.3. | 1.1.1.4 | 1.1.1.5 | 1.1.1.6 | 1.1.1.7 | 1.1.1.8. | 1.1.1.9 | 1.1.2.1 |
| 1.1.2.2 | 1.1.2.3 | 1.1.2.4 | 1.1.2.5 | 1.1.2.6 | 1.1.2.7 | 1.1.2.8 | 1.1.2.9 | 1.1.3.1 | 1.1.3.2 |
| 1.1.3.3 | 1.1.3.4 | 1.1.3.5 | 1.1.3.6 | 1.1.3.7 | 1.1.3.8 | 1.1.3.9 | 1.1.4.1 | 1.1.4.2 | 1.1.4.3 |
| 1.1.4.4 | 1.1.4.5 | 1.1.4.6 | 1.1.4.7 | 1.1.4.8 | 1.1.4.9 | 1.1.5.1 | 1.1.5.2 | 1.1.5.3 | 1.1.5.4 |
| 1.1.5.5 | 1.1.5.6 | 1.1.5.7 | 1.1.5.8 | 1.1.5.9 | 1.1.6.1 | 1.1.6.2 | 1.1.6.3 | 1.1.6.4 | 1.1.6.5 |
| 1.1.6.6 | 1.1.6.7 | 1.1.6.8 | 1.1.6.9 | 1.1.7.1 | 1.1.7.2 | 1.1.7.3 | 1.1.7.4 | 1.1.7.5 | 1.1.7.6 |
| 1.1.7.7 | 1.1.7.8 | 1.1.7.9 | 1.1.8.1 | 1.1.8.2 | 1.1.8.3 | 1.1.8.4 | 1.1.8.5 | 1.1.8.6 | 1.1.8.7 |
| 1.1.8.8 | 1.1.8.9 | 1.1.9.1 | 1.1.9.2 | 1.1.9.3 | 1.1.9.4 | 1.1.9.5 | 1.1.9.6 | 1.1.9.7 | 1.1.9.8 |
| 1.1.9.9 | 1.2.1.1 | 1.2.1.2 | 1.2.1.3 | 1.2.1.4 | 1.2.1.5 | 1.2.1.6 | 1.2.1.7 | 1.2.1.8 | 1.2.1.9 |
| 1.2.2.1 | 1.2.2.2 | 1.2.2.3 | 1.2.2.4 | 1.2.2.5 | 1.2.2.6 | 1.2.2.7 | 1.2.2.8 | 1.2.2.9 | 1.2.3.1 |
| 1.2.3.2 | 1.2.3.3 | 1.2.3.4 | 1.2.3.5 | 1.2.3.6 | 1.2.3.7 | 1.2.3.8 | 1.2.3.9 | 1.2.4.1 | 1.2.4.2 |
| 1.2.4.3 | 1.2.4.4 | 1.2.4.5 | 1.2.4.6 | 1.2.4.7 | 1.2.4.8 | 1.2.4.9 | 1.2.5.1 | 1.2.5.2 | 1.2.5.3 |
| 1.2.5.4 | 1.2.5.5 | 1.2.5.6 | 1.2.5.7 | 1.2.5.8 | 1.2.5.9 | 1.2.6.1 | 1.2.6.2 | 1.2.6.3 | 1.2.6.4 |
| 1.2.6.5 | 1.2.6.6 | 1.2.6.7 | 1.2.6.8 | 1.2.6.9 | 1.2.7.1 | 1.2.7.2 | 1.2.7.3 | 1.2.7.4 | 1.2.7.5 |
| 1.2.7.6 | 1.2.7.7 | 1.2.7.8 | 1.2.7.9 | 1.2.8.1 | 1.2.8.2 | 1.2.8.3 | 1.2.8.4 | 1.2.8.5 | 1.2.8.6 |
| 1.2.8.7 | 1.2.8.8 | 1.2.8.9 | 1.2.9.1 | 1.2.9.2 | 1.2.9.3 | 1.2.9.4 | 1.2.9.5 | 1.2.9.6 | 1.2.9.7 |
| 1.2.9.8 | 1.2.9.9 | 1.3.1.1 | 1.3.1.2 | 1.3.1.3 | 1.3.1.4 | 1.3.1.5 | 1.3.1.6 | 1.3.1.7 | 1.3.1.8 |
| 1.3.1.9 | 1.3.2.1 | 1.3.2.2 | 1.3.2.3 | 1.3.2.4 | 1.3.2.5 | 1.3.2.6 | 1.3.2.7 | 1.3.2.8 | 1.3.2.9 |
| 1.3.3.1 | 1.3.3.2. | 1.3.3.3 | 1.3.3.4 | 1.3.3.5 | 1.3.3.6 | 1.3.3.7 | 1.3.3.8 | 1.3.3.9 | 1.3.4.1 |
| 1.3.4.2 | 1.3.4.3 | 1.3.4.4 | 1.3.4.5 | 1.3.4.6 | 1.3.4.7 | 1.3.4.8 | 1.3.4.9 | 1.3.5.1 | 1.3.5.2 |
| 1.3.5.3 | 1.3.5.4 | 1.3.5.5 | 1.3.5.6 | 1.3.5.7 | 1.3.5.8 | 1.3.5.9 | 1.3.6.1 | 1.3.6.2 | 1.3.6.3 |
| 1.3.6.4 | 1.3.6.5 | 1.3.6.6 | 1.3.6.7 | 1.3.6.8 | 1.3.6.9 | 1.3.7.1 | 1.3.7.2 | 1.3.7.3 | 1.3.7.4 |
| 1.3.7.5 | 1.3.7.6 | 1.3.7.7 | 1.3.7.8 | 1.3.7.9 | 1.3.8.1 | 1.3.8.2 | 1.3.8.3 | 1.3.8.4 | 1.3.8.5 |

TABLE 1-continued

| | | | | | | | | |
|---|---|---|---|---|---|---|---|---|
| 1.3.8.6 | 1.3.8.7 | 1.3.8.8 | 1.3.8.9 | 1.3.9.1 | 1.3.9.2 | 1.3.9.3 | 1.3.9.4 | 1.3.9.5 | 1.3.9.6 |
| 1.3.9.7 | 1.3.9.8 | 1.3.9.9 | 1.4.1.1 | 1.4.1.2 | 1.4.1.3 | 1.4.1.4 | 1.4.1.5 | 1.4.1.6 | 1.4.1.7 |
| 1.4.1.8 | 1.4.1.9 | 1.4.2.1 | 1.4.2.2 | 1.4.2.3 | 1.4.2.4 | 1.4.2.5 | 1.4.2.6 | 1.4.2.7 | 1.4.2.8 |
| 1.4.2.9 | 1.4.3.1 | 1.4.3.2 | 1.4.3.3 | 1.4.3.4 | 1.4.3.5 | 1.4.3.6 | 1.4.3.7 | 1.4.3.8 | 1.4.3.9 |
| 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.6.1 | 1.4.6.2 |
| 1.4.6.3 | 1.4.6.4 | 1.4.6.5 | 1.4.6.6 | 1.4.6.7 | 1.4.6.8 | 1.4.6.9 | 1.4.7.1 | 1.4.7.2 | 1.4.7.3 |
| 1.4.7.4 | 1.4.7.5 | 1.4.7.6 | 1.4.7.7 | 1.4.7.8 | 1.4.7.9 | 1.4.8.1 | 1.4.8.2 | 1.4.8.3 | 1.4.8.4 |
| 1.4.8.5 | 1.4.8.6 | 1.4.8.7 | 1.4.8.8 | 1.4.8.9 | 1.4.9.1 | 1.4.9.2 | 1.4.9.3 | 1.4.9.4 | 1.4.9.5 |
| 1.4.9.6 | 1.4.9.7 | 1.4.9.8 | 1.4.9.9 | 1.5.1.1 | 1.5.1.2 | 1.5.1.3 | 1.5.1.4 | 1.5.1.5 | 1.5.1.6 |
| 1.5.1.7 | 1.5.1.8 | 1.5.1.9 | 1.5.2.1 | 1.5.2.2 | 1.5.2.3 | 1.5.2.4 | 1.5.2.5 | 1.5.2.6 | 1.5.2.7 |
| 1.5.2.8 | 1.5.2.9 | 1.5.3.1 | 1.5.3.2 | 1.5.3.3 | 1.5.3.4 | 1.5.3.5 | 1.5.3.6 | 1.5.3.7 | 1.5.3.8 |
| 1.5.3.9 | 1.5.4.1 | 1.5.4.2 | 1.5.4.3 | 1.5.4.4 | 1.5.4.5 | 1.5.4.6 | 1.5.4.7 | 1.5.4.8 | 1.5.4.9 |
| 1.5.5.1 | 1.5.5.2 | 1.5.5.3 | 1.5.5.4 | 1.5.5.5 | 1.5.5.6 | 1.5.5.7 | 1.5.5.8 | 1.5.5.9 | 1.5.6.1 |
| 1.5.6.2 | 1.5.6.3. | 1.5.6.4 | 1.5.6.5 | 1.5.6.6 | 1.5.6.7 | 1.5.6.8 | 1.5.6.9 | 1.5.7.1 | 1.5.7.2 |
| 1.5.7.3 | 1.5.7.4 | 1.5.7.5 | 1.5.7.6 | 1.5.7.7 | 1.5.7.8 | 1.5.7.9 | 1.5.8.1 | 1.5.8.2 | 1.5.8.3 |
| 1.5.8.4 | 1.5.8.5 | 1.5.8.6 | 1.5.8.7 | 1.5.8.8 | 1.5.8.9 | 1.5.9.1 | 1.5.9.2 | 1.5.9.3 | 1.5.9.4 |
| 1.5.9.5 | 1.5.9.6 | 1.5.9.7 | 1.5.9.8 | 1.5.9.9 | 1.6.1.1 | 1.6.1.2 | 1.6.1.3 | 1.6.1.4 | 1.6.1.5 |
| 1.6.1.6 | 1.6.1.7 | 1.6.1.8 | 1.6.1.9 | 1.6.2.1 | 1.6.2.2 | 1.6.2.3 | 1.6.2.4 | 1.6.2.5 | 1.6.2.6 |
| 1.6.2.7 | 1.6.2.8 | 1.6.2.9 | 1.6.3.1 | 1.6.3.2 | 1.6.3.3 | 1.6.3.4 | 1.6.3.5 | 1.6.3.6 | 1.6.3.7 |
| 1.6.3.8 | 1.6.3.9 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 |
| 1.6.6.1 | 1.6.6.2 | 1.6.6.3 | 1.6.6.4 | 1.6.6.5 | 1.6.6.6 | 1.6.6.7 | 1.6.6.8 | 1.6.6.9 | 1.6.7.1 |
| 1.6.7.2 | 1.6.7.3 | 1.6.7.4 | 1.6.7.5 | 1.6.7.6 | 1.6.7.7 | 1.6.7.8 | 1.6.7.9 | 1.6.8.1 | 1.6.8.2 |
| 1.6.8.3 | 1.6.8.4. | 1.6.8.5 | 1.6.8.6 | 1.6.8.7 | 1.6.8.8 | 1.6.8.9 | 1.6.9.1 | 1.6.9.2 | 1.6.9.3 |
| 1.6.9.4 | 1.6.9.5 | 1.6.9.6 | 1.6.9.7 | 1.6.9.8 | 1.6.9.9 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.2.1 | 1.7.2.2 | 1.7.2.3 | 1.7.2.4 | 1.7.2.5 |
| 1.7.2.6 | 1.7.2.7 | 1.7.2.8 | 1.7.2.9 | 1.7.3.1 | 1.7.3.2 | 1.7.3.3 | 1.7.3.4 | 1.7.3.5 | 1.7.3.6 |
| 1.7.3.7 | 1.7.3.8 | 1.7.3.9 | 1.7.4.1 | 1.7.4.2 | 1.7.4.3 | 1.7.4.4 | 1.7.4.5 | 1.7.4.6 | 1.7.4.7 |
| 1.7.4.8 | 1.7.4.9 | 1.7.5.1 | 1.7.5.2 | 1.7.5.3 | 1.7.5.4 | 1.7.5.5 | 1.7.5.6 | 1.7.5.7 | 1.7.5.8 |
| 1.7.5.9 | 1.7.6.1 | 1.7.6.2 | 1.7.6.3 | 1.7.6.4 | 1.7.6.5 | 1.7.6.6 | 1.7.6.7 | 1.7.6.8 | 1.7.6.9 |
| 1.7.7.1 | 1.7.7.2 | 1.7.7.3 | 1.7.7.4 | 1.7.7.5 | 1.7.7.6 | 1.7.7.7 | 1.7.7.8 | 1.7.7.9 | 1.7.8.1 |
| 1.7.8.2 | 1.7.8.3 | 1.7.8.4 | 1.7.8.5 | 1.7.8.6 | 1.7.8.7 | 1.7.8.8 | 1.7.8.9 | 1.7.9.1 | 1.7.9.2 |
| 1.7.9.3 | 1.7.9.4 | 1.7.9.5 | 1.7.9.6 | 1.7.9.7 | 1.7.9.8 | 1.7.9.9 | 1.8.1.1 | 1.8.1.2 | 1.8.1.3 |
| 1.8.1.4 | 1.8.1.5 | 1.8.1.6 | 1.8.1.7 | 1.8.1.8 | 1.8.1.9 | 1.8.2.1 | 1.8.2.2 | 1.8.2.3 | 1.8.2.4 |
| 1.8.2.5 | 1.8.2.6 | 1.8.2.7 | 1.8.2.8 | 1.8.2.9 | 1.8.3.1 | 1.8.3.2 | 1.8.3.3 | 1.8.3.4 | 1.8.3.5 |
| 1.8.3.6 | 1.8.3.7 | 1.8.3.8 | 1.8.3.9 | 1.8.4.1 | 1.8.4.2. | 1.8.4.3. | 1.8.4.4 | 1.8.4.5 | 1.8.4.6 |
| 1.8.4.7 | 1.8.4.8 | 1.8.4.9 | 1.8.5.1 | 1.8.5.2 | 1.8.5.3 | 1.8.5.4 | 1.8.5.5 | 1.8.5.6 | 1.8.5.7 |
| 1.8.5.8 | 1.8.5.9 | 1.8.6.1 | 1.8.6.2 | 1.8.6.3 | 1.8.6.4 | 1.8.6.5 | 1.8.6.6 | 1.8.6.7 | 1.8.6.8 |
| 1.8.6.9 | 1.8.7.1 | 1.8.7.2 | 1.8.7.3 | 1.8.7.4 | 1.8.7.5 | 1.8.7.6 | 1.8.7.7 | 1.8.7.8 | 1.8.7.9 |
| 1.8.8.1 | 1.8.8.2 | 1.8.8.3 | 1.8.8.4 | 1.8.8.5 | 1.8.8.6 | 1.8.8.7 | 1.8.8.8 | 1.8.8.9 | 1.8.9.1 |
| 1.8.9.2 | 1.8.9.3 | 1.8.9.4 | 1.8.9.5 | 1.8.9.6 | 1.8.9.7 | 1.8.9.8 | 1.8.9.9 | 1.9.1.1 | 1.9.1.2 |
| 1.9.1.3 | 1.9.1.4 | 1.9.1.5 | 1.9.1.6 | 1.9.1.7 | 1.9.1.8 | 1.9.1.9 | 1.9.2.1 | 1.9.2.2 | 1.9.2.3 |
| 1.9.2.4 | 1.9.2.5 | 1.9.2.6 | 1.9.2.7 | 1.9.2.8 | 1.9.2.9 | 1.9.3.1 | 1.9.3.2 | 1.9.3.3 | 1.9.3.4 |
| 1.9.3.5 | 1.9.3.6 | 1.9.3.7 | 1.9.3.8 | 1.9.3.9 | 1.9.4.1 | 1.9.4.2 | 1.9.4.3 | 1.9.4.4 | 1.9.4.5 |
| 1.9.4.6 | 1.9.4.7 | 1.9.4.8 | 1.9.4.9 | 1.9.5.1 | 1.9.5.2 | 1.9.5.3 | 1.9.5.4 | 1.9.5.5 | 1.9.5.6 |
| 1.9.5.7 | 1.9.5.8 | 1.9.5.9 | 1.9.6.1 | 1.9.6.2 | 1.9.6.3 | 1.9.6.4 | 1.9.6.5 | 1.9.6.6 | 1.9.6.7 |
| 1.9.6.8 | 1.9.6.9 | 1.9.7.1 | 1.9.7.2 | 1.9.7.3 | 1.9.7.4 | 1.9.7.5 | 1.9.7.6 | 1.9.7.7 | 1.9.7.8 |
| 1.9.7.9 | 1.9.8.1 | 1.9.8.2 | 1.9.8.3 | 1.9.8.4 | 1.9.8.5 | 1.9.8.6 | 1.9.8.7 | 1.9.8.8 | 1.9.8.9 |
| 1.9.9.1 | 1.9.9.2 | 1.9.9.3 | 1.9.9.4 | 1.9.9.5 | 1.9.9.6 | 1.9.9.7 | 1.9.9.8 | 1.9.9.9 | 2.1.1.1 |
| 2.1.1.2 | 2.1.1.3 | 2.1.1.4 | 2.1.1.5 | 2.1.1.6 | 2.1.1.7 | 2.1.1.8 | 2.1.1.9 | 2.1.2.1 | 2.1.2.2 |
| 2.1.2.3 | 2.1.2.4 | 2.1.2.5 | 2.1.2.6 | 2.1.2.7 | 2.1.2.8 | 2.1.2.9 | 2.1.3.1 | 2.1.3.2 | 2.1.3.3 |
| 2.1.3.4 | 2.1.3.5 | 2.1.3.6 | 2.1.3.7 | 2.1.3.8 | 2.1.3.9 | 2.1.4.1 | 2.1.4.2 | 2.1.4.3 | 2.1.4.4 |
| 2.1.4.5 | 2.1.4.6 | 2.1.4.7 | 2.1.4.8 | 2.1.4.9 | 2.1.5.1 | 2.1.5.2 | 2.1.5.3 | 2.1.5.4 | 2.1.5.5 |
| 2.1.5.6 | 2.1.5.7 | 2.1.5.8 | 2.1.5.9 | 2.1.6.1 | 2.1.6.2 | 2.1.6.3 | 2.1.6.4 | 2.1.6.5 | 2.1.6.6 |
| 2.1.6.7 | 2.1.6.8 | 2.1.6.9 | 2.1.7.1 | 2.1.7.2 | 2.1.7.3 | 2.1.7.4 | 2.1.7.5 | 2.1.7.6 | 2.1.7.7 |
| 2.1.7.8 | 2.1.7.9 | 2.1.8.1 | 2.1.8.2 | 2.1.8.3 | 2.1.8.4 | 2.1.8.5 | 2.1.8.6 | 2.1.8.7 | 2.1.8.8 |
| 2.1.8.9 | 2.1.9.1 | 2.1.9.2 | 2.1.9.3 | 2.1.9.4 | 2.1.9.5 | 2.1.9.6 | 2.1.9.7 | 2.1.9.8 | 2.1.9.9 |
| 2.2.1.1 | 2.2.1.2 | 2.2.1.3 | 2.2.1.4 | 2.2.1.5 | 2.2.1.6 | 2.2.1.7 | 2.2.1.8 | 2.2.1.9 | 2.2.2.1 |
| 2.2.2.2 | 2.2.2.3 | 2.2.2.4 | 2.2.2.5 | 2.2.2.6 | 2.2.2.7 | 2.2.2.8 | 2.2.2.9 | 2.2.3.1 | 2.2.3.2 |
| 2.2.3.3 | 2.2.3.4 | 2.2.3.5 | 2.2.3.6 | 2.2.3.7 | 2.2.3.8 | 2.2.3.9 | 2.2.4.1 | 2.2.4.2 | 2.2.4.3 |
| 2.2.4.4 | 2.2.4.5 | 2.2.4.6 | 2.2.4.7 | 2.2.4.8 | 2.2.4.9 | 2.2.5.1 | 2.2.5.2 | 2.2.5.3 | 2.2.5.4 |
| 2.2.5.5 | 2.2.5.6 | 2.2.5.7 | 2.2.5.8 | 2.2.5.9 | 2.2.6.1 | 2.2.6.2 | 2.2.6.3 | 2.2.6.4 | 2.2.6.5 |
| 2.2.6.6 | 2.2.6.7 | 2.2.6.8 | 2.2.6.9 | 2.2.7.1 | 2.2.7.2 | 2.2.7.3 | 2.2.7.4 | 2.2.7.5 | 2.2.7.6 |
| 2.2.7.7 | 2.2.7.8 | 2.2.7.9 | 2.2.8.1 | 2.2.8.2 | 2.2.8.3 | 2.2.8.4 | 2.2.8.5 | 2.2.8.6 | 2.2.8.7 |
| 2.2.8.8 | 2.2.8.9 | 2.2.9.1 | 2.2.9.2 | 2.2.9.3 | 2.2.9.4 | 2.2.9.5 | 2.2.9.6 | 2.2.9.7 | 2.2.9.8 |
| 2.2.9.9 | 2.3.1.1 | 2.3.1.2 | 2.3.1.3 | 2.3.1.4 | 2.3.1.5 | 2.3.1.6 | 2.3.1.7 | 2.3.1.8 | 2.3.1.9 |
| 2.3.2.1 | 2.3.2.2 | 2.3.2.3 | 2.3.2.4 | 2.3.2.5 | 2.3.2.6 | 2.3.2.7 | 2.3.2.8 | 2.3.2.9 | 2.3.3.1 |
| 2.3.3.2 | 2.3.3.3 | 2.3.3.4 | 2.3.3.5 | 2.3.3.6 | 2.3.3.7 | 2.3.3.8 | 2.3.3.9 | 2.3.4.1 | 2.3.4.2 |
| 2.3.4.3 | 2.3.4.4 | 2.3.4.5 | 2.3.4.6 | 2.3.4.7 | 2.3.4.8 | 2.3.4.9 | 2.3.5.1 | 2.3.5.2 | 2.3.5.3 |
| 2.3.5.4 | 2.3.5.5 | 2.3.5.6 | 2.3.5.7 | 2.3.5.8 | 2.3.5.9 | 2.3.6.1 | 2.3.6.2 | 2.3.6.3 | 2.3.6.4 |
| 2.3.6.5 | 2.3.6.6 | 2.3.6.7 | 2.3.6.8 | 2.3.6.9 | 2.3.7.1 | 2.3.7.2 | 2.3.7.3 | 2.3.7.4 | 2.3.7.5 |
| 2.3.7.6 | 2.3.7.7 | 2.3.7.8 | 2.3.7.9 | 2.3.8.1 | 2.3.8.2 | 2.3.8.3 | 2.3.8.4 | 2.3.8.5 | 2.3.8.6 |
| 2.3.8.7 | 2.3.8.8 | 2.3.8.9 | 2.3.9.1 | 2.3.9.2 | 2.3.9.3 | 2.3.9.4 | 2.3.9.5 | 2.3.9.6 | 2.3.9.7 |
| 2.3.9.8 | 2.3.9.9 | 2.4.1.1 | 2.4.1.2 | 2.4.1.3 | 2.4.1.4 | 2.4.1.5 | 2.4.1.6 | 2.4.1.7 | 2.4.1.8 |
| 2.4.1.9 | 2.4.2.1 | 2.4.2.2 | 2.4.2.3 | 2.4.2.4 | 2.4.2.5 | 2.4.2.6 | 2.4.2.7 | 2.4.2.8 | 2.4.2.9 |
| 2.4.3.1 | 2.4.3.2 | 2.4.3.3 | 2.4.3.4 | 2.4.3.5 | 2.4.3.6 | 2.4.3.7 | 2.4.3.8 | 2.4.3.9 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.5.1 | 2.4.5.2 |
| 2.4.5.3 | 2.4.5.4 | 2.4.5.5 | 2.4.5.6 | 2.4.5.7 | 2.4.5.8 | 2.4.5.9 | 2.4.6.1 | 2.4.6.2 | 2.4.6.3 |
| 2.4.6.4 | 2.4.6.5 | 2.4.6.6 | 2.4.6.7 | 2.4.6.8 | 2.4.6.9 | 2.4.7.1 | 2.4.7.2 | 2.4.7.3 | 2.4.7.4 |

TABLE 1-continued

| | | | | | | | | | |
|---|---|---|---|---|---|---|---|---|---|
| 2.4.7.5 | 2.4.7.6 | 2.4.7.7 | 2.4.7.8 | 2.4.7.9 | 2.4.8.1 | 2.4.8.2 | 2.4.8.3 | 2.4.8.4 | 2.4.8.5 |
| 2.4.8.6 | 2.4.8.7 | 2.4.8.8 | 2.4.8.9 | 2.4.9.1 | 2.4.9.2 | 2.4.9.3 | 2.4.9.4 | 2.4.9.5 | 2.4.9.6 |
| 2.4.9.7 | 2.4.9.8 | 2.4.9.9 | 2.5.1.1 | 2.5.1.2 | 2.5.1.3 | 2.5.1.4 | 2.5.1.5 | 2.5.1.6 | 2.5.1.7 |
| 2.5.1.8 | 2.5.1.9 | 2.5.2.1 | 2.5.2.2 | 2.5.2.3 | 2.5.2.4 | 2.5.2.5 | 2.5.2.6 | 2.5.2.7 | 2.5.2.8 |
| 2.5.2.9 | 2.5.3.1 | 2.5.3.2 | 2.5.3.3 | 2.5.3.4 | 2.5.3.5 | 2.5.3.6 | 2.5.3.7 | 2.5.3.8 | 2.5.3.9 |
| 2.5.4.1 | 2.5.4.2 | 2.5.4.3 | 2.5.4.4 | 2.5.4.5 | 2.5.4.6 | 2.5.4.7 | 2.5.4.8 | 2.5.4.9 | 2.5.5.1 |
| 2.5.5.2 | 2.5.5.3 | 2.5.5.4 | 2.5.5.5 | 2.5.5.6 | 2.5.5.7 | 2.5.5.8 | 2.5.5.9 | 2.5.6.1 | 2.5.6.2 |
| 2.5.6.3 | 2.5.6.4 | 2.5.6.5 | 2.5.6.6 | 2.5.6.7 | 2.5.6.8 | 2.5.6.9 | 2.5.7.1 | 2.5.7.2 | 2.5.7.3 |
| 2.5.7.4 | 2.5.7.5 | 2.5.7.6 | 2.5.7.7 | 2.5.7.8 | 2.5.7.9 | 2.5.8.1 | 2.5.8.2 | 2.5.8.3 | 2.5.8.4 |
| 2.5.8.5 | 2.5.8.6 | 2.5.8.7 | 2.5.8.8 | 2.5.8.9 | 2.5.9.1 | 2.5.9.2 | 2.5.9.3 | 2.5.9.4 | 2.5.9.5 |
| 2.5.9.6 | 2.5.9.7 | 2.5.9.8 | 2.5.9.9 | 2.6.1.1 | 2.6.1.2 | 2.6.1.3 | 2.6.1.4 | 2.6.1.5 | 2.6.1.6 |
| 2.6.1.7 | 2.6.1.8 | 2.6.1.9 | 2.6.2.1 | 2.6.2.2 | 2.6.2.3 | 2.6.2.4 | 2.6.2.5 | 2.6.2.6 | 2.6.2.7 |
| 2.6.2.8 | 2.6.2.9 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 |
| 2.6.5.1 | 2.6.5.2 | 2.6.5.3 | 2.6.5.4 | 2.6.5.5 | 2.6.5.6 | 2.6.5.7 | 2.6.5.8 | 2.6.5.9 | 2.6.6.1 |
| 2.6.6.2 | 2.6.6.3 | 2.6.6.4 | 2.6.6.5 | 2.6.6.6 | 2.6.6.7 | 2.6.6.8 | 2.6.6.9 | 2.6.7.1 | 2.6.7.2 |
| 2.6.7.3 | 2.6.7.4 | 2.6.7.5 | 2.6.7.6 | 2.6.7.7 | 2.6.7.8 | 2.6.7.9 | 2.6.8.1 | 2.6.8.2 | 2.6.8.3 |
| 2.6.8.4 | 2.6.8.5 | 2.6.8.6 | 2.6.8.7 | 2.6.8.8 | 2.6.8.9 | 2.6.9.1 | 2.6.9.2 | 2.6.9.3 | 2.6.9.4 |
| 2.6.9.5 | 2.6.9.6 | 2.6.9.7 | 2.6.9.8 | 2.6.9.9 | 2.7.1.1 | 2.7.1.2 | 2.7.1.3 | 2.7.1.4 | 2.7.1.5 |
| 2.7.1.6 | 2.7.1.7 | 2.7.1.8 | 2.7.1.9 | 2.7.2.1 | 2.7.2.2 | 2.7.2.3 | 2.7.2.4 | 2.7.2.5 | 2.7.2.6 |
| 2.7.2.7 | 2.7.2.8 | 2.7.2.9 | 2.7.3.1 | 2.7.3.2 | 2.7.3.3 | 2.7.3.4 | 2.7.3.5 | 2.7.3.6 | 2.7.3.7 |
| 2.7.3.8 | 2.7.3.9 | 2.7.4.1 | 2.7.4.2 | 2.7.4.3 | 2.7.4.4 | 2.7.4.5 | 2.7.4.6 | 2.7.4.7 | 2.7.4.8 |
| 2.7.4.9 | 2.7.5.1 | 2.7.5.2 | 2.7.5.3 | 2.7.5.4 | 2.7.5.5 | 2.7.5.6 | 2.7.5.7 | 2.7.5.8 | 2.7.5.9 |
| 2.7.6.1 | 2.7.6.2 | 2.7.6.3 | 2.7.6.4 | 2.7.6.5 | 2.7.6.6 | 2.7.6.7 | 2.7.6.8 | 2.7.6.9 | 2.7.7.1 |
| 2.7.7.2 | 2.7.7.3 | 2.7.7.4 | 2.7.7.5 | 2.7.7.6 | 2.7.7.7 | 2.7.7.8 | 2.7.7.9 | 2.7.8.1 | 2.7.8.2 |
| 2.7.8.3 | 2.7.8.4 | 2.7.8.5 | 2.7.8.6 | 2.7.8.7 | 2.7.8.8 | 2.7.8.9 | 2.7.9.1 | 2.7.9.2 | 2.7.9.3 |
| 2.7.9.4 | 2.7.9.5 | 2.7.9.6 | 2.7.9.7 | 2.7.9.8 | 2.7.9.9 | 2.8.1.1 | 2.8.1.2 | 2.8.1.3 | 2.8.1.4 |
| 2.8.1.5 | 2.8.1.6 | 2.8.1.7 | 2.8.1.8 | 2.8.1.9 | 2.8.2.1 | 2.8.2.2 | 2.8.2.3 | 2.8.2.4 | 2.8.2.5 |
| 2.8.2.6 | 2.8.2.7 | 2.8.2.8 | 2.8.2.9 | 2.8.3.1 | 2.8.3.2 | 2.8.3.3 | 2.8.3.4 | 2.8.3.5 | 2.8.3.6 |
| 2.8.3.7 | 2.8.3.8 | 2.8.3.9 | 2.8.4.1 | 2.8.4.2 | 2.8.4.3 | 2.8.4.4 | 2.8.4.5 | 2.8.4.6 | 2.8.4.7 |
| 2.8.4.8 | 2.8.4.9 | 2.8.5.1 | 2.8.5.2 | 2.8.5.3 | 2.8.5.4 | 2.8.5.5 | 2.8.5.6 | 2.8.5.7 | 2.8.5.8 |
| 2.8.5.9 | 2.8.6.1 | 2.8.6.2 | 2.8.6.3 | 2.8.6.4 | 2.8.6.5 | 2.8.6.6 | 2.8.6.7 | 2.8.6.8 | 2.8.6.9 |
| 2.8.7.1 | 2.8.7.2 | 2.8.7.3 | 2.8.7.4 | 2.8.7.5 | 2.8.7.6 | 2.8.7.7 | 2.8.7.8 | 2.8.7.9 | 2.8.8.1 |
| 2.8.8.2 | 2.8.8.3 | 2.8.8.4 | 2.8.8.5 | 2.8.8.6 | 2.8.8.7 | 2.8.8.8 | 2.8.8.9 | 2.8.9.1 | 2.8.9.2 |
| 2.8.9.3 | 2.8.9.4 | 2.8.9.5 | 2.8.9.6 | 2.8.9.7 | 2.8.9.8 | 2.8.9.9 | 2.9.1.1 | 2.9.1.2 | 2.9.1.3 |
| 2.9.1.4 | 2.9.1.5 | 2.9.1.6 | 2.9.1.7 | 2.9.1.8 | 2.9.1.9 | 2.9.2.1 | 2.9.2.2 | 2.9.2.3 | 2.9.2.4 |
| 2.9.2.5 | 2.9.2.6 | 2.9.2.7 | 2.9.2.8 | 2.9.2.9 | 2.9.3.1 | 2.9.3.2 | 2.9.3.3 | 2.9.3.4 | 2.9.3.5 |
| 2.9.3.6 | 2.9.3.7 | 2.9.3.8 | 2.9.3.9 | 2.9.4.1 | 2.9.4.2 | 2.9.4.3 | 2.9.4.4 | 2.9.4.5 | 2.9.4.6 |
| 2.9.4.7 | 2.9.4.8 | 2.9.4.9 | 2.9.5.1 | 2.9.5.2 | 2.9.5.3 | 2.9.5.4 | 2.9.5.5 | 2.9.5.6 | 2.9.5.7 |
| 2.9.5.8 | 2.9.5.9 | 2.9.6.1 | 2.9.6.2 | 2.9.6.3 | 2.9.6.4 | 2.9.6.5 | 2.9.6.6 | 2.9.6.7 | 2.9.6.8 |
| 2.9.6.9 | 2.9.7.1 | 2.9.7.2 | 2.9.7.3 | 2.9.7.4 | 2.9.7.5 | 2.9.7.6 | 2.9.7.7 | 2.9.7.8 | 2.9.7.9 |
| 2.9.8.1 | 2.9.8.2 | 2.9.8.3 | 2.9.8.4 | 2.9.8.5 | 2.9.8.6 | 2.9.8.7 | 2.9.8.8 | 2.9.8.9 | 2.9.9.1 |
| 2.9.9.2 | 2.9.9.3 | 2.9.9.4 | 2.9.9.5 | 2.9.9.6 | 2.9.9.7 | 2.9.9.8 | 2.9.9.9 | 3.1.1.1 | 3.1.1.2 |
| 3.1.1.3 | 3.1.1.4 | 3.1.1.5 | 3.1.1.6 | 3.1.1.7 | 3.1.1.8 | 3.1.1.9 | 3.1.2.1 | 3.1.2.2 | 3.1.2.3 |
| 3.1.2.4 | 3.1.2.5 | 3.1.2.6 | 3.1.2.7 | 3.1.2.8 | 3.1.2.9 | 3.1.3.1 | 3.1.3.2 | 3.1.3.3 | 3.1.3.4 |
| 3.1.3.5 | 3.1.3.6 | 3.1.3.7 | 3.1.3.8 | 3.1.3.9 | 3.1.4.1 | 3.1.4.2 | 3.1.4.3 | 3.1.4.4 | 3.1.4.5 |
| 3.1.4.6 | 3.1.4.7 | 3.1.4.8 | 3.1.4.9 | 3.1.5.1 | 3.1.5.2 | 3.1.5.3 | 3.1.5.4 | 3.1.5.5 | 3.1.5.6 |
| 3.1.5.7 | 3.1.5.8 | 3.1.5.9 | 3.1.6.1 | 3.1.6.2 | 3.1.6.3 | 3.1.6.4 | 3.1.6.5 | 3.1.6.6 | 3.1.6.7 |
| 3.1.6.8 | 3.1.6.9 | 3.1.7.1 | 3.1.7.2 | 3.1.7.3 | 3.1.7.4 | 3.1.7.5 | 3.1.7.6 | 3.1.7.7 | 3.1.7.8 |
| 3.1.7.9 | 3.1.8.1 | 3.1.8.2 | 3.1.8.3 | 3.1.8.4 | 3.1.8.5 | 3.1.8.6 | 3.1.8.7 | 3.1.8.8 | 3.1.8.9 |
| 3.1.9.1 | 3.1.9.2 | 3.1.9.3 | 3.1.9.4 | 3.1.9.5 | 3.1.9.6 | 3.1.9.7 | 3.1.9.8 | 3.1.9.9 | 3.2.1.1 |
| 3.2.1.2 | 3.2.1.3 | 3.2.1.4 | 3.2.1.5 | 3.2.1.6 | 3.2.1.7 | 3.2.1.8 | 3.2.1.9 | 3.2.2.1 | 3.2.2.2 |
| 3.2.2.3 | 3.2.2.4 | 3.2.2.5 | 3.2.2.6 | 3.2.2.7 | 3.2.2.8 | 3.2.2.9 | 3.2.3.1 | 3.2.3.2 | 3.2.3.3 |
| 3.2.3.4 | 3.2.3.5 | 3.2.3.6 | 3.2.3.7 | 3.2.3.8 | 3.2.3.9 | 3.2.4.1 | 3.2.4.2 | 3.2.4.3 | 3.2.4.4 |
| 3.2.4.5 | 3.2.4.6 | 3.2.4.7 | 3.2.4.8 | 3.2.4.9 | 3.2.5.1 | 3.2.5.2 | 3.2.5.3 | 3.2.5.4 | 3.2.5.5 |
| 3.2.5.6 | 3.2.5.7 | 3.2.5.8 | 3.2.5.9 | 3.2.6.1 | 3.2.6.2 | 3.2.6.3 | 3.2.6.4 | 3.2.6.5 | 3.2.6.6 |
| 3.2.6.7 | 3.2.6.8 | 3.2.6.9 | 3.2.7.1 | 3.2.7.2 | 3.2.7.3 | 3.2.7.4 | 3.2.7.5 | 3.2.7.6 | 3.2.7.7 |
| 3.2.7.8 | 3.2.7.9 | 3.2.8.1 | 3.2.8.2 | 3.2.8.3 | 3.2.8.4 | 3.2.8.5 | 3.2.8.6 | 3.2.8.7 | 3.2.8.8 |
| 3.2.8.9 | 3.2.9.1 | 3.2.9.2 | 3.2.9.3 | 3.2.9.4 | 3.2.9.5 | 3.2.9.6 | 3.2.9.7 | 3.2.9.8 | 3.2.9.9 |
| 3.3.1.1 | 3.3.1.2 | 3.3.1.3 | 3.3.1.4 | 3.3.1.5 | 3.3.1.6 | 3.3.1.7 | 3.3.1.8 | 3.3.1.9 | 3.3.2.1 |
| 3.3.2.2 | 3.3.2.3 | 3.3.2.4 | 3.3.2.5 | 3.3.2.6 | 3.3.2.7 | 3.3.2.8 | 3.3.2.9 | 3.3.3.1 | 3.3.3.2 |
| 3.3.3.3 | 3.3.3.4 | 3.3.3.5 | 3.3.3.6 | 3.3.3.7 | 3.3.3.8 | 3.3.3.9 | 3.3.4.1 | 3.3.4.2 | 3.3.4.3 |
| 3.3.4.4 | 3.3.4.5 | 3.3.4.6 | 3.3.4.7 | 3.3.4.8 | 3.3.4.9 | 3.3.5.1 | 3.3.5.2 | 3.3.5.3 | 3.3.5.4 |
| 3.3.5.5 | 3.3.5.6 | 3.3.5.7 | 3.3.5.8 | 3.3.5.9 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.7.1 | 3.3.7.2 | 3.3.7.3 | 3.3.7.4 | 3.3.7.5 | 3.3.7.6 |
| 3.3.7.7 | 3.3.7.8 | 3.3.7.9 | 3.3.8.1 | 3.3.8.2 | 3.3.8.3 | 3.3.8.4 | 3.3.8.5 | 3.3.8.6 | 3.3.8.7 |
| 3.3.8.8 | 3.3.8.9 | 3.3.9.1 | 3.3.9.2 | 3.3.9.3 | 3.3.9.4 | 3.3.9.5 | 3.3.9.6 | 3.3.9.7 | 3.3.9.8 |
| 3.3.9.9 | 3.4.1.1 | 3.4.1.2 | 3.4.1.3 | 3.4.1.4 | 3.4.1.5 | 3.4.1.6 | 3.4.1.7 | 3.4.1.8 | 3.4.1.9 |
| 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.4.1 | 3.4.4.2 |
| 3.4.4.3 | 3.4.4.4 | 3.4.4.5 | 3.4.4.6 | 3.4.4.7 | 3.4.4.8 | 3.4.4.9 | 3.4.5.1 | 3.4.5.2 | 3.4.5.3 |
| 3.4.5.4 | 3.4.5.5 | 3.4.5.6 | 3.4.5.7 | 3.4.5.8 | 3.4.5.9 | 3.4.6.1 | 3.4.6.2 | 3.4.6.3 | 3.4.6.4 |
| 3.4.6.5 | 3.4.6.6 | 3.4.6.7 | 3.4.6.8 | 3.4.6.9 | 3.4.7.1 | 3.4.7.2 | 3.4.7.3 | 3.4.7.4 | 3.4.7.5 |
| 3.4.7.6 | 3.4.7.7 | 3.4.7.8 | 3.4.7.9 | 3.4.8.1 | 3.4.8.2 | 3.4.8.3 | 3.4.8.4 | 3.4.8.5 | 3.4.8.6 |
| 3.4.8.7 | 3.4.8.8 | 3.4.8.9 | 3.4.9.1 | 3.4.9.2 | 3.4.9.3 | 3.4.9.4 | 3.4.9.5 | 3.4.9.6 | 3.4.9.7 |
| 3.4.9.8 | 3.4.9.9 | 3.5.1.1 | 3.5.1.2 | 3.5.1.3 | 3.5.1.4 | 3.5.1.5 | 3.5.1.6 | 3.5.1.7 | 3.5.1.8 |
| 3.5.1.9 | 3.5.2.1 | 3.5.2.2 | 3.5.2.3 | 3.5.2.4 | 3.5.2.5 | 3.5.2.6 | 3.5.2.7 | 3.5.2.8 | 3.5.2.9 |
| 3.5.3.1 | 3.5.3.2 | 3.5.3.3 | 3.5.3.4 | 3.5.3.5 | 3.5.3.6 | 3.5.3.7 | 3.5.3.8 | 3.5.3.9 | 3.5.4.1 |
| 3.5.4.2 | 3.5.4.3 | 3.5.4.4 | 3.5.4.5 | 3.5.4.6 | 3.5.4.7 | 3.5.4.8 | 3.5.4.9 | 3.5.5.1 | 3.5.5.2 |
| 3.5.5.3 | 3.5.5.4 | 3.5.5.5 | 3.5.5.6 | 3.5.5.7 | 3.5.5.8 | 3.5.5.9 | 3.5.6.1 | 3.5.6.2 | 3.5.6.3 |

TABLE 1-continued

| | | | | | | | | |
|---|---|---|---|---|---|---|---|---|
| 3.5.6.4 | 3.5.6.5 | 3.5.6.6 | 3.5.6.7 | 3.5.6.8 | 3.5.6.9 | 3.5.7.1 | 3.5.7.2 | 3.5.7.3 | 3.5.7.4 |
| 3.5.7.5 | 3.5.7.6 | 3.5.7.7 | 3.5.7.8 | 3.5.7.9 | 3.5.8.1 | 3.5.8.2 | 3.5.8.3 | 3.5.8.4 | 3.5.8.5 |
| 3.5.8.6 | 3.5.8.7 | 3.5.8.8 | 3.5.8.9 | 3.5.9.1 | 3.5.9.2 | 3.5.9.3 | 3.5.9.4 | 3.5.9.5 | 3.5.9.6 |
| 3.5.9.7 | 3.5.9.8 | 3.5.9.9 | 3.6.1.1 | 3.6.1.2 | 3.6.1.3 | 3.6.1.4 | 3.6.1.5 | 3.6.1.6 | 3.6.1.7 |
| 3.6.1.8 | 3.6.1.9 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 |
| 3.6.4.1 | 3.6.4.2 | 3.6.4.3 | 3.6.4.4 | 3.6.4.5 | 3.6.4.6 | 3.6.4.7 | 3.6.4.8 | 3.6.4.9 | 3.6.5.1 |
| 3.6.5.2 | 3.6.5.3 | 3.6.5.4 | 3.6.5.5 | 3.6.5.6 | 3.6.5.7 | 3.6.5.8 | 3.6.5.9 | 3.6.6.1 | 3.6.6.2 |
| 3.6.6.3 | 3.6.6.4 | 3.6.6.5 | 3.6.6.6 | 3.6.6.7 | 3.6.6.8 | 3.6.6.9 | 3.6.7.1 | 3.6.7.2 | 3.6.7.3 |
| 3.6.7.4 | 3.6.7.5 | 3.6.7.6 | 3.6.7.7 | 3.6.7.8 | 3.6.7.9 | 3.6.8.1 | 3.6.8.2 | 3.6.8.3 | 3.6.8.4 |
| 3.6.8.5 | 3.6.8.6 | 3.6.8.7 | 3.6.8.8 | 3.6.8.9 | 3.6.9.1 | 3.6.9.2 | 3.6.9.3 | 3.6.9.4 | 3.6.9.5 |
| 3.6.9.6 | 3.6.9.7 | 3.6.9.8 | 3.6.9.9 | 3.7.1.1 | 3.7.1.2 | 3.7.1.3 | 3.7.1.4 | 3.7.1.5 | 3.7.1.6 |
| 3.7.1.7 | 3.7.1.8 | 3.7.1.9 | 3.7.2.1 | 3.7.2.2 | 3.7.2.3 | 3.7.2.4 | 3.7.2.5 | 3.7.2.6 | 3.7.2.7 |
| 3.7.2.8 | 3.7.2.9 | 3.7.3.1 | 3.7.3.2 | 3.7.3.3 | 3.7.3.4 | 3.7.3.5 | 3.7.3.6 | 3.7.3.7 | 3.7.3.8 |
| 3.7.3.9 | 3.7.4.1 | 3.7.4.2 | 3.7.4.3 | 3.7.4.4 | 3.7.4.5 | 3.7.4.6 | 3.7.4.7 | 3.7.4.8 | 3.7.4.9 |
| 3.7.5.1 | 3.7.5.2 | 3.7.5.3 | 3.7.5.4 | 3.7.5.5 | 3.7.5.6 | 3.7.5.7 | 3.7.5.8 | 3.7.5.9 | 3.7.6.1 |
| 3.7.6.2 | 3.7.6.3 | 3.7.6.4 | 3.7.6.5 | 3.7.6.6 | 3.7.6.7 | 3.7.6.8 | 3.7.6.9 | 3.7.7.1 | 3.7.7.2 |
| 3.7.7.3 | 3.7.7.4 | 3.7.7.5 | 3.7.7.6 | 3.7.7.7 | 3.7.7.8 | 3.7.7.9 | 3.7.8.1 | 3.7.8.2 | 3.7.8.3 |
| 3.7.8.4 | 3.7.8.5 | 3.7.8.6 | 3.7.8.7 | 3.7.8.8 | 3.7.8.9 | 3.7.9.1 | 3.7.9.2 | 3.7.9.3 | 3.7.9.4 |
| 3.7.9.5 | 3.7.9.6 | 3.7.9.7 | 3.7.9.8 | 3.7.9.9 | 3.8.1.1 | 3.8.1.2 | 3.8.1.3 | 3.8.1.4 | 3.8.1.5 |
| 3.8.1.6 | 3.8.1.7 | 3.8.1.8 | 3.8.1.9 | 3.8.2.1 | 3.8.2.2 | 3.8.2.3 | 3.8.2.4 | 3.8.2.5 | 3.8.2.6 |
| 3.8.2.7 | 3.8.2.8 | 3.8.2.9 | 3.8.3.1 | 3.8.3.2 | 3.8.3.3 | 3.8.3.4 | 3.8.3.5 | 3.8.3.6 | 3.8.3.7 |
| 3.8.3.8 | 3.8.3.9 | 3.8.4.1 | 3.8.4.2 | 3.8.4.3 | 3.8.4.4 | 3.8.4.5 | 3.8.4.6 | 3.8.4.7 | 3.8.4.8 |
| 3.8.4.9 | 3.8.5.1 | 3.8.5.2 | 3.8.5.3 | 3.8.5.4 | 3.8.5.5 | 3.8.5.6 | 3.8.5.7 | 3.8.5.8 | 3.8.5.9 |
| 3.8.6.1 | 3.8.6.2 | 3.8.6.3 | 3.8.6.4 | 3.8.6.5 | 3.8.6.6 | 3.8.6.7 | 3.8.6.8 | 3.8.6.9 | 3.8.7.1 |
| 3.8.7.2 | 3.8.7.3 | 3.8.7.4 | 3.8.7.5 | 3.8.7.6 | 3.8.7.7 | 3.8.7.8 | 3.8.7.9 | 3.8.8.1 | 3.8.8.2 |
| 3.8.8.3 | 3.8.8.4 | 3.8.8.5 | 3.8.8.6 | 3.8.8.7 | 3.8.8.8 | 3.8.8.9 | 3.8.9.1 | 3.8.9.2 | 3.8.9.3 |
| 3.8.9.4 | 3.8.9.5 | 3.8.9.6 | 3.8.9.7 | 3.8.9.8 | 3.8.9.9 | 3.9.1.1 | 3.9.1.2 | 3.9.1.3 | 3.9.1.4 |
| 3.9.1.5 | 3.9.1.6 | 3.9.1.7 | 3.9.1.8 | 3.9.1.9 | 3.9.2.1 | 3.9.2.2 | 3.9.2.3 | 3.9.2.4 | 3.9.2.5 |
| 3.9.2.6 | 3.9.2.7 | 3.9.2.8 | 3.9.2.9 | 3.9.3.1 | 3.9.3.2 | 3.9.3.3 | 3.9.3.4 | 3.9.3.5 | 3.9.3.6 |
| 3.9.3.7 | 3.9.3.8 | 3.9.3.9 | 3.9.4.1 | 3.9.4.2 | 3.9.4.3 | 3.9.4.4 | 3.9.4.5 | 3.9.4.6 | 3.9.4.7 |
| 3.9.4.8 | 3.9.4.9 | 3.9.5.1 | 3.9.5.2 | 3.9.5.3 | 3.9.5.4 | 3.9.5.5 | 3.9.5.6 | 3.9.5.7 | 3.9.5.8 |
| 3.9.5.9 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.7.1 | 3.9.7.2 | 3.9.7.3 | 3.9.7.4 | 3.9.7.5 | 3.9.7.6 | 3.9.7.7 | 3.9.7.8 | 3.9.7.9 | 3.9.8.1 |
| 3.9.8.2 | 3.9.8.3 | 3.9.8.4 | 3.9.8.5 | 3.9.8.6 | 3.9.8.7 | 3.9.8.8 | 3.9.8.9 | 3.9.9.1 | 3.9.9.2 |
| 3.9.9.3 | 3.9.9.4 | 3.9.9.5 | 3.9.9.6 | 3.9.9.7 | 3.9.9.8 | 3.9.9.9 | 4.1.1.1 | 4.1.1.2 | 4.1.1.3 |
| 4.1.1.4 | 4.1.1.5 | 4.1.1.6 | 4.1.1.7 | 4.1.1.8 | 4.1.1.9 | 4.1.2.1 | 4.1.2.2 | 4.1.2.3 | 4.1.2.4 |
| 4.1.2.5 | 4.1.2.6 | 4.1.2.7 | 4.1.2.8 | 4.1.2.9 | 4.1.3.1 | 4.1.3.2 | 4.1.3.3 | 4.1.3.4 | 4.1.3.5 |
| 4.1.3.6 | 4.1.3.7 | 4.1.3.8 | 4.1.3.9 | 4.1.4.1 | 4.1.4.2 | 4.1.4.3 | 4.1.4.4 | 4.1.4.5 | 4.1.4.6 |
| 4.1.4.7 | 4.1.4.8 | 4.1.4.9 | 4.1.5.1 | 4.1.5.2 | 4.1.5.3 | 4.1.5.4 | 4.1.5.5 | 4.1.5.6 | 4.1.5.7 |
| 4.1.5.8 | 4.1.5.9 | 4.1.6.1 | 4.1.6.2 | 4.1.6.3 | 4.1.6.4 | 4.1.6.5 | 4.1.6.6 | 4.1.6.7 | 4.1.6.8 |
| 4.1.6.9 | 4.1.7.1 | 4.1.7.2 | 4.1.7.3 | 4.1.7.4 | 4.1.7.5 | 4.1.7.6 | 4.1.7.7 | 4.1.7.8 | 4.1.7.9 |
| 4.1.8.1 | 4.1.8.2 | 4.1.8.3 | 4.1.8.4 | 4.1.8.5 | 4.1.8.6 | 4.1.8.7 | 4.1.8.8 | 4.1.8.9 | 4.1.9.1 |
| 4.1.9.2 | 4.1.9.3 | 4.1.9.4 | 4.1.9.5 | 4.1.9.6 | 4.1.9.7 | 4.1.9.8 | 4.1.9.9 | 4.2.1.1 | 4.2.1.2 |
| 4.2.1.3 | 4.2.1.4 | 4.2.1.5 | 4.2.1.6 | 4.2.1.7 | 4.2.1.8 | 4.2.1.9 | 4.2.2.1 | 4.2.2.2 | 4.2.2.3 |
| 4.2.2.4 | 4.2.2.5 | 4.2.2.6 | 4.2.2.7 | 4.2.2.8 | 4.2.2.9 | 4.2.3.1 | 4.2.3.2 | 4.2.3.3 | 4.2.3.4 |
| 4.2.3.5 | 4.2.3.6 | 4.2.3.7 | 4.2.3.8 | 4.2.3.9 | 4.2.4.1 | 4.2.4.2 | 4.2.4.3 | 4.2.4.4 | 4.2.4.5 |
| 4.2.4.6 | 4.2.4.7 | 4.2.4.8 | 4.2.4.9 | 4.2.5.1 | 4.2.5.2 | 4.2.5.3 | 4.2.5.4 | 4.2.5.5 | 4.2.5.6 |
| 4.2.5.7 | 4.2.5.8 | 4.2.5.9 | 4.2.6.1 | 4.2.6.2 | 4.2.6.3 | 4.2.6.4 | 4.2.6.5 | 4.2.6.6 | 4.2.6.7 |
| 4.2.6.8 | 4.2.6.9 | 4.2.7.1 | 4.2.7.2 | 4.2.7.3 | 4.2.7.4 | 4.2.7.5 | 4.2.7.6 | 4.2.7.7 | 4.2.7.8 |
| 4.2.7.9 | 4.2.8.1 | 4.2.8.2 | 4.2.8.3 | 4.2.8.4 | 4.2.8.5 | 4.2.8.6 | 4.2.8.7 | 4.2.8.8 | 4.2.8.9 |
| 4.2.9.1 | 4.2.9.2 | 4.2.9.3 | 4.2.9.4 | 4.2.9.5 | 4.2.9.6 | 4.2.9.7 | 4.2.9.8 | 4.2.9.9 | 4.3.1.1 |
| 4.3.1.2 | 4.3.1.3 | 4.3.1.4 | 4.3.1.5 | 4.3.1.6 | 4.3.1.7 | 4.3.1.8 | 4.3.1.9 | 4.3.2.1 | 4.3.2.2 |
| 4.3.2.3 | 4.3.2.4 | 4.3.2.5 | 4.3.2.6 | 4.3.2.7 | 4.3.2.8 | 4.3.2.9 | 4.3.3.1 | 4.3.3.2 | 4.3.3.3 |
| 4.3.3.4 | 4.3.3.5 | 4.3.3.6 | 4.3.3.7 | 4.3.3.8 | 4.3.3.9 | 4.3.4.1 | 4.3.4.2 | 4.3.4.3 | 4.3.4.4 |
| 4.3.4.5 | 4.3.4.6 | 4.3.4.7 | 4.3.4.8 | 4.3.4.9 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.6.1 | 4.3.6.2 | 4.3.6.3 | 4.3.6.4 | 4.3.6.5 | 4.3.6.6 |
| 4.3.6.7 | 4.3.6.8 | 4.3.6.9 | 4.3.7.1 | 4.3.7.2 | 4.3.7.3 | 4.3.7.4 | 4.3.7.5 | 4.3.7.6 | 4.3.7.7 |
| 4.3.7.8 | 4.3.7.9 | 4.3.8.1 | 4.3.8.2 | 4.3.8.3 | 4.3.8.4 | 4.3.8.5 | 4.3.8.6 | 4.3.8.7 | 4.3.8.8 |
| 4.3.8.9 | 4.3.9.1 | 4.3.9.2 | 4.3.9.3 | 4.3.9.4 | 4.3.9.5 | 4.3.9.6 | 4.3.9.7 | 4.3.9.8 | 4.3.9.9 |
| 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.3.1 | 4.4.3.2 |
| 4.4.3.3 | 4.4.3.4 | 4.4.3.5 | 4.4.3.6 | 4.4.3.7 | 4.4.3.8 | 4.4.3.9 | 4.4.4.1 | 4.4.4.2 | 4.4.4.3 |
| 4.4.4.4 | 4.4.4.5 | 4.4.4.6 | 4.4.4.7 | 4.4.4.8 | 4.4.4.9 | 4.4.5.1 | 4.4.5.2 | 4.4.5.3 | 4.4.5.4 |
| 4.4.5.5 | 4.4.5.6 | 4.4.5.7 | 4.4.5.8 | 4.4.5.9 | 4.4.6.1 | 4.4.6.2 | 4.4.6.3 | 4.4.6.4 | 4.4.6.5 |
| 4.4.6.6 | 4.4.6.7 | 4.4.6.8 | 4.4.6.9 | 4.4.7.1 | 4.4.7.2 | 4.4.7.3 | 4.4.7.4 | 4.4.7.5 | 4.4.7.6 |
| 4.4.7.7 | 4.4.7.8 | 4.4.7.9 | 4.4.8.1 | 4.4.8.2 | 4.4.8.3 | 4.4.8.4 | 4.4.8.5 | 4.4.8.6 | 4.4.8.7 |
| 4.4.8.8 | 4.4.8.9 | 4.4.9.1 | 4.4.9.2 | 4.4.9.3 | 4.4.9.4 | 4.4.9.5 | 4.4.9.6 | 4.4.9.7 | 4.4.9.8 |
| 4.4.9.9 | 4.5.1.1 | 4.5.1.2 | 4.5.1.3 | 4.5.1.4 | 4.5.1.5 | 4.5.1.6 | 4.5.1.7 | 4.5.1.8 | 4.5.1.9 |
| 4.5.2.1 | 4.5.2.2 | 4.5.2.3 | 4.5.2.4 | 4.5.2.5 | 4.5.2.6 | 4.5.2.7 | 4.5.2.8 | 4.5.2.9 | 4.5.3.1 |
| 4.5.3.2 | 4.5.3.3 | 4.5.3.4 | 4.5.3.5 | 4.5.3.6 | 4.5.3.7 | 4.5.3.8 | 4.5.3.9 | 4.5.4.1 | 4.5.4.2 |
| 4.5.4.3 | 4.5.4.4 | 4.5.4.5 | 4.5.4.6 | 4.5.4.7 | 4.5.4.8 | 4.5.4.9 | 4.5.5.1 | 4.5.5.2 | 4.5.5.3 |
| 4.5.5.4 | 4.5.5.5 | 4.5.5.6 | 4.5.5.7 | 4.5.5.8 | 4.5.5.9 | 4.5.6.1 | 4.5.6.2 | 4.5.6.3 | 4.5.6.4 |
| 4.5.6.5 | 4.5.6.6 | 4.5.6.7 | 4.5.6.8 | 4.5.6.9 | 4.5.7.1 | 4.5.7.2 | 4.5.7.3 | 4.5.7.4 | 4.5.7.5 |
| 4.5.7.6 | 4.5.7.7 | 4.5.7.8 | 4.5.7.9 | 4.5.8.1 | 4.5.8.2 | 4.5.8.3 | 4.5.8.4 | 4.5.8.5 | 4.5.8.6 |
| 4.5.8.7 | 4.5.8.8 | 4.5.8.9 | 4.5.9.1 | 4.5.9.2 | 4.5.9.3 | 4.5.9.4 | 4.5.9.5 | 4.5.9.6 | 4.5.9.7 |
| 4.5.9.8 | 4.5.9.9 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 |
| 4.6.3.1 | 4.6.3.2 | 4.6.3.3 | 4.6.3.4 | 4.6.3.5 | 4.6.3.6 | 4.6.3.7 | 4.6.3.8 | 4.6.3.9 | 4.6.4.1 |
| 4.6.4.2 | 4.6.4.3 | 4.6.4.4 | 4.6.4.5 | 4.6.4.6 | 4.6.4.7 | 4.6.4.8 | 4.6.4.9 | 4.6.5.1 | 4.6.5.2 |

TABLE 1-continued

| | | | | | | | | |
|---|---|---|---|---|---|---|---|---|
| 4.6.5.3 | 4.6.5.4 | 4.6.5.5 | 4.6.5.6 | 4.6.5.7 | 4.6.5.8 | 4.6.5.9 | 4.6.6.1 | 4.6.6.2 | 4.6.6.3 |
| 4.6.6.4 | 4.6.6.5 | 4.6.6.6 | 4.6.6.7 | 4.6.6.8 | 4.6.6.9 | 4.6.7.1 | 4.6.7.2 | 4.6.7.3 | 4.6.7.4 |
| 4.6.7.5 | 4.6.7.6 | 4.6.7.7 | 4.6.7.8 | 4.6.7.9 | 4.6.8.1 | 4.6.8.2 | 4.6.8.3 | 4.6.8.4 | 4.6.8.5 |
| 4.6.8.6 | 4.6.8.7 | 4.6.8.8 | 4.6.8.9 | 4.6.9.1 | 4.6.9.2 | 4.6.9.3 | 4.6.9.4 | 4.6.9.5 | 4.6.9.6 |
| 4.6.9.7 | 4.6.9.8 | 4.6.9.9 | 4.7.1.1 | 4.7.1.2 | 4.7.1.3 | 4.7.1.4 | 4.7.1.5 | 4.7.1.6 | 4.7.1.7 |
| 4.7.1.8 | 4.7.1.9 | 4.7.2.1 | 4.7.2.2 | 4.7.2.3 | 4.7.2.4 | 4.7.2.5 | 4.7.2.6 | 4.7.2.7 | 4.7.2.8 |
| 4.7.2.9 | 4.7.3.1 | 4.7.3.2 | 4.7.3.3 | 4.7.3.4 | 4.7.3.5 | 4.7.3.6 | 4.7.3.7 | 4.7.3.8 | 4.7.3.9 |
| 4.7.4.1 | 4.7.4.2 | 4.7.4.3 | 4.7.4.4 | 4.7.4.5 | 4.7.4.6 | 4.7.4.7 | 4.7.4.8 | 4.7.4.9 | 4.7.5.1 |
| 4.7.5.2 | 4.7.5.3 | 4.7.5.4 | 4.7.5.5 | 4.7.5.6 | 4.7.5.7 | 4.7.5.8 | 4.7.5.9 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.7.1 | 4.7.7.2 | 4.7.7.3 |
| 4.7.7.4 | 4.7.7.5 | 4.7.7.6 | 4.7.7.7 | 4.7.7.8 | 4.7.7.9 | 4.7.8.1 | 4.7.8.2 | 4.7.8.3 | 4.7.8.4 |
| 4.7.8.5 | 4.7.8.6 | 4.7.8.7 | 4.7.8.8 | 4.7.8.9 | 4.7.9.1 | 4.7.9.2 | 4.7.9.3 | 4.7.9.4 | 4.7.9.5 |
| 4.7.9.6 | 4.7.9.7 | 4.7.9.8 | 4.7.9.9 | 4.8.1.1 | 4.8.1.2 | 4.8.1.3 | 4.8.1.4 | 4.8.1.5 | 4.8.1.6 |
| 4.8.1.7 | 4.8.1.8 | 4.8.1.9 | 4.8.2.1 | 4.8.2.2 | 4.8.2.3 | 4.8.2.4 | 4.8.2.5 | 4.8.2.6 | 4.8.2.7 |
| 4.8.2.8 | 4.8.2.9 | 4.8.3.1 | 4.8.3.2 | 4.8.3.3 | 4.8.3.4 | 4.8.3.5 | 4.8.3.6 | 4.8.3.7 | 4.8.3.8 |
| 4.8.3.9 | 4.8.4.1 | 4.8.4.2 | 4.8.4.3 | 4.8.4.4 | 4.8.4.5 | 4.8.4.6 | 4.8.4.7 | 4.8.4.8 | 4.8.4.9 |
| 4.8.5.1 | 4.8.5.2 | 4.8.5.3 | 4.8.5.4 | 4.8.5.5 | 4.8.5.6 | 4.8.5.7 | 4.8.5.8 | 4.8.5.9 | 4.8.6.1 |
| 4.8.6.2 | 4.8.6.3 | 4.8.6.4 | 4.8.6.5 | 4.8.6.6 | 4.8.6.7 | 4.8.6.8 | 4.8.6.9 | 4.8.7.1 | 4.8.7.2 |
| 4.8.7.3 | 4.8.7.4 | 4.8.7.5 | 4.8.7.6 | 4.8.7.7 | 4.8.7.8 | 4.8.7.9 | 4.8.8.1 | 4.8.8.2 | 4.8.8.3 |
| 4.8.8.4 | 4.8.8.5 | 4.8.8.6 | 4.8.8.7 | 4.8.8.8 | 4.8.8.9 | 4.8.9.1 | 4.8.9.2 | 4.8.9.3 | 4.8.9.4 |
| 4.8.9.5 | 4.8.9.6 | 4.8.9.7 | 4.8.9.8 | 4.8.9.9 | 4.9.1.1 | 4.9.1.2 | 4.9.1.3 | 4.9.1.4 | 4.9.1.5 |
| 4.9.1.6 | 4.9.1.7 | 4.9.1.8 | 4.9.1.9 | 4.9.2.1 | 4.9.2.2 | 4.9.2.3 | 4.9.2.4 | 4.9.2.5 | 4.9.2.6 |
| 4.9.2.7 | 4.9.2.8 | 4.9.2.9 | 4.9.3.1 | 4.9.3.2 | 4.9.3.3 | 4.9.3.4 | 4.9.3.5 | 4.9.3.6 | 4.9.3.7 |
| 4.9.3.8 | 4.9.3.9 | 4.9.4.1 | 4.9.4.2 | 4.9.4.3 | 4.9.4.4 | 4.9.4.5 | 4.9.4.6 | 4.9.4.7 | 4.9.4.8 |
| 4.9.4.9 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.7.1 |
| 4.9.7.2 | 4.9.7.3 | 4.9.7.4 | 4.9.7.5 | 4.9.7.6 | 4.9.7.7 | 4.9.7.8 | 4.9.7.9 | 4.9.8.1 | 4.9.8.2 |
| 4.9.8.3 | 4.9.8.4 | 4.9.8.5 | 4.9.8.6 | 4.9.8.7 | 4.9.8.8 | 4.9.8.9 | 4.9.9.1 | 4.9.9.2 | 4.9.9.3 |
| 4.9.9.4 | 4.9.9.5 | 4.9.9.6 | 4.9.9.7 | 4.9.9.8 | 4.9.9.9 | 5.1.1.1 | 5.1.1.2 | 5.1.1.3 | 5.1.1.4 |
| 5.1.1.5 | 5.1.1.6 | 5.1.1.7 | 5.1.1.8 | 5.1.1.9 | 5.1.2.1 | 5.1.2.2 | 5.1.2.3 | 5.1.2.4 | 5.1.2.5 |
| 5.1.2.6 | 5.1.2.7 | 5.1.2.8 | 5.1.2.9 | 5.1.3.1 | 5.1.3.2 | 5.1.3.3 | 5.1.3.4 | 5.1.3.5 | 5.1.3.6 |
| 5.1.3.7 | 5.1.3.8 | 5.1.3.9 | 5.1.4.1 | 5.1.4.2 | 5.1.4.3 | 5.1.4.4 | 5.1.4.5 | 5.1.4.6 | 5.1.4.7 |
| 5.1.4.8 | 5.1.4.9 | 5.1.5.1 | 5.1.5.2 | 5.1.5.3 | 5.1.5.4 | 5.1.5.5 | 5.1.5.6 | 5.1.5.7 | 5.1.5.8 |
| 5.1.5.9 | 5.1.6.1 | 5.1.6.2 | 5.1.6.3 | 5.1.6.4 | 5.1.6.5 | 5.1.6.6 | 5.1.6.7 | 5.1.6.8 | 5.1.6.9 |
| 5.1.7.1 | 5.1.7.2 | 5.1.7.3 | 5.1.7.4 | 5.1.7.5 | 5.1.7.6 | 5.1.7.7 | 5.1.7.8 | 5.1.7.9 | 5.1.8.1 |
| 5.1.8.2 | 5.1.8.3 | 5.1.8.4 | 5.1.8.5 | 5.1.8.6 | 5.1.8.7 | 5.1.8.8 | 5.1.8.9 | 5.1.9.1 | 5.1.9.2 |
| 5.1.9.3 | 5.1.9.4 | 5.1.9.5 | 5.1.9.6 | 5.1.9.7 | 5.1.9.8 | 5.1.9.9 | 5.2.1.1 | 5.2.1.2 | 5.2.1.3 |
| 5.2.1.4 | 5.2.1.5 | 5.2.1.6 | 5.2.1.7 | 5.2.1.8 | 5.2.1.9 | 5.2.2.1 | 5.2.2.2 | 5.2.2.3 | 5.2.2.4 |
| 5.2.2.5 | 5.2.2.6 | 5.2.2.7 | 5.2.2.8 | 5.2.2.9 | 5.2.3.1 | 5.2.3.2 | 5.2.3.3 | 5.2.3.4 | 5.2.3.5 |
| 5.2.3.6 | 5.2.3.7 | 5.2.3.8 | 5.2.3.9 | 5.2.4.1 | 5.2.4.2 | 5.2.4.3 | 5.2.4.4 | 5.2.4.5 | 5.2.4.6 |
| 5.2.4.7 | 5.2.4.8 | 5.2.4.9 | 5.2.5.1 | 5.2.5.2 | 5.2.5.3 | 5.2.5.4 | 5.2.5.5 | 5.2.5.6 | 5.2.5.7 |
| 5.2.5.8 | 5.2.5.9 | 5.2.6.1 | 5.2.6.2 | 5.2.6.3 | 5.2.6.4 | 5.2.6.5 | 5.2.6.6 | 5.2.6.7 | 5.2.6.8 |
| 5.2.6.9 | 5.2.7.1 | 5.2.7.2 | 5.2.7.3 | 5.2.7.4 | 5.2.7.5 | 5.2.7.6 | 5.2.7.7 | 5.2.7.8 | 5.2.7.9 |
| 5.2.8.1 | 5.2.8.2 | 5.2.8.3 | 5.2.8.4 | 5.2.8.5 | 5.2.8.6 | 5.2.8.7 | 5.2.8.8 | 5.2.8.9 | 5.2.9.1 |
| 5.2.9.2 | 5.2.9.3 | 5.2.9.4 | 5.2.9.5 | 5.2.9.6 | 5.2.9.7 | 5.2.9.8 | 5.2.9.9 | 5.3.1.1 | 5.3.1.2 |
| 5.3.1.3 | 5.3.1.4 | 5.3.1.5 | 5.3.1.6 | 5.3.1.7 | 5.3.1.8 | 5.3.1.9 | 5.3.2.1 | 5.3.2.2 | 5.3.2.3 |
| 5.3.2.4 | 5.3.2.5 | 5.3.2.6 | 5.3.2.7 | 5.3.2.8 | 5.3.2.9 | 5.3.3.1 | 5.3.3.2 | 5.3.3.3 | 5.3.3.4 |
| 5.3.3.5 | 5.3.3.6 | 5.3.3.7 | 5.3.3.8 | 5.3.3.9 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.5.1 | 5.3.5.2 | 5.3.5.3 | 5.3.5.4 | 5.3.5.5 | 5.3.5.6 |
| 5.3.5.7 | 5.3.5.8 | 5.3.5.9 | 5.3.6.1 | 5.3.6.2 | 5.3.6.3 | 5.3.6.4 | 5.3.6.5 | 5.3.6.6 | 5.3.6.7 |
| 5.3.6.8 | 5.3.6.9 | 5.3.7.1 | 5.3.7.2 | 5.3.7.3 | 5.3.7.4 | 5.3.7.5 | 5.3.7.6 | 5.3.7.7 | 5.3.7.8 |
| 5.3.7.9 | 5.3.8.1 | 5.3.8.2 | 5.3.8.3 | 5.3.8.4 | 5.3.8.5 | 5.3.8.6 | 5.3.8.7 | 5.3.8.8 | 5.3.8.9 |
| 5.3.9.1 | 5.3.9.2 | 5.3.9.3 | 5.3.9.4 | 5.3.9.5 | 5.3.9.6 | 5.3.9.7 | 5.3.9.8 | 5.3.9.9 | 5.4.1.1 |
| 5.4.1.2 | 5.4.1.3 | 5.4.1.4 | 5.4.1.5 | 5.4.1.6 | 5.4.1.7 | 5.4.1.8 | 5.4.1.9 | 5.4.2.1 | 5.4.2.2 |
| 5.4.2.3 | 5.4.2.4 | 5.4.2.5 | 5.4.2.6 | 5.4.2.7 | 5.4.2.8 | 5.4.2.9 | 5.4.3.1 | 5.4.3.2 | 5.4.3.3 |
| 5.4.3.4 | 5.4.3.5 | 5.4.3.6 | 5.4.3.7 | 5.4.3.8 | 5.4.3.9 | 5.4.4.1 | 5.4.4.2 | 5.4.4.3 | 5.4.4.4 |
| 5.4.4.5 | 5.4.4.6 | 5.4.4.7 | 5.4.4.8 | 5.4.4.9 | 5.4.5.1 | 5.4.5.2 | 5.4.5.3 | 5.4.5.4 | 5.4.5.5 |
| 5.4.5.6 | 5.4.5.7 | 5.4.5.8 | 5.4.5.9 | 5.4.6.1 | 5.4.6.2 | 5.4.6.3 | 5.4.6.4 | 5.4.6.5 | 5.4.6.6 |
| 5.4.6.7 | 5.4.6.8 | 5.4.6.9 | 5.4.7.1 | 5.4.7.2 | 5.4.7.3 | 5.4.7.4 | 5.4.7.5 | 5.4.7.6 | 5.4.7.7 |
| 5.4.7.8 | 5.4.7.9 | 5.4.8.1 | 5.4.8.2 | 5.4.8.3 | 5.4.8.4 | 5.4.8.5 | 5.4.8.6 | 5.4.8.7 | 5.4.8.8 |
| 5.4.8.9 | 5.4.9.1 | 5.4.9.2 | 5.4.9.3 | 5.4.9.4 | 5.4.9.5 | 5.4.9.6 | 5.4.9.7 | 5.4.9.8 | 5.4.9.9 |
| 5.5.1.1 | 5.5.1.2 | 5.5.1.3 | 5.5.1.4 | 5.5.1.5 | 5.5.1.6 | 5.5.1.7 | 5.5.1.8 | 5.5.1.9 | 5.5.2.1 |
| 5.5.2.2 | 5.5.2.3 | 5.5.2.4 | 5.5.2.5 | 5.5.2.6 | 5.5.2.7 | 5.5.2.8 | 5.5.2.9 | 5.5.3.1 | 5.5.3.2 |
| 5.5.3.3 | 5.5.3.4 | 5.5.3.5 | 5.5.3.6 | 5.5.3.7 | 5.5.3.8 | 5.5.3.9 | 5.5.4.1 | 5.5.4.2 | 5.5.4.3 |
| 5.5.4.4 | 5.5.4.5 | 5.5.4.6 | 5.5.4.7 | 5.5.4.8 | 5.5.4.9 | 5.5.5.1 | 5.5.5.2 | 5.5.5.3 | 5.5.5.4 |
| 5.5.5.5 | 5.5.5.6 | 5.5.5.7 | 5.5.5.8 | 5.5.5.9 | 5.5.6.1 | 5.5.6.2 | 5.5.6.3 | 5.5.6.4 | 5.5.6.5 |
| 5.5.6.6 | 5.5.6.7 | 5.5.6.8 | 5.5.6.9 | 5.5.7.1 | 5.5.7.2 | 5.5.7.3 | 5.5.7.4 | 5.5.7.5 | 5.5.7.6 |
| 5.5.7.7 | 5.5.7.8 | 5.5.7.9 | 5.5.8.1 | 5.5.8.2 | 5.5.8.3 | 5.5.8.4 | 5.5.8.5 | 5.5.8.6 | 5.5.8.7 |
| 5.5.8.8 | 5.5.8.9 | 5.5.9.1 | 5.5.9.2 | 5.5.9.3 | 5.5.9.4 | 5.5.9.5 | 5.5.9.6 | 5.5.9.7 | 5.5.9.8 |
| 5.5.9.9 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 |
| 5.6.2.1 | 5.6.2.2 | 5.6.2.3 | 5.6.2.4 | 5.6.2.5 | 5.6.2.6 | 5.6.2.7 | 5.6.2.8 | 5.6.2.9 | 5.6.3.1 |
| 5.6.3.2 | 5.6.3.3 | 5.6.3.4 | 5.6.3.5 | 5.6.3.6 | 5.6.3.7 | 5.6.3.8 | 5.6.3.9 | 5.6.4.1 | 5.6.4.2 |
| 5.6.4.3 | 5.6.4.4 | 5.6.4.5 | 5.6.4.6 | 5.6.4.7 | 5.6.4.8 | 5.6.4.9 | 5.6.5.1 | 5.6.5.2 | 5.6.5.3 |
| 5.6.5.4 | 5.6.5.5 | 5.6.5.6 | 5.6.5.7 | 5.6.5.8 | 5.6.5.9 | 5.6.6.1 | 5.6.6.2 | 5.6.6.3 | 5.6.6.4 |
| 5.6.6.5 | 5.6.6.6 | 5.6.6.7 | 5.6.6.8 | 5.6.6.9 | 5.6.7.1 | 5.6.7.2 | 5.6.7.3 | 5.6.7.4 | 5.6.7.5 |
| 5.6.7.6 | 5.6.7.7 | 5.6.7.8 | 5.6.7.9 | 5.6.8.1 | 5.6.8.2 | 5.6.8.3 | 5.6.8.4 | 5.6.8.5 | 5.6.8.6 |
| 5.6.8.7 | 5.6.8.8 | 5.6.8.9 | 5.6.9.1 | 5.6.9.2 | 5.6.9.3 | 5.6.9.4 | 5.6.9.5 | 5.6.9.6 | 5.6.9.7 |
| 5.6.9.8 | 5.6.9.9 | 5.7.1.1 | 5.7.1.2 | 5.7.1.3 | 5.7.1.4 | 5.7.1.5 | 5.7.1.6 | 5.7.1.7 | 5.7.1.8 |
| 5.7.1.9 | 5.7.2.1 | 5.7.2.2 | 5.7.2.3 | 5.7.2.4 | 5.7.2.5 | 5.7.2.6 | 5.7.2.7 | 5.7.2.8 | 5.7.2.9 |
| 5.7.3.1 | 5.7.3.2 | 5.7.3.3 | 5.7.3.4 | 5.7.3.5 | 5.7.3.6 | 5.7.3.7 | 5.7.3.8 | 5.7.3.9 | 5.7.4.1 |

TABLE 1-continued

| | | | | | | | | |
|---|---|---|---|---|---|---|---|---|
| 5.7.4.2 | 5.7.4.3 | 5.7.4.4 | 5.7.4.5 | 5.7.4.6 | 5.7.4.7 | 5.7.4.8 | 5.7.4.9 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.6.1 | 5.7.6.2 | 5.7.6.3 |
| 5.7.6.4 | 5.7.6.5 | 5.7.6.6 | 5.7.6.7 | 5.7.6.8 | 5.7.6.9 | 5.7.7.1 | 5.7.7.2 | 5.7.7.3 | 5.7.7.4 |
| 5.7.7.5 | 5.7.7.6 | 5.7.7.7 | 5.7.7.8 | 5.7.7.9 | 5.7.8.1 | 5.7.8.2 | 5.7.8.3 | 5.7.8.4 | 5.7.8.5 |
| 5.7.8.6 | 5.7.8.7 | 5.7.8.8 | 5.7.8.9 | 5.7.9.1 | 5.7.9.2 | 5.7.9.3 | 5.7.9.4 | 5.7.9.5 | 5.7.9.6 |
| 5.7.9.7 | 5.7.9.8 | 5.7.9.9 | 5.8.1.1 | 5.8.1.2 | 5.8.1.3 | 5.8.1.4 | 5.8.1.5 | 5.8.1.6 | 5.8.1.7 |
| 5.8.1.8 | 5.8.1.9 | 5.8.2.1 | 5.8.2.2 | 5.8.2.3 | 5.8.2.4 | 5.8.2.5 | 5.8.2.6 | 5.8.2.7 | 5.8.2.8 |
| 5.8.2.9 | 5.8.3.1 | 5.8.3.2 | 5.8.3.3 | 5.8.3.4 | 5.8.3.5 | 5.8.3.6 | 5.8.3.7 | 5.8.3.8 | 5.8.3.9 |
| 5.8.4.1 | 5.8.4.2 | 5.8.4.3 | 5.8.4.4 | 5.8.4.5 | 5.8.4.6 | 5.8.4.7 | 5.8.4.8 | 5.8.4.9 | 5.8.5.1 |
| 5.8.5.2 | 5.8.5.3 | 5.8.5.4 | 5.8.5.5 | 5.8.5.6 | 5.8.5.7 | 5.8.5.8 | 5.8.5.9 | 5.8.6.1 | 5.8.6.2 |
| 5.8.6.3 | 5.8.6.4 | 5.8.6.5 | 5.8.6.6 | 5.8.6.7 | 5.8.6.8 | 5.8.6.9 | 5.8.7.1 | 5.8.7.2 | 5.8.7.3 |
| 5.8.7.4 | 5.8.7.5 | 5.8.7.6 | 5.8.7.7 | 5.8.7.8 | 5.8.7.9 | 5.8.8.1 | 5.8.8.2 | 5.8.8.3 | 5.8.8.4 |
| 5.8.8.5 | 5.8.8.6 | 5.8.8.7 | 5.8.8.8 | 5.8.8.9 | 5.8.9.1 | 5.8.9.2 | 5.8.9.3 | 5.8.9.4 | 5.8.9.5 |
| 5.8.9.6 | 5.8.9.7 | 5.8.9.8 | 5.8.9.9 | 5.9.1.1 | 5.9.1.2 | 5.9.1.3 | 5.9.1.4 | 5.9.1.5 | 5.9.1.6 |
| 5.9.1.7 | 5.9.1.8 | 5.9.1.9 | 5.9.2.1 | 5.9.2.2 | 5.9.2.3 | 5.9.2.4 | 5.9.2.5 | 5.9.2.6 | 5.9.2.7 |
| 5.9.2.8 | 5.9.2.9 | 5.9.3.1 | 5.9.3.2 | 5.9.3.3 | 5.9.3.4 | 5.9.3.5 | 5.9.3.6 | 5.9.3.7 | 5.9.3.8 |
| 5.9.3.9 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.6.1 |
| 5.9.6.2 | 5.9.6.3 | 5.9.6.4 | 5.9.6.5 | 5.9.6.6 | 5.9.6.7 | 5.9.6.8 | 5.9.6.9 | 5.9.7.1 | 5.9.7.2 |
| 5.9.7.3 | 5.9.7.4 | 5.9.7.5 | 5.9.7.6 | 5.9.7.7 | 5.9.7.8 | 5.9.7.9 | 5.9.8.1 | 5.9.8.2 | 5.9.8.3 |
| 5.9.8.4 | 5.9.8.5 | 5.9.8.6 | 5.9.8.7 | 5.9.8.8 | 5.9.8.9 | 5.9.9.1 | 5.9.9.2 | 5.9.9.3 | 5.9.9.4 |
| 5.9.9.5 | 5.9.9.6 | 5.9.9.7 | 5.9.9.8 | 5.9.9.9 | 6.1.1.1 | 6.1.1.2 | 6.1.1.3 | 6.1.1.4 | 6.1.1.5 |
| 6.1.1.6 | 6.1.1.7 | 6.1.1.8 | 6.1.1.9 | 6.1.2.1 | 6.1.2.2 | 6.1.2.3 | 6.1.2.4 | 6.1.2.5 | 6.1.2.6 |
| 6.1.2.7 | 6.1.2.8 | 6.1.2.9 | 6.1.3.1 | 6.1.3.2 | 6.1.3.3 | 6.1.3.4 | 6.1.3.5 | 6.1.3.6 | 6.1.3.7 |
| 6.1.3.8 | 6.1.3.9 | 6.1.4.1 | 6.1.4.2 | 6.1.4.3 | 6.1.4.4 | 6.1.4.5 | 6.1.4.6 | 6.1.4.7 | 6.1.4.8 |
| 6.1.4.9 | 6.1.5.1 | 6.1.5.2 | 6.1.5.3 | 6.1.5.4 | 6.1.5.5 | 6.1.5.6 | 6.1.5.7 | 6.1.5.8 | 6.1.5.9 |
| 6.1.6.1 | 6.1.6.2 | 6.1.6.3 | 6.1.6.4 | 6.1.6.5 | 6.1.6.6 | 6.1.6.7 | 6.1.6.8 | 6.1.6.9 | 6.1.7.1 |
| 6.1.7.2 | 6.1.7.3 | 6.1.7.4 | 6.1.7.5 | 6.1.7.6 | 6.1.7.7 | 6.1.7.8 | 6.1.7.9 | 6.1.8.1 | 6.1.8.2 |
| 6.1.8.3 | 6.1.8.4 | 6.1.8.5 | 6.1.8.6 | 6.1.8.7 | 6.1.8.8 | 6.1.8.9 | 6.1.9.1 | 6.1.9.2 | 6.1.9.3 |
| 6.1.9.4 | 6.1.9.5 | 6.1.9.6 | 6.1.9.7 | 6.1.9.8 | 6.1.9.9 | 6.2.1.1 | 6.2.1.2 | 6.2.1.3 | 6.2.1.4 |
| 6.2.1.5 | 6.2.1.6 | 6.2.1.7 | 6.2.1.8 | 6.2.1.9 | 6.2.2.1 | 6.2.2.2 | 6.2.2.3 | 6.2.2.4 | 6.2.2.5 |
| 6.2.2.6 | 6.2.2.7 | 6.2.2.8 | 6.2.2.9 | 6.2.3.1 | 6.2.3.2 | 6.2.3.3 | 6.2.3.4 | 6.2.3.5 | 6.2.3.6 |
| 6.2.3.7 | 6.2.3.8 | 6.2.3.9 | 6.2.4.1 | 6.2.4.2 | 6.2.4.3 | 6.2.4.4 | 6.2.4.5 | 6.2.4.6 | 6.2.4.7 |
| 6.2.4.8 | 6.2.4.9 | 6.2.5.1 | 6.2.5.2 | 6.2.5.3 | 6.2.5.4 | 6.2.5.5 | 6.2.5.6 | 6.2.5.7 | 6.2.5.8 |
| 6.2.5.9 | 6.2.6.1 | 6.2.6.2 | 6.2.6.3 | 6.2.6.4 | 6.2.6.5 | 6.2.6.6 | 6.2.6.7 | 6.2.6.8 | 6.2.6.9 |
| 6.2.7.1 | 6.2.7.2 | 6.2.7.3 | 6.2.7.4 | 6.2.7.5 | 6.2.7.6 | 6.2.7.7 | 6.2.7.8 | 6.2.7.9 | 6.2.8.1 |
| 6.2.8.2 | 6.2.8.3 | 6.2.8.4 | 6.2.8.5 | 6.2.8.6 | 6.2.8.7 | 6.2.8.8 | 6.2.8.9 | 6.2.9.1 | 6.2.9.2 |
| 6.2.9.3 | 6.2.9.4 | 6.2.9.5 | 6.2.9.6 | 6.2.9.7 | 6.2.9.8 | 6.2.9.9 | 6.3.1.1 | 6.3.1.2 | 6.3.1.3 |
| 6.3.1.4 | 6.3.1.5 | 6.3.1.6 | 6.3.1.7 | 6.3.1.8 | 6.3.1.9 | 6.3.2.1 | 6.3.2.2 | 6.3.2.3 | 6.3.2.4 |
| 6.3.2.5 | 6.3.2.6 | 6.3.2.7 | 6.3.2.8 | 6.3.2.9 | 6.3.3.1 | 6.3.3.2 | 6.3.3.3 | 6.3.3.4 | 6.3.3.5 |
| 6.3.3.6 | 6.3.3.7 | 6.3.3.8 | 6.3.3.9 | 6.3.4.1 | 6.3.4.2 | 6.3.4.3 | 6.3.4.4 | 6.3.4.5 | 6.3.4.6 |
| 6.3.4.7 | 6.3.4.8 | 6.3.4.9 | 6.3.5.1 | 6.3.5.2 | 6.3.5.3 | 6.3.5.4 | 6.3.5.5 | 6.3.5.6 | 6.3.5.7 |
| 6.3.5.8 | 6.3.5.9 | 6.3.6.1 | 6.3.6.2 | 6.3.6.3 | 6.3.6.4 | 6.3.6.5 | 6.3.6.6 | 6.3.6.7 | 6.3.6.8 |
| 6.3.6.9 | 6.3.7.1 | 6.3.7.2 | 6.3.7.3 | 6.3.7.4 | 6.3.7.5 | 6.3.7.6 | 6.3.7.7 | 6.3.7.8 | 6.3.7.9 |
| 6.3.8.1 | 6.3.8.2 | 6.3.8.3 | 6.3.8.4 | 6.3.8.5 | 6.3.8.6 | 6.3.8.7 | 6.3.8.8 | 6.3.8.9 | 6.3.9.1 |
| 6.3.9.2 | 6.3.9.3 | 6.3.9.4 | 6.3.9.5 | 6.3.9.6 | 6.3.9.7 | 6.3.9.8 | 6.3.9.9 | 6.4.1.1 | 6.4.1.2 |
| 6.4.1.3 | 6.4.1.4 | 6.4.1.5 | 6.4.1.6 | 6.4.1.7 | 6.4.1.8 | 6.4.1.9 | 6.4.2.1 | 6.4.2.2 | 6.4.2.3 |
| 6.4.2.4 | 6.4.2.5 | 6.4.2.6 | 6.4.2.7 | 6.4.2.8 | 6.4.2.9 | 6.4.3.1 | 6.4.3.2 | 6.4.3.3 | 6.4.3.4 |
| 6.4.3.5 | 6.4.3.6 | 6.4.3.7 | 6.4.3.8 | 6.4.3.9 | 6.4.4.1 | 6.4.4.2 | 6.4.4.3 | 6.4.4.4 | 6.4.4.5 |
| 6.4.4.6 | 6.4.4.7 | 6.4.4.8 | 6.4.4.9 | 6.4.5.1 | 6.4.5.2 | 6.4.5.3 | 6.4.5.4 | 6.4.5.5 | 6.4.5.6 |
| 6.4.5.7 | 6.4.5.8 | 6.4.5.9 | 6.4.6.1 | 6.4.6.2 | 6.4.6.3 | 6.4.6.4 | 6.4.6.5 | 6.4.6.6 | 6.4.6.7 |
| 6.4.6.8 | 6.4.6.9 | 6.4.7.1 | 6.4.7.2 | 6.4.7.3 | 6.4.7.4 | 6.4.7.5 | 6.4.7.6 | 6.4.7.7 | 6.4.7.8 |
| 6.4.7.9 | 6.4.8.1 | 6.4.8.2 | 6.4.8.3 | 6.4.8.4 | 6.4.8.5 | 6.4.8.6 | 6.4.8.7 | 6.4.8.8 | 6.4.8.9 |
| 6.4.9.1 | 6.4.9.2 | 6.4.9.3 | 6.4.9.4 | 6.4.9.5 | 6.4.9.6 | 6.4.9.7 | 6.4.9.8 | 6.4.9.9 | 6.5.1.1 |
| 6.5.1.2 | 6.5.1.3 | 6.5.1.4 | 6.5.1.5 | 6.5.1.6 | 6.5.1.7 | 6.5.1.8 | 6.5.1.9 | 6.5.2.1 | 6.5.2.2 |
| 6.5.2.3 | 6.5.2.4 | 6.5.2.5 | 6.5.2.6 | 6.5.2.7 | 6.5.2.8 | 6.5.2.9 | 6.5.3.1 | 6.5.3.2 | 6.5.3.3 |
| 6.5.3.4 | 6.5.3.5 | 6.5.3.6 | 6.5.3.7 | 6.5.3.8 | 6.5.3.9 | 6.5.4.1 | 6.5.4.2 | 6.5.4.3 | 6.5.4.4 |
| 6.5.4.5 | 6.5.4.6 | 6.5.4.7 | 6.5.4.8 | 6.5.4.9 | 6.5.5.1 | 6.5.5.2 | 6.5.5.3 | 6.5.5.4 | 6.5.5.5 |
| 6.5.5.6 | 6.5.5.7 | 6.5.5.8 | 6.5.5.9 | 6.5.6.1 | 6.5.6.2 | 6.5.6.3 | 6.5.6.4 | 6.5.6.5 | 6.5.6.6 |
| 6.5.6.7 | 6.5.6.8 | 6.5.6.9 | 6.5.7.1 | 6.5.7.2 | 6.5.7.3 | 6.5.7.4 | 6.5.7.5 | 6.5.7.6 | 6.5.7.7 |
| 6.5.7.8 | 6.5.7.9 | 6.5.8.1 | 6.5.8.2 | 6.5.8.3 | 6.5.8.4 | 6.5.8.5 | 6.5.8.6 | 6.5.8.7 | 6.5.8.8 |
| 6.5.8.9 | 6.5.9.1 | 6.5.9.2 | 6.5.9.3 | 6.5.9.4 | 6.5.9.5 | 6.5.9.6 | 6.5.9.7 | 6.5.9.8 | 6.5.9.9 |
| 6.6.1.1 | 6.6.1.2 | 6.6.1.3 | 6.6.1.4 | 6.6.1.5 | 6.6.1.6 | 6.6.1.7 | 6.6.1.8 | 6.6.1.9 | 6.6.2.1 |
| 6.6.2.2 | 6.6.2.3 | 6.6.2.4 | 6.6.2.5 | 6.6.2.6 | 6.6.2.7 | 6.6.2.8 | 6.6.2.9 | 6.6.3.1 | 6.6.3.2 |
| 6.6.3.3 | 6.6.3.4 | 6.6.3.5 | 6.6.3.6 | 6.6.3.7 | 6.6.3.8 | 6.6.3.9 | 6.6.4.1 | 6.6.4.2 | 6.6.4.3 |
| 6.6.4.4 | 6.6.4.5 | 6.6.4.6 | 6.6.4.7 | 6.6.4.8 | 6.6.4.9 | 6.6.5.1 | 6.6.5.2 | 6.6.5.3 | 6.6.5.4 |
| 6.6.5.5 | 6.6.5.6 | 6.6.5.7 | 6.6.5.8 | 6.6.5.9 | 6.6.6.1 | 6.6.6.2 | 6.6.6.3 | 6.6.6.4 | 6.6.6.5 |
| 6.6.6.6 | 6.6.6.7 | 6.6.6.8 | 6.6.6.9 | 6.6.7.1 | 6.6.7.2 | 6.6.7.3 | 6.6.7.4 | 6.6.7.5 | 6.6.7.6 |
| 6.6.7.7 | 6.6.7.8 | 6.6.7.9 | 6.6.8.1 | 6.6.8.2 | 6.6.8.3 | 6.6.8.4 | 6.6.8.5 | 6.6.8.6 | 6.6.8.7 |
| 6.6.8.8 | 6.6.8.9 | 6.6.9.1 | 6.6.9.2 | 6.6.9.3 | 6.6.9.4 | 6.6.9.5 | 6.6.9.6 | 6.6.9.7 | 6.6.9.8 |
| 6.6.9.9 | 6.7.1.1 | 6.7.1.2 | 6.7.1.3 | 6.7.1.4 | 6.7.1.5 | 6.7.1.6 | 6.7.1.7 | 6.7.1.8 | 6.7.1.9 |
| 6.7.2.1 | 6.7.2.2 | 6.7.2.3 | 6.7.2.4 | 6.7.2.5 | 6.7.2.6 | 6.7.2.7 | 6.7.2.8 | 6.7.2.9 | 6.7.3.1 |
| 6.7.3.2 | 6.7.3.3 | 6.7.3.4 | 6.7.3.5 | 6.7.3.6 | 6.7.3.7 | 6.7.3.8 | 6.7.3.9 | 6.7.4.1 | 6.7.4.2 |
| 6.7.4.3 | 6.7.4.4 | 6.7.4.5 | 6.7.4.6 | 6.7.4.7 | 6.7.4.8 | 6.7.4.9 | 6.7.5.1 | 6.7.5.2 | 6.7.5.3 |
| 6.7.5.4 | 6.7.5.5 | 6.7.5.6 | 6.7.5.7 | 6.7.5.8 | 6.7.5.9 | 6.7.6.1 | 6.7.6.2 | 6.7.6.3 | 6.7.6.4 |
| 6.7.6.5 | 6.7.6.6 | 6.7.6.7 | 6.7.6.8 | 6.7.6.9 | 6.7.7.1 | 6.7.7.2 | 6.7.7.3 | 6.7.7.4 | 6.7.7.5 |
| 6.7.7.6 | 6.7.7.7 | 6.7.7.8 | 6.7.7.9 | 6.7.8.1 | 6.7.8.2 | 6.7.8.3 | 6.7.8.4 | 6.7.8.5 | 6.7.8.6 |
| 6.7.8.7 | 6.7.8.8 | 6.7.8.9 | 6.7.9.1 | 6.7.9.2 | 6.7.9.3 | 6.7.9.4 | 6.7.9.5 | 6.7.9.6 | 6.7.9.7 |
| 6.7.9.8 | 6.7.9.9 | 6.8.1.1 | 6.8.1.2 | 6.8.1.3 | 6.8.1.4 | 6.8.1.5 | 6.8.1.6 | 6.8.1.7 | 6.8.1.8 |
| 6.8.1.9 | 6.8.2.1 | 6.8.2.2 | 6.8.2.3 | 6.8.2.4 | 6.8.2.5 | 6.8.2.6 | 6.8.2.7 | 6.8.2.8 | 6.8.2.9 |

TABLE 1-continued

| | | | | | | | | | |
|---|---|---|---|---|---|---|---|---|---|
| 6.8.3.1 | 6.8.3.2 | 6.8.3.3 | 6.8.3.4 | 6.8.3.5 | 6.8.3.6 | 6.8.3.7 | 6.8.3.8 | 6.8.3.9 | 6.8.4.1 |
| 6.8.4.2 | 6.8.4.3 | 6.8.4.4 | 6.8.4.5 | 6.8.4.6 | 6.8.4.7 | 6.8.4.8 | 6.8.4.9 | 6.8.5.1 | 6.8.5.2 |
| 6.8.5.3 | 6.8.5.4 | 6.8.5.5 | 6.8.5.6 | 6.8.5.7 | 6.8.5.8 | 6.8.5.9 | 6.8.6.1 | 6.8.6.2 | 6.8.6.3 |
| 6.8.6.4 | 6.8.6.5 | 6.8.6.6 | 6.8.6.7 | 6.8.6.8 | 6.8.6.9 | 6.8.7.1 | 6.8.7.2 | 6.8.7.3 | 6.8.7.4 |
| 6.8.7.5 | 6.8.7.6 | 6.8.7.7 | 6.8.7.8 | 6.8.7.9 | 6.8.8.1 | 6.8.8.2 | 6.8.8.3 | 6.8.8.4 | 6.8.8.5 |
| 6.8.8.6 | 6.8.8.7 | 6.8.8.8 | 6.8.8.9 | 6.8.9.1 | 6.8.9.2 | 6.8.9.3 | 6.8.9.4 | 6.8.9.5 | 6.8.9.6 |
| 6.8.9.7 | 6.8.9.8 | 6.8.9.9 | 6.9.1.1 | 6.9.1.2 | 6.9.1.3 | 6.9.1.4 | 6.9.1.5 | 6.9.1.6 | 6.9.1.7 |
| 6.9.1.8 | 6.9.1.9 | 6.9.2.1 | 6.9.2.2 | 6.9.2.3 | 6.9.2.4 | 6.9.2.5 | 6.9.2.6 | 6.9.2.7 | 6.9.2.8 |
| 6.9.2.9 | 6.9.3.1 | 6.9.3.2 | 6.9.3.3 | 6.9.3.4 | 6.9.3.5 | 6.9.3.6 | 6.9.3.7 | 6.9.3.8 | 6.9.3.9 |
| 6.9.4.1 | 6.9.4.2 | 6.9.4.3 | 6.9.4.4 | 6.9.4.5 | 6.9.4.6 | 6.9.4.7 | 6.9.4.8 | 6.9.4.9 | 6.9.5.1 |
| 6.9.5.2 | 6.9.5.3 | 6.9.5.4 | 6.9.5.5 | 6.9.5.6 | 6.9.5.7 | 6.9.5.8 | 6.9.5.9 | 6.9.6.1 | 6.9.6.2 |
| 6.9.6.3 | 6.9.6.4 | 6.9.6.5 | 6.9.6.6 | 6.9.6.7 | 6.9.6.8 | 6.9.6.9 | 6.9.7.1 | 6.9.7.2 | 6.9.7.3 |
| 6.9.7.4 | 6.9.7.5 | 6.9.7.6 | 6.9.7.7 | 6.9.7.8 | 6.9.7.9 | 6.9.8.1 | 6.9.8.2 | 6.9.8.3 | 6.9.8.4 |
| 6.9.8.5 | 6.9.8.6 | 6.9.8.7 | 6.9.8.8 | 6.9.8.9 | 6.9.9.1 | 6.9.9.2 | 6.9.9.3 | 6.9.9.4 | 6.9.9.5 |
| 6.9.9.6 | 6.9.9.7 | 6.9.9.8 | 6.9.9.9 | 7.1.1.1 | 7.1.1.2 | 7.1.1.3 | 7.1.1.4 | 7.1.1.5 | 7.1.1.6 |
| 7.1.1.7 | 7.1.1.8 | 7.1.1.9 | 7.1.2.1 | 7.1.2.2 | 7.1.2.3 | 7.1.2.4 | 7.1.2.5 | 7.1.2.6 | 7.1.2.7 |
| 7.1.2.8 | 7.1.2.9 | 7.1.3.1 | 7.1.3.2 | 7.1.3.3 | 7.1.3.4 | 7.1.3.5 | 7.1.3.6 | 7.1.3.7 | 7.1.3.8 |
| 7.1.3.9 | 7.1.4.1 | 7.1.4.2 | 7.1.4.3 | 7.1.4.4 | 7.1.4.5 | 7.1.4.6 | 7.1.4.7 | 7.1.4.8 | 7.1.4.9 |
| 7.1.5.1 | 7.1.5.2 | 7.1.5.3 | 7.1.5.4 | 7.1.5.5 | 7.1.5.6 | 7.1.5.7 | 7.1.5.8 | 7.1.5.9 | 7.1.6.1 |
| 7.1.6.2 | 7.1.6.3 | 7.1.6.4 | 7.1.6.5 | 7.1.6.6 | 7.1.6.7 | 7.1.6.8 | 7.1.6.9 | 7.1.7.1 | 7.1.7.2 |
| 7.1.7.3 | 7.1.7.4 | 7.1.7.5 | 7.1.7.6 | 7.1.7.7 | 7.1.7.8 | 7.1.7.9 | 7.1.8.1 | 7.1.8.2 | 7.1.8.3 |
| 7.1.8.4 | 7.1.8.5 | 7.1.8.6 | 7.1.8.7 | 7.1.8.8 | 7.1.8.9 | 7.1.9.1 | 7.1.9.2 | 7.1.9.3 | 7.1.9.4 |
| 7.1.9.5 | 7.1.9.6 | 7.1.9.7 | 7.1.9.8 | 7.1.9.9 | 7.2.1.1 | 7.2.1.2 | 7.2.1.3 | 7.2.1.4 | 7.2.1.5 |
| 7.2.1.6 | 7.2.1.7 | 7.2.1.8 | 7.2.1.9 | 7.2.2.1 | 7.2.2.2 | 7.2.2.3 | 7.2.2.4 | 7.2.2.5 | 7.2.2.6 |
| 7.2.2.7 | 7.2.2.8 | 7.2.2.9 | 7.2.3.1 | 7.2.3.2 | 7.2.3.3 | 7.2.3.4 | 7.2.3.5 | 7.2.3.6 | 7.2.3.7 |
| 7.2.3.8 | 7.2.3.9 | 7.2.4.1 | 7.2.4.2 | 7.2.4.3 | 7.2.4.4 | 7.2.4.5 | 7.2.4.6 | 7.2.4.7 | 7.2.4.8 |
| 7.2.4.9 | 7.2.5.1 | 7.2.5.2 | 7.2.5.3 | 7.2.5.4 | 7.2.5.5 | 7.2.5.6 | 7.2.5.7 | 7.2.5.8 | 7.2.5.9 |
| 7.2.6.1 | 7.2.6.2 | 7.2.6.3 | 7.2.6.4 | 7.2.6.5 | 7.2.6.6 | 7.2.6.7 | 7.2.6.8 | 7.2.6.9 | 7.2.7.1 |
| 7.2.7.2 | 7.2.7.3 | 7.2.7.4 | 7.2.7.5 | 7.2.7.6 | 7.2.7.7 | 7.2.7.8 | 7.2.7.9 | 7.2.8.1 | 7.2.8.2 |
| 7.2.8.3 | 7.2.8.4 | 7.2.8.5 | 7.2.8.6 | 7.2.8.7 | 7.2.8.8 | 7.2.8.9 | 7.2.9.1 | 7.2.9.2 | 7.2.9.3 |
| 7.2.9.4 | 7.2.9.5 | 7.2.9.6 | 7.2.9.7 | 7.2.9.8 | 7.2.9.9 | 7.3.1.1 | 7.3.1.2 | 7.3.1.3 | 7.3.1.4 |
| 7.3.1.5 | 7.3.1.6 | 7.3.1.7 | 7.3.1.8 | 7.3.1.9 | 7.3.2.1 | 7.3.2.2 | 7.3.2.3 | 7.3.2.4 | 7.3.2.5 |
| 7.3.2.6 | 7.3.2.7 | 7.3.2.8 | 7.3.2.9 | 7.3.3.1 | 7.3.3.2 | 7.3.3.3 | 7.3.3.4 | 7.3.3.5 | 7.3.3.6 |
| 7.3.3.7 | 7.3.3.8 | 7.3.3.9 | 7.3.4.1 | 7.3.4.2 | 7.3.4.3 | 7.3.4.4 | 7.3.4.5 | 7.3.4.6 | 7.3.4.7 |
| 7.3.4.8 | 7.3.4.9 | 7.3.5.1 | 7.3.5.2 | 7.3.5.3 | 7.3.5.4 | 7.3.5.5 | 7.3.5.6 | 7.3.5.7 | 7.3.5.8 |
| 7.3.5.9 | 7.3.6.1 | 7.3.6.2 | 7.3.6.3 | 7.3.6.4 | 7.3.6.5 | 7.3.6.6 | 7.3.6.7 | 7.3.6.8 | 7.3.6.9 |
| 7.3.7.1 | 7.3.7.2 | 7.3.7.3 | 7.3.7.4 | 7.3.7.5 | 7.3.7.6 | 7.3.7.7 | 7.3.7.8 | 7.3.7.9 | 7.3.8.1 |
| 7.3.8.2 | 7.3.8.3 | 7.3.8.4 | 7.3.8.5 | 7.3.8.6 | 7.3.8.7 | 7.3.8.8 | 7.3.8.9 | 7.3.9.1 | 7.3.9.2 |
| 7.3.9.3 | 7.3.9.4 | 7.3.9.5 | 7.3.9.6 | 7.3.9.7 | 7.3.9.8 | 7.3.9.9 | 7.4.1.1 | 7.4.1.2 | 7.4.1.3 |
| 7.4.1.4 | 7.4.1.5 | 7.4.1.6 | 7.4.1.7 | 7.4.1.8 | 7.4.1.9 | 7.4.2.1 | 7.4.2.2 | 7.4.2.3 | 7.4.2.4 |
| 7.4.2.5 | 7.4.2.6 | 7.4.2.7 | 7.4.2.8 | 7.4.2.9 | 7.4.3.1 | 7.4.3.2 | 7.4.3.3 | 7.4.3.4 | 7.4.3.5 |
| 7.4.3.6 | 7.4.3.7 | 7.4.3.8 | 7.4.3.9 | 7.4.4.1 | 7.4.4.2 | 7.4.4.3 | 7.4.4.4 | 7.4.4.5 | 7.4.4.6 |
| 7.4.4.7 | 7.4.4.8 | 7.4.4.9 | 7.4.5.1 | 7.4.5.2 | 7.4.5.3 | 7.4.5.4 | 7.4.5.5 | 7.4.5.6 | 7.4.5.7 |
| 7.4.5.8 | 7.4.5.9 | 7.4.6.1 | 7.4.6.2 | 7.4.6.3 | 7.4.6.4 | 7.4.6.5 | 7.4.6.6 | 7.4.6.7 | 7.4.6.8 |
| 7.4.6.9 | 7.4.7.1 | 7.4.7.2 | 7.4.7.3 | 7.4.7.4 | 7.4.7.5 | 7.4.7.6 | 7.4.7.7 | 7.4.7.8 | 7.4.7.9 |
| 7.4.8.1 | 7.4.8.2 | 7.4.8.3 | 7.4.8.4 | 7.4.8.5 | 7.4.8.6 | 7.4.8.7 | 7.4.8.8 | 7.4.8.9 | 7.4.9.1 |
| 7.4.9.2 | 7.4.9.3 | 7.4.9.4 | 7.4.9.5 | 7.4.9.6 | 7.4.9.7 | 7.4.9.8 | 7.4.9.9 | 7.5.1.1 | 7.5.1.2 |
| 7.5.1.3 | 7.5.1.4 | 7.5.1.5 | 7.5.1.6 | 7.5.1.7 | 7.5.1.8 | 7.5.1.9 | 7.5.2.1 | 7.5.2.2 | 7.5.2.3 |
| 7.5.2.4 | 7.5.2.5 | 7.5.2.6 | 7.5.2.7 | 7.5.2.8 | 7.5.2.9 | 7.5.3.1 | 7.5.3.2 | 7.5.3.3 | 7.5.3.4 |
| 7.5.3.5 | 7.5.3.6 | 7.5.3.7 | 7.5.3.8 | 7.5.3.9 | 7.5.4.1 | 7.5.4.2 | 7.5.4.3 | 7.5.4.4 | 7.5.4.5 |
| 7.5.4.6 | 7.5.4.7 | 7.5.4.8 | 7.5.4.9 | 7.5.5.1 | 7.5.5.2 | 7.5.5.3 | 7.5.5.4 | 7.5.5.5 | 7.5.5.6 |
| 7.5.5.7 | 7.5.5.8 | 7.5.5.9 | 7.5.6.1 | 7.5.6.2 | 7.5.6.3 | 7.5.6.4 | 7.5.6.5 | 7.5.6.6 | 7.5.6.7 |
| 7.5.6.8 | 7.5.6.9 | 7.5.7.1 | 7.5.7.2 | 7.5.7.3 | 7.5.7.4 | 7.5.7.5 | 7.5.7.6 | 7.5.7.7 | 7.5.7.8 |
| 7.5.7.9 | 7.5.8.1 | 7.5.8.2 | 7.5.8.3 | 7.5.8.4 | 7.5.8.5 | 7.5.8.6 | 7.5.8.7 | 7.5.8.8 | 7.5.8.9 |
| 7.5.9.1 | 7.5.9.2 | 7.5.9.3 | 7.5.9.4 | 7.5.9.5 | 7.5.9.6 | 7.5.9.7 | 7.5.9.8 | 7.5.9.9 | 7.6.1.1 |
| 7.6.1.2 | 7.6.1.3 | 7.6.1.4 | 7.6.1.5 | 7.6.1.6 | 7.6.1.7 | 7.6.1.8 | 7.6.1.9 | 7.6.2.1 | 7.6.2.2 |
| 7.6.2.3 | 7.6.2.4 | 7.6.2.5 | 7.6.2.6 | 7.6.2.7 | 7.6.2.8 | 7.6.2.9 | 7.6.3.1 | 7.6.3.2 | 7.6.3.3 |
| 7.6.3.4 | 7.6.3.5 | 7.6.3.6 | 7.6.3.7 | 7.6.3.8 | 7.6.3.9 | 7.6.4.1 | 7.6.4.2 | 7.6.4.3 | 7.6.4.4 |
| 7.6.4.5 | 7.6.4.6 | 7.6.4.7 | 7.6.4.8 | 7.6.4.9 | 7.6.5.1 | 7.6.5.2 | 7.6.5.3 | 7.6.5.4 | 7.6.5.5 |
| 7.6.5.6 | 7.6.5.7 | 7.6.5.8 | 7.6.5.9 | 7.6.6.1 | 7.6.6.2 | 7.6.6.3 | 7.6.6.4 | 7.6.6.5 | 7.6.6.6 |
| 7.6.6.7 | 7.6.6.8 | 7.6.6.9 | 7.6.7.1 | 7.6.7.2 | 7.6.7.3 | 7.6.7.4 | 7.6.7.5 | 7.6.7.6 | 7.6.7.7 |
| 7.6.7.8 | 7.6.7.9 | 7.6.8.1 | 7.6.8.2 | 7.6.8.3 | 7.6.8.4 | 7.6.8.5 | 7.6.8.6 | 7.6.8.7 | 7.6.8.8 |
| 7.6.8.9 | 7.6.9.1 | 7.6.9.2 | 7.6.9.3 | 7.6.9.4 | 7.6.9.5 | 7.6.9.6 | 7.6.9.7 | 7.6.9.8 | 7.6.9.9 |
| 7.7.1.1 | 7.7.1.2 | 7.7.1.3 | 7.7.1.4 | 7.7.1.5 | 7.7.1.6 | 7.7.1.7 | 7.7.1.8 | 7.7.1.9 | 7.7.2.1 |
| 7.7.2.2 | 7.7.2.3 | 7.7.2.4 | 7.7.2.5 | 7.7.2.6 | 7.7.2.7 | 7.7.2.8 | 7.7.2.9 | 7.7.3.1 | 7.7.3.2 |
| 7.7.3.3 | 7.7.3.4 | 7.7.3.5 | 7.7.3.6 | 7.7.3.7 | 7.7.3.8 | 7.7.3.9 | 7.7.4.1 | 7.7.4.2 | 7.7.4.3 |
| 7.7.4.4 | 7.7.4.5 | 7.7.4.6 | 7.7.4.7 | 7.7.4.8 | 7.7.4.9 | 7.7.5.1 | 7.7.5.2 | 7.7.5.3 | 7.7.5.4 |
| 7.7.5.5 | 7.7.5.6 | 7.7.5.7 | 7.7.5.8 | 7.7.5.9 | 7.7.6.1 | 7.7.6.2 | 7.7.6.3 | 7.7.6.4 | 7.7.6.5 |
| 7.7.6.6 | 7.7.6.7 | 7.7.6.8 | 7.7.6.9 | 7.7.7.1 | 7.7.7.2 | 7.7.7.3 | 7.7.7.4 | 7.7.7.5 | 7.7.7.6 |
| 7.7.7.7 | 7.7.7.8 | 7.7.7.9 | 7.7.8.1 | 7.7.8.2 | 7.7.8.3 | 7.7.8.4 | 7.7.8.5 | 7.7.8.6 | 7.7.8.7 |
| 7.7.8.8 | 7.7.8.9 | 7.7.9.1 | 7.7.9.2 | 7.7.9.3 | 7.7.9.4 | 7.7.9.5 | 7.7.9.6 | 7.7.9.7 | 7.7.9.8 |
| 7.7.9.9 | 7.8.1.1 | 7.8.1.2 | 7.8.1.3 | 7.8.1.4 | 7.8.1.5 | 7.8.1.6 | 7.8.1.7 | 7.8.1.8 | 7.8.1.9 |
| 7.8.2.1 | 7.8.2.2 | 7.8.2.3 | 7.8.2.4 | 7.8.2.5 | 7.8.2.6 | 7.8.2.7 | 7.8.2.8 | 7.8.2.9 | 7.8.3.1 |
| 7.8.3.2 | 7.8.3.3 | 7.8.3.4 | 7.8.3.5 | 7.8.3.6 | 7.8.3.7 | 7.8.3.8 | 7.8.3.9 | 7.8.4.1 | 7.8.4.2 |
| 7.8.4.3 | 7.8.4.4 | 7.8.4.5 | 7.8.4.6 | 7.8.4.7 | 7.8.4.8 | 7.8.4.9 | 7.8.5.1 | 7.8.5.2 | 7.8.5.3 |
| 7.8.5.4 | 7.8.5.5 | 7.8.5.6 | 7.8.5.7 | 7.8.5.8 | 7.8.5.9 | 7.8.6.1 | 7.8.6.2 | 7.8.6.3 | 7.8.6.4 |
| 7.8.6.5 | 7.8.6.6 | 7.8.6.7 | 7.8.6.8 | 7.8.6.9 | 7.8.7.1 | 7.8.7.2 | 7.8.7.3 | 7.8.7.4 | 7.8.7.5 |
| 7.8.7.6 | 7.8.7.7 | 7.8.7.8 | 7.8.7.9 | 7.8.8.1 | 7.8.8.2 | 7.8.8.3 | 7.8.8.4 | 7.8.8.5 | 7.8.8.6 |
| 7.8.8.7 | 7.8.8.8 | 7.8.8.9 | 7.8.9.1 | 7.8.9.2 | 7.8.9.3 | 7.8.9.4 | 7.8.9.5 | 7.8.9.6 | 7.8.9.7 |
| 7.8.9.8 | 7.8.9.9 | 7.9.1.1 | 7.9.1.2 | 7.9.1.3 | 7.9.1.4 | 7.9.1.5 | 7.9.1.6 | 7.9.1.7 | 7.9.1.8 |

TABLE 1-continued

| | | | | | | | | |
|---|---|---|---|---|---|---|---|---|
| 7.9.1.9 | 7.9.2.1 | 7.9.2.2 | 7.9.2.3 | 7.9.2.4 | 7.9.2.5 | 7.9.2.6 | 7.9.2.7 | 7.9.2.8 | 7.9.2.9 |
| 7.9.3.1 | 7.9.3.2 | 7.9.3.3 | 7.9.3.4 | 7.9.3.5 | 7.9.3.6 | 7.9.3.7 | 7.9.3.8 | 7.9.3.9 | 7.9.4.1 |
| 7.9.4.2 | 7.9.4.3 | 7.9.4.4 | 7.9.4.5 | 7.9.4.6 | 7.9.4.7 | 7.9.4.8 | 7.9.4.9 | 7.9.5.1 | 7.9.5.2 |
| 7.9.5.3 | 7.9.5.4 | 7.9.5.5 | 7.9.5.6 | 7.9.5.7 | 7.9.5.8 | 7.9.5.9 | 7.9.6.1 | 7.9.6.2 | 7.9.6.3 |
| 7.9.6.4 | 7.9.6.5 | 7.9.6.6 | 7.9.6.7 | 7.9.6.8 | 7.9.6.9 | 7.9.7.1 | 7.9.7.2 | 7.9.7.3 | 7.9.7.4 |
| 7.9.7.5 | 7.9.7.6 | 7.9.7.7 | 7.9.7.8 | 7.9.7.9 | 7.9.8.1 | 7.9.8.2 | 7.9.8.3 | 7.9.8.4 | 7.9.8.5 |
| 7.9.8.6 | 7.9.8.7 | 7.9.8.8 | 7.9.8.9 | 7.9.9.1 | 7.9.9.2 | 7.9.9.3 | 7.9.9.4 | 7.9.9.5 | 7.9.9.6 |
| 7.9.9.7 | 7.9.9.8 | 7.9.9.9 | 8.1.1.1 | 8.1.1.2 | 8.1.1.3 | 8.1.1.4 | 8.1.1.5 | 8.1.1.6 | 8.1.1.7 |
| 8.1.1.8 | 8.1.1.9 | 8.1.2.1 | 8.1.2.2 | 8.1.2.3 | 8.1.2.4 | 8.1.2.5 | 8.1.2.6 | 8.1.2.7 | 8.1.2.8 |
| 8.1.2.9 | 8.1.3.1 | 8.1.3.2 | 8.1.3.3 | 8.1.3.4 | 8.1.3.5 | 8.1.3.6 | 8.1.3.7 | 8.1.3.8 | 8.1.3.9 |
| 8.1.4.1 | 8.1.4.2 | 8.1.4.3 | 8.1.4.4 | 8.1.4.5 | 8.1.4.6 | 8.1.4.7 | 8.1.4.8 | 8.1.4.9 | 8.1.5.1 |
| 8.1.5.2 | 8.1.5.3 | 8.1.5.4 | 8.1.5.5 | 8.1.5.6 | 8.1.5.7 | 8.1.5.8 | 8.1.5.9 | 8.1.6.1 | 8.1.6.2 |
| 8.1.6.3 | 8.1.6.4 | 8.1.6.5 | 8.1.6.6 | 8.1.6.7 | 8.1.6.8 | 8.1.6.9 | 8.1.7.1 | 8.1.7.2 | 8.1.7.3 |
| 8.1.7.4 | 8.1.7.5 | 8.1.7.6 | 8.1.7.7 | 8.1.7.8 | 8.1.7.9 | 8.1.8.1 | 8.1.8.2 | 8.1.8.3 | 8.1.8.4 |
| 8.1.8.5 | 8.1.8.6 | 8.1.8.7 | 8.1.8.8 | 8.1.8.9 | 8.1.9.1 | 8.1.9.2 | 8.1.9.3 | 8.1.9.4 | 8.1.9.5 |
| 8.1.9.6 | 8.1.9.7 | 8.1.9.8 | 8.1.9.9 | 8.2.1.1 | 8.2.1.2 | 8.2.1.3 | 8.2.1.4 | 8.2.1.5 | 8.2.1.6 |
| 8.2.1.7 | 8.2.1.8 | 8.2.1.9 | 8.2.2.1 | 8.2.2.2 | 8.2.2.3 | 8.2.2.4 | 8.2.2.5 | 8.2.2.6 | 8.2.2.7 |
| 8.2.2.8 | 8.2.2.9 | 8.2.3.1 | 8.2.3.2 | 8.2.3.3 | 8.2.3.4 | 8.2.3.5 | 8.2.3.6 | 8.2.3.7 | 8.2.3.8 |
| 8.2.3.9 | 8.2.4.1 | 8.2.4.2 | 8.2.4.3 | 8.2.4.4 | 8.2.4.5 | 8.2.4.6 | 8.2.4.7 | 8.2.4.8 | 8.2.4.9 |
| 8.2.5.1 | 8.2.5.2 | 8.2.5.3 | 8.2.5.4 | 8.2.5.5 | 8.2.5.6 | 8.2.5.7 | 8.2.5.8 | 8.2.5.9 | 8.2.6.1 |
| 8.2.6.2 | 8.2.6.3 | 8.2.6.4 | 8.2.6.5 | 8.2.6.6 | 8.2.6.7 | 8.2.6.8 | 8.2.6.9 | 8.2.7.1 | 8.2.7.2 |
| 8.2.7.3 | 8.2.7.4 | 8.2.7.5 | 8.2.7.6 | 8.2.7.7 | 8.2.7.8 | 8.2.7.9 | 8.2.8.1 | 8.2.8.2 | 8.2.8.3 |
| 8.2.8.4 | 8.2.8.5 | 8.2.8.6 | 8.2.8.7 | 8.2.8.8 | 8.2.8.9 | 8.2.9.1 | 8.2.9.2 | 8.2.9.3 | 8.2.9.4 |
| 8.2.9.5 | 8.2.9.6 | 8.2.9.7 | 8.2.9.8 | 8.2.9.9 | 8.3.1.1 | 8.3.1.2 | 8.3.1.3 | 8.3.1.4 | 8.3.1.5 |
| 8.3.1.6 | 8.3.1.7 | 8.3.1.8 | 8.3.1.9 | 8.3.2.1 | 8.3.2.2 | 8.3.2.3 | 8.3.2.4 | 8.3.2.5 | 8.3.2.6 |
| 8.3.2.7 | 8.3.2.8 | 8.3.2.9 | 8.3.3.1 | 8.3.3.2 | 8.3.3.3 | 8.3.3.4 | 8.3.3.5 | 8.3.3.6 | 8.3.3.7 |
| 8.3.3.8 | 8.3.3.9 | 8.3.4.1 | 8.3.4.2 | 8.3.4.3 | 8.3.4.4 | 8.3.4.5 | 8.3.4.6 | 8.3.4.7 | 8.3.4.8 |
| 8.3.4.9 | 8.3.5.1 | 8.3.5.2 | 8.3.5.3 | 8.3.5.4 | 8.3.5.5 | 8.3.5.6 | 8.3.5.7 | 8.3.5.8 | 8.3.5.9 |
| 8.3.6.1 | 8.3.6.2 | 8.3.6.3 | 8.3.6.4 | 8.3.6.5 | 8.3.6.6 | 8.3.6.7 | 8.3.6.8 | 8.3.6.9 | 8.3.7.1 |
| 8.3.7.2 | 8.3.7.3 | 8.3.7.4 | 8.3.7.5 | 8.3.7.6 | 8.3.7.7 | 8.3.7.8 | 8.3.7.9 | 8.3.8.1 | 8.3.8.2 |
| 8.3.8.3 | 8.3.8.4 | 8.3.8.5 | 8.3.8.6 | 8.3.8.7 | 8.3.8.8 | 8.3.8.9 | 8.3.9.1 | 8.3.9.2 | 8.3.9.3 |
| 8.3.9.4 | 8.3.9.5 | 8.3.9.6 | 8.3.9.7 | 8.3.9.8 | 8.3.9.9 | 8.4.1.1 | 8.4.1.2 | 8.4.1.3 | 8.4.1.4 |
| 8.4.1.5 | 8.4.1.6 | 8.4.1.7 | 8.4.1.8 | 8.4.1.9 | 8.4.2.1 | 8.4.2.2 | 8.4.2.3 | 8.4.2.4 | 8.4.2.5 |
| 8.4.2.6 | 8.4.2.7 | 8.4.2.8 | 8.4.2.9 | 8.4.3.1 | 8.4.3.2 | 8.4.3.3 | 8.4.3.4 | 8.4.3.5 | 8.4.3.6 |
| 8.4.3.7 | 8.4.3.8 | 8.4.3.9 | 8.4.4.1 | 8.4.4.2 | 8.4.4.3 | 8.4.4.4 | 8.4.4.5 | 8.4.4.6 | 8.4.4.7 |
| 8.4.4.8 | 8.4.4.9 | 8.4.5.1 | 8.4.5.2 | 8.4.5.3 | 8.4.5.4 | 8.4.5.5 | 8.4.5.6 | 8.4.5.7 | 8.4.5.8 |
| 8.4.5.9 | 8.4.6.1 | 8.4.6.2 | 8.4.6.3 | 8.4.6.4 | 8.4.6.5 | 8.4.6.6 | 8.4.6.7 | 8.4.6.8 | 8.4.6.9 |
| 8.4.7.1 | 8.4.7.2 | 8.4.7.3 | 8.4.7.4 | 8.4.7.5 | 8.4.7.6 | 8.4.7.7 | 8.4.7.8 | 8.4.7.9 | 8.4.8.1 |
| 8.4.8.2 | 8.4.8.3 | 8.4.8.4 | 8.4.8.5 | 8.4.8.6 | 8.4.8.7 | 8.4.8.8 | 8.4.8.9 | 8.4.9.1 | 8.4.9.2 |
| 8.4.9.3 | 8.4.9.4 | 8.4.9.5 | 8.4.9.6 | 8.4.9.7 | 8.4.9.8 | 8.4.9.9 | 8.5.1.1 | 8.5.1.2 | 8.5.1.3 |
| 8.5.1.4 | 8.5.1.5 | 8.5.1.6 | 8.5.1.7 | 8.5.1.8 | 8.5.1.9 | 8.5.2.1 | 8.5.2.2 | 8.5.2.3 | 8.5.2.4 |
| 8.5.2.5 | 8.5.2.6 | 8.5.2.7 | 8.5.2.8 | 8.5.2.9 | 8.5.3.1 | 8.5.3.2 | 8.5.3.3 | 8.5.3.4 | 8.5.3.5 |
| 8.5.3.6 | 8.5.3.7 | 8.5.3.8 | 8.5.3.9 | 8.5.4.1 | 8.5.4.2 | 8.5.4.3 | 8.5.4.4 | 8.5.4.5 | 8.5.4.6 |
| 8.5.4.7 | 8.5.4.8 | 8.5.4.9 | 8.5.5.1 | 8.5.5.2 | 8.5.5.3 | 8.5.5.4 | 8.5.5.5 | 8.5.5.6 | 8.5.5.7 |
| 8.5.5.8 | 8.5.5.9 | 8.5.6.1 | 8.5.6.2 | 8.5.6.3 | 8.5.6.4 | 8.5.6.5 | 8.5.6.6 | 8.5.6.7 | 8.5.6.8 |
| 8.5.6.9 | 8.5.7.1 | 8.5.7.2 | 8.5.7.3 | 8.5.7.4 | 8.5.7.5 | 8.5.7.6 | 8.5.7.7 | 8.5.7.8 | 8.5.7.9 |
| 8.5.8.1 | 8.5.8.2 | 8.5.8.3 | 8.5.8.4 | 8.5.8.5 | 8.5.8.6 | 8.5.8.7 | 8.5.8.8 | 8.5.8.9 | 8.5.9.1 |
| 8.5.9.2 | 8.5.9.3 | 8.5.9.4 | 8.5.9.5 | 8.5.9.6 | 8.5.9.7 | 8.5.9.8 | 8.5.9.9 | 8.6.1.1 | 8.6.1.2 |
| 8.6.1.3 | 8.6.1.4 | 8.6.1.5 | 8.6.1.6 | 8.6.1.7 | 8.6.1.8 | 8.6.1.9 | 8.6.2.1 | 8.6.2.2 | 8.6.2.3 |
| 8.6.2.4 | 8.6.2.5 | 8.6.2.6 | 8.6.2.7 | 8.6.2.8 | 8.6.2.9 | 8.6.3.1 | 8.6.3.2 | 8.6.3.3 | 8.6.3.4 |
| 8.6.3.5 | 8.6.3.6 | 8.6.3.7 | 8.6.3.8 | 8.6.3.9 | 8.6.4.1 | 8.6.4.2 | 8.6.4.3 | 8.6.4.4 | 8.6.4.5 |
| 8.6.4.6 | 8.6.4.7 | 8.6.4.8 | 8.6.4.9 | 8.6.5.1 | 8.6.5.2 | 8.6.5.3 | 8.6.5.4 | 8.6.5.5 | 8.6.5.6 |
| 8.6.5.7 | 8.6.5.8 | 8.6.5.9 | 8.6.6.1 | 8.6.6.2 | 8.6.6.3 | 8.6.6.4 | 8.6.6.5 | 8.6.6.6 | 8.6.6.7 |
| 8.6.6.8 | 8.6.6.9 | 8.6.7.1 | 8.6.7.2 | 8.6.7.3 | 8.6.7.4 | 8.6.7.5 | 8.6.7.6 | 8.6.7.7 | 8.6.7.8 |
| 8.6.7.9 | 8.6.8.1 | 8.6.8.2 | 8.6.8.3 | 8.6.8.4 | 8.6.8.5 | 8.6.8.6 | 8.6.8.7 | 8.6.8.8 | 8.6.8.9 |
| 8.6.9.1 | 8.6.9.2 | 8.6.9.3 | 8.6.9.4 | 8.6.9.5 | 8.6.9.6 | 8.6.9.7 | 8.6.9.8 | 8.6.9.9 | 8.7.1.1 |
| 8.7.1.2 | 8.7.1.3 | 8.7.1.4 | 8.7.1.5 | 8.7.1.6 | 8.7.1.7 | 8.7.1.8 | 8.7.1.9 | 8.7.2.1 | 8.7.2.2 |
| 8.7.2.3 | 8.7.2.4 | 8.7.2.5 | 8.7.2.6 | 8.7.2.7 | 8.7.2.8 | 8.7.2.9 | 8.7.3.1 | 8.7.3.2 | 8.7.3.3 |
| 8.7.3.4 | 8.7.3.5 | 8.7.3.6 | 8.7.3.7 | 8.7.3.8 | 8.7.3.9 | 8.7.4.1 | 8.7.4.2 | 8.7.4.3 | 8.7.4.4 |
| 8.7.4.5 | 8.7.4.6 | 8.7.4.7 | 8.7.4.8 | 8.7.4.9 | 8.7.5.1 | 8.7.5.2 | 8.7.5.3 | 8.7.5.4 | 8.7.5.5 |
| 8.7.5.6 | 8.7.5.7 | 8.7.5.8 | 8.7.5.9 | 8.7.6.1 | 8.7.6.2 | 8.7.6.3 | 8.7.6.4 | 8.7.6.5 | 8.7.6.6 |
| 8.7.6.7 | 8.7.6.8 | 8.7.6.9 | 8.7.7.1 | 8.7.7.2 | 8.7.7.3 | 8.7.7.4 | 8.7.7.5 | 8.7.7.6 | 8.7.7.7 |
| 8.7.7.8 | 8.7.7.9 | 8.7.8.1 | 8.7.8.2 | 8.7.8.3 | 8.7.8.4 | 8.7.8.5 | 8.7.8.6 | 8.7.8.7 | 8.7.8.8 |
| 8.7.8.9 | 8.7.9.1 | 8.7.9.2 | 8.7.9.3 | 8.7.9.4 | 8.7.9.5 | 8.7.9.6 | 8.7.9.7 | 8.7.9.8 | 8.7.9.9 |
| 8.8.1.1 | 8.8.1.2 | 8.8.1.3 | 8.8.1.4 | 8.8.1.5 | 8.8.1.6 | 8.8.1.7 | 8.8.1.8 | 8.8.1.9 | 8.8.2.1 |
| 8.8.2.2 | 8.8.2.3 | 8.8.2.4 | 8.8.2.5 | 8.8.2.6 | 8.8.2.7 | 8.8.2.8 | 8.8.2.9 | 8.8.3.1 | 8.8.3.2 |
| 8.8.3.3 | 8.8.3.4 | 8.8.3.5 | 8.8.3.6 | 8.8.3.7 | 8.8.3.8 | 8.8.3.9 | 8.8.4.1 | 8.8.4.2 | 8.8.4.3 |
| 8.8.4.4 | 8.8.4.5 | 8.8.4.6 | 8.8.4.7 | 8.8.4.8 | 8.8.4.9 | 8.8.5.1 | 8.8.5.2 | 8.8.5.3 | 8.8.5.4 |
| 8.8.5.5 | 8.8.5.6 | 8.8.5.7 | 8.8.5.8 | 8.8.5.9 | 8.8.6.1 | 8.8.6.2 | 8.8.6.3 | 8.8.6.4 | 8.8.6.5 |
| 8.8.6.6 | 8.8.6.7 | 8.8.6.8 | 8.8.6.9 | 8.8.7.1 | 8.8.7.2 | 8.8.7.3 | 8.8.7.4 | 8.8.7.5 | 8.8.7.6 |
| 8.8.7.7 | 8.8.7.8 | 8.8.7.9 | 8.8.8.1 | 8.8.8.2 | 8.8.8.3 | 8.8.8.4 | 8.8.8.5 | 8.8.8.6 | 8.8.8.7 |
| 8.8.8.8 | 8.8.8.9 | 8.8.9.1 | 8.8.9.2 | 8.8.9.3 | 8.8.9.4 | 8.8.9.5 | 8.8.9.6 | 8.8.9.7 | 8.8.9.8 |
| 8.8.9.9 | 8.9.1.1 | 8.9.1.2 | 8.9.1.3 | 8.9.1.4 | 8.9.1.5 | 8.9.1.6 | 8.9.1.7 | 8.9.1.8 | 8.9.1.9 |
| 8.9.2.1 | 8.9.2.2 | 8.9.2.3 | 8.9.2.4 | 8.9.2.5 | 8.9.2.6 | 8.9.2.7 | 8.9.2.8 | 8.9.2.9 | 8.9.3.1 |
| 8.9.3.2 | 8.9.3.3 | 8.9.3.4 | 8.9.3.5 | 8.9.3.6 | 8.9.3.7 | 8.9.3.8 | 8.9.3.9 | 8.9.4.1 | 8.9.4.2 |
| 8.9.4.3 | 8.9.4.4 | 8.9.4.5 | 8.9.4.6 | 8.9.4.7 | 8.9.4.8 | 8.9.4.9 | 8.9.5.1 | 8.9.5.2 | 8.9.5.3 |
| 8.9.5.4 | 8.9.5.5 | 8.9.5.6 | 8.9.5.7 | 8.9.5.8 | 8.9.5.9 | 8.9.6.1 | 8.9.6.2 | 8.9.6.3 | 8.9.6.4 |
| 8.9.6.5 | 8.9.6.6 | 8.9.6.7 | 8.9.6.8 | 8.9.6.9 | 8.9.7.1 | 8.9.7.2 | 8.9.7.3 | 8.9.7.4 | 8.9.7.5 |
| 8.9.7.6 | 8.9.7.7 | 8.9.7.8 | 8.9.7.9 | 8.9.8.1 | 8.9.8.2 | 8.9.8.3 | 8.9.8.4 | 8.9.8.5 | 8.9.8.6 |
| 8.9.8.7 | 8.9.8.8 | 8.9.8.9 | 8.9.9.1 | 8.9.9.2 | 8.9.9.3 | 8.9.9.4 | 8.9.9.5 | 8.9.9.6 | 8.9.9.7 |

TABLE 1-continued

| | | | | | | | | | |
|---|---|---|---|---|---|---|---|---|---|
| 8.9.9.8 | 8.9.9.9 | 9.1.1.1 | 9.1.1.2 | 9.1.1.3 | 9.1.1.4 | 9.1.1.5 | 9.1.1.6 | 9.1.1.7 | 9.1.1.8 |
| 9.1.1.9 | 9.1.2.1 | 9.1.2.2 | 9.1.2.3 | 9.1.2.4 | 9.1.2.5 | 9.1.2.6 | 9.1.2.7 | 9.1.2.8 | 9.1.2.9 |
| 9.1.3.1 | 9.1.3.2 | 9.1.3.3 | 9.1.3.4 | 9.1.3.5 | 9.1.3.6 | 9.1.3.7 | 9.1.3.8 | 9.1.3.9 | 9.1.4.1 |
| 9.1.4.2 | 9.1.4.3 | 9.1.4.4 | 9.1.4.5 | 9.1.4.6 | 9.1.4.7 | 9.1.4.8 | 9.1.4.9 | 9.1.5.1 | 9.1.5.2 |
| 9.1.5.3 | 9.1.5.4 | 9.1.5.5 | 9.1.5.6 | 9.1.5.7 | 9.1.5.8 | 9.1.5.9 | 9.1.6.1 | 9.1.6.2 | 9.1.6.3 |
| 9.1.6.4 | 9.1.6.5 | 9.1.6.6 | 9.1.6.7 | 9.1.6.8 | 9.1.6.9 | 9.1.7.1 | 9.1.7.2 | 9.1.7.3 | 9.1.7.4 |
| 9.1.7.5 | 9.1.7.6 | 9.1.7.7 | 9.1.7.8 | 9.1.7.9 | 9.1.8.1 | 9.1.8.2 | 9.1.8.3 | 9.1.8.4 | 9.1.8.5 |
| 9.1.8.6 | 9.1.8.7 | 9.1.8.8 | 9.1.8.9 | 9.1.9.1 | 9.1.9.2 | 9.1.9.3 | 9.1.9.4 | 9.1.9.5 | 9.1.9.6 |
| 9.1.9.7 | 9.1.9.8 | 9.1.9.9 | 9.2.1.1 | 9.2.1.2 | 9.2.1.3 | 9.2.1.4 | 9.2.1.5 | 9.2.1.6 | 9.2.1.7 |
| 9.2.1.8 | 9.2.1.9 | 9.2.2.1 | 9.2.2.2 | 9.2.2.3 | 9.2.2.4 | 9.2.2.5 | 9.2.2.6 | 9.2.2.7 | 9.2.2.8 |
| 9.2.2.9 | 9.2.3.1 | 9.2.3.2 | 9.2.3.3 | 9.2.3.4 | 9.2.3.5 | 9.2.3.6 | 9.2.3.7 | 9.2.3.8 | 9.2.3.9 |
| 9.2.4.1 | 9.2.4.2 | 9.2.4.3 | 9.2.4.4 | 9.2.4.5 | 9.2.4.6 | 9.2.4.7 | 9.2.4.8 | 9.2.4.9 | 9.2.5.1 |
| 9.2.5.2 | 9.2.5.3 | 9.2.5.4 | 9.2.5.5 | 9.2.5.6 | 9.2.5.7 | 9.2.5.8 | 9.2.5.9 | 9.2.6.1 | 9.2.6.2 |
| 9.2.6.3 | 9.2.6.4 | 9.2.6.5 | 9.2.6.6 | 9.2.6.7 | 9.2.6.8 | 9.2.6.9 | 9.2.7.1 | 9.2.7.2 | 9.2.7.3 |
| 9.2.7.4 | 9.2.7.5 | 9.2.7.6 | 9.2.7.7 | 9.2.7.8 | 9.2.7.9 | 9.2.8.1 | 9.2.8.2 | 9.2.8.3 | 9.2.8.4 |
| 9.2.8.5 | 9.2.8.6 | 9.2.8.7 | 9.2.8.8 | 9.2.8.9 | 9.2.9.1 | 9.2.9.2 | 9.2.9.3 | 9.2.9.4 | 9.2.9.5 |
| 9.2.9.6 | 9.2.9.7 | 9.2.9.8 | 9.2.9.9 | 9.3.1.1 | 9.3.1.2 | 9.3.1.3 | 9.3.1.4 | 9.3.1.5 | 9.3.1.6 |
| 9.3.1.7 | 9.3.1.8 | 9.3.1.9 | 9.3.2.1 | 9.3.2.2 | 9.3.2.3 | 9.3.2.4 | 9.3.2.5 | 9.3.2.6 | 9.3.2.7 |
| 9.3.2.8 | 9.3.2.9 | 9.3.3.1 | 9.3.3.2 | 9.3.3.3 | 9.3.3.4 | 9.3.3.5 | 9.3.3.6 | 9.3.3.7 | 9.3.3.8 |
| 9.3.3.9 | 9.3.4.1 | 9.3.4.2 | 9.3.4.3 | 9.3.4.4 | 9.3.4.5 | 9.3.4.6 | 9.3.4.7 | 9.3.4.8 | 9.3.4.9 |
| 9.3.5.1 | 9.3.5.2 | 9.3.5.3 | 9.3.5.4 | 9.3.5.5 | 9.3.5.6 | 9.3.5.7 | 9.3.5.8 | 9.3.5.9 | 9.3.6.1 |
| 9.3.6.2 | 9.3.6.3 | 9.3.6.4 | 9.3.6.5 | 9.3.6.6 | 9.3.6.7 | 9.3.6.8 | 9.3.6.9 | 9.3.7.1 | 9.3.7.2 |
| 9.3.7.3 | 9.3.7.4 | 9.3.7.5 | 9.3.7.6 | 9.3.7.7 | 9.3.7.8 | 9.3.7.9 | 9.3.8.1 | 9.3.8.2 | 9.3.8.3 |
| 9.3.8.4 | 9.3.8.5 | 9.3.8.6 | 9.3.8.7 | 9.3.8.8 | 9.3.8.9 | 9.3.9.1 | 9.3.9.2 | 9.3.9.3 | 9.3.9.4 |
| 9.3.9.5 | 9.3.9.6 | 9.3.9.7 | 9.3.9.8 | 9.3.9.9 | 9.4.1.1 | 9.4.1.2 | 9.4.1.3 | 9.4.1.4 | 9.4.1.5 |
| 9.4.1.6 | 9.4.1.7 | 9.4.1.8 | 9.4.1.9 | 9.4.2.1 | 9.4.2.2 | 9.4.2.3 | 9.4.2.4 | 9.4.2.5 | 9.4.2.6 |
| 9.4.2.7 | 9.4.2.8 | 9.4.2.9 | 9.4.3.1 | 9.4.3.2 | 9.4.3.3 | 9.4.3.4 | 9.4.3.5 | 9.4.3.6 | 9.4.3.7 |
| 9.4.3.8 | 9.4.3.9 | 9.4.4.1 | 9.4.4.2 | 9.4.4.3 | 9.4.4.4 | 9.4.4.5 | 9.4.4.6 | 9.4.4.7 | 9.4.4.8 |
| 9.4.4.9 | 9.4.5.1 | 9.4.5.2 | 9.4.5.3 | 9.4.5.4 | 9.4.5.5 | 9.4.5.6 | 9.4.5.7 | 9.4.5.8 | 9.4.5.9 |
| 9.4.6.1 | 9.4.6.2 | 9.4.6.3 | 9.4.6.4 | 9.4.6.5 | 9.4.6.6 | 9.4.6.7 | 9.4.6.8 | 9.4.6.9 | 9.4.7.1 |
| 9.4.7.2 | 9.4.7.3 | 9.4.7.4 | 9.4.7.5 | 9.4.7.6 | 9.4.7.7 | 9.4.7.8 | 9.4.7.9 | 9.4.8.1 | 9.4.8.2 |
| 9.4.8.3 | 9.4.8.4 | 9.4.8.5 | 9.4.8.6 | 9.4.8.7 | 9.4.8.8 | 9.4.8.9 | 9.4.9.1 | 9.4.9.2 | 9.4.9.3 |
| 9.4.9.4 | 9.4.9.5 | 9.4.9.6 | 9.4.9.7 | 9.4.9.8 | 9.4.9.9 | 9.5.1.1 | 9.5.1.2 | 9.5.1.3 | 9.5.1.4 |
| 9.5.1.5 | 9.5.1.6 | 9.5.1.7 | 9.5.1.8 | 9.5.1.9 | 9.5.2.1 | 9.5.2.2 | 9.5.2.3 | 9.5.2.4 | 9.5.2.5 |
| 9.5.2.6 | 9.5.2.7 | 9.5.2.8 | 9.5.2.9 | 9.5.3.1 | 9.5.3.2 | 9.5.3.3 | 9.5.3.4 | 9.5.3.5 | 9.5.3.6 |
| 9.5.3.7 | 9.5.3.8 | 9.5.3.9 | 9.5.4.1 | 9.5.4.2 | 9.5.4.3 | 9.5.4.4 | 9.5.4.5 | 9.5.4.6 | 9.5.4.7 |
| 9.5.4.8 | 9.5.4.9 | 9.5.5.1 | 9.5.5.2 | 9.5.5.3 | 9.5.5.4 | 9.5.5.5 | 9.5.5.6 | 9.5.5.7 | 9.5.5.8 |
| 9.5.5.9 | 9.5.6.1 | 9.5.6.2 | 9.5.6.3 | 9.5.6.4 | 9.5.6.5 | 9.5.6.6 | 9.5.6.7 | 9.5.6.8 | 9.5.6.9 |
| 9.5.7.1 | 9.5.7.2 | 9.5.7.3 | 9.5.7.4 | 9.5.7.5 | 9.5.7.6 | 9.5.7.7 | 9.5.7.8 | 9.5.7.9 | 9.5.8.1 |
| 9.5.8.2 | 9.5.8.3 | 9.5.8.4 | 9.5.8.5 | 9.5.8.6 | 9.5.8.7 | 9.5.8.8 | 9.5.8.9 | 9.5.9.1 | 9.5.9.2 |
| 9.5.9.3 | 9.5.9.4 | 9.5.9.5 | 9.5.9.6 | 9.5.9.7 | 9.5.9.8 | 9.5.9.9 | 9.6.1.1 | 9.6.1.2 | 9.6.1.3 |
| 9.6.1.4 | 9.6.1.5 | 9.6.1.6 | 9.6.1.7 | 9.6.1.8 | 9.6.1.9 | 9.6.2.1 | 9.6.2.2 | 9.6.2.3 | 9.6.2.4 |
| 9.6.2.5 | 9.6.2.6 | 9.6.2.7 | 9.6.2.8 | 9.6.2.9 | 9.6.3.1 | 9.6.3.2 | 9.6.3.3 | 9.6.3.4 | 9.6.3.5 |
| 9.6.3.6 | 9.6.3.7 | 9.6.3.8 | 9.6.3.9 | 9.6.4.1 | 9.6.4.2 | 9.6.4.3 | 9.6.4.4 | 9.6.4.5 | 9.6.4.6 |
| 9.6.4.7 | 9.6.4.8 | 9.6.4.9 | 9.6.5.1 | 9.6.5.2 | 9.6.5.3 | 9.6.5.4 | 9.6.5.5 | 9.6.5.6 | 9.6.5.7 |
| 9.6.5.8 | 9.6.5.9 | 9.6.6.1 | 9.6.6.2 | 9.6.6.3 | 9.6.6.4 | 9.6.6.5 | 9.6.6.6 | 9.6.6.7 | 9.6.6.8 |
| 9.6.6.9 | 9.6.7.1 | 9.6.7.2 | 9.6.7.3 | 9.6.7.4 | 9.6.7.5 | 9.6.7.6 | 9.6.7.7 | 9.6.7.8 | 9.6.7.9 |
| 9.6.8.1 | 9.6.8.2 | 9.6.8.3 | 9.6.8.4 | 9.6.8.5 | 9.6.8.6 | 9.6.8.7 | 9.6.8.8 | 9.6.8.9 | 9.6.9.1 |
| 9.6.9.2 | 9.6.9.3 | 9.6.9.4 | 9.6.9.5 | 9.6.9.6 | 9.6.9.7 | 9.6.9.8 | 9.6.9.9 | 9.7.1.1 | 9.7.1.2 |
| 9.7.1.3 | 9.7.1.4 | 9.7.1.5 | 9.7.1.6 | 9.7.1.7 | 9.7.1.8 | 9.7.1.9 | 9.7.2.1 | 9.7.2.2 | 9.7.2.3 |
| 9.7.2.4 | 9.7.2.5 | 9.7.2.6 | 9.7.2.7 | 9.7.2.8 | 9.7.2.9 | 9.7.3.1 | 9.7.3.2 | 9.7.3.3 | 9.7.3.4 |
| 9.7.3.5 | 9.7.3.6 | 9.7.3.7 | 9.7.3.8 | 9.7.3.9 | 9.7.4.1 | 9.7.4.2 | 9.7.4.3 | 9.7.4.4 | 9.7.4.5 |
| 9.7.4.6 | 9.7.4.7 | 9.7.4.8 | 9.7.4.9 | 9.7.5.1 | 9.7.5.2 | 9.7.5.3 | 9.7.5.4 | 9.7.5.5 | 9.7.5.6 |
| 9.7.5.7 | 9.7.5.8 | 9.7.5.9 | 9.7.6.1 | 9.7.6.2 | 9.7.6.3 | 9.7.6.4 | 9.7.6.5 | 9.7.6.6 | 9.7.6.7 |
| 9.7.6.8 | 9.7.6.9 | 9.7.7.1 | 9.7.7.2 | 9.7.7.3 | 9.7.7.4 | 9.7.7.5 | 9.7.7.6 | 9.7.7.7 | 9.7.7.8 |
| 9.7.7.9 | 9.7.8.1 | 9.7.8.2 | 9.7.8.3 | 9.7.8.4 | 9.7.8.5 | 9.7.8.6 | 9.7.8.7 | 9.7.8.8 | 9.7.8.9 |
| 9.7.9.1 | 9.7.9.2 | 9.7.9.3 | 9.7.9.4 | 9.7.9.5 | 9.7.9.6 | 9.7.9.7 | 9.7.9.8 | 9.7.9.9 | 9.8.1.1 |
| 9.8.1.2 | 9.8.1.3 | 9.8.1.4 | 9.8.1.5 | 9.8.1.6 | 9.8.1.7 | 9.8.1.8 | 9.8.1.9 | 9.8.2.1 | 9.8.2.2 |
| 9.8.2.3 | 9.8.2.4 | 9.8.2.5 | 9.8.2.6 | 9.8.2.7 | 9.8.2.8 | 9.8.2.9 | 9.8.3.1 | 9.8.3.2 | 9.8.3.3 |
| 9.8.3.4 | 9.8.3.5 | 9.8.3.6 | 9.8.3.7 | 9.8.3.8 | 9.8.3.9 | 9.8.4.1 | 9.8.4.2 | 9.8.4.3 | 9.8.4.4 |
| 9.8.4.5 | 9.8.4.6 | 9.8.4.7 | 9.8.4.8 | 9.8.4.9 | 9.8.5.1 | 9.8.5.2 | 9.8.5.3 | 9.8.5.4 | 9.8.5.5 |
| 9.8.5.6 | 9.8.5.7 | 9.8.5.8 | 9.8.5.9 | 9.8.6.1 | 9.8.6.2 | 9.8.6.3 | 9.8.6.4 | 9.8.6.5 | 9.8.6.6 |
| 9.8.6.7 | 9.8.6.8 | 9.8.6.9 | 9.8.7.1 | 9.8.7.2 | 9.8.7.3 | 9.8.7.4 | 9.8.7.5 | 9.8.7.6 | 9.8.7.7 |
| 9.8.7.8 | 9.8.7.9 | 9.8.8.1 | 9.8.8.2 | 9.8.8.3 | 9.8.8.4 | 9.8.8.5 | 9.8.8.6 | 9.8.8.7 | 9.8.8.8 |
| 9.8.8.9 | 9.8.9.1 | 9.8.9.2 | 9.8.9.3 | 9.8.9.4 | 9.8.9.5 | 9.8.9.6 | 9.8.9.7 | 9.8.9.8 | 9.8.9.9 |
| 9.9.1.1 | 9.9.1.2 | 9.9.1.3 | 9.9.1.4 | 9.9.1.5 | 9.9.1.6 | 9.9.1.7 | 9.9.1.8 | 9.9.1.9 | 9.9.2.1 |
| 9.9.2.2 | 9.9.2.3 | 9.9.2.4 | 9.9.2.5 | 9.9.2.6 | 9.9.2.7 | 9.9.2.8 | 9.9.2.9 | 9.9.3.1 | 9.9.3.2 |
| 9.9.3.3 | 9.9.3.4 | 9.9.3.5 | 9.9.3.6 | 9.9.3.7 | 9.9.3.8 | 9.9.3.9 | 9.9.4.1 | 9.9.4.2 | 9.9.4.3 |
| 9.9.4.4 | 9.9.4.5 | 9.9.4.6 | 9.9.4.7 | 9.9.4.8 | 9.9.4.9 | 9.9.5.1 | 9.9.5.2 | 9.9.5.3 | 9.9.5.4 |
| 9.9.5.5 | 9.9.5.6 | 9.9.5.7 | 9.9.5.8 | 9.9.5.9 | 9.9.6.1 | 9.9.6.2 | 9.9.6.3 | 9.9.6.4 | 9.9.6.5 |
| 9.9.6.6 | 9.9.6.7 | 9.9.6.8 | 9.9.6.9 | 9.9.7.1 | 9.9.7.2 | 9.9.7.3 | 9.9.7.4 | 9.9.7.5 | 9.9.7.6 |
| 9.9.7.7 | 9.9.7.8 | 9.9.7.9 | 9.9.8.1 | 9.9.8.2 | 9.9.8.3 | 9.9.8.4 | 9.9.8.5 | 9.9.8.6 | 9.9.8.7 |
| 9.9.8.8 | 9.9.8.9 | 9.9.9.1 | 9.9.9.2 | 9.9.9.3 | 9.9.9.4 | 9.9.9.5 | 9.9.9.6 | 9.9.9.7 | 9.9.9.8 |
| 9.9.9.9 | | | | | | | | | |

Another group of preferred compounds are named in Table 2 and designated by numbers assigned to the variables of formula I using the following convention: $M^1.Y/Y'.V/Z/W$.

The compounds are shown without depiction of stereochemistry since the compounds are biologically active as the diastereomeric mixture or as a single stereoisomer. $M^1$ is a variable that represents compounds of the formula M-H which have a specific hydroxyl group that is phosphorylated with a group P(O)[Y—CH(V)CH(Z)CH(W)—Y'] to make compounds of formula I or $M^1$ is a variable that represents phosphonic acids of the formula M-PO$_3$= which are transformed to compounds of formula I by replacing two oxygens in the PO$_3$= group with Y—CH(V)CH(Z)CH(W)—Y'.

The structures for variable $M^1$ are the same as described above.

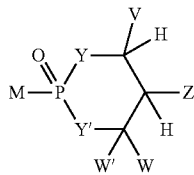

Variable Y/Y'
1) Y=NH; Y'=oxygen
2) Y=oxygen; Y'=NH
3) Y=NH; Y'=NH
4) Y=N—CH$_3$; Y'=oxygen
5) Y=oxygen; Y'=NCH3
6) Y=N—CH2CH3; Y'=oxygen
7) Y=N-phenyl; Y'=oxygen
8) Y=Ni-propyl; Y'=oxygen
9) Y=oxygen; Y'=N—CH2CH3

Variable V/Z/W: Group V/Z/W1
1) V=phenyl; Z=methyl; W=hydrogen
2) V=3,5-dichlorophenyl; Z=methyl; W=hydrogen
3) V=4-pyridyl; Z=methyl; W=hydrogen
4) V=phenyl; Z=methoxy; W=hydrogen
5) V=3,5-dichlorophenyl; Z=methoxy; W=hydrogen
6) V=4-pyridyl; Z=methoxy; W=hydrogen
7) V=phenyl; Z=hydrogen; W=phenyl
8) V=3,5-dichlorophenyl; Z=hydrogen; W=3,5-dichlorophenyl
9) V=4-pyridyl; Z=hydrogen; W=4-pyridyl Variable V/Z/W: Group V/Z/W2
1) V=phenyl; Z=NHAc; W=hydrogen
2) V=3,5-dichlorophenyl; Z=NHAc; W=hydrogen
3) V=4-pyridyl; Z=NHAc; W=hydrogen
4) V=phenyl; Z=hydrogen; W=methyl
5) V=3,5-dichlorophenyl; Z=hydrogen; W=methyl
6) V=4-pyridyl; Z=hydrogen; W=methyl
7) V=phenyl; Z=hydroxy; W=hydrogen
8) V=3,5-dichlorophenyl; Z=hydroxy; W=hydrogen
9) V=4-pyridyl; Z=hydroxy; W=hydrogen Variable V/Z/W: Group V/Z/W3
1) V=hydrogen; Z=CH2OH; W=hydrogen
2) V=hydrogen; Z=CH2OC(O)CH3; W=hydrogen
3) V=hydrogen; Z=CH2OC(O)OCH3; W=hydrogen
4) V=methyl; Z=CH2OH; W=hydrogen
5) V=methyl; Z=CH2OC(O)CH3; W=hydrogen
6) V=methyl; Z=CH2OC(O)OCH3; W=hydrogen
7) Z=hydrogen; V and W=—CH2-CH(OH)CH2-
8) Z=hydrogen; V and W=—CH2-CH(OAc)CH2-
9) Z=hydrogen; V and W=—CH2-CH(OCO2CH2CH3)CH2-

Preferred compounds are compounds listed in Table 2 using groups $M^1$1 and V/Z/W1. For example, compound 1.1.3 represents structure 1 of group $M^1$1, i.e. 3TC; structure 1 of the variable Y/Y', i.e. Y=NH and Y'=oxygen; structure 3 of group V/Z/W1, i.e. V=4-pyridyl, Z=methyl and W=hydrogen. The compound 1.1.3. therefore is 3TC with the P(O)(N(H)—CH(4-pyridyl)CH(CH3)CH2O) attached to the primary hydroxyl.

Preferred compounds are also compounds listed in Table 2 using groups $M^1$1 and V/Z/W2. Preferred compounds are also compounds listed in Table 2 using groups $M^1$1 and V/Z/W3. Preferred compounds are also compounds listed in Table 2 using groups $M^1$2 and V/Z/W1. Preferred compounds are also compounds listed in Table 2 using groups $M^1$2 and V/Z/W 2. Preferred compounds are also compounds listed in Table 2 using groups $M^1$2 and V/Z/W 3. Preferred compounds are also compounds listed in Table 2 using groups $M^1$3 and V/Z/W1. Preferred compounds are also compounds listed in Table 2 using groups $M^1$3 and V/Z/W 2. Preferred compounds are also compounds listed in Table 2 using groups $M^1$3 and V/Z/W 3.

TABLE 2

| | | | | | | | | | | | |
|---|---|---|---|---|---|---|---|---|---|---|---|
| 1.1.1 | 1.1.2 | 1.1.3 | 1.1.4 | 1.1.5 | 1.1.6 | 1.1.7 | 1.1.8 | 1.1.9 | 1.2.1 | 1.2.2 | 1.2.3 |
| 1.2.4 | 1.2.5 | 1.2.6 | 1.2.7 | 1.2.8 | 1.2.9 | 1.3.1 | 1.3.2 | 1.3.3 | 1.3.4 | 1.3.5 | 1.3.6 |
| 1.3.7 | 1.3.8 | 1.3.9 | 1.4.1 | 1.4.2 | 1.4.3 | 1.4.4 | 1.4.5 | 1.4.6 | 1.4.7 | 1.4.8 | 1.4.9 |
| 1.5.1 | 1.5.2 | 1.5.3 | 1.5.4 | 1.5.5 | 1.5.6 | 1.5.7 | 1.5.8 | 1.5.9 | 1.6.1 | 1.6.2 | 1.6.3 |
| 1.6.4 | 1.6.5 | 1.6.6 | 1.6.7 | 1.6.8 | 1.6.9 | 1.7.1 | 1.7.2 | 1.7.3 | 1.7.4 | 1.7.5 | 1.7.6 |
| 1.7.7 | 1.7.8 | 1.7.9 | 1.8.1 | 1.8.2 | 1.8.3 | 1.8.4 | 1.8.5 | 1.8.6 | 1.8.7 | 1.8.8 | 1.8.9 |
| 1.9.1 | 1.9.2 | 1.9.3 | 1.9.4 | 1.9.5 | 1.9.6 | 1.9.7 | 1.9.8 | 1.9.9 | 2.1.1 | 2.1.2 | 2.1.3 |
| 2.1.4 | 2.1.5 | 2.1.6 | 2.1.7 | 2.1.8 | 2.1.9 | 2.2.1 | 2.2.2 | 2.2.3 | 2.2.4 | 2.2.5 | 2.2.6 |
| 2.2.7 | 2.2.8 | 2.2.9 | 2.3.1 | 2.3.2 | 2.3.3 | 2.3.4 | 2.3.5 | 2.3.6 | 2.3.7 | 2.3.8 | 2.3.9 |
| 2.4.1 | 2.4.2 | 2.4.3 | 2.4.4 | 2.4.5 | 2.4.6 | 2.4.7 | 2.4.8 | 2.4.9 | 2.5.1 | 2.5.2 | 2.5.3 |
| 2.5.4 | 2.5.5 | 2.5.6 | 2.5.7 | 2.5.8 | 2.5.9 | 2.6.1 | 2.6.2 | 2.6.3 | 2.6.4 | 2.6.5 | 2.6.6 |
| 2.6.7 | 2.6.8 | 2.6.9 | 2.7.1 | 2.7.2 | 2.7.3 | 2.7.4 | 2.7.5 | 2.7.6 | 2.7.7 | 2.7.8 | 2.7.9 |
| 2.8.1 | 2.8.2 | 2.8.3 | 2.8.4 | 2.8.5 | 2.8.6 | 2.8.7 | 2.8.8 | 2.8.9 | 2.9.1 | 2.9.2 | 2.9.3 |
| 2.9.4 | 2.9.5 | 2.9.6 | 2.9.7 | 2.9.8 | 2.9.9 | 3.1.1 | 3.1.2 | 3.1.3 | 3.1.4 | 3.1.5 | 3.1.6 |
| 3.1.7 | 3.1.8 | 3.1.9 | 3.2.1 | 3.2.2 | 3.2.3 | 3.2.4 | 3.2.5 | 3.2.6 | 3.2.7 | 3.2.8 | 3.2.9 |
| 3.3.1 | 3.3.2 | 3.3.3 | 3.3.4 | 3.3.5 | 3.3.6 | 3.3.7 | 3.3.8 | 3.3.9 | 3.4.1 | 3.4.2 | 3.4.3 |
| 3.4.4 | 3.4.5 | 3.4.6 | 3.4.7 | 3.4.8 | 3.4.9 | 3.5.1 | 3.5.2 | 3.5.3 | 3.5.4 | 3.5.5 | 3.5.6 |
| 3.5.7 | 3.5.8 | 3.5.9 | 3.6.1 | 3.6.2 | 3.6.3 | 3.6.4 | 3.6.5 | 3.6.6 | 3.6.7 | 3.6.8 | 3.6.9 |
| 3.7.1 | 3.7.2 | 3.7.3 | 3.7.4 | 3.7.5 | 3.7.6 | 3.7.7 | 3.7.8 | 3.7.9 | 3.8.1 | 3.8.2 | 3.8.3 |
| 3.8.4 | 3.8.5 | 3.8.6 | 3.8.7 | 3.8.8 | 3.8.9 | 3.9.1 | 3.9.2 | 3.9.3 | 3.9.4 | 3.9.5 | 3.9.6 |
| 3.9.7 | 3.9.8 | 3.9.9 | 4.1.1 | 4.1.2 | 4.1.3 | 4.1.4 | 4.1.5 | 4.1.6 | 4.1.7 | 4.1.8 | 4.1.9 |
| 4.2.1 | 4.2.2 | 4.2.3 | 4.2.4 | 4.2.5 | 4.2.6 | 4.2.7 | 4.2.8 | 4.2.9 | 4.3.1 | 4.3.2 | 4.3.3 |
| 4.3.4 | 4.3.5 | 4.3.6 | 4.3.7 | 4.3.8 | 4.3.9 | 4.4.1 | 4.4.2 | 4.4.3 | 4.4.4 | 4.4.5 | 4.4.6 |
| 4.4.7 | 4.4.8 | 4.4.9 | 4.5.1 | 4.5.2 | 4.5.3 | 4.5.4 | 4.5.5 | 4.5.6 | 4.5.7 | 4.5.8 | 4.5.9 |
| 4.6.1 | 4.6.2 | 4.6.3 | 4.6.4 | 4.6.5 | 4.6.6 | 4.6.7 | 4.6.8 | 4.6.9 | 4.7.1 | 4.7.2 | 4.7.3 |
| 4.7.4 | 4.7.5 | 4.7.6 | 4.7.7 | 4.7.8 | 4.7.9 | 4.8.1 | 4.8.2 | 4.8.3 | 4.8.4 | 4.8.5 | 4.8.6 |
| 4.8.7 | 4.8.8 | 4.8.9 | 4.9.1 | 4.9.2 | 4.9.3 | 4.9.4 | 4.9.5 | 4.9.6 | 4.9.7 | 4.9.8 | 4.9.9 |
| 5.1.1 | 5.1.2 | 5.1.3 | 5.1.4 | 5.1.5 | 5.1.6 | 5.1.7 | 5.1.8 | 5.1.9 | 5.2.1 | 5.2.2 | 5.2.3 |

TABLE 2-continued

| | | | | | | | | | | | |
|---|---|---|---|---|---|---|---|---|---|---|---|
| 5.2.4 | 5.2.5 | 5.2.6 | 5.2.7 | 5.2.8 | 5.2.9 | 5.3.1 | 5.3.2 | 5.3.3 | 5.3.4 | 5.3.5 | 5.3.6 |
| 5.3.7 | 5.3.8 | 5.3.9 | 5.4.1 | 5.4.2 | 5.4.3 | 5.4.4 | 5.4.5 | 5.4.6 | 5.4.7 | 5.4.8 | 5.4.9 |
| 5.5.1 | 5.5.2 | 5.5.3 | 5.5.4 | 5.5.5 | 5.5.6 | 5.5.7 | 5.5.8 | 5.5.9 | 5.6.1 | 5.6.2 | 5.6.3 |
| 5.6.4 | 5.6.5 | 5.6.6 | 5.6.7 | 5.6.8 | 5.6.9 | 5.7.1 | 5.7.2 | 5.7.3 | 5.7.4 | 5.7.5 | 5.7.6 |
| 5.7.7 | 5.7.8 | 5.7.9 | 5.8.1 | 5.8.2 | 5.8.3 | 5.8.4 | 5.8.5 | 5.8.6 | 5.8.7 | 5.8.8 | 5.8.9 |
| 5.9.1 | 5.9.2 | 5.9.3 | 5.9.4 | 5.9.5 | 5.9.6 | 5.9.7 | 5.9.8 | 5.9.9 | 6.1.1 | 6.1.2 | 6.1.3 |
| 6.1.4 | 6.1.5 | 6.1.6 | 6.1.7 | 6.1.8 | 6.1.9 | 6.2.1 | 6.2.2 | 6.2.3 | 6.2.4 | 6.2.5 | 6.2.6 |
| 6.2.7 | 6.2.8 | 6.2.9 | 6.3.1 | 6.3.2 | 6.3.3 | 6.3.4 | 6.3.5 | 6.3.6 | 6.3.7 | 6.3.8 | 6.3.9 |
| 6.4.1 | 6.4.2 | 6.4.3 | 6.4.4 | 6.4.5 | 6.4.6 | 6.4.7 | 6.4.8 | 6.4.9 | 6.5.1 | 6.5.2 | 6.5.3 |
| 6.5.4 | 6.5.5 | 6.5.6 | 6.5.7 | 6.5.8 | 6.5.9 | 6.6.1 | 6.6.2 | 6.6.3 | 6.6.4 | 6.6.5 | 6.6.6 |
| 6.6.7 | 6.6.8 | 6.6.9 | 6.7.1 | 6.7.2 | 6.7.3 | 6.7.4 | 6.7.5 | 6.7.6 | 6.7.7 | 6.7.8 | 6.7.9 |
| 6.8.1 | 6.8.2 | 6.8.3 | 6.8.4 | 6.8.5 | 6.8.6 | 6.8.7 | 6.8.8 | 6.8.9 | 6.9.1 | 6.9.2 | 6.9.3 |
| 6.9.4 | 6.9.5 | 6.9.6 | 6.9.7 | 6.9.8 | 6.9.9 | 7.1.1 | 7.1.2 | 7.1.3 | 7.1.4 | 7.1.5 | 7.1.6 |
| 7.1.7 | 7.1.8 | 7.1.9 | 7.2.1 | 7.2.2 | 7.2.3 | 7.2.4 | 7.2.5 | 7.2.6 | 7.2.7 | 7.2.8 | 7.2.9 |
| 7.3.1 | 7.3.2 | 7.3.3 | 7.3.4 | 7.3.5 | 7.3.6 | 7.3.7 | 7.3.8 | 7.3.9 | 7.4.1 | 7.4.2 | 7.4.3 |
| 7.4.4 | 7.4.5 | 7.4.6 | 7.4.7 | 7.4.8 | 7.4.9 | 7.5.1 | 7.5.2 | 7.5.3 | 7.5.4 | 7.5.5 | 7.5.6 |
| 7.5.7 | 7.5.8 | 7.5.9 | 7.6.1 | 7.6.2 | 7.6.3 | 7.6.4 | 7.6.5 | 7.6.6 | 7.6.7 | 7.6.8 | 7.6.9 |
| 7.7.1 | 7.7.2 | 7.7.3 | 7.7.4 | 7.7.5 | 7.7.6 | 7.7.7 | 7.7.8 | 7.7.9 | 7.8.1 | 7.8.2 | 7.8.3 |
| 7.8.4 | 7.8.5 | 7.8.6 | 7.8.7 | 7.8.8 | 7.8.9 | 7.9.1 | 7.9.2 | 7.9.3 | 7.9.4 | 7.9.5 | 7.9.6 |
| 7.9.7 | 7.9.8 | 7.9.9 | 8.1.1 | 8.1.2 | 8.1.3 | 8.1.4 | 8.1.5 | 8.1.6 | 8.1.7 | 8.1.8 | 8.1.9 |
| 8.2.1 | 8.2.2 | 8.2.3 | 8.2.4 | 8.2.5 | 8.2.6 | 8.2.7 | 8.2.8 | 8.2.9 | 8.3.1 | 8.3.2 | 8.3.3 |
| 8.3.4 | 8.3.5 | 8.3.6 | 8.3.7 | 8.3.8 | 8.3.9 | 8.4.1 | 8.4.2 | 8.4.3 | 8.4.4 | 8.4.5 | 8.4.6 |
| 8.4.7 | 8.4.8 | 8.4.9 | 8.5.1 | 8.5.2 | 8.5.3 | 8.5.4 | 8.5.5 | 8.5.6 | 8.5.7 | 8.5.8 | 8.5.9 |
| 8.6.1 | 8.6.2 | 8.6.3 | 8.6.4 | 8.6.5 | 8.6.6 | 8.6.7 | 8.6.8 | 8.6.9 | 8.7.1 | 8.7.2 | 8.7.3 |
| 8.7.4 | 8.7.5 | 8.7.6 | 8.7.7 | 8.7.8 | 8.7.9 | 8.8.1 | 8.8.2 | 8.8.3 | 8.8.4 | 8.8.5 | 8.8.6 |
| 8.8.7 | 8.8.8 | 8.8.9 | 8.9.1 | 8.9.2 | 8.9.3 | 8.9.4 | 8.9.5 | 8.9.6 | 8.9.7 | 8.9.8 | 8.9.9 |
| 9.1.1 | 9.1.2 | 9.1.3 | 9.1.4 | 9.1.5 | 9.1.6 | 9.1.7 | 9.1.8 | 9.1.9 | 9.2.1 | 9.2.2 | 9.2.3 |
| 9.2.4 | 9.2.5 | 9.2.6 | 9.2.7 | 9.2.8 | 9.2.9 | 9.3.1 | 9.3.2 | 9.3.3 | 9.3.4 | 9.3.5 | 9.3.6 |
| 9.3.7 | 9.3.8 | 9.3.9 | 9.4.1 | 9.4.2 | 9.4.3 | 9.4.4 | 9.4.5 | 9.4.6 | 9.4.7 | 9.4.8 | 9.4.9 |
| 9.5.1 | 9.5.2 | 9.5.3 | 9.5.4 | 9.5.5 | 9.5.6 | 9.5.7 | 9.5.8 | 9.5.9 | 9.6.1 | 9.6.2 | 9.6.3 |
| 9.6.4 | 9.6.5 | 9.6.6 | 9.6.7 | 9.6.8 | 9.6.9 | 9.7.1 | 9.7.2 | 9.7.3 | 9.7.4 | 9.7.5 | 9.7.6 |
| 9.7.7 | 9.7.8 | 9.7.9 | 9.8.1 | 9.8.2 | 9.8.3 | 9.8.4 | 9.8.5 | 9.8.6 | 9.8.7 | 9.8.8 | 9.8.9 |
| 9.9.1 | 9.9.2 | 9.9.3 | 9.9.4 | 9.9.5 | 9.9.6 | 9.9.7 | 9.9.8 | 9.9.9 | | | |

Syntheses of Compounds of Formula I

Synthesis of the compounds encompassed by the present invention includes: I). synthesis of prodrugs; and II). synthesis of substituted 1,3-hydroxyamines and 1,3-diamines.

I) Syntheses of Prodrugs:

The following procedures on the preparation of prodrugs illustrate the general procedures used to prepare the prodrugs of the invention which apply to all phosphate, phosphonate- and phosphoramidate containing drugs. Prodrugs can be introduced at different stages of synthesis of a drug. Most often they are made at a later stage, because of the general sensitivity of these groups to various reaction conditions. Optically pure prodrugs containing single isomer at phosphorus center can be made either by separation of the diastereomers by a combination of column chromatography and/or crystallization, or by enantioselective synthesis of chiral activated phosphoramide intermediates.

The preparation of prodrugs is further organized into 1) synthesis via activated P(V) intermediates, 2) synthesis via activated P(III) intermediates, 3) synthesis via phosph(on)ate diacid, and 4) miscellaneous methods. Some of the general synthetic methods described in here are utilized for phosphate and phosphonate ester synthesis. However, these methods are equally applicable in phosphoramidate case also when the nitrogen in the prodrug moiety is appropriately protected and/or substituted.

I.1. Synthesis Via Activated P(V) Intermediate:

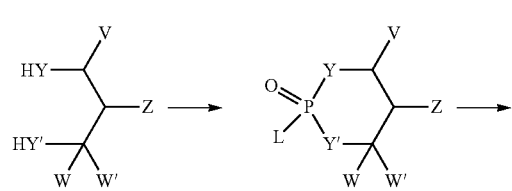

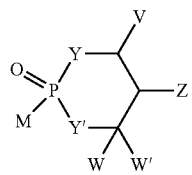

I.1.a. Synthesis of Activated P(V) Intermediates:

Most preferred synthesis of phosphoramidate nucleotide prodrugs is the reaction of MH hydroxy group with 4-nitrophenyl phosphoramidate (where L is nitrophenyl) in presence of a strong base such as sodium hydride or lithium hydride. The activated precursor is prepared by reaction of commercially available 4-nitrophenyl phosphorochloridate with a substituted 1,3-aminoalcohol or 1,3-diamine. In general, synthesis of phosphoroamidate prodrug is achieved by coupling the alcohol with the corresponding activated phosphoroamidate precursor for example, Chlorophosphoroamidate (L=chloro) addition on to 5'-hydroxy of nucleoside is a well known method for preparation of phosphoroamidates (Stepanov et al., Tetrahedron Lett., 1989, 30, 5125). The activated precursor can be prepared by several well known methods. Chlorophosphoroamidates useful for synthesis of the prodrugs are prepared from the substituted-1,3-propanediamine or 1,3-aminoalcohol (Kirsten, et al, J. Org. Chem., 1997, 62, 6882). Chlorophosphoroamidate may also be made by oxidation of the corresponding P(III) intermediates (Ozaki, et al, Bull. Chem. Soc. Jpn., 1989, 62, 3869) which are obtained by reaction of appropriately protected and/or substituted 1,3-aminoalcohol or 1,3-diamine with phosphorus trichloride. Alternatively, the chlorophosphoroamidate agent is made by treating substituted-1,3-aminoalcohol or 1,3-diamine with phosphorusoxychloride (Welch, et al., J. Org. Chem., 1990, 55, 5991). Chlorophosphoroamidate species may also be generated in situ from corresponding phosphites (Jung, et al., *Nucleosides and Nucleotides,* 1994, 13, 1597). Phosphoroflouridate intermediate prepared from phosphoroamidic acid may also act as a precursor in preparation of cyclic prodrugs (Watanabe et al., *Tetrahedron lett.,* 1988, 29, 5763).

Phosphoramidates (L=NRR') can also be used as intermediates in the case of phosphoramidate prodrugs as in the synthesis of phosphate esters where the nitrogen is substituted or in the protected form. Monoalkyl or dialkylphosphoramidate (Watanabe, et al, *Chem Pharm Bull.,* 1990, 38, 562), triazolophosphoramidate (Yamakage, et al., *Tetrahedron,* 1989, 45, 5459) and pyrrolidinophosphoramidate (Nakayama, et al, *J. Am. Chem. Soc.,* 1990, 112, 6936) are some of the known intermediates used for the preparation of phosphate esters. Another effective phosphorylating procedure is a metal catalyzed addition of cyclic chlorophosphoroamidate adduct of 2-oxazolone. This type of intermediate attains high selectivity in phosphorylation of primary hydroxy group in presence of secondary hydroxyl group (Nagamatsu, et al, *Tetrahedron Lett.,* 1987, 28, 2375). These agents are obtained by reaction of a chlorophosphoroamidate with the amine or alternatively by formation of the corresponding phosphoramidite followed by oxidation.

I.b. Synthesis of Chiral Activated Phosphoramidate:

Phosphorylation of an enantiomerically pure substituted 1,3-aminoalcohol or 1,3-diamine with for example, a commercially available phosphorodichloridate R—OP(O)Cl$_2$, where RO is a leaving group, preferably aryl substituted with electron withdrawing groups, such as a nitro or a chloro, produces two diastereomeric intermediates that can be separated by a combination of column chromatography and/or crystallization. Such a method may also be utilized in preparing chiral chlorophosphoroamidate. Chiral phosphoramidate intermediates can be obtained by utilization of optically pure amine as the chiral auxiliary. This type of intermediate are known to undergo stereospecific substitution in the phosphate formation (Nakayama, et al. *J. Am. Chem. Soc.,* 1990, 112, 6936). The relative configuration of the phosphorus atom can be determined by comparison of the $^{31}$P NMR spectra. The chemical shift of the equatorial phosphoryloxy moiety (trans-isomer) is always more upfield than the one of the axial isomer (cis-isomer) (Verkade, et al, *J. Org. Chem.,* 1977, 42, 1549).

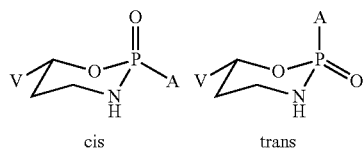

cis      trans

I.1.c. Synthesis of Prodrugs Using Activated Phosphoramidates:

Coupling of activated phosphoramidates with alcohols (MH) is accomplished in the presence of an organic base. For example, Chloro phosphoramidates synthesized as described in the earlier section react with an alcohol in the presence of a base such as pyridines or N-methylimidazole. In some cases phosphorylation is enhanced by in situ generation of iodophosphoramidates from chloro (Stomberg, et al., *Nucleosides & Nucleotides.,* 1987, 5: 815). Phosphoroflouridate intermediates have also been used in phosphorylation reactions in the presence of a base such as CsF or n-BuLi to generate cyclic prodrugs (Watanabe et al., *Tetrahedron lett.,* 1988, 29, 5763). Phosphoramidate intermediates are shown to couple by transition metal catalysis (Nagamatsu, et al., *Tetrahedron Lett.,* 1987, 28, 2375).

Reaction of the optically pure diastereomer of phosphoramidate intermediate with the hydroxyl of drug in the presence of an acid produces the optically pure phosphate prodrug by direct S$_N$2(P) reaction (Nakayama, et al., *J. Am. Chem. Soc.,* 1990, 112, 6936). Alternatively, reaction of the optically pure phosphoramidate precursor with a fluoride source, preferably cesium fluoride or tetrabutylammonium fluoride, produces the more reactive phosphorofluoridate which reacts with the hydroxyl of the drug to give the optically pure prodrug configuration at the phosphorus atom (Ogilvie, et al., *J. Am. Chem. Soc.,* 1977, 99, 1277).

I.2 Synthesis Via Phosphoramidite Intermediate:

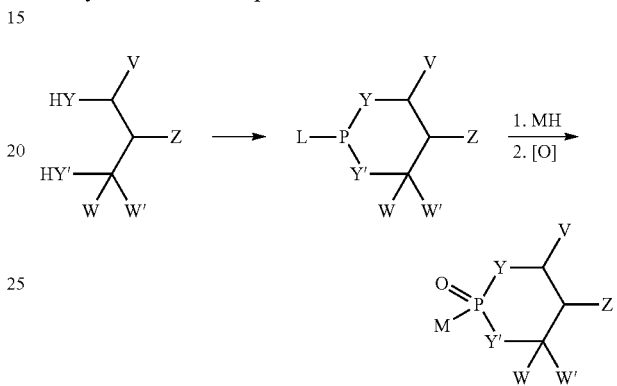

I.2.a. Synthesis of Activated P(III) Intermediates:

Phosphorylation of hydroxy and amino groups is achieved using cyclic phosphorylating agents where the agent is at the P(III) oxidation state. One preferred phosphorylating agent is a chloro phosphoramidite (L' chloro). Cyclic chlorophosphoramidites are prepared under mild conditions by reaction of phosphorus trichloride with substituted 1,3-aminoalcohols or 1,3-diamines (Wada, et al, *Tetrahedron Lett.,* 1990, 31, 6363). Alternatively phosphoramidites can be used as the phosphorylating agent (Beaucage, et al., *Tetrahedron,* 1993, 49, 6123). Appropriately substituted phosphoramidites can be prepared by reacting cyclic chlorophosphoramidite with N,N-dialkylamine (Perich, et al., *Aust. J. Chem.,* 1990, 43, 1623. Perich, et al., *Synthesis,* 1988, 2, 142) or by reaction of commercially available dialkylaminophosphorochloridate with substituted propyl-1,3-aminoalcohols or 1,3-diamines.

I.2.b. Synthesis of Chiral Activated P(III) Intermediate:

In the cases where unsymmetrical 1,3-aminoalcohols or 1,3-diamines are used, the cyclic phosphoramidites are expected to form a mixture of chiral isomers. When an optically active pure amino alcohol or diamine is used a chromatographically separable mixture of two stable diastereomers with the leaving group (NRR') axial and equatorial on the phosphorous atom is expected (Brown et al., *Tet.,* 1990, 46, 4877). Pure diasteromers can usually be obtained by chromatographic separation. These intermediates may also be prepared through chirality induction by an optically active amine.

I.2.c. Synthesis of Prodrugs Using Activated Phosphoramidites:

Appropriately substituted chlorophosphoramidites are used to phosphorylate alcohols on nucleosides in the presence of an organic base (e.g., triethylamine, pyridine). Alternatively, the phosphoramidite can be obtained by coupling the nucleoside with a phosphoramidate in the presence of a coupling promoter such as tetrazole or benzimidazolium triflate (Hayakawa et al., *J. Org. Chem.,* 1996, 61, 7996). Since condensation of alcohols with chloro phosphoramidites or phosphoramidites is an $S_N2(P)$ reaction, the product is expected to have an inverted configuration. This allows for the stereoselective synthesis of cyclic phosphoramidites of prodrugs. Isomeric mixtures of phosphorylation reactions can also be equilibrated (e.g. thermal equilibration) to a more thermodynamically stable isomer.

The resulting phosphoramidites of prodrugs are subsequently oxidized to the corresponding phosphoramidate prodrugs using an oxidant such as molecular oxygen or t-butylhydroperoxide (Ozaki et al., Tetrahedron. Lett., 1989, 30, 5899). Oxidation of optically pure P(III) intermediate is expected to stereoselectively provide optically active prodrugs (Mikolajczyk, et al., J. Org. Chem., 1978, 43, 2132. Cullis, P. M. J. Chem. Soc., Chem. Commun., 1984, 1510, Verfurth, et al., Chem. Ber., 1991, 129, 1627).

I.3 Synthesis of Phosphoramidate Prodrugs Via Diacids:

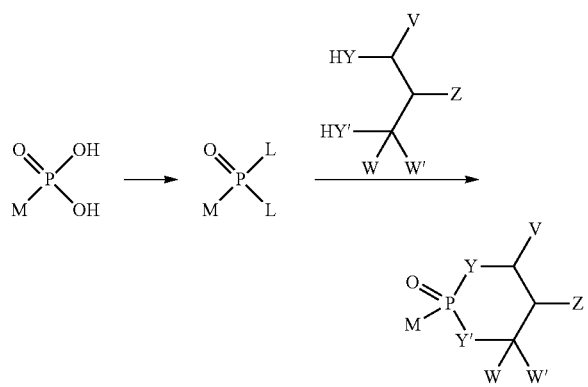

Prodrugs of formula I are synthesized by reaction of the corresponding phosphodichloridate and an 1,3-aminoalcohol or 1,3-diamine (Khamnei, et al., J. Med. Chem., 1996, 39:4109). For example, the reaction of a phosphodichloridate with substituted 1,3-aminoalcohols or diamines in the presence of base (such as pyridine, triethylamine, etc) yields compounds of formula I. These conditions can also be applied in the synthesis of cyclophosphamide analogs where commercially available bis(2-chloroethyl)phosphoramidic dichloride is coupled with corresponding substituted 1,3-amino alcohols or 1,3-diamines.

Such reactive dichloridate intermediates, can be prepared from the corresponding acids and the chlorinating agents e.g. thionyl chloride (Starrett, et al., J. Med. Chem., 1994, 1857), oxalyl chloride (Stowell, et al., Tetrahedron Lett., 1990, 31: 3261), and phosphorus pentachloride (Quast, et al., Synthesis, 1974, 490). Alternatively, these dichlorophosphonates can also be generated from disilyl esters (Bhongle, et al., Synth. Commun., 1987, 17: 1071) and dialkyl esters (Still, et al., Tetrahedron Lett., 1983, 24: 4405; Patois, et al., Bull. Soc. Chim. Fr., 1993, 130: 485).

Alternatively, acid coupling reagents including, but not limited to, carbodiimides (Alexander, et al., Collect. Czech. Chem. Commun., 1994, 59: 1853; Casara, et al., Bioorg. Med. Chem. Lett., 1992, 2: 145; Ohashi, et al., Tetrahedron Lett., 1988, 29: 1189; Hoffman, M., Synthesis, 1988, 62), and benzotriazolyloxytris-(dimethylamino)phosphonium salts (Campagne, et al., Tetrahedron Lett., 1993, 34: 6743) are also used in the synthesis of compounds of formula I starting from phosphate or phosphonate diacids.

Chiral phosphonoamidate prodrugs can be synthesized by either resolution (Pogatnic, et al., Tetrahedron Lett., 1997, 38, 3495) or by chirality induction (Taapken, et al., Tetrahedron Lett., 1995, 36, 6659; J. Org. Chem., 1998, 63, 8284).

1.4. Miscellaneous Methods:

Phosphorylation of an alcohol is also achieved under Mitsunobu reaction conditions using the cyclic 1',3'-propanyl phosphoramidic acid in the presence of triphenylphosphine and diethylazodicarboxylate (Kimura et al., Bull. Chem. Soc. Jpn., 1979, 52, 1191). Furthermore, phosphate prodrugs can be made by conversion of nucleoside to the dichloridate intermediate with phosphoryl chloride in presence of triethylphosphite and quenching with substituted-1,3-aminoalcohols (Farquhar et al., J. Org. Chem., 1983, 26, 1153).

Phosphorylation can also be achieved by making the mixed anhydride of the cyclic diester of phosphoramidic acid and a sulfonyl chloride, preferably 8-quinolinesulfonyl chloride, and reacting the hydroxyl of the drug in the presence of a base, preferably methylimidazole (Takaku, et al., J. Org. Chem., 1982, 47, 4937). In addition, starting from a chiral cyclic phosphoramidic acid, obtained by chiral resolution (Wynberg, et al., J. Org. Chem., 1985, 50, 4508) is also a source for chiral phosphoramidate prodrugs.

III. Synthesis of Substituted 1,3-Hydroxyamines and 1,3-Diamines:

A large number of synthetic methods are available for the preparation of substituted 1,3-hydroxyamines and 1,3-diamines due to the ubiquitous nature of these functionalities in naturally occurring compounds. Following are some of these methods organized into:

1. synthesis of substituted 1,3-hydroxy amines; 2. synthesis of substituted 1,3-diamines and 3. synthesis of chiral substituted 1,3-hydroxyamines and 1,3-diamines.

III.1. Synthesis of Substituted 1,3-Hydroxy Amines:

A general synthetic procedure for 3-aryl-3-hydroxy-propan-1-amine type of prodrug moiety involves aldol type condensation of aryl esters with alkyl nitriles followed by reduction of resulting benzoylacetonitrile (Shih et al., Heterocycles, 1986, 24, 1599). The procedure can also be adapted for formation 2-substituted aminopropanols by using substituted alkylnitrile. In another approach, 3-aryl-3-amino-propan-1-ol type of prodrug groups are synthesized from aryl aldehydes by condensation of malonic acid in presence of ammonium acetate followed by reduction of resulting substituted b-amino acids. Both these methods enable to introduce wide variety of substitution of aryl group (Shih, et al., Heterocycles., 1978, 9, 1277). In an alternate approach, -substituted organolithium compounds of 1-amino-1-aryl ethyl dianion generated from styrene type of compounds undergo addition with carbonyl compounds to give variety of W, W' substitution by variation of the carbonyl compounds (Barluenga, et al., J. Org. Chem., 1979, 44, 4798).

Large number of synthetic methods are known for the preparation of racemic or chiral 1,3-diols. These methods may be utilized in the synthesis of corresponding substituted 1,3-aminoalcohols or 1,3 diamines by converting hydroxy functionality to a leaving group and treating with anhydrous ammonia or required primary or secondary amines (Corey, et al., Tetrahedron Lett., 1989, 30, 5207: Gao, et al., J. Org. Chem., 1988, 53, 4081). A similar transformation may also be achieved directly from alcohols in Mitsunobu type of reaction conditions (Hughes, D. L., Org. React., 1992, 42).

A variety of synthetic methods are known to prepare the following types of 1,3-diols: a) 1-substituted; b) 2-substituted; and c) 1,2- or 1,3-annulated in their racemic or chiral form. Substitution of V, W, Z groups of formula I, can be introduced or modified either during synthesis of aminoalcohols or after the synthesis of prodrugs.

III.1a) 1-Substituted 1,3-Diols:

1,3-Dihydroxy compounds can be synthesized by several well known methods in literature. Aryl Grignard additions to 1-hydroxy propan-3-al give 1-aryl-substituted propan-1,3-diols. This method will enable conversion of various substituted aryl halides to 1-aryl substituted-1,3-propane diols (Coppi, et al., *J. Org. Chem.*, 1988, 53, 911). Aryl halides can also be used to synthesize 1-substituted propanediols by Heck coupling of 1,3-diox-4-ene followed by reduction and hydrolysis (Sakamoto, et al., *Tetrahedron Lett.*, 1992, 33, 6845). Substituted 1,3-diols can be generated enantioselective reduction of vinyl ketone and hydroboration or by kinetic resolution of allylic alcohol. Variety of aromatic aldehydes can be converted to 1-substituted-1,3-diols by vinyl Grignard addition followed by hydroboration. Substituted aromatic aldehydes are also utilized by lithium-t-butylacetate addition followed by ester reduction (Turner., *J. Org. Chem.*, 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure 1,3-diols (Gao, et al., *J. Org. Chem.*, 1980, 53, 4081). Alternatively, enantiomerically pure 1,3-diols can be obtained by chiral borane reduction of hydroxyethyl aryl ketone derivatives (Ramachandran, et al., *Tetrahedron Lett.*, 1997, 38 761). Pyridyl, quinoline, isoquinoline propan-3-ol derivatives can be oxygenated to 1-substituted-1,3-diol by N-oxide formation followed by rearrangement in acetic anhydride conditions (Yamamoto, et al., *Tetrahedron*, 1981, 37, 1871). Aldol condensation is another well described method for synthesis of the 1,3-oxygenated functionality (Mukaiyama, *Org. React.*, 1982, 28, 203). Chral substituted diols can also be made by enantioselective reduction of carbonyl compounds, by chiral aldol condensation or by enzyme promoted kinetic resolution.

III.1b) 2-Substituted 1,3-Diols:

Various 2-substituted-1,3-diols can be made from commercially available 2-(hydroxymethyl)-1,3-propane diol. Pentaerythritol can be converted to triol via decarboxylation of diacid followed by reduction (Werle, et al., *Liebigs. Ann. Chem.*, 1986, 944) or diol-monocarboxylic acid derivatives can also be obtained by decarboxylation under known conditions (Iwata, et al., *Tetrahedron lett.* 1987, 28, 3131). Nitrotriol is also known to give triol by reductive elimination (Latour, et al., *Synthesis*, 1987, 8, 742). The triol can be derivatised by mono acetylation or carbonate formation by treatment with alkanoyl chloride, or alkylchloroformate (Greene and Wuts, *Protective groups in organic synthesis*, John Wiley, New York, 1990). Aryl substitution can be affected by oxidation to aldehyde and aryl Grignard additions. Aldehydes can also be converted to substituted amines by reductive amination reaction.

III.1c) Cyclic-1,3-diols:

Compounds of formula I where V—Z or V—W are fused by four carbons are made from Cyclohexane derivatives. Commercially available cis,cis-1,3,5-cyclohexane triol can be used as is or modified as described in case of 2-substituted propan-1,3-diols to give various analogues. These modifications can either be made before or after ester formation. Various 1,3-cyclohexane diols can be made by Diels-Alder methodology using pyrone as diene (Posner, et al., *Tetrahedron Lett.*, 1991, 32, 5295). Cyclohexyl diol derivatives are also made by nitrile oxide-olefin additions (Curran, et al., *J. Am. Chem. Soc.*, 1985, 107, 6023). Alternatively, cyclohexyl precursors are also made from commercially available quinic acid (Rao, et al., *Tetrahedron Lett.*, 1991, 32, 547.)

III.2. Synthesis of Substituted 1,3-Diamines:

Substituted 1,3-diamines are synthesized starting from variety of substrates. Arylglutaronitriles can be transformed to 1-substituted diamines by hydrolysis to amide and Hoffman rearrangement conditions (Bertochio, et al., *Bull. Soc. Chim. Fr*, 1962, 1809). Whereas, malononitrile substitution will enable variety of Z substitution by electrophile introduction followed by hydride reduction to corresponding diamines. In another approach, cinnamaldehydes react with hydrazines or substituted hydrazines to give corresponding pyrazolines which upon catalytic hydrogenation result in substituted 1,3-diamines (Weinhardt, et al., *J. Med. Chem.*, 1985, 28, 694). High trans-diastereoselectivity of 1,3-substitution is also attainable by aryl Grignard addition on to pyrazolines followed by reduction (Alexakis, et al., *J. Org. Chem.*, 1992, 576, 4563). 1-Aryl-1,3-diaminopropanes are also prepared by diborane reduction of 3-amino-3-arylacrylonitriles which in turn are made from nitrile substituted aromatic compounds (Dornow, et al., *Chem. Ber.*, 1949, 82, 254). Reduction of 1,3-diimines obtained from corresponding 1,3-carbonyl compounds are another source of 1,3-diamine prodrug moiety which allows a wide variety of activating groups V and/or Z (Barluenga, et al., *J. Org. Chem.*, 1983, 48, 2255).

III.3. Synthesis of Chiral Substituted 1,3-Hydroxyamines and 1,3-Diamines:

Enantiomerically pure 3-aryl-3-hydroxypropan-1-amines are synthesized by CBS enantioselective catalytic reaction of β-chloropropiophenone followed by displacement of halo group to make secondary or primary amines as required (Corey, et al., *Tetrahedron Lett.*, 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., *J. Org. Chem.*, 1982, 47, 4005). Chiral induction in 1,3-polar additions to form substituted isoxazolidines is also attained by chiral phosphine palladium complexes resulting in enatioselective formation of δ-amino alcohol (Hori, et al., *J. Org. Chem.*, 1999, 64, 5017). Alternatively, optically pure 1-aryl substituted amino alcohols are obtained by selective ring opening of corresponding chiral epoxy alcohols with desired amines (Canas et al., *Tetrahedron Lett.*, 1991, 32, 6931).

Several methods are known for diastereoselective synthesis of 1,3-disubstituted aminoalcohols. For example, treatment of (E)-N-cinnamyltrichloroacetamide with hypochlorus acid results in trans-dihydrooxazine which is readily hydrolysed to erythro-β-chloro-α-hydroxy-δ-phenylpropanamine in high diastereoselectivity (Commercon et al., *Tetrahedron Lett.*, 1990, 31, 3871). Diastereoselective formation of 1,3-aminoalcohols is also achieved by reductive amination of optically pure 3-hydroxy ketones (Haddad et al., *Tetrahedron Lett.*, 1997, 38, 5981). In an alternate approach, 3-aminoketones are transformed to 1,3-disubstituted aminoalcohols in high stereoselectivity by a selective hydride reduction (Barluenga et al., *J. Org. Chem.*, 1992, 57, 1219).

All the above mentioned methods can also be applied to prepare corresponding V—Z or V—W annulated chiral aminoalcohols. Furthermore, such optically pure amino alcohols are also a source to obtain optically pure diamines by the procedures described earlier in the section.

Formulations

Compounds of the invention are administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient may be preferred. The dose may be administered in as many divided doses as is convenient. When other methods are used (e.g. intravenous administration), compounds are administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

EXAMPLES

The prodrug compounds of this invention, their intermediates, and their preparation can be understood further by the examples which illustrate some of the processes by which these compounds are prepared. These examples should not however be construed as specifically limiting the invention and variations of the compounds, now known or later developed, are considered to fall within the scope of the present invention as hereinafter claimed.

Compounds of formula I are prepared using procedures detailed in the following examples.

Example 1

General Procedure for Phosphoramidate Prodrugs of Phosphonic Acid Containing Drugs A suspension of 5-Isobutyl-2-methyl-4-(2-(5-phosphono) furanyl)thiazole (200 mg, 0.6 mmol) in 2.5 mL of thionyl chloride was heated at reflux temperature for 4 h. The reaction mixture was cooled and evaporated to dryness followed by azeotroping with toluene. To the solution of the resulting residue in 4 ml of methylene chloride was added a solution of amino alcohol (82 mg, 0.54 mmol) and pyridine (0.5 ml, 6 mmol) in 1 mL of methylene chloride.

After stirring at 25° C. for 4 h the reaction was evaporated and coevaporated with toluene. The crude product was chromatographed by eluting with 10% methanol-dichloromethane to give 52 mg (20.8%) of a less polar isomer and 48 mg (19.2%) of a more polar isomer.

The following compounds were prepared in this manner:
1.1: 5-Isobutyl-2-methyl-4-{2-[5-(1-phenyl-1,3-propyl) phosphorimido]-furanyl}thiazole, less polar isomer. Rf=0.76 in 10% MeOH/CH2Cl2. Anal. Cald. for C21H25N2O3PS+0.25H2O+0.1HCl: C, 59.40; H, 6.08; N, 6.60. Found: C, 59.42; H, 5.72; N, 6.44.
1.2: 5-Isobutyl-2-methyl-4-{2-[5-(1-phenyl-1,3-propyl) phosphorimido]-furanyl}thiazole, more polar isomer. Rf=0.7 in MeOH/CH2Cl2. Anal. Cald. for C21H25N2O3PS+0.25H2O: C, 59.91; H, 6.1; N, 6.65. Found: C, 60.17; H, 5.81; N, 6.52.
1.3: 2-Amino-5-isobutyl-4-{2-[5-(1-phenyl-1,3-propyl) phosphoramido]furanyl}thiazole. Rf=0.53 (silica, 9:1 CH2Cl2/MeOH). Anal. cald. for C20 H24 N3 O3 P S+0.2CH2Cl2+0.25H2O: C, 55.27; H, 5.72; N, 9.57. Found: C, 55.03; H, 5.42; N, 9.37.
1.4: 2-Amino-5-isobutyl-4-{2-[5-(1-phenyl-1,3-propyl) phosphoramido]furanyl}thiazole, less polar isomer. Rf=0.57 (silica, 9:1 CH2Cl2/MeOH). Anal. cald. for C20 H24 N3 O3 P S+0.15 CH2Cl2: C, 56.26; H, 5.69; N, 9.77. Found: C, 56.36; H, 5.46; N, 9.59.
1.5: 2-Amino-5-methylthio-4-{2-[5-(1-phenyl-1,3-propyl) phosphoramido-]furanyl}thiazole, less polar isomer. Rf=0.59 (silica, 9:1 CH2Cl2/MeOH). Anal. cald. for C17 H18 N3 O3 P S2+0.4HCl: C, 48.38; H, 4.39; N, 9.96. Found: C, 48.47; H, 4.21; N, 9.96.
1.6: 2-Amino-5-methylthio-4-{2-[5-(1-phenyl-1,3-propyl) phosphoramido]furanyl}thiazole, more polar isomer. Rf=0.56 (silica, 9:1 CH2Cl2/MeOH). Anal. cald. for C17 H18 N3 O3 P S2: C, 50.11; H, 4.45; N, 10.31. Found: C, 49.84; H, 4.19; N, 10.13.
1.7: 2-Amino-5-methylthio-4-{2-[5-(N-methyl-1-phenyl-1, 3-propyl)phos-phoramido]furanyl}thiazole. Rf=0.56 (silica, 9:1 CH2Cl2/MeOH). Anal. cald. for C18 H20 N3 O3 P S2+0.25HCl C: 50.21; H, 4.74; N, 9.76. Found: C, 50.31; H, 4.46; N, 9.79.
1.8: 2-Amino-5-isobutyl-4-{2-[5-(1-phenyl-1,3-propyl)-N-acetylphosph-oramido]furanyl}thiazole. Rf=0.62 (silica, 9:1 CH2Cl2/MeOH). Anal. cald. for C22 H26 N3 O4 P S+1.25H2O: C, 54.82; H, 5.96; N, 8.72. Found: C, 55.09; H, 5.99; N, 8.39.

1.9: 2-Amino-5-isobutyl-4-{2-[5-(1-[2,4-dichlorophenyl]-propan-1,3-yl)phosphoramido]furanyl}thiazole. mp 235-237 C (decomp). Rf=0.35 (silica, 3:2 EtOAc/CH2Cl2). Anal. cald. for C20 H22 Cl2 N3 O3 P S: C, 49.39; H, 4.56; N, 8.64. Found: C, 49.04; H, 4.51; N, 8.37.

1.10: 188-189 9-{2-[1-phenyl-1-aza-3-oxa-2-phosphorinanyl-2-methyloxy]ethyl}adenine. mp 188-189 C. Rf=0.25 (silica, 9:1 CHCl2/MeOH). Anal. cald. for C17 H21 N6 O3 P+0.5H2O: C, 51.38; H, 5.58; N, 21.15. Found: C, 51.05; H, 5.28; N, 20.77.

1.11: 2-Amino-5-isobutyl-4-{2-[5-(1-(3-chlorophenyl)-propan-1,3-yl)phosphoradia-mido]furanyl}thiazole. Light yellow solid; Rf=0.45 (Silica, 5:95 Methanol/dichloromethane); $^1$H NMR (200 MHz, DMSO-d6) δ 7.35 (m, 4H); 7.1 (m, 1H), 6.6 (m, 1H); 5.55 (m, 1H), 2.8 (d, 2H), 0.9 (d, 6H).

Example 2

Step A

A solution of 3-amino-3-phenyl-1-propanol (1 g, 6.6 mmol) and triethylamine (3 ml, 21.8 mmol) in tetrahydrofuran (60 ml) was added dropwise over 20 minutes into a solution of 4-nitrophenyl phosphorodichloridate in tetrahydrofuran at 0° C. A white precipitate quickly forms. The yellow heterogeneous mixture was stirred at 0° C. for 1 hour then warmed slowly to rt. After stirring at rt for 60 hours, the precipitate was dissolved with water (40 ml). The clear yellow solution was concentrated to ca 40 ml. The resulting mixture was diluted with a saturated aqueous solution of sodium bicarbonate and extracted twice with ethyl acetate. The combined organic extracts were washed with a saturated aqueous solution of sodium bicarbonate and brine. The aqueous washes were back extracted and the organic extracts combined. The combined organic extracts were dried over sodium sulfate, concentrated and purified by column chromatography (silica gel, hexanes/ethyl acetate) to give fast eluting trans isomer (995 mg, 45%) and slow eluting cis isomer (1 g, 45%) and);

Step B

A mixture of 2',3'-dideoxy-adenosine (50 mg, 0.21 mmol), cesium fluoride (323 mg, 2.1 mmol) and fast eluting (4-Nitrophenoxy)-4-phenyl-1,3,2-oxazaphosphorinan-2-one (142 mg, 0.4 mmol) in tent-butanol was heated at 80° C. After 48 hours, more (4-Nitrophenoxy)-4-phenyl-1,3,2-oxazaphosphorinan-2-one (70 mg) was added and stirring was continued at 80° C. After 5 days, the cooled yellow heterogeneous mixture was diluted with 50/50 methanol/dichloromethane, filtered through a pad of silica and rinsed with 50/50 methanol/dichloromethane. The combined filtrates were concentrated and the residue was purified by column chromatography (silica gel, methanol/dichloromethane) to give the prodrug which was re crystallized from dichloromethane and hexanes: 42 mg (47% yield).

The following compounds are prepared in this manner:
2.1 2',3'-Dideoxy-5'-O-(2-oxo-4-phenyl-1,3,2-oxazaphosphorin-2-yl)-adenosine. mp 119-122. Rf=0.25 (silica gel, 1/9 methanol/dichloromethane). Anal. Cald. for $C_{19}H_{23}N_6O_4P$+0.9 mol dichloromethane: C, 47.16; H, 4.93; N, 16.58. Found: C, 47.03; H, 4.98; N, 16.61.

2.2 3'-Azido-3'-deoxy-5'-O-(4-phenyl-2-oxo-1,3,2-oxazaphosphorin-2-y-l)-thymidine. mp 85-105. Rf=0.5 (silica gel, 1/9 methanol/dichloromethane). Anal. cald. for $C_{19}H_{23}N_6O_6P$: C, 49.35; H, 5.01; N, 18.17. Found: C, 49.32; H, 5.17; N, 17.89.

Example 3

Step A

Same as step A of example 2.

Step B

Lithium hydride (15 mg, 1.52 mmol) was added to a solution of 9-β-D-arabinofuranosyl-adenine (100 mg, 0.37 mmol) and fast eluting (4-nitrophenoxy)-4-phenyl-1,3,2-oxazaphosphorinan-2-one (250 mg, 0.74 mmol) in dimethylformamide at room temperature. After 6 hours the yellow heterogeneous mixture was neutralized with acetic acid. The clear yellow solution was concentrated and the residue was purified by column chromatography (silica gel, methanol/dichloromethane). The isolated product was further purified by preparative TLC and recrystallized from ethanol to give the prodrug: 18 mg (11% yield);

The following compound is prepared in this manner:
3.1 5'-O-(2-oxo-4-Phenyl-1,3,2-oxazaphosphorin-2-yl)-9-β-D-arabinofuranosyl-adenine. mp>250. Rf=0.25 (silica gel, 2/8 methanol/dichloromethane). Anal. cald. for $C_{19}H_{23}N_6O_6P$: C, 49.35; H, 5.01; N, 18.17. Found: C, 49.22; H, 4.89; N, 18.03.

The following compounds are made in a similar manner with the exception that the reactions were neutralized with 1N solution of hydrochloric acid during work up.
3.2 9-[(2-(4-Phenyl-2-oxo-1,3,2-oxazaphosphorinan-2-oxy)-ethoxy)methyl]-guanin: mp 151-165; Rf=0.2 (silica gel, 2/8 methanol/dichloromethane); Anal. cald. for $C_{17}H_{21}N_6O_5P$+2H2O: C, 44.74; H, 5.52; N, 18.41. Found: C, 44.45; H, 5.40; N, 18.14.
3.3 2'-Deoxy-5-fluoro-5'-O-(4-phenyl-2-oxo-1,3,2-oxazaphosphorin-2-yl)-uridine. mp 188-195 Dec. Rf=0.25 (silica gel, 1/9 methanol/dichloromethane). MS cald. for $C_{18}H_{21}FN_3O_7P$+Na$^+$: 464. Found: 464; MS cald. for $C_{18}H_{21}FN_3O_7P$—H: 440. Found: 440.

Example 4

General Procedure for Formation of Nucleotide Prodrugs by P(III) Intermediates

To a solution of 1(aryl)-1-(1-alkyl or acyl amino) propanol (1 mmol) in dichloromethane (10 mL) is added phosphorus trichloride at 0° C. The reaction is warmed to room temperature and allowed to stir for 3 h. Reaction mixture is concentrated, azeotroped with toluene (2×10 mL) and dried. Crude chlorophosphoramidite is used in the next step without further purification.

To a solution of nucleoside (1 mmol) in DMF (10 mL) is added diisopropylethylamine (2 mmol) at −40° C. To this mixture is added crude cyclic chlorophoramidite (1 mmole) in 2 mL of DMF. The mixture is warmed to room temperature and stirred for 2 h. The reaction is cooled back to −40° C. and 5-6M t-butylhydroperoxide in decane (2 mmol) is added and left at room temperature. After overnight stirring, the reaction is concentrated and crude mixture is chromatographed.

Example 5

General Procedure for Preparation of 3-Aryl-3-Aminoprolpanols from Aryl Aldehydes (Shih, et al., *Heterocycles*, 1978, 9, 1277)

Step A:

A mixture of an appropriate aryl aldehyde (10 mmol), malonic acid (10 mmol), and ammonium acetate (10 mmol) in 50 mL of 95% ethanol is heated in a water bath at 80° C. Carbon dioxide begins to evolve at 55° C. and the reaction is complete in 5-7 h. The white solid is collected by suction and recrystallized from aqueous ethanol to obtain the 3-aryl-3-aminopropionic acid.

Step B:

To a suspension of lithium aluminum hydride (50 mmol) in anhydrous tetrahydrofuran (40 mL) is added a 3-aryl-3-aminopropionic acid (20 mmol) with cooling and stirring. The mixture is refluxed for 3 h, allowed to stand overnight, and treated with moist ether and then with water to decompose the excess of lithium aluminum hydride. The organic layer is decanted, and the material left in the flask is extracted with hot ethylacetate (3×50 mL). The organic solutions are combined and rotary evaporated. The residue is vacuum distilled or recrystallized to obtain 3-aryl-3-aminopropanol.

Example 6

General Procedure for Preparation of 3-Aryl-3-Hydroxypropylamines from Epoxy Cinnamyl Alcohols (Gao, et al., *J. Org. Chem.*, 1988, 53, 4084)

Step A:

To a solution of commercial (−)-(2S,3S)-2,3-epoxycinnamyl alcohol (10.0 mmol) in dimethoxyethane (50 mL) is added a 3.4 M solution of sodium bis(2-methoxyethoxy) aluminum hydride (Red-Al) in toluene (10.5 mmol) dropwise under nitrogen at 0° C. After stirring at room temperature for 3 h, the solution is diluted with ether and quenched with 5% HCl solution. After further stirring at room temperature for 30 min, the white precipitate formed is removed by filtration and boiled with ethyl acetate and filtered again. The combined organic extracts are dried with magnesium sulfate and concentrated to give (R)-3-phenyl-1,3-dihydroxypropane.

Step B:

To a solution of (R)-3-phenyl-1,3-dihydroxypropane (17.8 mmol) and triethylamine (25.6 mmol) in ether (90 mL) is added dropwise MsCl (18.7 mmol) under nitrogen at −10° C. After stirring at −10 to 0° C. for 3 h, the mixture is poured into ice water (30 mL), organic layer was washed with 20% $H_2SO_4$, saturated aqueous $NaHCO_3$, and brine, and dried over magnesium sulfate. The crude product is purified by chromatography on a silica gel column.

Step C:

A solution of (R)-3-phenyl-3-(hydroxy)-propyl methanesulfonate (3 mmol) and methylamine (10 mL, 40% in water) in THF (10 mL) is heated at 65° C. for 3 h. After cooling, the solution is diluted with ether, washed with saturated aqueous sodium bicarbonate and brine, and dried with anhydrous potassium carbonate. Concentration of extract provides (R)-3-phenyl-3-(hydroxy)-propyl amine.

Example 7

General Procedure for Preparation of 3-Aryl-Propylenediamines from Cinnamyl Aldehydes (Weinhardt, et al., *J. Med. Chem.*, 1985, 28, 694)

Step A:

To a solution of cinnamaldehyde (10 mmol) in 100 mL of EtOH is added substituted hydrazine (10 mmol). The reaction is stirred at room temperature for 45 min. Solvents are removed on a rotatory evaporator and saturated $NaHCO_3$ was added to the residue. The crude product is extracted into ether. The organic layer is washed, dried and evaporated. Crude products from chromatography results in a pure pyrazoline adduct.

Step B:

A solution of 3-phenylpyrazoline (10 mmol) in 50 mL of AcOH and 10 mL of 10% HCl is hydrogenated at atmospheric pressure over 500 mg of 5% Pt/C. The reaction is stirred under hydrogen for 6 h. The catalyst is removed by filtration and the filtrate is concentrated. The crude product is purified by column to give pure 3-Aryl-propylenediamines derivative.

Example 8

General Procedure for 1,3-Amino Alcohols for 2-Substituted Prodrugs (V, W and W'=H and Z=—$CHR^2OH$)

Step A:

To a solution of commercially available 2-(hydroxymethyl)-1,3-propane diol (1 mmol) in pyridine (5 mL) is added methanesulfonyl chloride (1 mmol) and stirred at room temperature until the reaction is complete. The mixture is concentrated, extracted and product is purified by column chromatography.

Step B:

A solution of 2-(methylsulfonyloxymethylene)-1,3-propane diol (1 mmol) and ammonium hydroxide (10 mL, 30% in water) in THF (10 mL) is heated at 100° C. in a sealed reactor. After cooling, the mixture is concentrated, extracted and product is purified by column chromatography to give 2-substituted-1,3-amino alcohol. Appropriate amines may be used in step B to vary —$NR^6$ substitution. 2-substituted-1,3-diamines may also be synthesized using Step A and B from 2-(hydroxymethyl)-1,3-propane diol using appropriate stoichiometry of reagents.

Step C:

Prodrugs of 2-substituted-1,3-amino alcohols or 2-substituted-1,3-diamines are synthesized by following coupling procedures as described in example 1 or example 2 (steps A and B) or example 3 (step B) or example 4 depending on the parent compound.

Example 9

General Procedure for Cyclic 1,3-Amino Alcohols (Together V and W are Connected)

Step A:

Commercially available cis,cis-1,3,5-cyclohexane triol is converted to a mono mesylate as described in example 8, step A.

Step B:

cis,cis-1-(methylsulfonyloxy)cyclohexane-3,5-diol is transformed to corresponding amino alcohol as described in example 8, step B. Appropriate amines may be used in step B to vary —NR$^6$ substitution. 1-Hydroxy-3,5-diamino cyclohexane may also be synthesized using Step A and B from cis, cis-1,3,5-cyclohexane triol using appropriate stoichiometry of reagents.

Step C:

Prodrugs of cyclohexyl-1,3-amino alcohols or 1,3-diamines are synthesized by following procedures as described in example 1 or example 2 (steps A and B) or example 3 (step B) or example 4 depending on the parent compound.

Example 10

Preparation of 2-substituted 4-[2'-(5'-phosphono)furanyl]thiazoles

Step A:

A solution of furan (1.3 mmole) in toluene was treated with 4-methyl pentanoic acid (1 mmole), trifluoroacetic anhydride (1.2 mmole) and boron trifluoride etherate (0.1 mmole) at 56° C. for 3.5 h. The cooled reaction mixture was quenched with aqueous sodium bicarbonate (1.9 mmole), filtered through a celite pad. Extraction, evaporation and distillation gave 2-[(4-methyl-1-oxo)pentyl]furan as a brown oil (bp 65-77° C., 0.1 mmHg).

Step B:

A solution of 2-[(4-methyl-1-oxo)pentyl]furan (1 mmole) in benzene was treated with ethylene glycol (2.1 mmole) and p-toluenesulfonic acid (0.05 mmole) at reflux for 60 h while removing water via a Dean-Stark trap. Triethyl orthoformate (0.6 mmole) was added and resulting mixture was heated at reflux for an additional hour. Extraction and evaporation gave 2-(2-furanyl)-2-[(3-methyl)butyl]-1,3-dioxolane as an orange liquid.

Step C:

A solution of 2-(2-furanyl)-2-[(3-methyl)butyl]-1,3-dioxolane (1 mmole) in THF was treated with TMEDA (1 mmole) and nBuLi (1.1 mmole) at −45° C., and the resulting reaction mixture was stirred at −5 to 0° C. for 1 h. The resulting reaction mixture was cooled to −45° C., and cannulated into a solution of diethyl chlorophosphate in THF at −45° C. The reaction mixture was gradually warmed to ambient temperature over 1.25 h. Extraction and evaporation gave 2-[2-(5-diethylphosphono)furanyl]-2-[(3-methyl)butyl]-1,3-dioxolane as a dark oil.

Step D:

A solution of 2-[2-(5-diethylphosphono)furanyl]-2-[(3-methyl)butyl]-1,3-dioxolane (1 mmole) in methanol was treated with 1 N hydrochloric acid (0.2 mmole) at 60° C. for 18 h. Extraction and distillation gave 5-diethylphosphono-2-[(4-methyl-1-oxo)pentyl]furan as a light orange oil (bp 152-156° C., 0.1 mmHg).

Step E:

A solution of compound gave 5-diethylphosphono-2-[(4-methyl-1-oxo)pentyl]furan (1 mmole) in ethanol was treated with copper (II) bromide (2.2 mmole) at reflux for 3 h. The cooled reaction mixture was filtered and the filtrate was evaporated to dryness. The resulting dark oil was purified by chromatography to give 5-diethylphosphono-2-[(2-bromo-4-methyl-1-oxo)pentyl]furan as an orange oil.

Step F:

A solution of 5-diethylphosphono-2-[(2-bromo-4-methyl-1-oxo)pentyl]furan (1 mmole) and thiourea (2 mmole) in ethanol was heated at reflux for 2 h. The cooled reaction mixture was evaporated to dryness and the resulting yellow foam was suspended in saturated sodium bicarbonate and water (pH=8). The resulting yellow solid was collected through filtration to give 2-amino-5-isobutyl-4-[2-(5-diethylphosphono)furanyl]thiazole.

Step G:

A solution of 2-amino-5-isobutyl-4-[2-(5-diethylphosphono)-furanyl]thiazole (1 mmole) in methylene chloride was treated with bromotrimethylsilane (10 mmole) at 25° C. for 8 h. The reaction mixture was evaporated to dryness and the residue was suspended in water. The resulting solid was collected through filtration to give 2-amino-5-isobutyl-4-[2-(5-phosphono)furanyl]thiazole as an off-white solid.

10.1 2-amino-5-isobutyl-4-[2'-(5'-phosphono)furanyl]thiazole mp>250° C. Anal. calcd. for $C_{11}H_{15}N_2O_4PS$+1.25HBr: C, 32.75; H, 4.06; N, 6.94. Found: C, 32.39; H, 4.33; N, 7.18.

The following compounds were prepared according to similar procedure:

10.2 2-Methyl-5-isobutyl-4-[2'-(5'-phosphono)furanyl]thiazole. Anal. calcd. for $C_{12}H_{16}NO_4PS$+HBr+0.1$CH_2Cl_2$: C, 37.20; H, 4.44; N, 3.58. Found: C, 37.24; H, 4.56; N, 3.30.

10.3 2-Amino-5-methylthio-4-[2'-(5'-phosphono)furanyl]thiazole. mp 181-184° C. Anal. calcd. for $C_8H_9N_2O_4PS_2$+0.4$H_2O$: C, 32.08; H, 3.30; N, 9.35.
Found: C, 32.09; H, 3.31; N, 9.15.

Example 11

General Procedure for the Synthesis of Cyclophosphamide Analogs (Boyd, et al., *J. Med. Chem.* 1980, 23, 372)

A solution of bis(2-chloroethyl)phosphoramidic dichloride (10 mmol) in ethyl acetate (100 mL) is added dropwise to a solution of commercial 3 methylamino-1-phenyl-1-propanol (10 mmol) and triethylamine (20 mmol) in ethyl acetate (100 mL) at rt. After stirring at rt for 3 days, the salts are filtered off and the combined filtrates are concentrated under vacuum. The crude product is purified by column chromatography on silica.

Example 12

Phosphoramide Prodrugs of 1-Methylamino-1-phenyl-3-propanol

Step A:

The reagent N-methyl-2-(4-nitrophenoxy)-2-oxo-6-phenyl-1,3,2-oxazaphosphorinane was made using the same procedure as the one described for step A of example 2:

Fast eluting isomer: White solid, mp 135° C.; Rf=0.4 (Silica, Ethyl acetate/Hexanes 1/1). Slow eluting isomer: White solid, mp 128-129; Rf=0.15 (Silica, Ethyl acetate/Hexanes 1/1).

Step B:

The coupling step with the nucleoside was accomplished in a manner similar to the one described in step B of example 3 except that the reaction mixture was stirred at 100.degree. C. for 5 hours.

The following compound was prepared in this manner:

12.1: 9-[(2-(N-Methyl-2-oxo-6-phenyl-1,3,2-oxazaphosphorin-2-oxy)-ethoxy)methyl]-guanine: pale yellow amorphous solid; Rf=0.45 (Silica, Methanol/dichloromethane 2/8); $^1$H NMR (200 MHz, DMSO $d_6$) δ 7.8 (bs, 1H); 7.3 (bs, 5H), 6.75 (bs, 2H, exchangeable with $D_2O$); 5.35 (bs, 3H).

The following compound was prepared in this manner:

12.2: 5-(N-Methyl-2-oxo-6-phenyl-1,3,2-oxazaphosphorin-2-yl)-9-β-D-arabino-furanosyladenine: Off white amorphous solid; Rf=0.2 (Silica, Methanol/dichloromethane 1/9); $^1$H NMR (200 MHz, DMSO d$_6$) δ 7.4-7.1 (m, 5H); 5.75 (s, 1H), 5.25 (m, 1H); 4.8 (m, 1H).

Example 13

Phosphoramide Prodrugs of
3-amino-1-hydroxy-1-phenyl propane

Step A:

A mixture of 3-phenyl-3-hydroxypropylmethanesulfonate (1.71 g, Gao, et al., *J. Org. Chem.*, 1988, 53, 4081), tetrahydrofuran (10 mL) and 28% ammonium hydroxide (30 mL) was heated in a bomb at 65° C. for 16 hours. After cooling, the volatiles were eliminated to leave the aqueous solution which was extracted with ether. The aqueous layer was concentrated under reduced pressure, azeotroped twice with anhydrous acetonitrile and dried under vacuum to give 3-amino-1-phenyl-1-propanol (1.04 g) as a white solid: mp 92-94° C., Rf=0.1 (silica, methanol/ethyl acetate 1/1).

Step B:

The reagent 2-(4-nitrophenoxy)-2-oxo-6-phenyl-1,3,2-oxazaphosphorinane (13.1) was made using the same procedure as the one described for step A of example 2: Fast eluting isomer: Rf=0.6 (Silica, Ethyl acetate), $^1$H NMR (200 MHz, DMSO d$_6$) δ 8.22 (m, 2H); 7.48 (m, 2H), 7.35 (m, 5H); 5.52 (m, 1H).

Step C:

The coupling step with the nucleoside is accomplished in a manner similar to the one described in step B of example 3.

The following compounds are made in this manner:

9-[(2-(N-Methyl-2-oxo-6-phenyl-1,3,2-oxazaphosphorin-2-oxy)-ethoxy)methyl]-guanine;

5-(N-Methyl-2-oxo-6-phenyl-1,3,2-oxazaphosphorin-2-yl)-9-β-D-arabinofuranosyladenine.

Examples of use of the method of the invention includes the following. It will be understood that these examples are exemplary and that the method of the invention is not limited solely to these examples.

For the purposes of clarity and brevity, chemical compounds are referred to as synthetic example numbers in the biological examples below.

BIOLOGICAL EXAMPLES

Example A

Chemical Stability of an Antidiabetic Phosphoramidate Prodrug

Methods: Aliquots of a 10 μg/mL solution of Compound 1.3 in potassium phosphate buffers at pH 3 and 7 (room temperature) were sampled hourly for 12 hours. Samples were analyzed by reverse phase HPLC with use of a Beckman Ultrasphere C8 column (4.6×250 mm). The column was equilibrated and eluted with a gradient from 50 mM sodium phosphate pH 5.5 to 80% acetonitrile at a flow rate of 1.0 mL/min. Detection was at 254 nm. Under these conditions, Compound 1.3 was separated from 2-Amino-5-isobutyl-4-[2-(5-phosphonomonoamide)furanyl]thiazole, and from 2-Amino-5-isobutyl-4-(2-furanyl)thiazole (retention times=17, 15.8, and 15.6 min., respectively).

Results: The half-life of Compound 1.3 at pH 3.0 was 3.8 h; prodrug decomposed to an unidentified metabolite at this pH. Compound 1.3 was fully stable at pH 7.0; there was no evidence of decomposition throughout the 12-hour incubation.

Example B

Stability of Phosphoramidate Prodrugs to Esterases, Phosphatases, Adenosine Deaminase, and Plasma Methods: Carboxylesterase (porcine liver) and alkaline phosphatase (calf intestinal mucose) are purchased from Sigma Chemical Co. (St. Louis, Mo.). Carboxylesterase activity is measured in 0.1 M Tris-HCl buffer at pH 8.0. Activity towards p-nitrophenyl acetate, a known substrate and positive control in the reactions is measured as described for example by Matsushima M., et al. [*FEBS Lett.* (1991)293 (1-2): 37-41]. Alkaline phosphatase activity is measured in a 0.1 M diethanolamine buffer, pH 9.8, containing 0.5 mM MgCl$_2$. Activity towards p-nitrophenyl phosphate, a known substrate and positive control in the reactions, is measured as described [e.g. Brenna O., et at (1975) *Biochem J.* 151(2): 291-6]. Adenosine deaminase activity is measured as described by e.g. Gustin N C, et al. [*Anal. Biochem.* (1976) 71: 527-532]. Adenosine is used as a positive control in these reactions. Plasma is prepared by centrifugation from fresh, heparinized rat or human blood. Prodrugs are incubated at a concentration of, for example, 25 μM in appropriate reaction mixtures containing carboxylesterase, alkaline phosphatase, adenosine deaminase, or rat or human plasma. In the case of the esterase, phosphatase, and adenosine deaminase assays, parallel reactions are run with known substrates of the enzymes as described.

Aliqouts are removed from the reaction mixture at various time points and the reaction stopped by addition of methanol to 60%. Following centrifugation and filtration, the methanolic aliquots are analyzed for generation of MPO$_2$—(NHR$^{6-}$) or other metabolites by standard reverse phase, ion-pairing, or ion exchange HPLC methods.

Results: MPO$_2$—(NHR$^{6-}$) or metabolites thereof are not detected following exposure of the prodrugs to carboxylesterase, alkaline phosphatase or plasma.

Example C

Activation of Phosphoramidate Prodrugs by Rat Liver Microsomes

Methods: The microsomal fraction is prepared from fresh, saline-perfused rat liver. Liver tissue is homogenized in three volumes (w/v) of 0.2 M KH$_2$PO$_4$ buffer pH 7.5, containing 2 mM MgCl$_2$ and 1 mM EGTA. The homogenate is centrifuged at 10,000 g for 1 hour and the supernatant recovered. The supernatant fraction is then recentrifuged at 100,000 g to pellet the microsomal fraction. The pellet is resuspended in homogenization buffer and recentrifuged. This process is repeated twice to ensure complete removal of cytosolic enzyme activities. After the last centrifugation, the microsomal pellet is resuspended in homogenization buffer at a final protein concentration of about 14 mg/ml. Reaction mixtures (0.5 ml) consist of 0.2 M KH$_2$PO$_4$ pH 7.5, 13 Mm glucose-6-phosphate, 2.2 mM NADP+, 1 unit of glucose-6-phosphate dehydrogenase, 0-2.5 mg/ml microsomal protein and 100 μM 7.1. Reactions are carried out at 37° C. Aliquots are removed from the reaction mixtures at appropriate time points, and extracted with 60% methanol. The methanolic extracts are centrifuged at 14,000 rpm, and filtered (0.2 μM) prior to analysis by HPLC. Standard HPLC techniques including reverse phase, ion-pairing, or ion exchange chromatography are used. Eluted peaks are quantified relative to authentic standards of known concentration.

Alternatively, the activation of prodrugs is monitored by the depletion of NADPH, an essential cofactor in the reaction. This assay is performed in reactions mixtures consisting of 0.2 M $KH_2PO_4$, 0.22 mM NADPH, 0-2.5 mg/ml microsomal protein, and 100 µM 28.4 or 30.1. Reactions are monitored spectrophotometrically at 340 nm. A decrease in absorbance is indicative of cofactor depletion and thus of the enzymatic oxidation of prodrug to $MPO_2$—$(NHR^{6-})$.

Results: Prodrugs are converted to $MPO_2$—$(NHR^{6-})$ in the presence, but not in the absence of, NADP+ (this cofactor is enzymatically reduced to NADPH by the dehydrogenase present in the reaction mixtures). This result indicates that an oxidative step is involved in the activation of the prodrug. The rate of activation of prodrugs to $MPO_2$—$(NHR^{6-})$ is linearly dependent on microsomal protein concentration, confirming that activation occurs by an enzyme-dependent mechanism.

Example D

Activation of Phosphoramidate Prodrugs by Human Microsomes and the Identification and Tissue Distribution of the Microsomal Enzymes Involved in Activation Methods: Human liver microsomes and cloned human P450 enzymes representing all major isoforms are obtained from In Vitro Technologies and Gentest Inc., respectively. Reaction mixtures typically contain 100 mM potassium phosphate buffer, pH 7.4, 2 mM NADPH, 0-2 mg/ml microsomal protein or cloned microsomal isozyme, and the prodrug at, for example, a 100 µM concentration. Formation of $MPO_2$—$(NHR^{6-})$ is monitored by standard reverse phase, ion pairing, or anion exchange HPLC methods. $MPO_2(NHR^{6-})$ is detected by uv absorbance and quantified relative to authentic standards. To determine the tissue distribution of the activating enzyme, homogenates are prepared from key tissues including the liver, lung, intestine, kidney, heart, and skeletal muscle. The rate of conversion of prodrug to $MPO_2$—$(NHR^{6-})$ in each homogenate is assessed as described for the microsomal reactions above. Alternatively, once the major catalytic isoform is identified, immunohistological methods using antibodies raised against the specific enzyme (Waziers et al 1989, *J. Pharm. Exp. Ther.* 254: 387), or molecular biological methods using PCR techniques (Sumida et al 2000, *BBRC* 267: 756) are employed to determine the tissue distribution of the activity.

Results: Prodrugs are transformed to $MPO_2$—$(NHR^{6-})$ in the human microme-catalyzed reaction at a readily measurable rate. In the screen of cloned microsomal isozymes, the CYP3A4 isozyme catalyzes activation of the prodrugs at the highest rate although other isozymes also show some activity towards the prodrugs. The tissue distribution studies indicate a high activity or abundance of the activating enzyme in the liver relative to other tissues.

Example E

Identification of the P450 Isozyme Involved in Phosphoramidate Prodrug Activation with Use of Specific Enzyme Inhibitors Prodrugs are evaluated for human microsome-catalyzed conversion to $MPO_2$—$(NHR^{6-})$ in the absence and presence of specific inhibitors of three major P450 isozymes: ketoconazole (CYP3A4), furafylline (CYPIA2), and sulfaphenazole CYP2C9).

Methods: Reactions (0.5 ml@37° C.) consist of 0.2 M $KH_2PO_4$, 13 mM glucose-6-phosphate, 2.2 mM NADP+, 1 unit of glucose-6-phosphate dehydrogenase, 0-2.5 mg/ml human microsomal protein (In Vitro Technologies, Inc.), 250 µM prodrug, and 0-100 µM P450 isozyme inhibitor. Reactions are stopped by addition of methanol to a concentration of 60%, and filtered (0.2 µM filter). $MPO_2$—$(NHR^{6-})$ is quantified by standard reverse phase, ion-pairing, or ion exchange HPLC methods. Eluted peaks are quantified relative to authentic standards of known concentration.

Results: Ketoconazole inhibits the formation of $MPO_2$—$(NHR^{6-})$ in a dose-dependent fashion. The other inhibitors, furafylline and sulfaphenazole, show no significant inhibition. The results indicate that CYP3A4 is the primary P450 isoform responsible for activation phosphoramidate prodrugs in human liver.

Example F

Activation of Compound 1.3 by Recombinant CYP3A4

Activation of 1.3 was evaluated in reactions containing microsomes from baculovirus-infected insect cells co-expressing human recombinant CYP3A4 and cytochrome p450 reductase (Panvera Corp., Madison, Wis.).

Methods: Reaction mixture composition was similar to that described in Example D. Reactions were terminated by addition of methanol to a final concentration of 60% and products were analyzed by HPLC as described in Example A.

Results: 2-Amino-5-isobutyl-4-[2-(5-phosphonomonoamide)furanyl]thiazole was generated from 1.3 at a rate of 4.2 nmoles/min./nmole CYP3A4.

Example G

Activation of Antiviral Phosphoramidate Prodrugs in Isolated Rat Hepatocytes

The activation of 3.1 and 3.2 was evaluated by monitoring the intracellular generation of the corresponding nucleoside triphosphates in rat hepatocytes.

Methods: Hepatocytes were prepared from fed, dexamethasone-induced Sprague-Dawley rats (300 g) according to the procedure of Berry and Friend (Berry, M. N., Friend, D. S. *J. Cell Biol.* 43, 506-520 (1969)) as modified by Groen (Groen, A. K. et al. *Eur J. Biochem* 122, 87-93 (1982)). Hepatocytes (62 mg wet weight/ml) were incubated in 2 ml Krebs bicarbonate buffer containing 10 mM glucose, and 1 mg/ml BSA. Incubations were carried out in a 95% oxygen, 5% carbon dioxide atmosphere in closed, 50-ml Falcon tubes submerged in a rapidly shaking water bath (37° C.). 3.1 and 3.2 were dissolved in methanol to yield 25 mM stock solutions, and then diluted into the cell suspension to yield a final concentration of 250 µM. Two hours following administration, aliquots of the cell suspension were removed and spun through a silicon/mineral oil layer into 10% perchloric acid. The cell extracts in the acid layers were neutralized by the addition of 0.3 volumes of 3M KOH/3M $KHCO_3$, and the extract was then centrifuged, filtered (0.2 micron) and loaded onto an anion exchange HPLC column equilibrated with 70% A (10 mM ammonium phosphate pH 3.5, 6% ETOH) and 30% B (1 M ammonium phosphate pH 3.5, 6% ETOH). AraATP and acyclovir-triphosphate, the expected metabolites of 3.1 and 3.2, respectively, were eluted from the column with a linear gradient to 80% B in 20 minutes. Detection was by uv absorbance at 254 nm. Peak areas were quantified by comparison of peak areas to authentic standards spiked into naive hepatocyte extracts.

Results: Both prodrugs generated their respective triphosphates in isolated rat hepatocytes. Levels formed following two hours of incubation are summarized below:

| Compound | Intracellular concentration nmoles/g |
|---|---|
| 3.1 | 15.7 ± 16 |
| 3.2 | 13.3 ± 3 |

Example H

Kinase Bypass

The generation of acyclovir triphosphate from a phosphoramidate prodrug of acyclovir (Compound 3.2) and acyclovir itself was compared in rat hepatocytes.

Methods: 3.2 and acyclovir were evaluated in isolated rat hepatocytes at 250 µM as described in Example G.

Results: Levels of acyclovir triphosphate formed following two hours of incubation are summarized below:

| Compound | Intracellular concentration nmoles/g |
|---|---|
| acyclovir | <2 |
| 3.2 | 13.3 ± 3 |

The results demonstrate that a phosphoramidate prodrug of a parent nucleoside such as acyclovir, that is poorly phosphorylated in cells, can bypass the nucleoside phosphorylation step and thus generate higher intracellular levels of triphosphate than the free nucleoside.

Example I

Inhibition of Glucose Production in Rat Hepatocytes by Compound 1.3

Compound 1.3 and its phosphonic acid parent compound, 2-Amino-5-isobutyl-4-(2-furanyl)thiazole, were tested in isolated rat hepatocytes for inhibition of glucose production.

Methods: Isolated rat hepatocytes were prepared from fasted Sprague Dawley rats (250-300 g) as described in Example G. Hepatocytes (75 mg wet weight/ml) were incubated in 1 ml Krebs bicarbonate buffer containing 10 mM glucose, and 1 mg/ml BSA. Incubations were carried out in a 95% oxygen, 5% carbon dioxide atmosphere in closed, 50-ml Falcon tubes submerged in a rapidly shaking water bath (37° C.). After 10 minutes of equilibration, lactate and pyruvate were added to 10 mM and 1 mM concentrations, respectively. Addition of these gluconeogenic substrates was immediately followed by the addition of test compound to concentrations ranging from 1-100 µM. After 1 hour, an aliquot (0.25 ml) was removed, and transferred to an Eppendorf tube and centrifuged. The resulting supernatant (50 µA) was then assayed for glucose content using a Glucose Oxidase kit (Sigma Chemical Co.) as per the manufacturer's instructions.

Results: 1.3 and 2-Amino-5-isobutyl-4-(2-furanyl)thiazole inhibited glucose production in a dose dependent manner with IC50's of 8.5 and 2.5 µM, respectively. Since 1.3 is not an inhibitor of FBPase in vitro, inhibition of gluconeogenesis in hepatocytes confirms that prodrug was converted to 2-Amino-5-isobutyl-4-(2-furanyl)thiazole intracellularly. The ~3-fold lower potency of 1.3 relative to 2-Amino-5-isobutyl-4-(2-furanyl)thiazole is consistent with time-dependent activation of prodrug to parent compound in cells.

Example J

Activation of Antidiabetic and Antiviral Phosphoramidate Prodrugs in Induced Rat Hepatocytes Compounds 1.7 and 12.1 was tested for activation in hepatocytes isolated from rats in which CYP3A4 expression was induced by treatment with dexamethasone. This treatment results in more extensive intracellular activation of phosphoramidate prodrugs.

Methods: Rats were treated with dexamethasone (50 mg/kg, intraperitoneally) for 4 days as described (Brain E G C et al 1998, *Br. J. Cancer* 7: 1768). Isolated hepatocytes were prepared, and prodrugs tested for activation as described in Example G.

Results: 1.7 activated to yield 20.5±3 nmole/g levels of 2-Amino-5-methylthio-4-[2-(5 phosphono)furanyl]thiazole following two hours of incubation. 12.1 generated 110±0.2 mmoles 1 g acyclovir triphosphate.

Example K

Cytotoxicity Testing of Phosphoramidate Prodrugs in Non-CYP3A4 Expressing Cell Lines Administration of a drug in a plasma-stable prodrug form can reduce systemic toxicities by limiting exposure to free $MPO_2$—$(NHR^{6-})$ and metabolites. This potential advantage of prodrug delivery is demonstrated by comparing the toxicity profile of the prodrug and the corresponding parent compound in a cell line which does not express the CYP3A4 enzyme required for prodrug activation.

Methods: The choice of cell line is dictated by the known toxicity profile of the parent compound. If the toxicity profile of a parent compound is unknown, a panel of different cultured cell lines can be tested. Cells are exposed to a range of prodrug and parent compound concentrations for hours to days. Viability is the measured by Trypan blue exclusion, enzyme marker leakage, incorporation of labeled thymidine into DNA or other standard method.

Results: Phosphoramidate prodrugs are either noncytotoxic or cytotoxic at considerably higher concentrations than the corresponding parent compound. The latter profile suggests that even if systemic exposure to the prodrug is high, it is likely to show reduced peripheral toxicity in vivo relative to free parent compound. Testing prodrugs in this manner allows an assessment of the intrinsic toxicity of the prodrug and can be used to select prodrugs with favorable cellular safety profiles.

Example L

Cytotoxicity Testing in Cellular Systems that Catalyze Phosphoramidate Prodrug Activation Cytotoxicity testing in systems in which phosphoramidate prodrugs are activated allows an assessment of the safety of $MPO_2$—$(NHR^{6-})$ and other metabolites of the prodrug or parent compound that are generated. Several cellular systems are useful for testing: (a) fresh primary cultures of hepatocytes of human or other origin in which CYP3A4 expression is maintained with an appropriate inducer such as Rifampicin, (b) cell lines in to which CYP3A4 and the requisite reductase are cotransfected, (c) cell lines that are coincubated with primary hepatocytes that express CYP3A4, (d) cell lines that are coincubated with CYP3A4 containing micromal fractions or a cloned CYP3A4 preparation in addition to a standard NADPH recycling system. Prodrugs are incubated in these systems for hours or days. Cytotoxicity is assessed by standard methods such as the Trypan blue exclusion technique, the leakage of enzyme markers, the incorporation of labeled precursors into cellular DNA, etc.

Example M

Byproduct Toxicity Testing, In Vitro

Activation of certain phosphoramidate prodrugs, in addition to generating $MPO_2$—$(NHR^{6-})$, also results in the formation of an electrophilic byproduct capable of alkylating cellular constituents. As the prodrugs in question are activated primarily in the liver, primary rat hepatocytes, known to contain both the microsomal enzymes required for prodrug activation as well as critical detoxification mechanisms, are the cell type of choice for testing the potential toxicity of the byproduct formed.

Methods: Isolated rat hepatocytes are prepared and incubated with test compound as described in Example G. Acetaminophen (0-10 mM) is used as a positive control in these tests since its microsomal metabolism is also known to generate an electrophilic metabolite in these cells (Smolarek T A et al 1989, *Metabolism and Disposition* 18: 659). This metabolite is detoxified by addition to glutathione, a protective thiol present in mM concentrations in liver cells. Incubations with acetaminophen and phosphoramidate prodrugs are for 4 hours. Cellular viability is assessed by lactate dehydrogenase or other liver enzyme leakage and/or by Trypan blue exclusion. Intracellular glutathione stores are also quantified as described (Baker M A et al 1990, *Anal. Biochem.* 190: 360).

Results: Acetaminophen depleted intracellular glutatione levels by 90% at the highest dose tested (10 mM) but did not compromise cellular viability as measured by Trypan blue exclusion. The data suggest that the byproduct generated as a result of acetaminophen metabolism was readily detoxified in the hepatocytes, and that the cellular capacity for detoxicification was not exceeded. Activation of phosphoramidate prodrugs does not cause byproduct-related toxicities in this hepatocyte system.

Example N

Byproduct Toxicity Testing In Vivo

Toxicity of the electrophile generated following microsomal activation of certain phosphoramidate prodrugs is tested in the mouse.

Methods: Mice are administered various doses of prodrug and acetaminophen (a positive control, see Example M) and serially sacrificed at various time points following drug administration. Livers are removed and processed for glutathione analysis as described in Example M, and for drug analysis by standard reverse phase, ion-pairing, or ion exchange HPLC methods. Plasma samples are subjected to a standard chemistry panel in which markers of liver function are evaluated.

Results: Acetaminophen exposure (50, 250 and 500 mg/kg) resulted in a dose-dependent reduction of hepatic glutathione. Liver toxicity in the form of liver enzyme elevations and the appearance of necrotic lesions was evident only at the highest dose, which depleted hepatic glutathione by >80%. This is in accordance with the literature; glutathione forms an adduct with the electrophilic acetaminophen metabolite formed, and protects against liver injury until a threshold level of depletion is reached (Mitchell J R et al 1973, *J. Pharm. and Exp. Ther* 187: 211). Phosphoramidate prodrug administration also results in glutathione depletion, indicating that the byproduct formed is efficiently detoxified. Liver injury is apparent only at very high doses well above the projected therapeutic doses in man. The data also show dose-dependent accumulation of $MPO_2$—$(NHR^{6-})$ and/or its metabolites following phosphoramidate prodrug administration.

Example O

Enhanced Delivery of Drugs to the Liver in Animals Pretreated with CYP3A-Inducing Agents Hepatic CYP3A enzymes are induced in rats by treatment with dexamethasone or other suitable agent. Enhanced expression of CYP3A will result in a higher rate of prodrug activation and thus enhance the distribution of $MPO_2$—$(NHR^{6-})$ and/or its metabolites to this organ.

Methods: Rats are treated with dexamethasone (50 mg/kg, intraperitoneally) for 4 days as described (Brain E G C et al 1998, *Br. J. Cancer* 7: 1768). Other CYP-inducing agents such as phenobarbital or rifampicin may also be used. The induced animals are then administered prodrug orally or sytemically and serially sacrificed at various time points. Livers are removed and homogenized in perchloric acid (10%). Following clarification by centrifugation and neutralization, $MPO_2$—$(NHR^{6-})$ and/or its metabolites in the homogenates are quantified by standard HPLC methods. A similar study is conducted in uninduced animals.

Results: The AUC of $MPO_2$—$(NHR^{6-})$ and/or its metabolites in livers of induced rats will exceed that of uninduced rats. Enhanced liver delivery of $MPO_2$—$(NHR^{6-})$ and/or its metabolites resulting from CYP3A induction is expected to result in increased efficacy.

Example P

Oral Bioavailability of Phosphoramidate Prodrugs

The oral bioavailability (OBAV) of phosphoramidate prodrugs is estimated by comparison of the area under the curve (AUC) of $MPO_2$—$(NHR^{6-})$ and/or its metabolites generated in liver following oral administration to that generated following intravenous administration. Alternatively, OBAV is determined by means of a urinary excretion assay of $MPO_2$—$(NHR^{6-})$ and/or its metabolites following prodrug administration.

Methods: Rats are dosed orally and systemically with a phosphoramidate prodrug in a suitable vehicle and serially sacrificed at appropriate time point following drug administration. Liver and plasma samples are obtained, processed, and analyzed for $MPO_2$—$(NHR^{6-})$ and/or its metabolites by standard reverse phase, ion-pairing, or ion exchange HPLC methods. Alternatively, animals are placed in metabolic cages following drug administration, and urine is collected for 24-48 hours. The quantity of $MPO_2$—$(NHR^{6-})$ and/or its metabolites excreted into urine is then determined by HPLC analysis. Oral bioavailability is calculated either by comparing the AUC of $MPO_2$—$(NHR^{6-})$ and/or its metabolites in the liver or the quantity in urine following oral and systemic administration.

Results: The data indicate that phosphoramidate prodrugs are suitable for the oral delivery of $MPO_2$—$(NHR^{6-})$ and/or its metabolites.

Example Q

Enhanced Liver Delivery and Reduced Systemic Exposure of $MPO_2$—$(NHR^{6-})$ and/or its Metabolites Following Administration of Phosphoramidate Prodrugs Method: Rats are dosed either orally or systemically with a phosphoramidate prodrug, $MPO_2(NHR^{6-})$, and/or its metabolites. Animals are serially sacrificed at appropriate time points following drug administration. Liver and plasma samples are obtained, processed, and analyzed for $MPO_2$ $(NHR^{6-})$ and/or its metabolites by standard reverse phase, ion-pairing, or ion exchange HPLC.

Results: Administration of phosphoramidate prodrugs results in the generation of higher levels of $MPO_2$—$(NHR^{6-})$ and/or its metabolites in liver and their reduced concentrations in plasma than when free $MPO_2$—$(NHR^{6-})$ is administered.

Example R

Reduced Renal Excretion of $MPO_2$—$(NHR^{6-})$ and/or its Metabolites Following Administration of Phosphoramidate Prodrugs Methods: Phosphoramidate prodrugs and respective $MPO_2$—$(NHR^{6-})$ are administered systemically to rats. Rats are subsequently caged in metabolic cages and urine collected over a 24-48 hour period. $MPO_2$—$(NHR^{6-})$ and/or its metabolites are quantified in urine by means of standard reverse phase, ion-pairing, or ion exchange HPLC methods. By relating the amount of parent compound/metabolites excreted in urine to the dose administered, the % renal clearance is calculated.

Results: Renal excretion of $MPO_2$—$(NHR^{6-})$ and/or its metabolites following phosphoramidate prodrug administration is lower than when parent compound is administered. This result indicates that the renal exposure and thus the renal toxicity associated with certain parent compounds and/or their metabolites may be avoided by administration of the compound in phosphoramidate prodrug form.

Example S

Sustained Liver Drug Levels

Methods: Rats are dosed orally and systemically with a phosphoramidate prodrug or the corresponding $MPO_2$— $(NHR^{6-})$ and serially sacrificed at appropriate time point following drug administration. Liver samples are obtained, processed, and analyzed for $MPO_2$—$(NHR^{6-})$ and/or its metabolites by standard reverse phase, ion-pairing, or ion exchange HPLC. Liver half-lives are determined with the aid of WinNonLin 1.1 software (Scientific Consulting, Inc.).

Results: The half-life of $MPO_2$—$(NHR^{6-})$ and/or its metabolites in liver is longer when administered in phosphoramidate prodrug form than when free $MPO_2$—$(NHR^{6-})$ is administered. This result is consistent with the prodrug serving as a $MPO_2$—$(NHR^{6-})$ reservoir and, by virtue of a prolonged in vivo half-life, providing sustained release of $MPO_2$—$(NHR^{6-})$ and/or its metabolites to the liver.

We claim:
1. A compound of formula I:

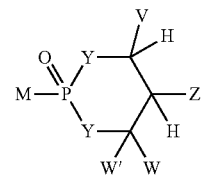

wherein:
V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)$ $OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH (CH=$CR^2_2$)OH, —CH(C≡$CR^2$)OH, —$R^2$, —$NR^2_2$, —$OCOR^3$, —$OCO_2R^3$, —$SCOR^3$, —$SCO_2R^3$, —NH-$COR^2$, —$NHCO_2R^3$, —$CH_2$NHaryl, —$(CH_2)_p$-$OR^{12}$, and —$(CH_2)_p$—$SR^{12}$;

p is an integer 2 or 3;
with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;
$R^3$ is selected from the group consisting of alkyl, aryl, alicyclic, and aralkyl;
$R^6$ is selected from the group consisting of —H, and lower alkyl, acyloxyalkyl, alkoxycarbonyloxy alkyl and lower acyl;

$R^{12}$ is selected from the group consisting of —H, and lower acyl;

each Y is independently selected from the group consisting of —O—, —$NR^6$— with the proviso that at least one Y is —$NR^6$—;

M is an agent selected from the group that when attached to H, $PO_3^{2-}$, $P_2O_6^{3-}$, $P_3O_9^{4-}$ or $P(O)(NHR^6)O^-$ is a biologically active agent, but is not an FBPase inhibitor, and is attached to the phosphorus in formula I via a carbon, oxygen, sulfur or nitrogen atom of the M group;

with the provisos that:

1) M is not —NH(lower alkyl), —N(lower alkyl)$_2$, —NH (lower alkylhalide), —N(lower alkylhalide)$_2$, or —N(lower alkyl)(lower alkylhalide); and 2) $R^6$ is not lower alkylhalide;

and pharmaceutically acceptable salts thereof.

2. The compounds of claim 1 wherein M is an agent selected from M-$P(O)(NHR^6)O^-$, M-$PO_3^{2-}$, M-$P_2O_6^{3-}$, and M-$P_3O_9^{4-}$, such that M-$P(O)(NHR^6)O^-$, M-$PO_3^{2-}$, M-$P_2O_6^{3-}$, and M-$P_3O_9^{4}$ is a biologically active agent selected from the group consisting of an antiviral, anticancer, antihyperlipidemic, antifibrotic, antiparasitic agents, metalloprotease inhibitor, and TS inhibitor.

3. The compounds of claim 2 wherein M is an agent selected from M-H, such that M-H is a biologically active agent selected from the group consisting of LdC, LdT, araA, AZT, d4T, ddI, ddA, ddC, L-ddC, L-FddC, L-d4C, L-Fd4C, 3TC, ribavirin, penciclovir, 5-fluoro-2'-deoxyuridine, FIAU, FIAC, BHCG, 2'R,5'S(−)-1-[2-(hydroxymethyl)oxathiolan-5-yl]cytosine, (−)-b-L-2',3'-dideoxycytidine, (−)-b-L-2',3'-dideoxy-5-fluorocytidine, FMAU, BvaraU, E-5-(2-bromovinyl)-2'-deoxyuridine, Cobucavir, TFT, 5-propynyl-1-arabinosyluracil, CDG, DAPD, FDOC, d4C, DXG, FEAU, FLG, FLT, FTC, 5-yl-carbocyclic 2'-deoxyguanosine, Cytallene, Oxetanocin A, Oxetanocin G, Cyclobut A, Cyclobut G, fluorodeoxyuridine, dFdC, araC, bromodeoxyuridine, IDU, CdA, F-araA, 5-FdUMP, Coformycin, 2'-deoxycoformycin, ACV, GCV, penciclovir, (R)-9-(3,4 dihydroxybutyl) guanine, and cytallene.

4. The compounds of claim 1 wherein M is selected from an agent selected from M-$PO_3^{2-}$, such that M-$PO_3^{2-}$ is a biologically active agent selected from the group consisting of PMEA, PMEDAP, HPMPC, HPMPA, FPMPA, and PMPA.

5. The compounds of claim 1 wherein $MP(O)(NH R^6)O$, $MPO_3^{2-}$, $MP_2O_6^{3-}$, or $MP_3O_9^{4-}$ is useful for the treatment of diseases of the liver or metabolic diseases where the liver is responsible for the overproduction of a biochemical end product.

6. The compounds of claim 5 wherein said disease of the liver or metabolic disease is selected from the group consisting of hepatitis, cancer, fibrosis, malaria, gallstones, chronic cholecystalithiasis, diabetes, atherosclerosis, and obesity.

7. The compounds of claim 5 wherein said biochemical end product is selected from the group consisting of glucose, cholesterol, fatty acids, and triglycerides.

8. The compounds of claim 7 wherein $MPO_3^{2-}$ or $MP(O)(NHR^6)O^-$ is an AMP activated protein kinase activator.

9. The compounds of claim 1 wherein Y is —O— located adjacent to the W' and W groups.

10. The compounds of claim 1 wherein Y is —O— located adjacent to the V group.

11. The compounds of claim 1 wherein both Y groups are —$NR^6$—.

12. The compounds of claim 1 wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus.

13. The compounds of claim 12 wherein V is selected from the group consisting of aryl, substituted aryl, heteroaryl, substituted heteroaryl; or together V and W are connected via an additional 3 carbon atoms to form a cyclic substituted group containing 6 carbon atoms and mono-substituted with a substituent selected from the group consisting of hydroxyl, acyloxy, alkoxycarbonyloxy, alkylthiocarbonyloxy, and aryloxycarbonyloxy attached to one of said additional carbon atoms that is three atoms from an Y attached to the phosphorus.

14. The compounds of claim 13 wherein V is selected from the group consisting of aryl, substituted aryl, heteroaryl, and substituted heteroaryl.

15. The compounds of claim 14 wherein Z, W, and W' are H; and $R^6$ is selected from the group consisting of —H, and lower alkyl.

16. The compounds of claim 14 wherein V is selected from the group consisting of phenyl, and substituted phenyl.

17. The compounds of claim 14 wherein V is selected from the group consisting of 3,5-dichlorophenyl, 3-bromo-4-fluorophenyl, 3-chlorophenyl, 3-bromophenyl, 3,5-difluorophenyl, and 4-pyridyl.

18. The compounds of claim 13 wherein together V and W are connected via an additional 3 carbon atoms to form an optionally substituted cyclic group containing 6 carbon atoms and mono-substituted with one substituent selected from the group consisting of hydroxy, acyloxy, alkoxycarbonyloxy, alkylthiocarbonyloxy, and aryloxycarbonyloxy attached to one of said additional carbon atoms that is three atoms from an Y attached to the phosphorus.

19. The compounds of claim 18 wherein together V and W form a cyclic group selected from the group consisting of —$CH_2$—CH(OH)—$CH_2$—, —$CH_2CH(OCOR^3)$—$CH_2$—, and —$CH_2CH(OCO_2R^3)$—$CH_2$—.

20. The compounds of claim 12 wherein said compound is selected from a compound of formula VI:

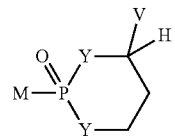

wherein

V is selected froth the group consisting of aryl, substituted aryl, heteroaryl, and substituted heteroaryl.

21. The compounds of claim 12 wherein said compound is selected from a compound of formula VII:

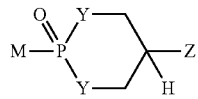 VII wherein

Z is selected from the group consisting of: —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, and —CH$_2$aryl.

22. The compounds of claim 12 wherein said compound is selected from a compound of formula VIII:

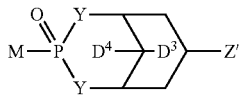 VIII wherein

Z' is selected from the group consisting of —OH, —OC(O)R$^3$, —OCO$_2$ R$^3$, and —OC(O)S R$^3$;

D$^3$ is —H;

D$^4$ is selected from the group consisting of —H, alkyl, —OH, and —OC(O)R$^3$.

23. The compounds of claim 12 wherein W' and Z are —H, W and V are both the same aryl, substituted aryl, heteroaryl, or substituted heteroaryl, and both Y groups are the same —NR$^6$—, such that the phosphonate moiety:

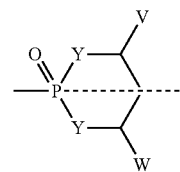

has a plane of symmetry through the phosphorus-oxygen double bond.

24. A method of enhancing oral bioavailability of a parent drug by administering to an animal a compound of claim 1.

25. The method of claim 24 wherein said oral bioavailability is at least 10%.

26. The method of claim 24 wherein said oral bioavailability is enhanced by 50% compared to the parent drug administered orally.

* * * * *